(12) United States Patent
Janetka et al.

(10) Patent No.: US 11,130,780 B2
(45) Date of Patent: Sep. 28, 2021

(54) INHIBITORS OF GROWTH FACTOR ACTIVATION ENZYMES

(71) Applicants: James W. Janetka, St. Louis, MO (US); Zhenfu Han, St. Louis, MO (US); Peter Harris, St. Louis, MO (US); Partha Karmakar, St. Louis, MO (US)

(72) Inventors: James W. Janetka, University City, MO (US); Zhenfu Han, St. Louis, MO (US); Peter Harris, Chesterfield, MO (US); Partha Karmakar, St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 15/556,804

(22) PCT Filed: Mar. 2, 2016

(86) PCT No.: PCT/US2016/020516
§ 371 (c)(1),
(2) Date: Sep. 8, 2017

(87) PCT Pub. No.: WO2016/144654
PCT Pub. Date: Sep. 15, 2016

(65) Prior Publication Data
US 2018/0066015 A1    Mar. 8, 2018

Related U.S. Application Data

(60) Provisional application No. 62/220,998, filed on Sep. 19, 2015, provisional application No. 62/130,117, filed on Mar. 9, 2015.

(51) Int. Cl.
| | | |
|---|---|---|
| A61K 51/04 | (2006.01) | |
| A61K 51/08 | (2006.01) | |
| C07K 5/12 | (2006.01) | |
| A61K 38/00 | (2006.01) | |
| C07K 5/09 | (2006.01) | |
| C07K 5/11 | (2006.01) | |
| C07K 5/103 | (2006.01) | |
| C07K 5/097 | (2006.01) | |
| G01N 33/58 | (2006.01) | |
| A61K 47/64 | (2017.01) | |
| A61K 49/00 | (2006.01) | |
| C07B 59/00 | (2006.01) | |
| C07D 277/64 | (2006.01) | |
| C07K 5/072 | (2006.01) | |
| C07K 5/078 | (2006.01) | |
| C07K 5/107 | (2006.01) | |

(52) U.S. Cl.
CPC ............ *C07K 5/0815* (2013.01); *A61K 47/64* (2017.08); *A61K 49/0052* (2013.01); *A61K 49/0056* (2013.01); *A61K 51/0453* (2013.01); *A61K 51/08* (2013.01); *C07B 59/002* (2013.01); *C07B 59/008* (2013.01); *C07D 277/64* (2013.01); *C07K 5/06095* (2013.01); *C07K 5/06156* (2013.01); *C07K 5/0817* (2013.01); *C07K 5/0821* (2013.01); *C07K 5/101* (2013.01); *C07K 5/1005* (2013.01); *C07K 5/1013* (2013.01); *C07K 5/1016* (2013.01); *C07K 5/1019* (2013.01); *C07K 5/126* (2013.01); *G01N 33/582* (2013.01); *A61K 38/00* (2013.01); *C07B 2200/05* (2013.01); *G01N 2800/7028* (2013.01)

(58) Field of Classification Search
CPC ............ A61K 2121/00; A61K 2123/00; A61K 38/00; A61K 49/00; A61K 49/0052; A61K 49/0056; A61K 51/00; A61K 51/0453; A61K 51/08; A61K 51/088; A61K 47/00; A61K 47/64; C07K 5/0815; C07K 5/101; C07K 5/126; C07K 5/06095; C07K 5/06156; C07K 5/1016; C07K 5/1013; C07K 5/0817; C07K 5/1019; C07K 5/0821; C07K 5/1005; C07B 59/002; C07B 59/008; C07B 2200/05; C07D 277/64; G01N 33/582; G01N 2800/7028
USPC .......... 424/1.11, 1.65, 1.69, 1.81, 1.85, 1.89, 424/9.1, 9.2, 9.3, 9.4, 9.5, 9.6; 514/1, 514/1.1, 19.2, 19.3, 19.4, 19.5, 19.6, 21.9, 514/21.8; 530/300
See application file for complete search history.

(56) References Cited

U.S. PATENT DOCUMENTS

| | | |
|---|---|---|
| 5,518,735 A | 5/1996 | Stürzebecher et al. |
| 5,607,937 A | 3/1997 | Stürzebecher et al. |

(Continued)

FOREIGN PATENT DOCUMENTS

| | | |
|---|---|---|
| WO | 03/064620 A2 | 8/2003 |
| WO | 03/070229 A2 | 8/2003 |

OTHER PUBLICATIONS

Han et al, ACS Med. Chem. Lett., Oct. 9, 2014, vol. 5, pp. 1219-1224 (Year: 2014).*

(Continued)

*Primary Examiner* — D. L. Jones
(74) *Attorney, Agent, or Firm* — Stinson LLP

(57) ABSTRACT

The present invention generally relates to compounds that are useful for inhibiting one or more of hepatocyte growth factor activator, matriptase, hepsin, Factor Xa, or thrombin. The present invention also relates to various methods of using the inhibitor compounds including treating a malignancy, a pre-malignant condition, or cancer by administering an effective amount of the inhibitor to a subject in need thereof.

23 Claims, 17 Drawing Sheets
Specification includes a Sequence Listing.

(56) References Cited

U.S. PATENT DOCUMENTS

| | | | |
|---|---|---|---|
| 6,495,358 | B1 | 12/2002 | Groutas |
| 6,677,377 | B2 | 1/2004 | Lin et al. |
| 7,019,019 | B2 | 3/2006 | Duncan et al. |
| 7,132,418 | B2* | 11/2006 | Costanzo ............. C07D 277/64 514/219 |
| 7,432,044 | B2 | 10/2008 | Kirchhofer et al. |
| 7,727,964 | B2 | 6/2010 | Bachovchin |
| 7,741,096 | B2 | 6/2010 | Eigenbrot, Jr. et al. |
| 7,745,441 | B1 | 6/2010 | Wikström et al. |
| 7,772,251 | B2 | 8/2010 | Stürzebecher et al. |
| 8,440,706 | B2 | 5/2013 | Cottrell et al. |
| 8,569,313 | B2 | 10/2013 | Steinmetzer et al. |
| 8,664,266 | B2 | 3/2014 | Vasioukhin et al. |
| 2004/0009911 | A1 | 1/2004 | Harris et al. |
| 2005/0222383 | A1 | 10/2005 | Harris et al. |
| 2011/0206704 | A1 | 8/2011 | Ganesan et al. |
| 2012/0270807 | A1 | 10/2012 | Marsault et al. |
| 2014/0086936 | A1 | 3/2014 | Richter et al. |

OTHER PUBLICATIONS

Duchene et al, Journal of Medicinal Chemistry, Nov. 2014, vol. 57, p. 10198-10204 (Year: 2014).*

Chevillet, J. R., et al., " Identification and Characterization of Small-Molecule Inhibitors of Hespin," 2008, Mol Cancer Ther, 7/10:3343-3351, 15 pages.

Colombo, É, et al., "Design and Synthesis of Potent, Selective Inhibitors of Matriptase," 2012, ACS Med Chem Lett, 3(7):530-534, 5 pages.

Duchene, D., et al., "Analysis of Sub-Pocket Selectivity and Identification of Potent Selective Inhibitors for Matriptase and Matriptase-2," 2014, J Med Chem, DOI: 10.1021/jm5015633, 12 pages.

Enyedy et al., "Structure-Based Approach for the Discovery of Bis-Benzamidines as Novel Inhibitors of Matriptase," 2001, J. Med. Chem., 44:1349-1355, Abstract Only. 2 pages.

Farady, J.F., et al., "The Mechanism of Inhibition of Antibody-Based Inhibitors of Membrane-Type Serine Protease 1 (MT-SP1)," 2007, J Mol Biol, 369:1041-1051, 11 pages.

Franco, F.M., et al., "Structure-Based Discovery of Small Molecule Hapsin and HGFA Protease Inhibitors: Evaluation of Potency and Selectivity Derived from Distinct Binding Pockets," 2015, Bioorganic & Med Chem, 23:2328-2343, 15 pages.

Gherardi, E., et al., "Targeting MET in Cancer: Rationale and Progress," 2012, Nature Reviews. Cancer, 12:89-103, 15 pages.

Hammami, M., Dissertation, "Development of New Inhibitors for the Type II Transmembrane Serine Protease Matriptase," 2012, Philipps University, Marburg, 196 pages.

Han, Z, et al., "Inhibitors of HGFA, Matriptase, and Hepsin Serine Proteases: A Nonkinase Strategy to Block Cell Signaling in Cancer," dx.doi.org/10.1021/ml500254r | ACS Med. Chem. Lett. Nov. 13, 2014; 5(11): 1219-1224.

Han, Z., et al., "Mechanism-based Inhibitors of HGFA Serine Protease: A Novel Strategy to Block Cancer Cell Receptor Tyrosine Kinase Signaling," Proceedings: AACR Annual Meeting 2014; Apr. 5-9, 2014; San Diego, CA, Oct. 2014, vol. 74, Issue 19 Supplement, 9 pages.

Li, W. et al., "Pegylated Kunitz Domain Inhibitor Suppresses Hepsin-Mediated Invasive Tumor Growth and Metastasis," 2009, Cancer Res, 69:8395-8403, 9 pages.

Owusu, B.Y., et al., Anticancer Activity of SRI 31215, a Novel Inhibitor of HGF Activation, Southern Research Institute, Abstract # 310, 2014, 1 page.

Parr, C., et al., "Hepatocyte Growth Factor Activation Inhibitors—Therapeutic Potential in Cancer," 2010, Anti-Cancer Agents in Med. Chem., 10:47-57, 11 pages.

Poręba, M., et al, "Chapter 2 Positional Scanning Substrate Combinatorial Library (PS-SCL) Approach to Define Caspase Substrate Specificity," 2014, Methods Mol Biol, Caspases, Paracaspases, and Metacaspases, Methods and Protocols, 1133, P.V. Bozhkov and G. Salvesen, Eds., pp. 41-59, 24 pages.

Shimomura, T., et al., "A Novel Protease Obtained from FBS-Containing Culture Supernatant, That Processes Single Chain Form Hepatocyte Growth Factor to Two Chain Form in Serum-Free Culture," 1992, Cytotechnology, 8/3:219-229, Abstract Only, 1 page.

Smyth, C., et al., "Emerging Molecular Targets in Oncology: Clinical Potential of Met/Hepatocyte Growth-Factor Inhibitors," 2014, OncoTargets Ther, 7:1001-1014, 14 pages.

Steinmetzer, T., et al., "Secondary Amides of Sulfonylated 3-Amidinophenylalanine. New Potent and Selective Inhibitors of Matriptase," 2006, J Med Chem, 49: 4116-4126, 11 pages.

Stürzebecher, J., et al., "Synthesis and Structure-Activity Relationships of Potent Thrombin Inhibitors: Piperazides of 3-Amidinophenylalanine," 1997, J Med Chem, 40/19:3091-3099. Abstract Only, 3 pages.

Venukadasula, P., et al., "A New Approach to Inhibit HGF/MET Oncogenic Signaling: SRI 31215 and Analogs are Triplex Inhibitors of the Serine Proteases Required for HGF Activiation," Abstract No. 804, Southern Research Institute Poster, 2014, 1 page.

PubChem Substance Record for SID 29871797, Create Date: Dec. 4, 2007, retrieved on Jun. 8, 2016, https://pubchem.ncbi.nlm.nih.gov/substance/29871797/version/1#section=Top>, 5 pages.

PubChem Substance Record for SID 231910502, Create Date: Feb. 12, 2015, retrieved on Apr. 14, 2016, https://pubchem.ncbi.nlm.nih.gov/substance/231910502/version/1#section=Top>, 7 pages.

PubChem Substance Record for SID 162750732, Create Date: May 22, 2013, retrieved on Apr. 14, 2016, https://pubchem.ncbi.nlm.nih.gov/substance/162750732/version/1#section=Top>, 7 pages.

International Search Report and Written Opinion issued in International PCT Application No. PCT/US2016/020516, dated Jul. 15, 2016, 12 pages.

* cited by examiner

|  | 0.2 nM Matriptase | 1.0 nM Matripatse |
|---|---|---|
| Vmax | 7.256e+006 | 1.793e+007 |
| Km | 101.6 | 106.4 |

|  | 0.2 nM Matriptase | 1.0 nM Matripatse |
|---|---|---|
| R square | 0.9950 | 0.9969 |

MRC5+MDA-MB-231    +AcKRLR-kbt V amide (1 µM)    +HAI-1 (10 nM)

INHIBITORS OF GROWTH FACTOR ACTIVATION ENZYMES

REFERENCE TO RELATED APPLICATIONS

This application is the 371 National Stage Application of International Application Serial No. PCT/US2016/020516, filed Mar. 2, 2016, and claims the benefit of U.S. Provisional Application Ser. No. 62/220,998, filed Sep. 19, 2015 and U.S. Provisional Application Ser. No. 62/130,117, filed Mar. 9, 2015, the contents of which are incorporated by reference herein.

FIELD OF THE INVENTION

The present invention generally relates to compounds that are useful for inhibiting one or more serine proteases including Hepatocyte Growth Factor Activator, matriptase, and hepsin. The present invention also relates to various methods of using the inhibitor compounds including treating a malignancy, a pre-malignant condition, or cancer by administering an effective amount of the inhibitor to a subject in need thereof.

BACKGROUND OF THE INVENTION

Proteases, also known as proteinases, peptidases, or proteolytic enzymes, are enzymes that degrade proteins by hydrolyzing peptide bonds between amino acid residues. It is known that proteases regulate numerous physiological processes which enable or stimulate the growth and metastasis of tumor cells. This involves the proteolytic degradation of the extracellular matrix proteins surrounding the tumor cells, which enables the invasion of tumor cells metastasizing from the tumors into the surrounding tissue and the lymph system or the blood system. Proteases are also involved in the activation of growth factors that stimulate the proliferation of cancer cells, thus enabling tumors to grow. Theses proteolytic enzymes include matrix metalloproteases, membrane-bound metalloproteases, lysosomal cysteine proteases, and a large number of serine proteases such as urokinase, plasmin, elastase, thrombin, and cathepsin G. In addition, a family of serine proteases called type II transmembrane serine proteases (TTSPs) has been found to be important in tissue homeostasis and in cancer, in particular with tumor metastasis.

One member of this enzyme class, matriptase (matriptase-1, MT-SP1, TADG-15, CAP3, epithin, and ST14), is a trypsin-like serine protease expressed by cells of epithelial origin and overexpressed in a wide variety of human cancers. Unlike most proteases, which are either secreted from or retained in the cell, matriptase, as a TTSP, is readily accessible on the cell surface and hence a good target for a variety of therapies, including vaccines, monoclonal antibodies and small molecule compounds. Inhibition of the enzyme results in concomitant inhibition of two crucial mediators of tumorigenesis, hepatocyte growth factor (HGF) and the urokinase-type plasminogen activator (uPA).

Hepsin is another member of the type II transmembrane serine protease family. Hepsin is thought to play a role in cell growth and is known to be produced at a particularly high level in the liver as well as in human hepatoma cells, some cancer cells, and nerve cells. Hepatocyte Growth Factor Activator (HGFA) is a trypsin-like protease but is a plasma protease.

Hepsin, matriptase and HGFA are differentially expressed and have upregulated function in numerous tumor types including multiple myeloma, breast, prostate, lung, liver, and pancreatic. These proteases cleave the single-chain zymogen precursors, pro-HGF (hepatocyte growth factor), and pro-MSP (macrophage stimulating protein) into active two-chain heterodimeric forms. Active HGF and MSP are activating ligands for the oncogenic receptor tyrosine kinases (RTKs), c-MET and RON, respectively.

Increased activity of hepsin, matriptase, and/or HGFA, resulting from either expression or upregulation of these proteases and/or downregulation of their endogenous serine protease inhibitors (serpins), HAI-1 (SPINT1), HAI-2 (SPINT2), and protein C inhibitor (PCI), has been demonstrated in almost every tumor type driven by c-MET and/or RON pathway signaling. This increased protease function has been clearly associated with increased metastatic cancer phenotypes and direct inhibition of this protease activity has been demonstrated to reduce this metastatic potential in multiple tumor types. The biological reason for the redundancy of activation by these three different proteases and the tight regulation by serpins in cancer is not yet understood. Furthermore, since HGF/c-MET and MSP/RON signaling are necessary for development and normal cell physiology, selective inhibitors of each protease involved in individual tumors need to be identified when developing as therapeutics in order to limit potential toxicities.

Matriptase inhibitors are of therapeutic importance, but development has been a challenging task. To date, a number of small molecule inhibitors and inhibitory antibodies have been reported. See, for example; Enyedy et al., *J. Med. Chem.* 2001, 44, 1349-1355; Steinmetzer et al., *J. Med. Chem.*, 2006, 49: 4116-4126, and Farady et al, *J Mol Biol.*, 2007, 369: 1041-1051. Also a series of peptide-based matriptase inhibitors was recently described by Marsault et al., ACS Med Chem. Lett., 2012, 3: 530-534.

As compared to matriptase, inhibitory antibodies have also been reported but relatively few inhibitors are known for hepsin and HFGA. Small molecule hepsin inhibitors were discovered through high-throughput screening (Chevillet, J. R., et al. *Mol. Cancer Ther.* 2008, 7, 3343) but the only reported HGFA inhibitors are the non-selective serine protease inhibitors, Nafamostat and Leupeptin (Shimomura, T., et al., *Cytotechnology,* 1992, 8, 219).

Although some progress has been made toward inhibitors of matriptase, hepsin, and HGFA, there remains a need for small molecular weight inhibitors of matriptase, hepsin, and HGFA that are both potent and selective for one of more of these enzymes. Such compounds have significant therapeutic value, in particular for the treatment of cancer and other conditions involving tumor progression and migration and abnormal cell differentiation and proliferation or hematological malignancies. Compounds having improved selectivity, solubility, metabolic stability, half-life, and oral bioavailability are particularly desirable.

SUMMARY OF THE INVENTION

Generally, the present invention relates to compounds that are useful for inhibiting one or more serine proteases including Hepatocyte Growth Factor Activator, matriptase, hepsin, thrombin, and Factor Xa along with various methods of use. In various aspects, the present invention is directed to compounds of Formula (I), as a single stereoisomer or as a mixture thereof:

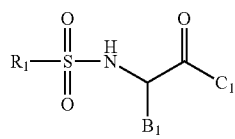

(I)

wherein R₁ is substituted or unsubstituted alkyl, substituted or unsubstituted aryl, or substituted or unsubstituted heteroaryl;

B₁ is selected from the group consisting of:

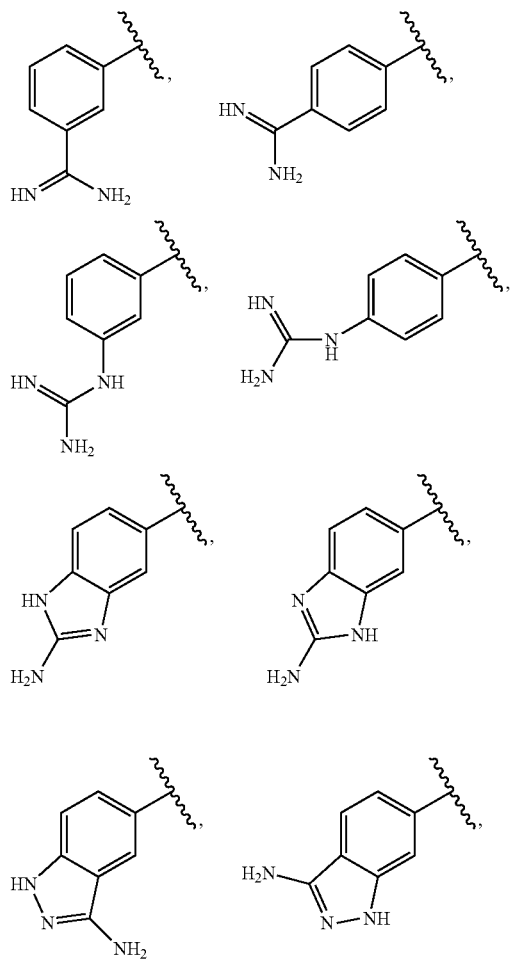

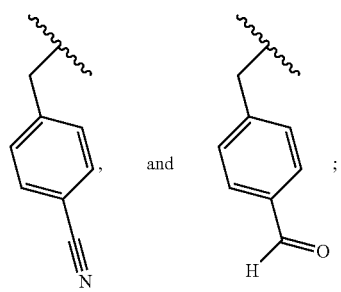

and

C₁ is a group selected from the group consisting of:

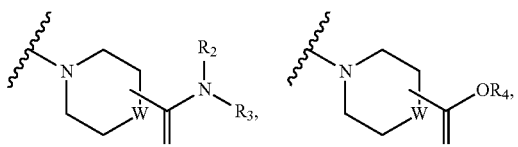

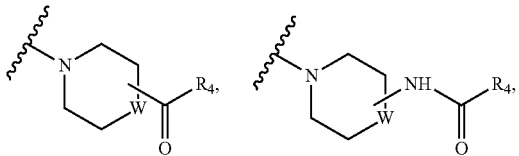

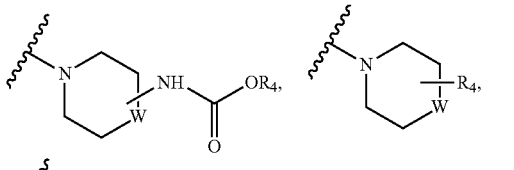

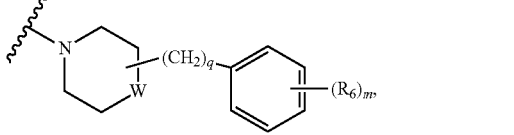

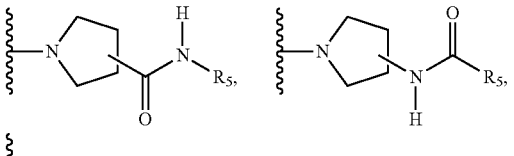

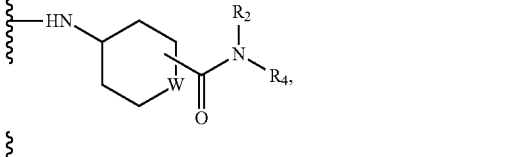

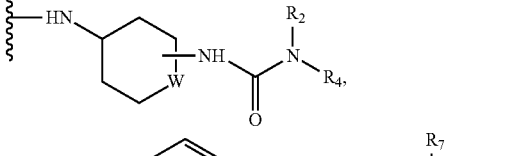

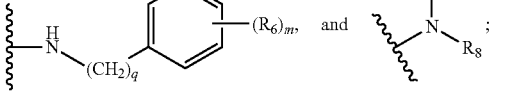

W is CH, CH₂, N, or NH;

R₂, R₃, R₄, R₅, R₆, R₇, and R₈ are each independently hydrogen, substituted or unsubstituted alkyl or cycloalkyl, substituted or unsubstituted alkylaryl, substituted or unsubstituted heterocyclic ring, substituted or unsubstituted aryl or heteroaryl, with the proviso that when R₂ is methyl, then R₃ cannot also be methyl and vice versa; and m is 0 to 5, or a pharmaceutically acceptable salt thereof.

The present invention also relates to compounds of Formula (II):

$$Y-(P_5)_b-(P_4)_n-(P_3)_m-P_2-P_1-Z \qquad (II)$$

wherein n is 0 or 1;

m is 0 or 1;

b is 0 or 1;

Y is H, acetyl, tert-butyloxycarbonyl, benzyloxymethyl acetyl, carboxybenzyl, benzyl, —C(O)R₉, —SOOR₉, —COOR₉, —C(O)NHR₉, —(CH₂)ₓaryl-R₉, heteroaryl-R₉, -cycloalkyl-R₉, a fluorophore, biotin, or a reporter tag;

x is 0, 1, or 2;

$R_9$ is $C_1$ to $C_{12}$ alkyl, cycloalkyl, alkylaryl, or aryl;

$P_1$ is a residue of an amino acid selected from the group consisting of Arg, D-Arg, Lys, substituted Lys, and an alpha-amino acid of the following:

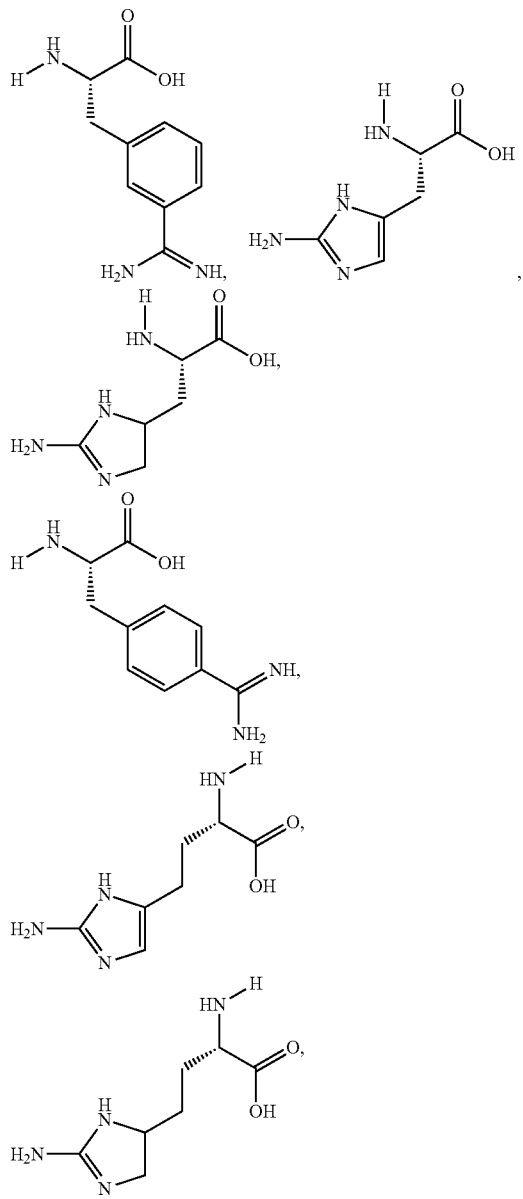

or an unnatural amino acid residue;

$P_2$ is a residue of an amino acid selected from the group consisting Leu, Phe, Met, Thr, Val, Tyr, Trp, Ser, Pro, His, Glu, Gln, Asp, Arg, Lys, Ile, Ala, Gly, Asn, hLeu, NptGly, L-Orm, L-Cha, Nle, hTyr, Nva, Orn, Cha, and an unnatural amino acid residue;

$P_3$ is a residue of an amino acid selected from the group consisting Asp, Glu, Arg, Lys, Met, Trp, Leu, Gln, Phe, Tyr, His, hArg, D-Trp, L-Orn, D-Gln, L-Met(O), L-Nle(OBzl), Agp, hCha, hTyr, hPhe, D-Arg, Nle(OBzl), Orn, Met(O), and an unnatural amino acid residue;

$P_4$ is a residue of an amino acid selected from the group consisting Arg, Lys, Met, Try, Trp, Ser, His, Phe, Thr, Asn, Pro, Gln, Asp, Glu, Chg, Idc, dhLeu, Agp, D-Ser, Agp, His(3-Bom), Lys(2-Cl—Z), L-Orn, L-Arg($NO_2$), L-Nle (OBzl), L-DAB(Z), and an unnatural amino acid residue;

$P_5$ is a residue of an amino acid selected from the group consisting Lys, Arg, Leu, Phe, Met, Thr, Val, Tyr, Trp, Ser, Pro, His, Glu, Gln, Asp, Ile, Ala, Gly, Asn, and an unnatural amino acid residue; and Z is Val, Ser, Lys, Ala, Gly, Trp, Tyr, Phe, Arg, Thr, Leu, Ile, Met, His, Nle, Phg, Pro, Gln, Asn, —$CH_2Cl$, or a substituted or unsubstituted ring substituent selected from the group consisting of:

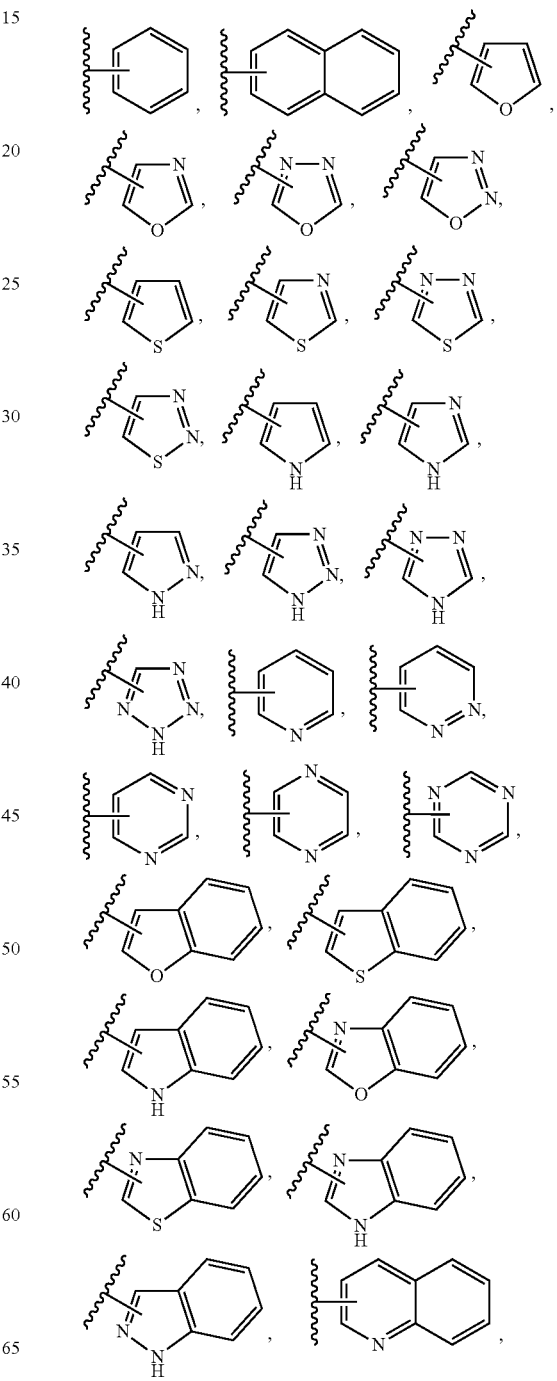

-continued

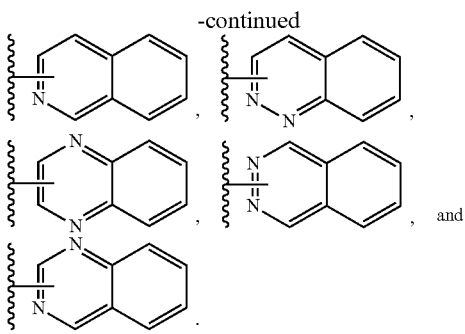

The present invention further relates to pharmaceutical compositions comprising a therapeutically effective amount of at least one compound as described herein.

The present invention also relates to various methods of use including a method of inhibiting matriptase, hepsin, or HGFA comprising administering to a subject in need thereof a pharmaceutical composition comprising a therapeutically effective amount of at least one compound as described herein. Another method includes a method of inhibiting HGF/MET oncogenic signaling comprising administering to a subject in need thereof a pharmaceutical composition comprising a therapeutically effective amount of at least one compound as described herein.

Other methods include a method of inhibiting carcinoma progression and a method of treating a malignancy, a pre-malignant condition, or cancer comprising administering to the subject in need thereof a pharmaceutical composition comprising a therapeutically effective amount of at least one compound as described herein.

Further, the present invention relates to imaging compositions comprising a radiolabeled compound of Formula (I) or (II) as described herein and a method of detecting cancer comprising administering to a subject an imaging composition comprising the radiolabeled compound; employing a nuclear imaging technique for monitoring or visualizing a distribution of the radiolabeled compound within the body or within a portion thereof; and correlating the distribution of the radiolabeled compound to the existence of cancer.

Additionally, the present invention relates to imaging compositions comprising a fluorescent compound of Formula (I) or (II) as described herein and a method of detecting cancer comprising administering to a subject an imaging composition comprising the fluorescent compound; employing an imaging technique for monitoring or visualizing a distribution of the fluorescent compound within the body of within a portion thereof; and correlating the distribution of the fluorescent compound to the existence of cancer.

Other objects and features will be in part apparent and in part pointed out hereinafter.

DESCRIPTION OF THE PREFERRED EMBODIMENTS

Figure 1:
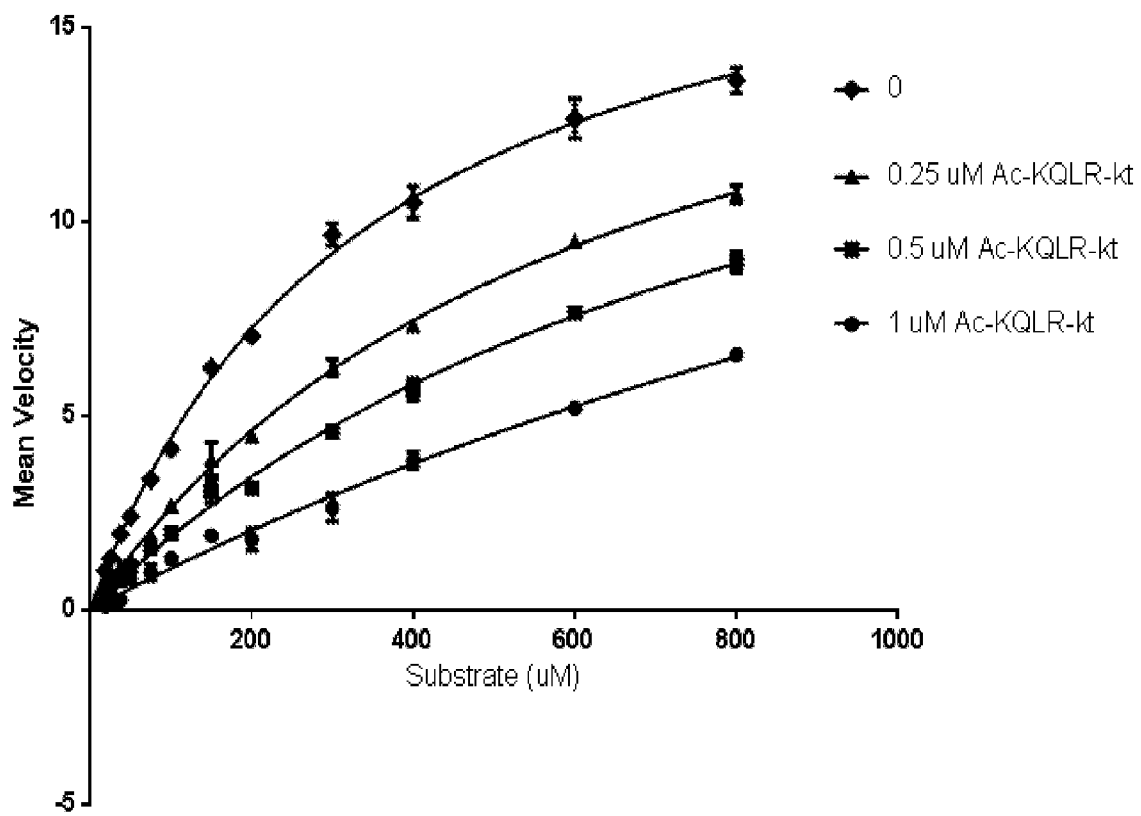
FIG. 1 presents a plot of the results for the HGFA competition assay of inhibitor Ac-KQLR (SEQ ID NO: 1)-Kt.

In various aspects, the present invention generally relates to compounds that are useful for inhibiting one or more serine proteases, including Hepatocyte Growth Factor Activator, matriptase, hepsin, thrombin, and Factor Xa along with various methods of use. In other aspects, the present invention also relates to various methods of using the inhibitor compounds including treating a malignancy, a pre-malignant condition, or cancer by administering an effective amount of the inhibitor to a subject in need thereof.

In accordance with the present invention, one class of compounds useful for inhibiting one or more of hepatocyte growth factor activator, matriptase, and hepsin includes benzamidine compounds of Formula (I), as a single stereoisomer or as a mixture thereof:

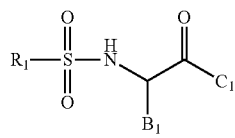
(I)

wherein $R_1$ is substituted or unsubstituted alkyl, substituted or unsubstituted aryl, or substituted or unsubstituted heteroaryl;

$B_1$ is selected from the group consisting of:

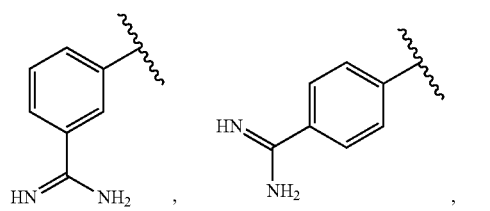

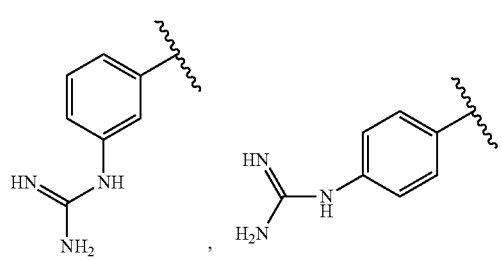

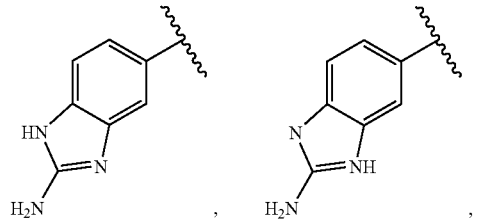

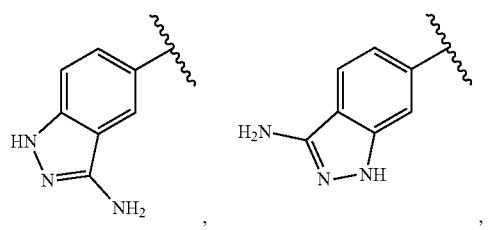

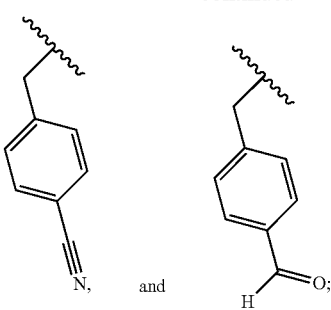

$C_1$ is a group selected from the group consisting of:

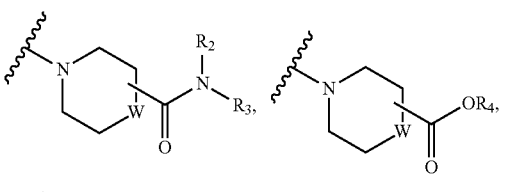

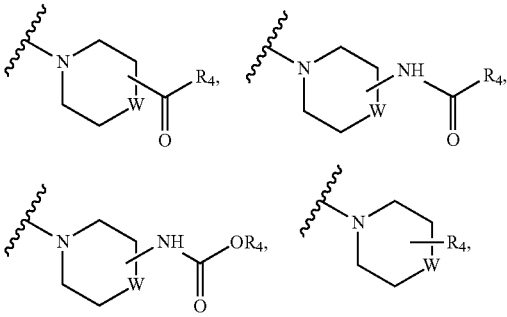

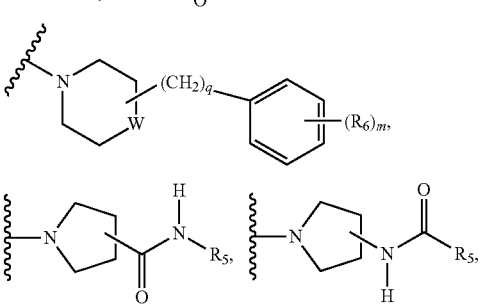

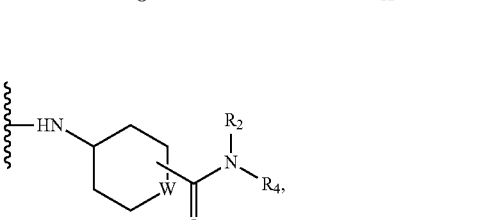

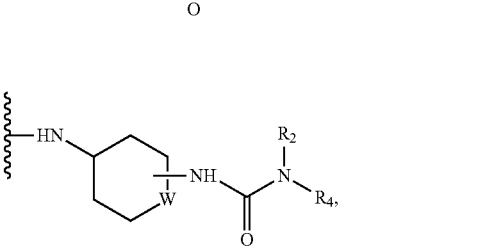

-continued

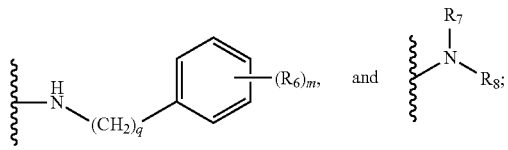 and 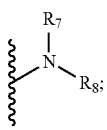

W is CH, CH$_2$, N, or NH;

R$_2$, R$_3$, R$_4$, R$_5$, R$_6$, R$_7$, and R$_8$ are each independently hydrogen, substituted or unsubstituted alkyl or cycloalkyl, substituted or unsubstituted alkylaryl, substituted or unsubstituted heterocyclic ring, substituted or unsubstituted aryl or heteroaryl, with the proviso that when R$_2$ is methyl, then R$_3$ cannot also be methyl and vice versa; and m is 0 to 5, or a pharmaceutically acceptable salt of Formula (I).

In various embodiments, R$_1$ is substituted or unsubstituted C$_1$-C$_6$ alkyl, substituted or unsubstituted C$_3$-C$_6$ cycloalkyl, substituted or unsubstituted phenyl, substituted or unsubstituted naphthyl, or a substituted or unsubstituted nitrogen-containing aromatic ring. For example, the substituted C$_1$-C$_6$ alkyl, substituted C$_3$-C$_6$ cycloalkyl, substituted phenyl, substituted naphthyl, or substituted nitrogen-containing aromatic ring can comprise one or more substituents comprising halo, hydroxy, C$_1$-C$_6$ alkyl, C$_1$-C$_6$ alkoxy, halo-substituted C$_1$-C$_4$ alkyl, or amino. In certain embodiments, R$_1$ is an group selected from the group consisting of:

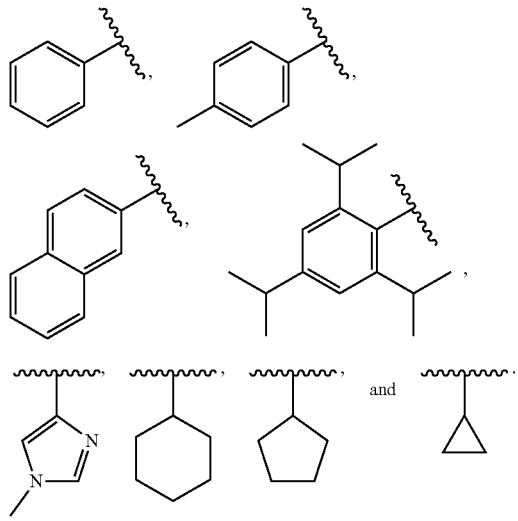

In some embodiments, C$_1$ is a group selected from the group consisting of:

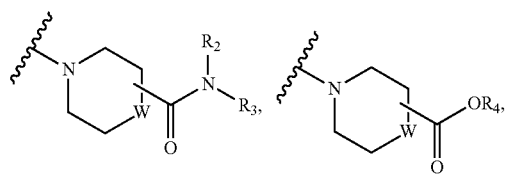

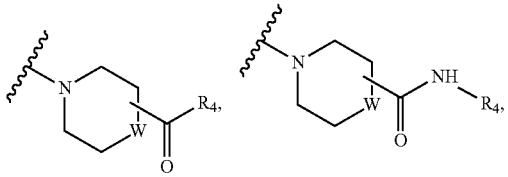

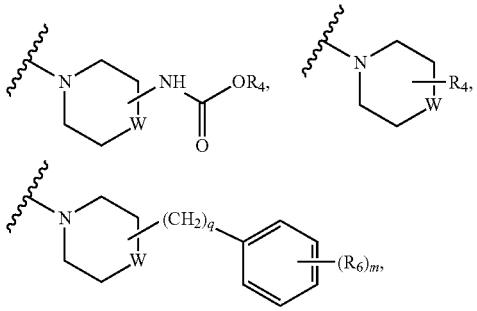

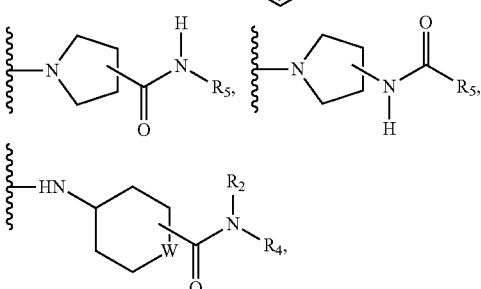

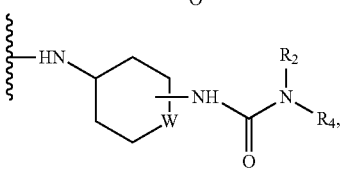

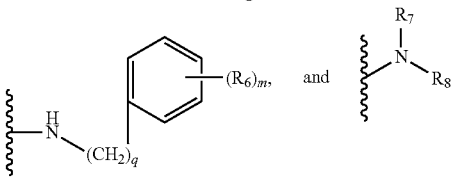 and 

W is CH or N;

R$_2$, R$_3$, R$_4$, R$_5$, R$_6$, R$_7$, and R$_8$ are each independently hydrogen, substituted or unsubstituted alkyl or cycloalkyl, substituted or unsubstituted alkylaryl, substituted or unsubstituted heterocyclic ring, substituted or unsubstituted aryl or heteroaryl, with the proviso that when R$_2$ is methyl, then R$_3$ cannot also be methyl and vice versa; and m is 0 to 5, or a pharmaceutically acceptable salt thereof.

In some embodiments, R$_2$, R$_3$, R$_4$, R$_5$, R$_6$, R$_7$, and R$_8$ are each independently hydrogen, substituted or unsubstituted C$_1$-C$_{10}$ alkyl or cycloalkyl, substituted or unsubstituted heterocyclic ring, substituted or unsubstituted aryl, or substituted or unsubstituted heteroaryl. In particular embodiments, R$_2$ is hydrogen; R$_3$ is hydrogen, C$_1$-C$_6$ alkyl, benzyl, or halo-substituted benzyl; R$_4$ and R$_5$ are each independently hydrogen, C$_1$-C$_6$ alkyl, halo- or alkoxy-substituted C$_1$-C$_6$ alkyl, phenyl, phenethyl, benzyl, halo- or alkoxy-substituted benzyl; substituted or unsubstituted 3-benzothiophenyl, or substituted or unsubstituted 1-morpholinyl; R$_6$ is hydrogen, C$_1$-C$_4$ alkoxy; and/or R$_7$ and R$_8$ are each independently hydrogen or C$_1$-C$_6$ alkyl.

In certain embodiments, $C_1$ is

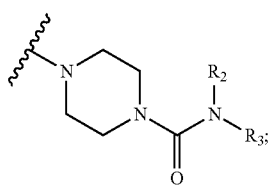

$R_2$ is hydrogen; and $R_3$ is hydrogen, $C_1$-$C_6$ alkyl, benzyl, or halo-substituted benzyl. In these and other embodiments, the compound of Formula (I) is a selective inhibitor of hepsin.

In accordance with the present invention, another class of compounds useful for inhibiting one or more of HGFA, matriptase, and hepsin includes polypeptide of Formula (II):

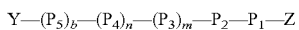

wherein n is 0 or 1;

m is 0 or 1;

b is 0 or 1;

Y is H, acetyl, tert-butyloxycarbonyl, benzyloxymethyl acetyl, carboxybenzyl, fluorene, benzyl, —C(O)$R_9$, —SOO$R_9$, —COO$R_9$, —C(O)NH$R_9$, —(CH$_2$)$_x$aryl-$R_9$, heteroaryl-$R_9$, -cycloalkyl-$R_9$, a fluorophore, biotin, or a reporter tag;

x is 0, 1, or 2;

$R_9$ is $C_1$ to $C_{12}$ alkyl, cycloalkyl, alkylaryl, or aryl;

$P_1$ is a residue of an amino acid selected from the group consisting of Arg, D-Arg, Lys, substituted Lys, and an alpha-amino acid of the following:

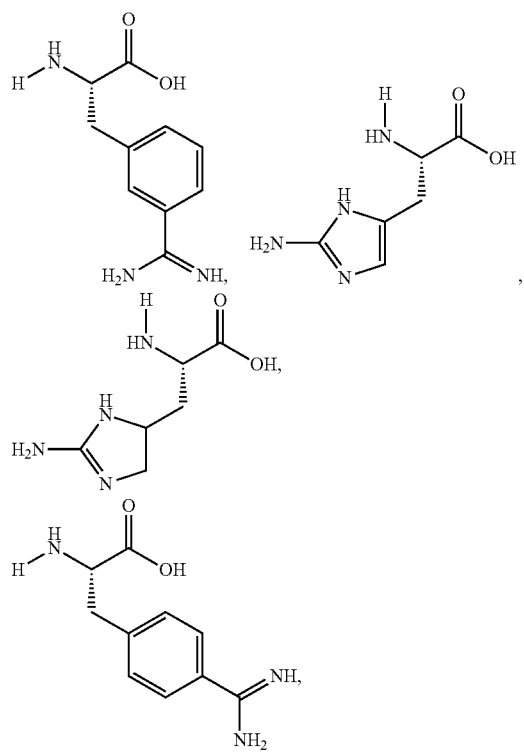

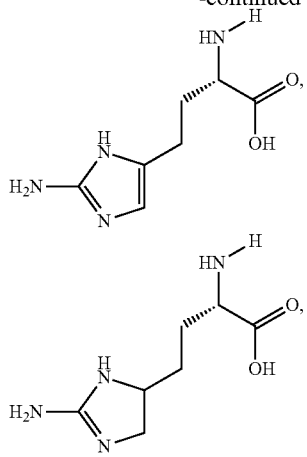

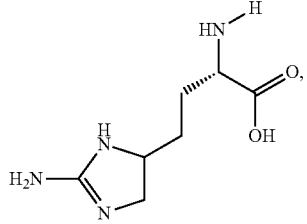

or an unnatural amino acid residue;

$P_2$ is a residue of an amino acid selected from the group consisting Leu, Phe, Met, Thr, Val, Tyr, Trp, Ser, Pro, His, Glu, Gln, Asp, Arg, Lys, Ile, Ala, Gly, Asn, hLeu, NptGly, L-Orn, L-Cha, Nle, hTyr, Nva, Om, Cha, and an unnatural amino acid residue;

$P_3$ is a residue of an amino acid selected from the group consisting Asp, Glu, Arg, Lys, Met, Trp, Leu, Gln, Phe, Tyr, His, hArg, D-Trp, L-Om, D-Gln, L-Met(O), L-Nle(OBzl), Agp, hCha, hTyr, hPhe, D-Arg, Nle(OBzl), Om, Met(O), and an unnatural amino acid residue; $P_4$ is a residue of an amino acid selected from the group consisting Arg, Lys, Met, Try, Trp, Ser, His, Phe, Thr, Asn, Pro, Gln, Asp, Glu, Chg, Idc, dhLeu, Agp, D-Ser, Agp, His(3-Bom), Lys(2-Cl—Z), L-Orn, L-Arg(NO$_2$), L-Nle(OBzl), L-DAB(Z), and an unnatural amino acid residue;

$P_5$ is a residue of an amino acid selected from the group consisting Lys, Arg, Leu, Phe, Met, Thr, Val, Tyr, Trp, Ser, Pro, His, Glu, Gln, Asp, Ile, Ala, Gly, Asn, and an unnatural amino acid residue; and Z is Val, Ser, Lys, Ala, Gly, Trp, Tyr, Phe, Arg, Thr, Leu, Ile, Met, His, Nle, Phg, Pro, Gln, Asn, —CH$_2$Cl, or a substituted or unsubstituted ring substituent selected from the group consisting of:

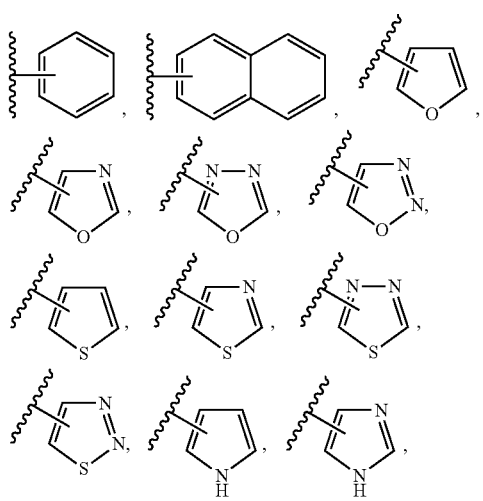

-continued

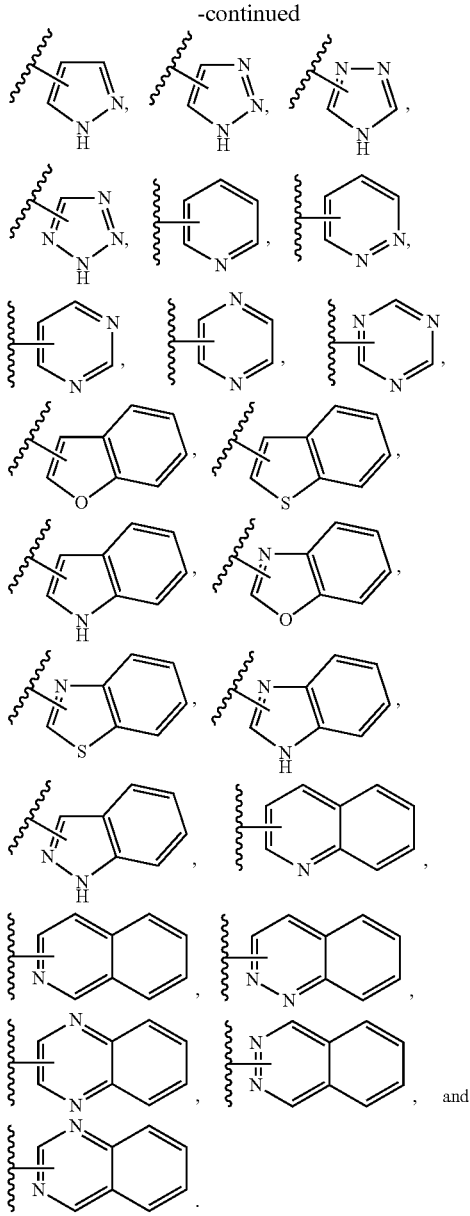

As understood herein, when two or more amino acids combine to form a peptide (e.g., of Formula (II)), the elements of water are removed, and what remains of each amino acid is called an amino-acid residue.

In various embodiments, the polypeptide of Formula (II) include one or more of the following:
Y is H, acetyl, tert-butyloxycarbonyl, benzyloxymethyl acetyl, carboxybenzyl, fluorene, benzyl, —C(O)R$_9$, —SOOR$_9$, —COOR$_9$, —C(O)NHR$_9$, —(CH$_2$)$_x$aryl-R$_9$, heteroaryl-R$_9$, -cycloalkyl-R$_9$, or a fluorophore;
x is 0, 1, or 2;
R$_9$ is C$_1$ to C$_{12}$ alkyl, cycloalkyl, alkylaryl, or aryl;
P$_2$ is a residue of an amino acid selected from the group consisting Leu, Phe, Met, Thr, Val, Tyr, Trp, Ser, Pro, His, Glu, Gln, Asp, Arg, Lys, Ile, Ala, Gly, Asn, hLeu, NptGly, L-Orn, L-Cha, Nle, hTyr, Nva, Om, Cha, and an unnatural amino acid residue;
P$_3$ is a residue of an amino acid selected from the group consisting Asp, Glu, Arg, Lys, Met, Trp, Leu, Gln, Phe, Tyr, His, hArg, D-Trp, L-Om, D-Gln, L-Met(O), L-Nle(OBzl), Agp, hCha, hTyr, hPhe, D-Arg, Nle(OBzl), Om, Met(O), and an unnatural amino acid residue; P$_4$ is a residue of an amino acid selected from the group consisting Arg, Lys, Met, Try, Trp, Ser, His, Phe, Thr, Asn, Pro, Gln, Asp, Glu, Chg, Idc, dhLeu, Agp, D-Ser, Agp, His(3-Bom), Lys(2-Cl—Z), L-Orn, L-Arg(NO$_2$), L-Nle(OBzl), L-DAB(Z), and an unnatural amino acid residue;
P$_5$ is a residue of an amino acid selected from the group consisting Lys, Arg, Leu, Phe, Met, Thr, Val, Tyr, Trp, Ser, Pro, His, Glu, Gln, Asp, Ile, Ala, Gly, Asn, and an unnatural amino acid residue; and
Z is Val, Ser, Lys, Ala, Gly, Trp, Tyr, Phe, Arg, Thr, Leu, Ile, Met, His, Nle, Phg, Pro, Gln, Asn, —CH$_2$Cl, a thiazole of Formula (III), or a benzothiazole of Formula (IV) or (V)

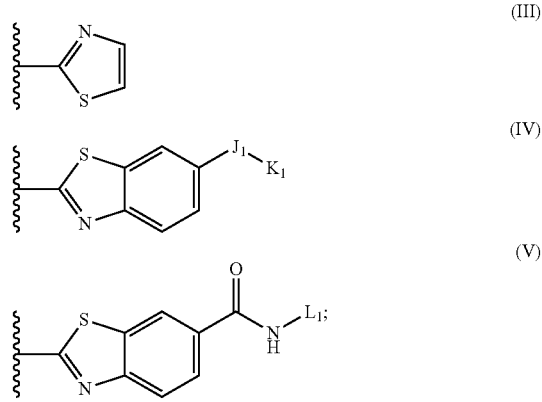

J$_1$ is C(O), SO$_2$, CH$_2$ or heterocyclo;
K$_1$ is a D- or L-amino acid, wherein the C-terminus is —COOH, —C(O)NH$_2$, —OH, —OR$_{10}$, —NH$_2$, —NR$_{11}$R$_{12}$, —H or heterocyclo;
R$_{10}$ is C$_1$ to C$_{12}$ alkyl, cycloalkyl, alkylaryl, or aryl;
R$_{11}$ and R$_{12}$ are each independently H, C$_1$ to C$_{12}$ alkyl, cycloalkyl, alkylaryl, aryl, or heterocyclo; and R$_{11}$ and R$_{12}$ together can form a ring; and/or
L$_1$ is H, alkyl, cycloalkyl, alkylaryl, benzyl, substituted benzyl, 2- or 3- or 4-piperdinyl, 2- or 3- or 4-pyridinyl, alkyl, cycloalkyl, aryl, heterocyclo, or heteroaryl.

In various embodiments, P$_1$, P$_2$, P$_3$, P$_4$ and P$_5$ can each independently be an unnatural amino acid residue. The unnatural amino acids can be selected from the group listed in the following Table. The unnatural amino acids can be the D- and/or L-isomers.

| Abbreviation | Structure |
|---|---|
| His(3-Bom) | 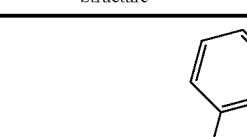 |

| Abbreviation | Structure |
|---|---|
| Agp | 2-amino-3-guanidinopropanoic acid |
| Lys(2-Cl-Z) | N6-(2-chlorobenzyloxycarbonyl)lysine |
| hArg | homoarginine |
| hTyr | homotyrosine |
| hPhe | homophenylalanine |
| hLeu | homoleucine |
| NptGly | neopentylglycine |
| DAB(Z) | 2,4-diaminobutanoic acid (Z-protected) |
| Nle(OBzl) | norleucine O-benzyl |
| Arg(NO₂) | nitroarginine |
| Hyp | hydroxyproline |

| Abbreviation | Structure |
|---|---|
| Oic | 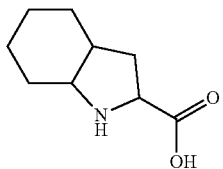 [SMILES: O=C(O)C1CC2CCCCC2N1] |
| hPro | 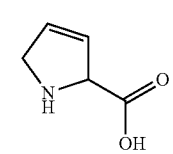 |
| Hyp(Bzl) | 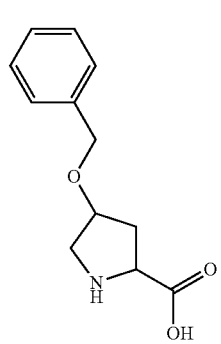 [SMILES: O=C(O)C1CC(OCc2ccccc2)CN1] |
| Asp(All) | 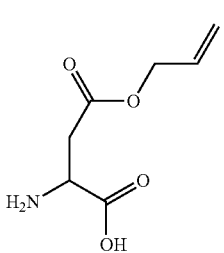 |
| Asp(Bzl) | 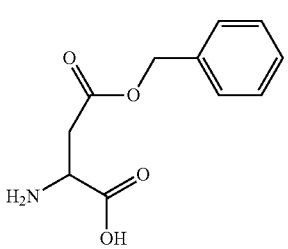 [SMILES: NC(CC(=O)OCc1ccccc1)C(=O)O] |
| Glu(Chx) | 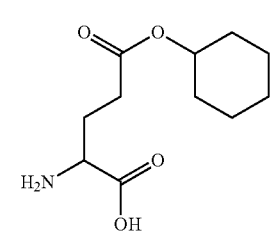 [SMILES: NC(CCC(=O)OC1CCCCC1)C(=O)O] |
| Abbreviation | Structure |
|---|---|
| Glu(Bzl) | 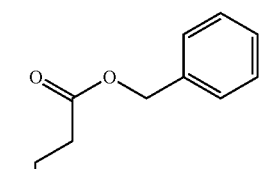 |
| Api | 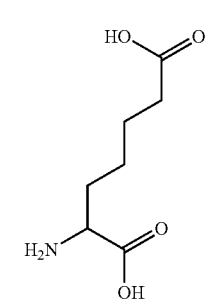 |
| Dap | 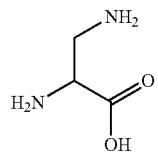 |
| Lys(TFA) | 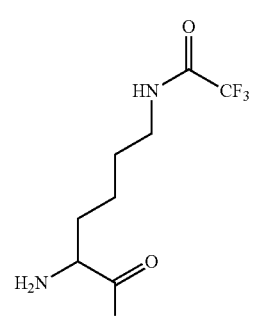 |
| His(Bzl) | 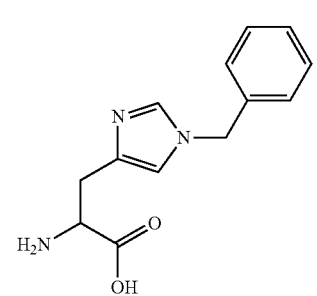 [SMILES: NC(Cc1cn(Cc2ccccc2)cn1)C(=O)O] |

| Abbreviation | Structure |
|---|---|
| Arg(Me)₂ | (structure) |
| 3-Pal | (structure) |
| 4-Pal | (structure) |
| Phe(4-F) | (structure) |
| Phe(3,4-F) | (structure) |
| Phe(F₅) | (structure) |

| Abbreviation | Structure |
|---|---|
| Phe(3,4-Cl) | (structure) |
| Phe(3-I) | (structure) |
| Phe(4-NO₂) | (structure) |
| Phe(4-guan) | (structure) |
| Ser(Bzl) | (structure) |

-continued

| Abbreviation | Structure |
|---|---|
| hSer(Bzl) | (structure) |
| Thr(Bzl) | (structure) |
| Cys(Bzl) | (structure) |
| Tyr(Me) | (structure) |
| hTyr(Me) | (structure) |

-continued

| Abbreviation | Structure |
|---|---|
| Tyr(2,6-Cl-Bzl) | (structure) |
| Bpa | (structure) |
| 1-Nal | (structure) |
| 2-Nal | (structure) |
| Abu | (structure) |
| Nva | (structure) |

-continued

| Abbreviation | Structure |
|---|---|
| 2-Aoc | 2-aminooctanoic acid structure (heptyl chain with α-amino acid) |
| Tle | tert-leucine structure |
| 4-NO₂-3-F—Phe | 4-nitro-3-fluoro-phenylalanine structure |
| Thyr | thyronine structure (two phenyl rings linked by ether, one with OH) |
| Inp | isonipecotic acid (piperidine-4-carboxylic acid) |
| Pip | pipecolic acid (piperidine-2-carboxylic acid) |

-continued

| Abbreviation | Structure |
|---|---|
| Phg | phenylglycine structure |
| 3-Pal | 3-pyridylalanine structure |
| 4-Pal | 4-pyridylalanine structure |
| hCha | homo-cyclohexylalanine structure |
| Orn | ornithine structure |
| Met(O) | methionine sulfoxide structure |

| Abbreviation | Structure |
|---|---|
| Cha | ![Cha structure: 2-amino-3-cyclohexylpropanoic acid] |
| Nle | ![Nle structure: norleucine] |
| MeAla | ![MeAla structure: N-methyl alanine] |
| βAla | ![βAla structure: beta-alanine] |
| Gla | ![Gla structure: gamma-carboxyglutamic acid] |
| Asp(Me) | ![Asp(Me) structure: aspartic acid methyl ester] |
| Glu(Me) | ![Glu(Me) structure: glutamic acid methyl ester] |
| Glu(All) | ![Glu(All) structure: glutamic acid allyl ester] |

| Abbreviation | Structure |
|---|---|
| Aad | ![Aad structure: 2-aminoadipic acid] |
| Cit | ![Cit structure: citrulline] |
| hCit | ![hCit structure: homocitrulline] |
| Lys(Ac) | ![Lys(Ac) structure: N-epsilon-acetyl lysine] |
| Lys(2Cl-Z) | ![Lys(2Cl-Z) structure: N-epsilon-(2-chlorobenzyloxycarbonyl) lysine] |

| Abbreviation | Structure |
|---|---|
| Arg(Me) | 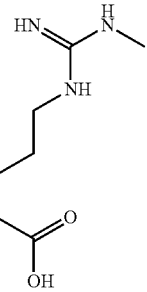 |
| Phe(4-NH₂) | 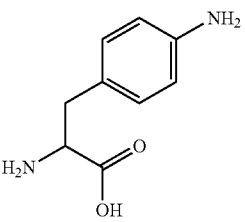 [SMILES: Nc1ccc(CC(N)C(=O)O)cc1] |
| Phe(2-F) | 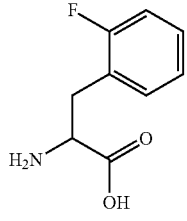 [SMILES: NC(Cc1ccccc1F)C(=O)O] |
| Phe(3-F) | 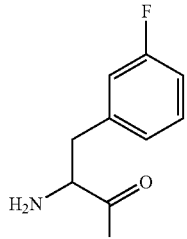 |
| Phe(2-Cl) |  |
| Phe(3-Cl) | 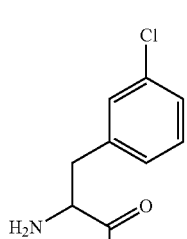 |
| Abbreviation | Structure |
|---|---|
| Phe(4-Cl) | 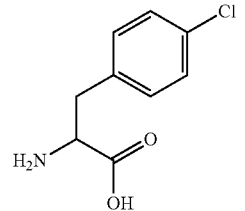 [SMILES: NC(Cc1ccc(Cl)cc1)C(=O)O] |
| Phe(4-I) | 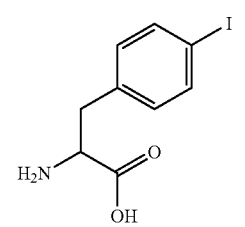 |
| Phe(4-Br) | 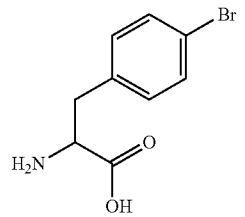 [SMILES: NC(Cc1ccc(Br)cc1)C(=O)O] |
| Phe(4-Me) | 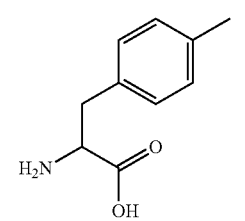 |
| Ala(2-th) | 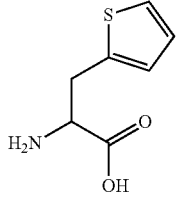 [SMILES: NC(Cc1cccs1)C(=O)O] |
| Cys(4-MeBzl) | 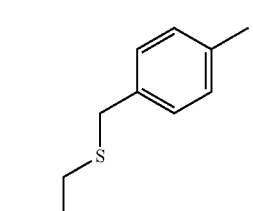 |

| Abbreviation | Structure |
|---|---|
| Cys(4-MeOBzl) | 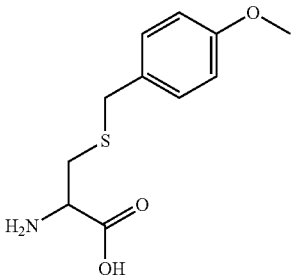 [SMILES: COc1ccc(CSCC(N)C(=O)O)cc1] |
| Tyr(Bzl) | 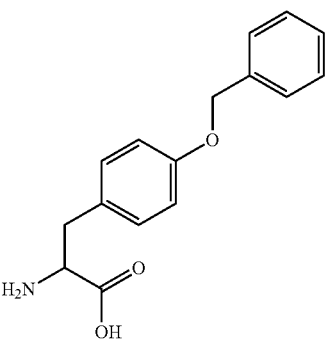 [SMILES: NC(Cc1ccc(OCc2ccccc2)cc1)C(=O)O] |
| Dht | 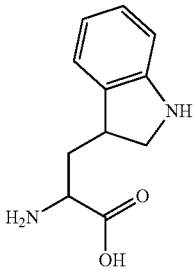 |
| Trp(Me) | 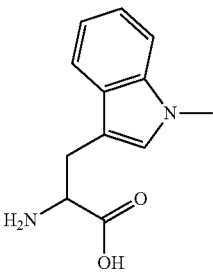 [SMILES: Cn1cc(CC(N)C(=O)O)c2ccccc21] |
| Abu(Bth) | 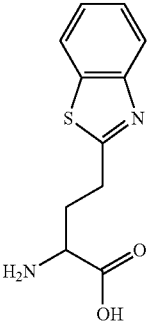 |
| Abbreviation | Structure |
|---|---|
| Bip | 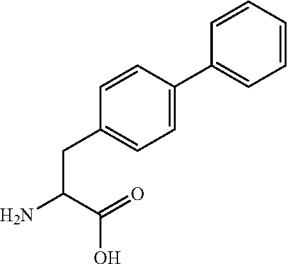 [SMILES: NC(Cc1ccc(-c2ccccc2)cc1)C(=O)O] |
| hSer | 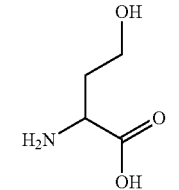 |
| Hnv | 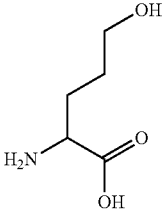 |
| Met(O$_2$) | 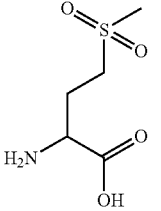 |
| AC5C | 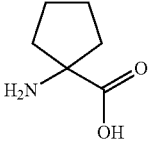 |
| Chg | 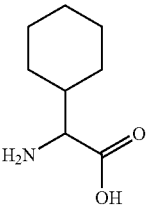 [SMILES: NC(C(=O)O)C1CCCCC1] |
| Tic | 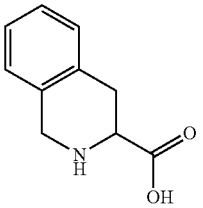 [SMILES: O=C(O)C1Cc2ccccc2CN1] |

33
-continued

| Abbreviation | Structure |
|---|---|
| AllyGly | 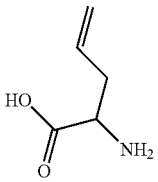 |

In accordance with the present invention, another class of compounds useful for inhibiting one or more of HGFA, matriptase, and hepsin includes cyclic peptides of Formula (II):

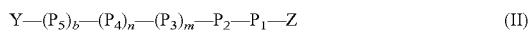

$$Y-(P_5)_b-(P_4)_n-(P_3)_m-P_2-P_1-Z \qquad (II)$$

wherein
n is 0 or 1;
m is 0 or 1;
b is 0 or 1;
Y is H, acetyl, tert-butyloxycarbonyl, benzyloxymethyl acetyl, carboxybenzyl, fluorene, benzyl, —C(O)R$_9$, —SOOR$_9$, —COOR$_9$, —C(O)NHR$_9$, —(CH$_2$)$_x$aryl-R$_9$, heteroaryl-R$_9$, -cycloalkyl-R$_9$, or a fluorophore;
x is 0, 1, or 2;
R$_9$ is C$_1$ to C$_{12}$ alkyl, cycloalkyl, alkylaryl, or aryl;
P$_1$ is a residue of an amino acid selected from the group consisting Arg, D-Arg, Lys, substituted Lys, and an unnatural amino acid residue;
P$_2$ is a residue of an amino acid selected from the group consisting Leu, Phe, Met, Thr, Val, Tyr, Trp, Ser, Pro, His, Glu, Gln, Asp, Arg, Lys, Ile, Ala, Gly, Asn, hLeu, NptGly, L-Orm, L-Cha, Nle, hTyr, Nva, Orn, Cha, and an unnatural amino acid residue;
P$_3$ is a residue of an amino acid selected from the group consisting Asp, Glu, Arg, Lys, Met, Trp, Leu, Gln, Phe, Tyr, His, hArg, D-Trp, L-Orn, D-Gln, L-Met(O), L-Nle(OBzl), Agp, hCha, hTyr, hPhe, D-Arg, Nle(OBzl), Orn, Met(O), and an unnatural amino acid residue;
P$_4$ is a residue of an amino acid selected from the group consisting Arg, Lys, Met, Try, Trp, Ser, His, Phe, Thr, Asn, Pro, Gln, Asp, Glu, Chg, Idc, dhLeu, Agp, D-Ser, Agp, His(3-Bom), Lys(2-Cl—Z), L-Orn, L-Arg(NO$_2$), L-Nle (OBzl), L-DAB(Z), and an unnatural amino acid residue;
P$_5$ is a residue of an amino acid selected from the group consisting Lys, Arg, Leu, Phe, Met, Thr, Val, Tyr, Trp, Ser, Pro, His, Glu, Gln, Asp, Ile, Ala, Gly, Asn, and an unnatural amino acid residue;
P$_3$ can bond with P$_5$ and form a cyclic peptide; and
P$_2$ can bond with P$_4$ and form a cyclic peptide.

In various embodiment, a compound useful for inhibiting HGFA includes a compound of Formula (II):

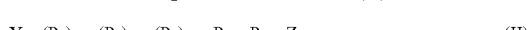

$$Y-(P_5)_b-(P_4)_n-(P_3)_m-P_2-P_1-Z \qquad (II)$$

wherein
n is 0 or 1;
m is 0 or 1;
b is 0 or 1;
Y is H, acetyl, tert-butyloxycarbonyl, benzyloxymethyl acetyl, carboxybenzyl, fluorene, benzyl, —C(O)R$_9$, —SOOR$_9$, —COOR$_9$, —C(O)NHR$_9$, —(CH$_2$)$_x$aryl-R$_9$, heteroaryl-R$_9$, -cycloalkyl-R$_9$, or a fluorophore;
x is 0, 1, or 2;
R$_9$ is C$_1$ to C$_{12}$ alkyl, cycloalkyl, alkylaryl, or aryl;
R$_1$ is Arg;

34

R$_2$ is selected from the group consisting of Leu, Met, Phe, Tyr, Trp, hLeu, NptGly, Nle, hTyr, and Nva;
P$_3$ is selected from the group consisting of His, Gln, Arg, Lys, Leu, Phe, Trp, Tyr, hArg, D-Trp, Agp, hCha, hTyr, hPhe, and D-Arg; and
P$_4$ is selected from the group consisting of Thr, Asn, Ser, Arg, Lys, Phe, Trp, His(Bom), Agp, Lys(2-Cl—Z), dhLeu, Idc, and Chg.

In other embodiments, a compound useful for inhibiting matriptase includes a compound of Formula (II):

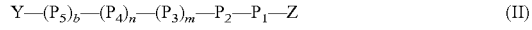

$$Y-(P_5)_b-(P_4)_n-(P_3)_m-P_2-P_1-Z \qquad (II)$$

wherein
n is 0 or 1;
m is 0 or 1;
b is 0 or 1;
Y is H, acetyl, tert-butyloxycarbonyl, benzyloxymethyl acetyl, carboxybenzyl, fluorene, benzyl, —C(O)R$_9$, —SOOR$_9$, —COOR$_9$, —C(O)NHR$_9$, —(CH$_2$)$_x$aryl-R$_9$, heteroaryl-R$_9$, -cycloalkyl-R$_9$, or a fluorophore;
x is 0, 1, or 2;
R$_9$ is C$_1$ to C$_{12}$ alkyl, cycloalkyl, alkylaryl, or aryl;
R$_1$ is selected from the group consisting of Arg, and Lys;
R$_2$ is selected from the group consisting of Phe, Ala, Arg, Asn, Gln, Glu, Gly, His, Leu, Lys, Met, Pro, and Ser;
R$_3$ is selected from the group consisting of Arg, Leu, Trp, Phe, His, Gln, Lys, D-Trp, and D-Arg; and
R$_4$ is selected from the group consisting of Pro, Phe, Thr, Asn, Trp, Gln, Ser, Lys, and Arg, His(Bom).

In further embodiments, a compound useful for inhibiting hepsin includes a compound of Formula (II):

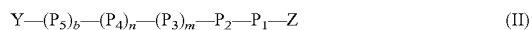

$$Y-(P_5)_b-(P_4)_n-(P_3)_m-P_2-P_1-Z \qquad (II)$$

wherein
n is 0 or 1;
m is 0 or 1;
b is 0 or 1;
Y is H, acetyl, tert-butyloxycarbonyl, benzyloxymethyl acetyl, carboxybenzyl, fluorene, benzyl, —C(O)R$_9$, —SOOR$_9$, —COOR$_9$, —C(O)NHR$_9$, —(CH$_2$)$_x$aryl-R$_9$, heteroaryl-R$_9$, -cycloalkyl-R$_9$, or a fluorophore;
x is 0, 1, or 2;
R$_9$ is C$_1$ to C$_{12}$ alkyl, cycloalkyl, alkylaryl, or aryl;
R$_1$ is Arg;
R$_2$ is selected from the group consisting of Pro, Arg, Asn, Asp, Gln, Ile, Leu, Lys, Phe, Thr, Trp, Tyr, Orn, Cha, Nle, and Nva;
R$_3$ is selected from the group consisting of Leu, Trp, Phe, His, Gln, Lys, Arg, D-Gln, Agp, Nle (OBzl), Orn, Met(O), D-Trp, and D-Arg; and
R$_4$ is selected from the group consisting of Pro, Phe, Thr, Asn, Trp, Gln, Ser, Arg, Lys, Agp, DAB(Z), Nle (OBzl), Orn, Arg(NO$_2$), and His(Bom).

In various embodiments, P$_1$ can be an amino acid residue of Arg. P$_2$ can be an amino acid residue of Leu, Phe or Met. P$_3$ can be an amino acid residue of Arg, Lys, Met, or Trp. P$_4$ can be an amino acid residue of Arg, Lys, or Try. In these and other embodiments, the compound of Formula (II) is a selective inhibitor of HGFA.

In various embodiments, Z is a benzothiazole of Formula (IV). In these and other embodiments, J$_1$ is C(O) and/or K$_1$ is an amino acid residue of Val.

In various embodiments, when Z is a benzothiazole of Formula (V), then L$_1$ is a substituted benzyl group. Exemplary substituted benzyl groups include, but are not limited to: 2-, 3-, and 4-carboxybenzyl and the C$_1$-C$_5$ esters thereof.

In some embodiments, m is 1, n is 1, and P$_4$—P$_3$—P$_2$—P$_1$ of Formula (II) is a tetrapeptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and mixtures thereof.

In some embodiments, the compound of Formula (II) is a tetrapeptide selected from the group consisting of:

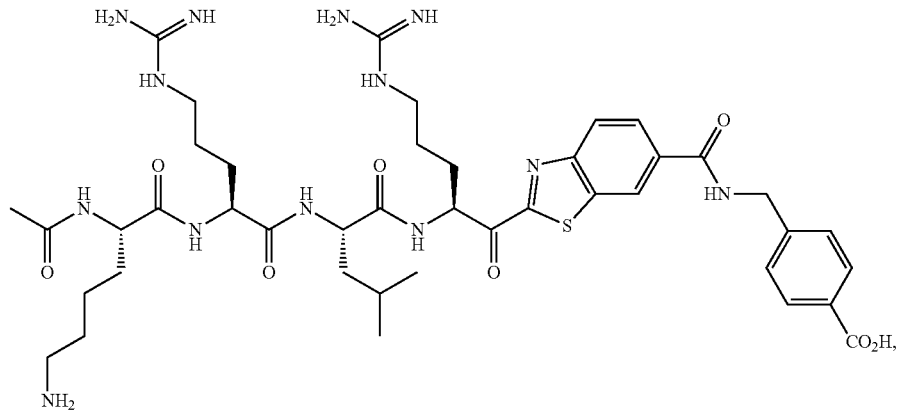

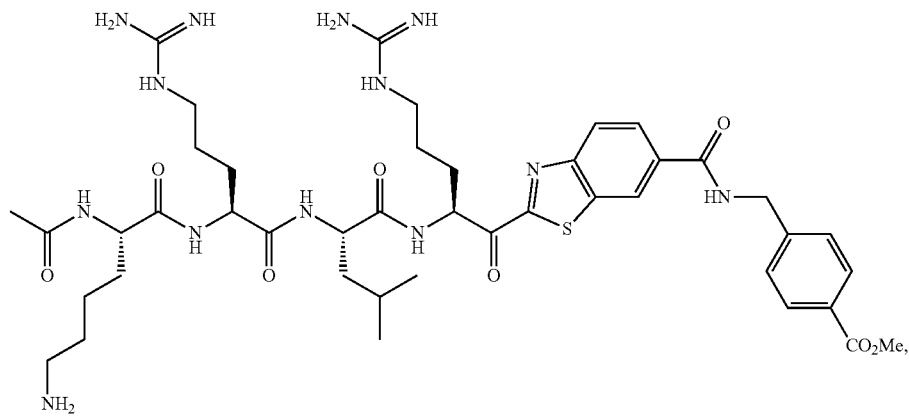

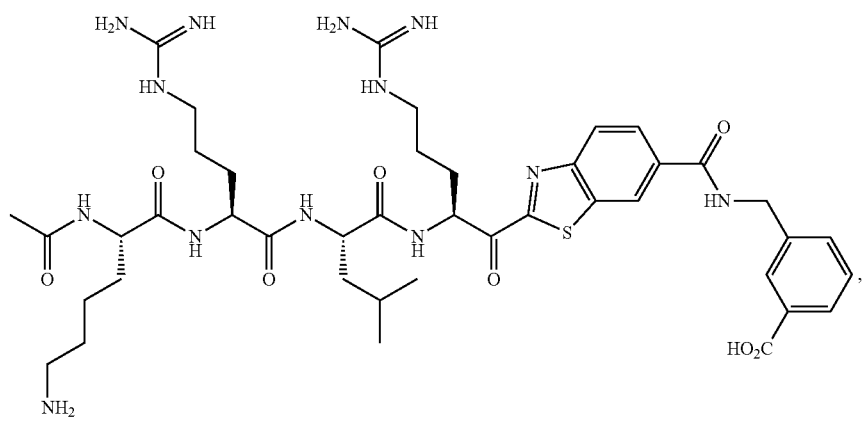

-continued
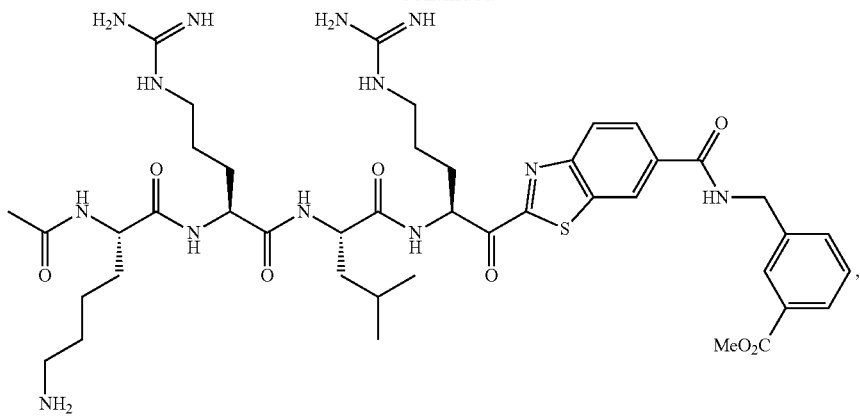
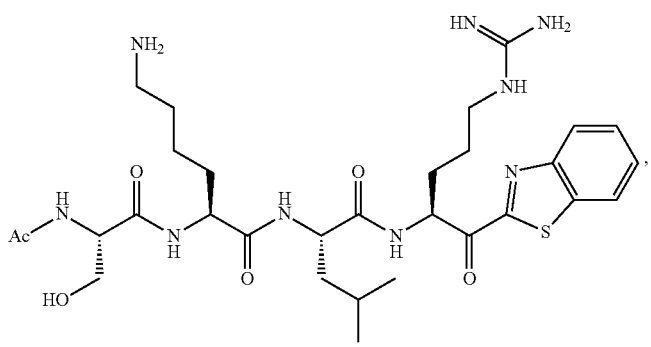
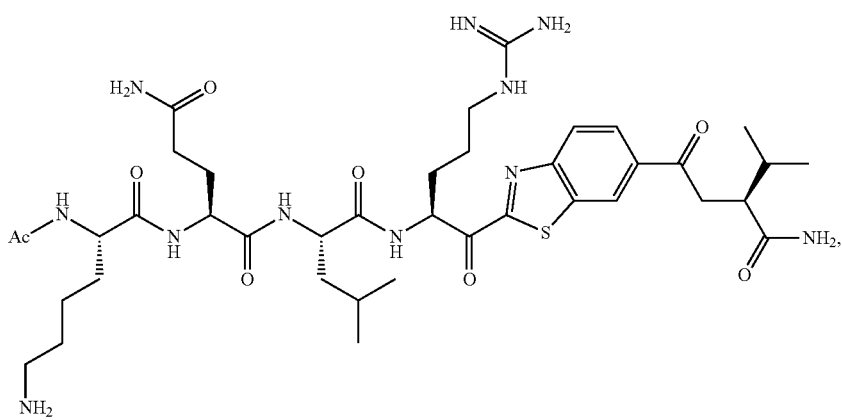
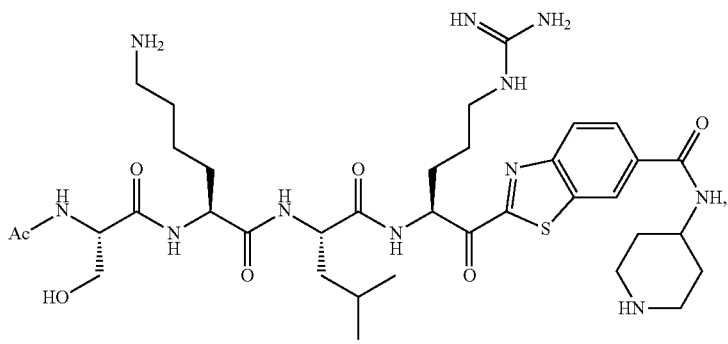

-continued
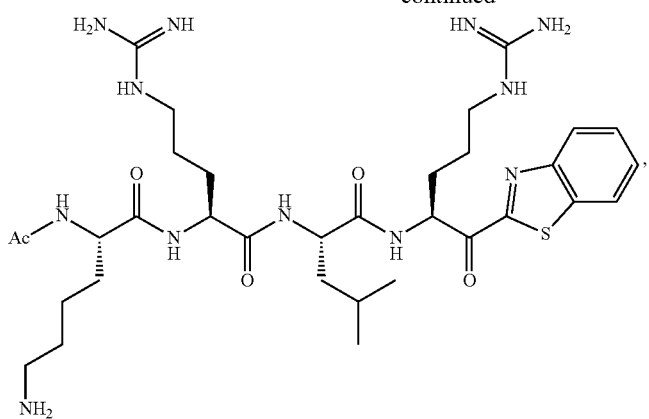
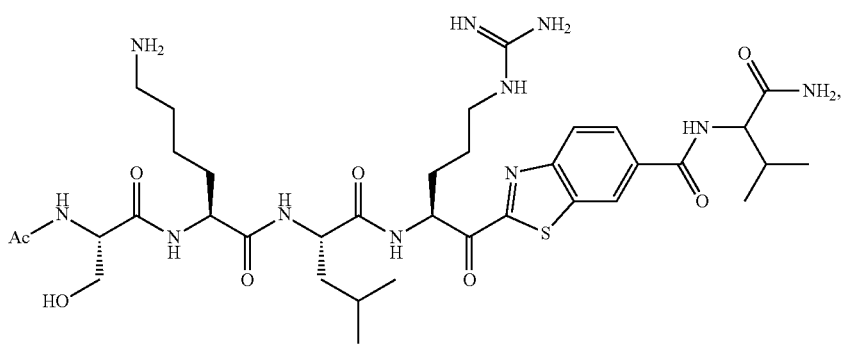
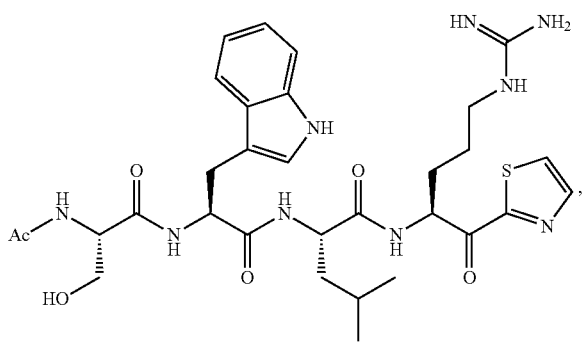
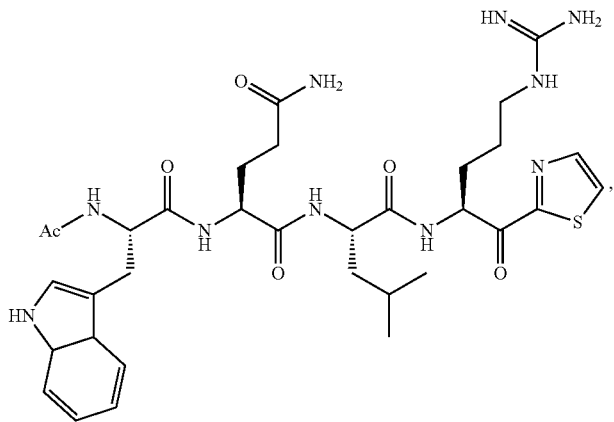

-continued
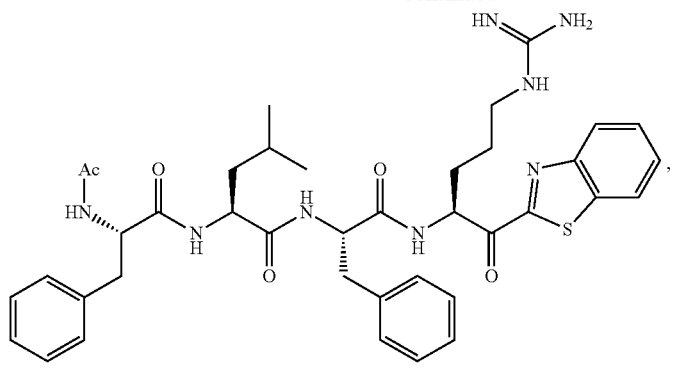
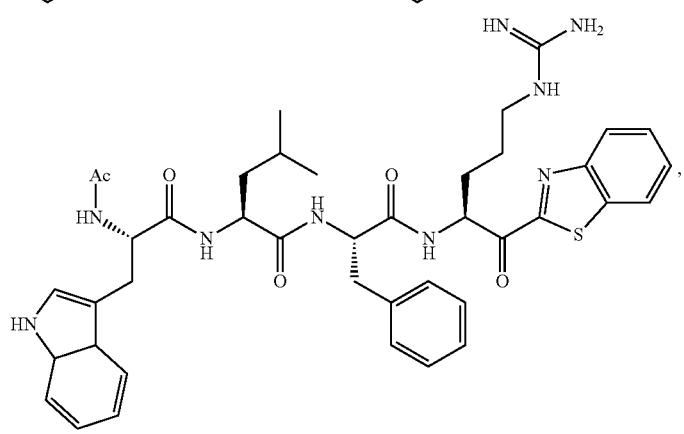
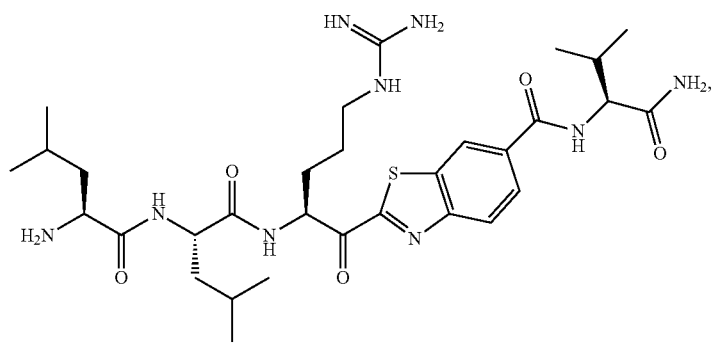
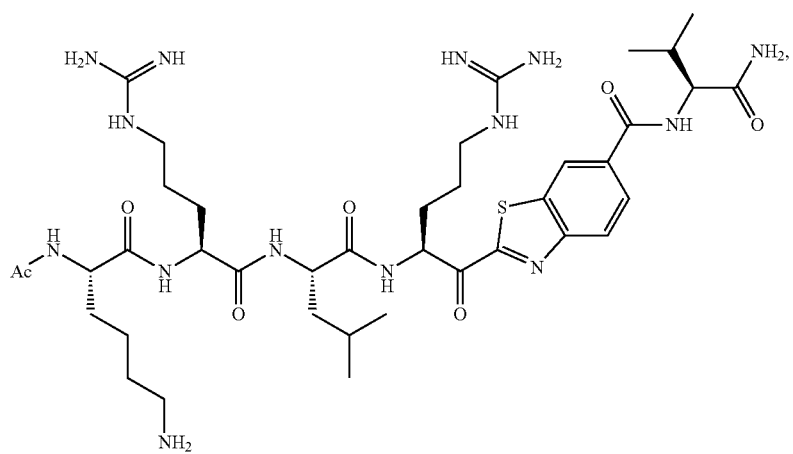

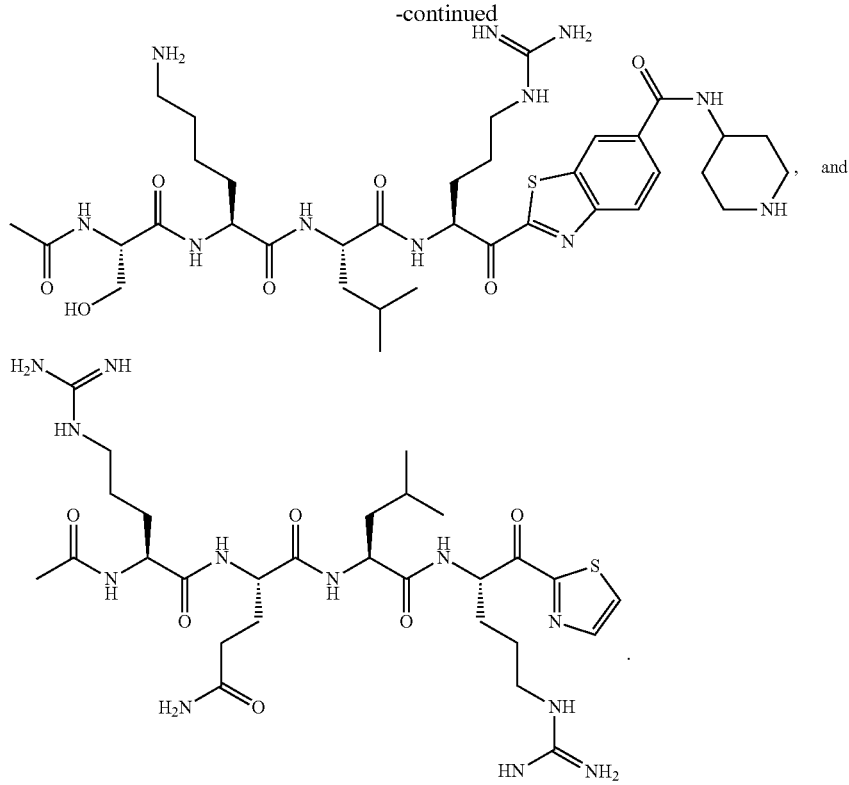
In some embodiments, the compound of Formula (II) is a tripeptide selected from the group consisting of:
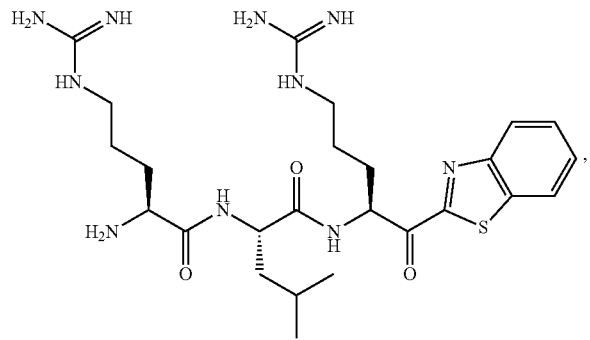
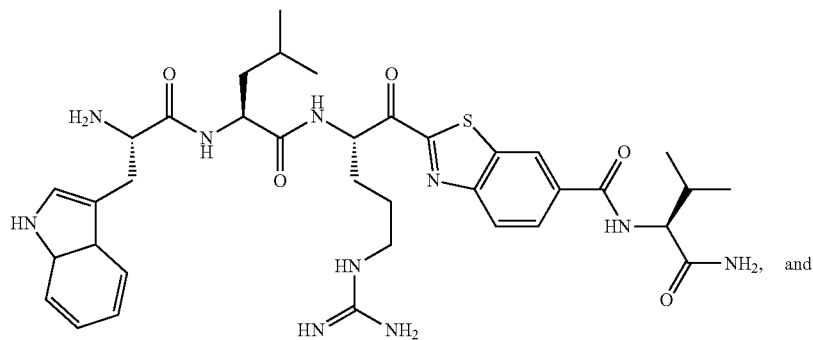
, and

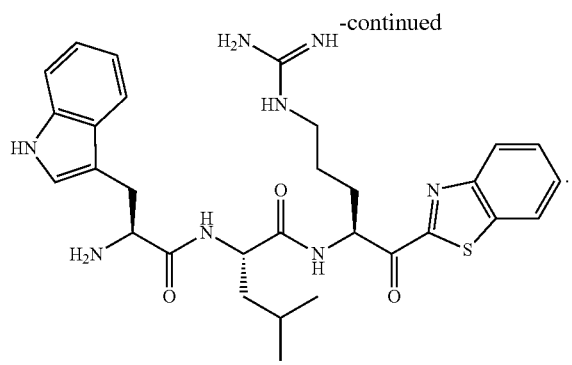

In some embodiments, the compound of Formula (II) is a dipeptide selected from the group consisting of:

In some embodiments, the compound of Formula (II) is a cyclic peptide of the following structure:

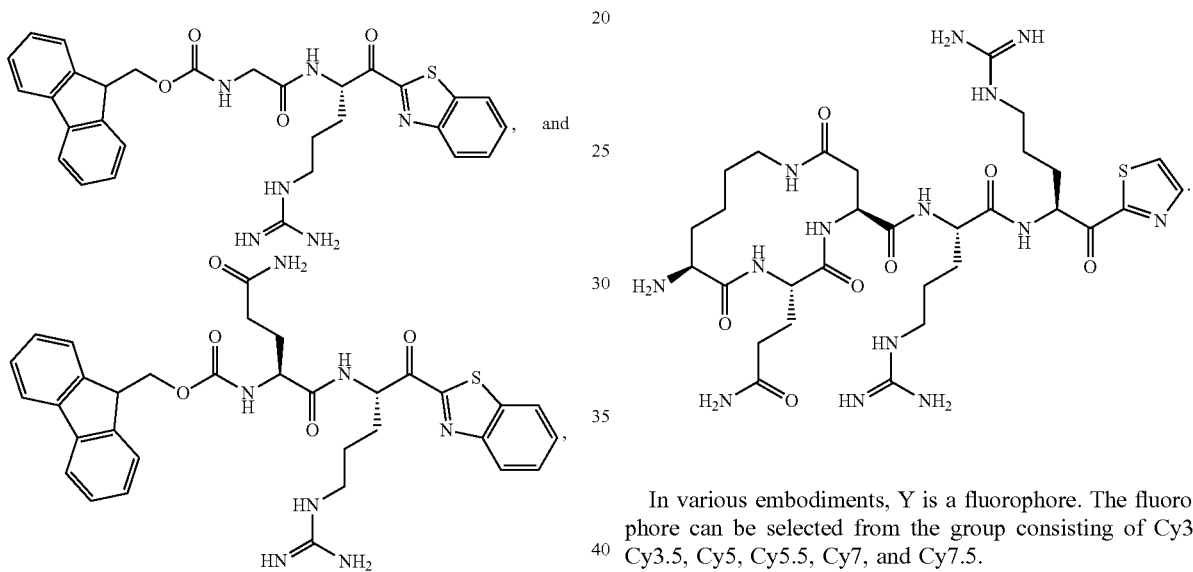

In various embodiments, Y is a fluorophore. The fluorophore can be selected from the group consisting of Cy3, Cy3.5, Cy5, Cy5.5, Cy7, and Cy7.5.

In some embodiments, the compound of Formula (II) is selected from the group consisting of:

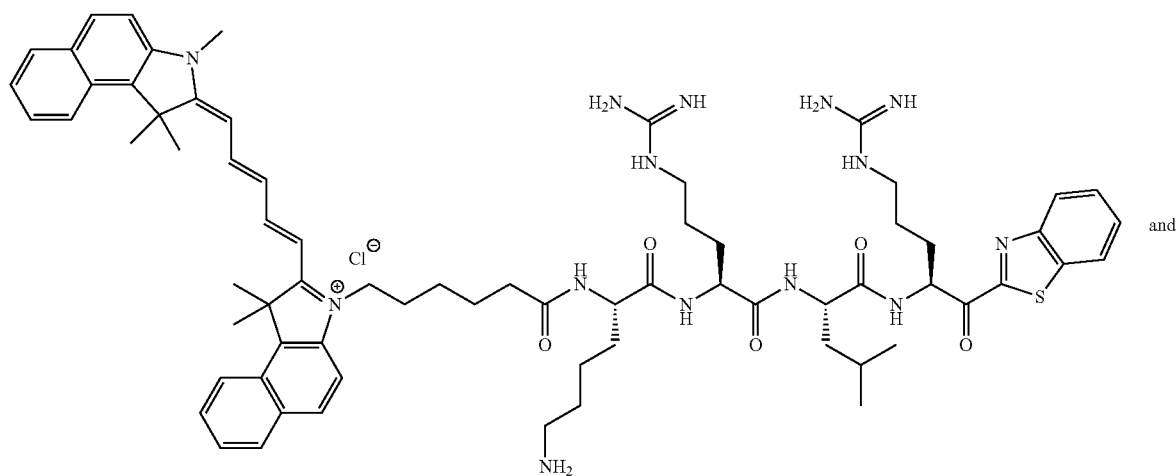

-continued

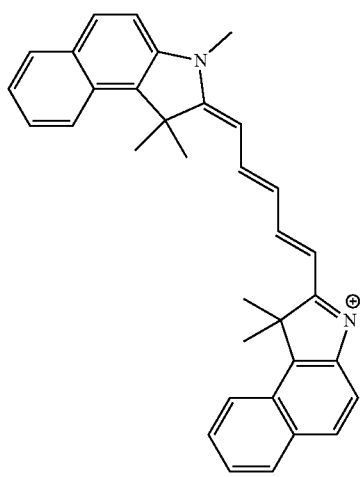
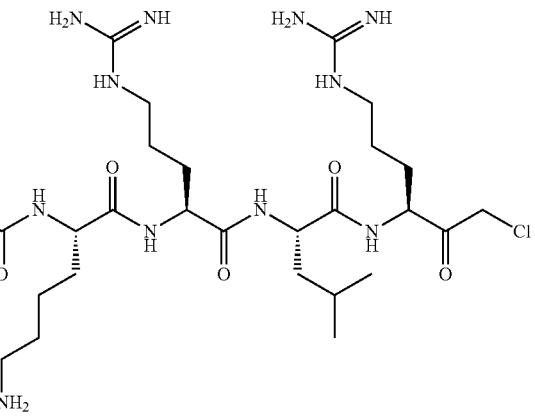

The compounds of Formulas (I) and (II) are useful for inhibiting one or more of matriptase, hepsin, and/or HGFA. Accordingly, the present invention is also directed to a method of inhibiting matriptase, hepsin, and/or HGFA comprising administering to a subject in need thereof a pharmaceutical composition comprising a therapeutically effective amount of at least one compound of Formula (I) or (II). In certain, embodiments the compounds are highly selective for one of matriptase, hepsin, or HGFA.

As noted, matriptase, hepsin, and/or HGFA are involved in various cancerous disease conditions. Thus, the present invention is directed to various methods of using the inhibitor compounds to treat cancer in a subject (e.g., a human). One method includes inhibiting HGF/MET oncogenic signaling by administering to a subject in need thereof a pharmaceutical composition comprising a therapeutically effective amount of at least one compound of Formula (I) or (II). Another method includes inhibiting MPS/RON oncogene signaling by administering to a subject in need thereof a pharmaceutical composition comprising a therapeutically effective amount of at least one compound of Formula (I) or (II). Yet another method including reversing resistance to a kinase inhibitor by blocking HGF and/or MPS production and/or activation by administering to a subject in need thereof a pharmaceutical composition comprising a therapeutically effective amount of at least one compound of Formula (I) or (II).

Another method includes inhibiting carcinoma progression comprising by administering to the subject in need thereof a pharmaceutical composition comprising a therapeutically effective amount of at least one compound of Formula (I) or (II).

A further method includes treating a malignancy, a pre-malignant condition, or cancer in a subject comprising administering to the subject in need thereof a pharmaceutical composition comprising a therapeutically effective amount of at least one compound of Formula (I) or (II). The cancer can be selected from the group consisting of breast, ovarian, prostate, endometrial, colon, pancreatic, head and neck, gastric, renal, brain, liver, bladder, kidney, lung, esophageal, leukemia, multiple myeloma, lymphoma, and melanoma. For example, the malignancy and the pre-malignant condition can be a condition of the breast. Also, the pre-malignant condition can be selected from the group consisting of a typical ductal hyperplasia of the breast, actinic keratosis, leukoplakia, Barrett's epithelium (columnar metaplasia) of the esophagus, ulcerative colitis, adenomatous colorectal polyps, erythroplasia of Queyrat, Bowen's disease, bowenoid papulosis, vulvar intraepthelial neoplasia, and dysplastic changes to the cervix. In various methods, the cancer can also be metastasized.

In the various methods of the present invention, the compounds of Formula (I) or (II) can also be administered in combination with an anticancer compound, radiation therapy, a compound that induces apoptosis, a surgical procedure, or any combination thereof.

In accordance with the various methods of the present invention, a pharmaceutical composition comprising an inhibitor compound of Formula (I) or (II) is administered to the subject in need thereof. The pharmaceutical composition can be administered by a routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. In various embodiments, administration is selected from the group consisting of oral, intranasal, intraperitoneal, intravenous, intramuscular, intratumoral, rectal, and transdermal.

The determination of a therapeutically effective dose for any one or more of the inhibitor compounds described herein is within the capability of those skilled in the art. A therapeutically effective dose refers to that amount of active ingredient which provides the desired result. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Typically, the normal dosage amount of the inhibitor can vary from about 0.05 to about 100 mg per kg body weight depending upon the route of administration. Guidance as to particular dosages and methods of delivery is provided in the literature and generally available to practitioners in the art.

It will generally be administered so that a daily oral dose in the range, for example, from about 0.1 mg to about 75 mg, from about 0.5 mg to about 50 mg, or from about 1 mg to about 25 mg per kg body weight is given. The active ingredient can be administered in a single dose per day, or alternatively, in divided does (e.g., twice per day, three time a day, four times a day, etc.). In general, lower doses can be administered when a parenteral route is employed. Thus, for example, for intravenous administration, a dose in the range, for example, from about 0.05 mg to about 30 mg, from about 0.1 mg to about 25 mg, or from about 0.1 mg to about 20 mg per kg body weight can be used.

A pharmaceutical composition for oral administration can be formulated using pharmaceutically acceptable carriers known in the art in dosages suitable for oral administration. Such carriers enable the pharmaceutical compositions to be formulated as tablets, pills, dragees, capsules, liquids, gels, syrups, slurries, suspensions, and the like, for ingestion by the subject. In certain embodiments, the composition is formulated for parenteral administration. Further details on techniques for formulation and administration can be found in the latest edition of REMINGTON'S PHARMACEUTICAL SCIENCES (Mack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

In addition to the active ingredients (e.g., the inhibitor compound), the pharmaceutical composition can contain suitable pharmaceutically acceptable carriers comprising excipients and auxiliaries that facilitate processing of the active compounds into preparations which can be used pharmaceutically. As used herein, the term "pharmaceutically acceptable carrier" means a non-toxic, inert solid, semi-solid or liquid filler, diluent, encapsulating material, or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil; and soybean oil; glycols such as propylene glycol; esters such as ethyl oleate and ethyl laurate; agar; detergents such as TWEEN 80; buffering agents such as magnesium hydroxide and aluminum hydroxide; alginic acid; pyrogen-free water; isotonic saline; Ringer's solution; ethyl alcohol; artificial cerebral spinal fluid (CSF), and phosphate buffer solutions, as well as other non-toxic compatible lubricants such as sodium lauryl sulfate and magnesium stearate, as well as coloring agents, releasing agents, coating agents, sweetening, flavoring, and perfuming agents, preservatives and antioxidants can also be present in the composition, according to the judgment of the formulator based on the desired route of administration.

The compounds of the present invention can also be used in various nuclear imaging techniques when labeled with a suitable radionuclide. Accordingly, an imaging composition in accordance with the present invention comprises a radiolabeled compound of Formula (I) or (II), wherein the labeled compound comprises a radioisotope selected from the group consisting of $^{13}C$, $^{13}N$, $^{15}O$, $^{18}F$, $^{75}Br$, $^{124}I$, $^{125}I$, and $^{131}I$. Methods known in the art for radiolabeling the compounds of the present invention may be used.

Imaging methods in accordance with the present invention include a method of detecting cancer comprising:

administering to a subject a radiolabeled compound of Formula (I) or (II);

employing a nuclear imaging technique for monitoring or visualizing a distribution of the radiolabeled compound within the body or within a portion thereof; and correlating the distribution of the radiolabeled compound to the existence of cancer. In various embodiments, the nuclear imaging technique is positron emission tomography (PET) or photon emission computed tomography (SPECT).

Imaging methods in accordance with the present invention include a method of detecting cancer comprising:

administering to a subject a fluorescent compound of Formula (I) or (II);

employing an imaging technique for monitoring or visualizing a distribution of the fluorescent compound within the body or within a portion thereof; and correlating the distribution of the fluorescent compound to the existence of cancer.

As used herein, the abbreviations of the naturally occurring amino acids are as follows:

| Amino acid | Three letter code | One letter code |
|---|---|---|
| alanine | Ala | A |
| arginine | Arg | R |
| asparagine | Asn | N |
| aspartic acid | Asp | D |
| cysteine | Cys | C |
| glutamic acid | Glu | E |
| glutamine | Gln | Q |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |
| tyrosine | Tyr | Y |
| valine | Val | V |

The naturally occurring amino acids described herein are the L-isomer unless denoted as a D-isomer.

Having described the invention in detail, it will be apparent that modifications and variations are possible without departing from the scope of the invention defined in the appended claims.

EXAMPLES

The following non-limiting examples are provided to further illustrate the present invention.

Example 1. General Synthesis, Purification, and Analytical Chemistry Procedures

Starting materials, reagents, and solvents were purchased from commercial vendors unless otherwise noted. $^1$H NMR spectra were measured on a Varian 400 MHz NMR instrument. The chemical shifts were reported ppm relative to tetramethylsilane (TMS) using residual solvent peak as the reference unless otherwise noted. The following abbreviations were used to express the multiplicities: s=singlet; d=doublet; t=triplet; q=quartet; m=multiplet; br=broad. High-performance liquid chromatography (HPLC) was carried out on GILSON GX-281 using Waters C18 5 µM, 4.6*50 mm and Waters Prep C18 5 µM, 19*150 mm reverse phase columns, eluted with a gradient system of 5:95 to 95:5 acetonitrile:water with a buffer consisting of 0.05% TFA. Purity assessment and mass spectra (MS) data were obtained using a Hewlett-Packard HPLC/MSD using electrospray ionization (ESI) for detection. All reactions were monitored by thin layer chromatography (TLC) carried out on Merck silica gel plates (0.25 mm thick, 60F254), visualized by using UV absorbance (254 nm) or dyes such as ninhydrin, KMnO$_4$, p-anisaldehyde or ceric ammonium molybdate (CAM). Silica gel chromatography was carried out on a Teledyne ISCO CombiFlash purification system using pre-packed silica gel columns (12 g-330 g sizes).

All compounds used for biological assays are greater than 95% purity based on NMR and HPLC by UV absorbance at 210 nm and 254 nm wavelengths.

Example 2. Synthesis of Tetrapeptide Ketothiazole Inhibitor Compounds

The tetrapeptide ketothiazoles (kt) listed in Table 2.1 were synthesized in accordance with the general schemes 2A and 2B shown below and the procedures described below.

TABLE 2.1

Tetrapeptide ketothiazoles.

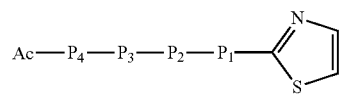

| Compound No. | Ac-P$_4$-P$_3$-P$_2$-P$_1$-kt |
|---|---|
| 5 | Ac-KQLR(SEQ ID NO: 1)-kt |
| 5-1 | Ac-KQLdR-kt |
| 5a | Ac-KHLR(SEQ ID NO: 2)-kt |
| 5a-1 | Ac-KHLdR-kt |
| 5b | Ac-WQLR(SEQ ID NO: 3)-kt |
| 5b-1 | Ac-WQLdR-kt |
| 5c | Ac-KQFR(SEQ ID NO: 4)-kt |
| 5c-1 | Ac-KQFdR-kt |
| 5d | Ac-KFLR(SEQ ID NO: 5)-kt |
| 5e | Ac-RQLR(SEQ ID NO: 6)-kt |
| 5e-1 | Ac-RQLdR-kt |
| 5f | Ac-SQLR(SEQ ID NO: 7)-kt |
| 5g | Ac-KRLR(SEQ ID NO: 8)-kt |
| 5h | Ac-WRLR(SEQ ID NO: 9)-kt |
| 6 | Ac-SKLR(SEQ ID NO: 10)-kt |
| 6-1 | Ac-SKLdR-kt |
| 6a | Ac-SHLR(SEQ ID NO: 11)-kt |
| 6a-1 | Ac-SHLdR-kt |
| 6b | Ac-WKLR(SEQ ID NO: 12)-kt |
| 6b-1 | Ac-WKLdR-kt |
| 6c | Ac-SKFR(SEQ ID NO: 13)-kt |
| 6c-1 | Ac-SKFdR-kt |
| 6d | Ac-NKLR(SEQ ID NO: 14)-kt |
| 6e | Ac-SRLR(SEQ ID NO: 15)-kt |
| 6e-1 | Ac-SdRLR-kt |
| 6e-2 | Ac-SRLdR-kt |
| 6e-3 | Ac-SdRLdR-kt |
| 6f | Ac-TKLR(SEQ ID NO: 16)-kt |
| 6g | Ac-SWLR(SEQ ID NO: 17)-kt |
| 6h | Ac-RKLR(SEQ ID NO: 18)-kt |

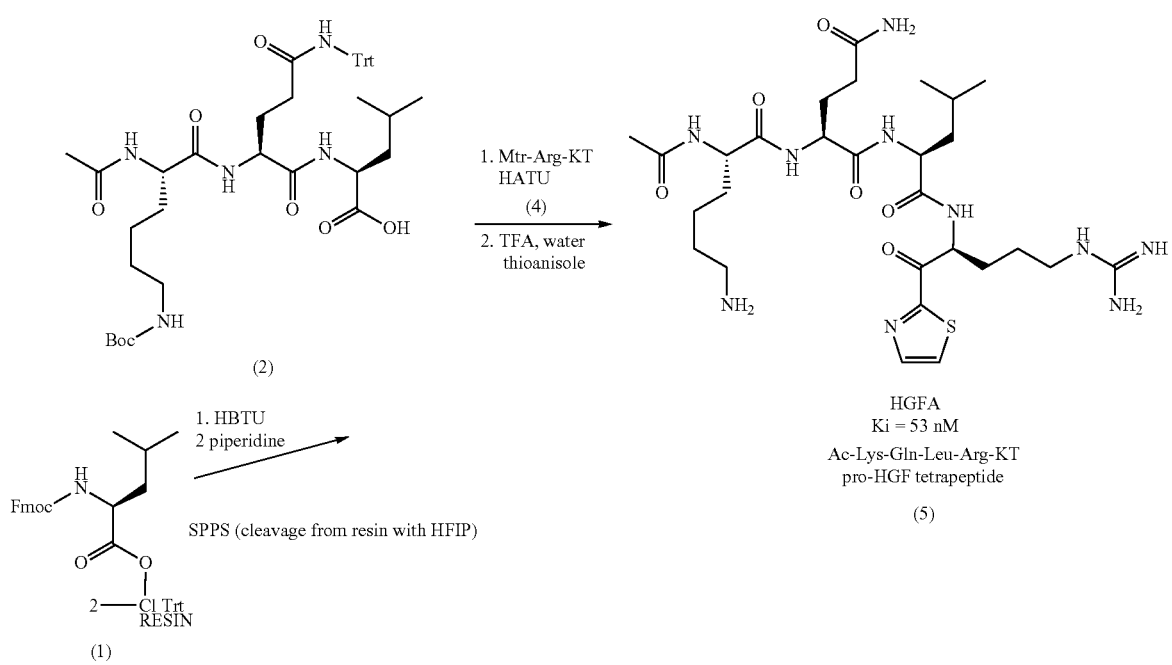

Scheme 2A. Synthesis of pro-HGF and pro-MSP P4-P1 tetrapeptide ketothiazoles

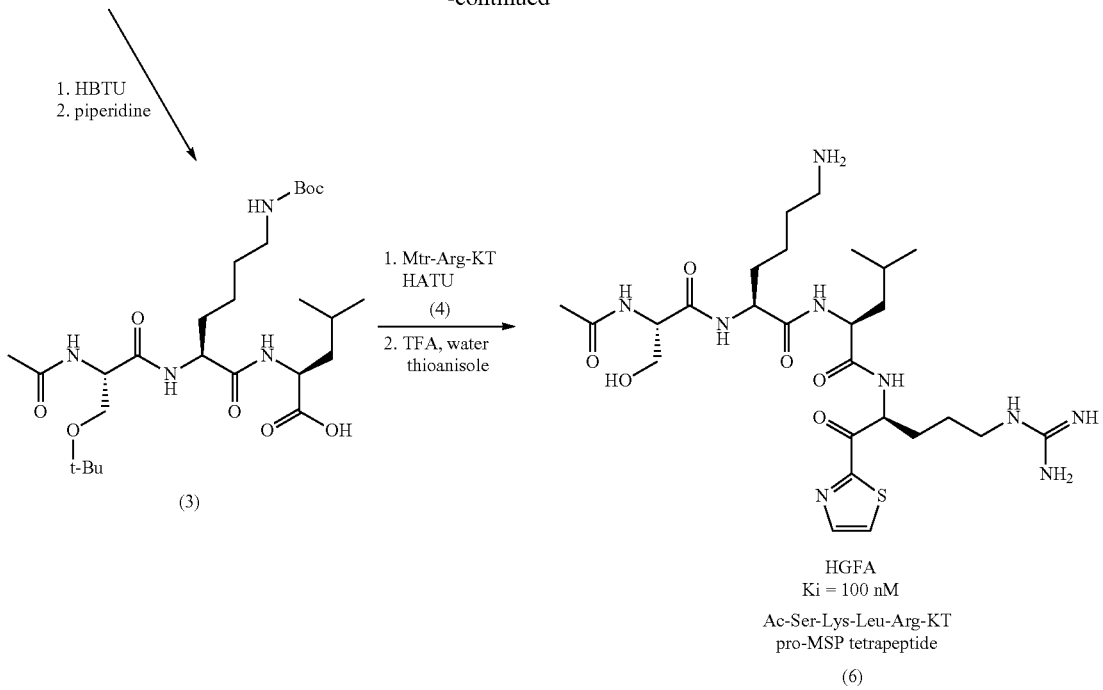

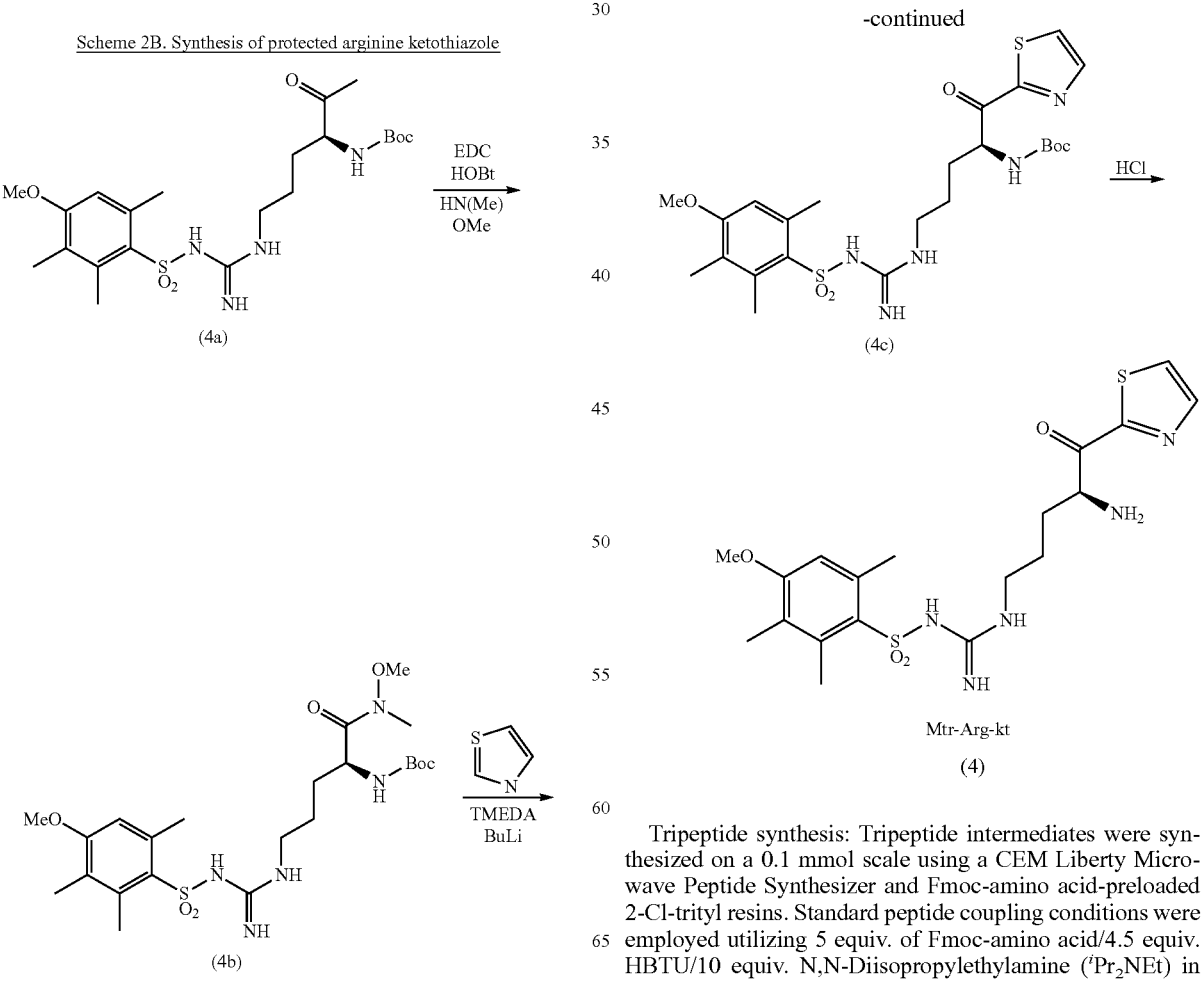

Tripeptide synthesis: Tripeptide intermediates were synthesized on a 0.1 mmol scale using a CEM Liberty Microwave Peptide Synthesizer and Fmoc-amino acid-preloaded 2-Cl-trityl resins. Standard peptide coupling conditions were employed utilizing 5 equiv. of Fmoc-amino acid/4.5 equiv. HBTU/10 equiv. N,N-Diisopropylethylamine ($^{i}Pr_2NEt$) in DMF was added and the mixture was heated at 75° C. for 5 minutes by microwave. Piperidine/DMF (20% v/v) was employed for the deprotection of the Fmoc protecting group using the microwave for 5 minutes.

Acetyl (Ac) Capping of the Tripeptides:

The tripeptide resin was suspended in 15 mL of 0.5 M Ac$_2$O/DMF and 1 M $^i$Pr$_2$NEt/DMF. The mixture was shaken at room temperature for 1 hour. The resin was filtered and washed with DMF (10 mL×4) followed by CH$_2$Cl$_2$ (10 mL×4).

Cleavage of Tripeptide Resin:

Ac-capped tripeptide resin was suspended and shaken in 15 mL of 25% v/v HFIP/CH$_2$Cl$_2$ for 1 hour. The mixture was filtered. The filtrate was concentrated then dried in vacuo, giving rise to crude Ac-capped tripeptide product.

Ac-KQFR (SEQ ID NO: 4) Ketothiazole (5c).

Under nitrogen atmosphere, at 0° C. anhydrous DMF (5 mL) was added into the round bottom flask containing Ac-capped KQF tripeptide (0.081 g, 0.1 mmol) and HATU (0.042 g, 0.11 mmol). After stirring for 10 minutes, arginine ketothiazole (0.042 g, 0.1 mmol), then N,N-diisopropylethylamine (0.065 g, 0.5 mmol) were added. The mixture was stirred overnight while being warmed to room temperature naturally. The majority of DMF was removed and to the resulting residue was added 20 mL of water. The precipitate that formed was filtered and dried. To this precipitate was added 5 mL of TFA/thioanisole/water (95/2.5/2.5(v/v/v)). The mixture was stirred at room temperature for 4 hours and then was added to 40 mL of cold ether. The precipitated crude product was collected by centrifugation, followed by carefully decanting out the ether solvent. The crude product was purified by HPLC (C18, 15*150 mm column; eluent: acetonitrile/water (0.1% TFA)) to give Ac-KQFR (SEQ ID NO: 4) ketothiazole (0.032 g) in 46% yield. At the same time the isomer KQFR (SEQ ID NO: 4)* ketothiazole (0.020 g) was also collected. $^1$H NMR (400 MHz, DEUTERIUM OXIDE) δ ppm 1.35 (m, 2H) 1.45-1.77 (m, 7H) 1.78-2.04 (m, 6H) 2.06-2.29 (m, 2H) 2.92 (t, J=7.63 Hz, 2H) 3.00 (m, 2H) 3.13 (m, 2H) 4.12-4.20 (m, 1H) 4.21-4.29 (m, 1H) 4.59 (t, J=7.63 Hz, 1H) 5.30-5.45 (m, 1H) 7.17 (m, 5H) 8.04 (br. s., 1H) 8.07 (br. s., 1H). MS (ESI): found: [M+H]$^+$, 687.5.

Ac-SQLR (SEQ ID NO: 7) Ketothiazole (5f)

(yield: 42%)$^1$H NMR (400 MHz, DEUTERIUM OXIDE) δ ppm 0.85 (d, J=5.87 Hz, 3H) 0.90 (d, J=5.87 Hz, 3H) 1.48-1.76 (m, 5H) 1.77-1.88 (m, 1H) 1.89-2.02 (m, 1H) 2.02-2.20 (m, 5H) 2.26-2.47 (m, 2H) 3.11-3.32 (m, 2H) 3.84 (tt, J=11.44, 5.77 Hz, 2H) 4.25-4.45 (m, 3H) 5.47 (dd, J=9.39, 4.30 Hz, 1H) 8.06 (d, J=3.13 Hz, 1H) 8.11 (d, J=3.13 Hz, 1H). MS (ESI): found: [M+H]$^+$, 612.5.

Ac-SRLR (SEQ ID NO: 15) ketothiazole (6e)

(yield: 26%)$^1$H NMR (400 MHz, DEUTERIUM OXIDE) δ ppm 0.85 (d, J=5.87 Hz, 3H) 0.91 (d, J=5.87 Hz, 3H) 1.52-1.77 (m, 8H) 1.79-1.89 (m, 2H) 1.99-2.18 (m, 4H) 3.09-3.34 (m, 4H) 3.83 (tt, J=11.35, 5.67 Hz, 2H) 4.29-4.45 (m, 3H) 5.46 (dd, J=9.20, 4.11 Hz, 1H) 8.06 (d, J=3.13 Hz, 1H) 8.12 (d, J=3.13 Hz, 1H). MS (ESI): found: [M+H]$^+$, 640.5.

Ac-TKLR (SEQ ID NO: 16) Ketothiazole (6f)

(yield: 59%)$^1$H NMR (400 MHz, DEUTERIUM OXIDE) δ ppm 0.85 (d, J=5.87 Hz, 3H) 0.91 (d, J=5.48 Hz, 3H) 1.12-1.24 (m, 3H) 1.32-1.90 (m, 12H) 1.99-2.18 (m, 4H) 2.98 (t, J=7.43 Hz, 2H) 3.15-3.30 (m, 2H) 4.07-4.19 (m, 1H) 4.24 (d, J=5.48 Hz, 1H) 4.34 (td, J=8.90, 5.67 Hz, 2H) 5.45 (dd, J=9.19, 4.50 Hz, 1H) 8.07 (d, J=3.13 Hz, 1H) 8.12 (d, J=3.13 Hz, 1H). MS (ESI): found: [M+H]$^+$, 626.5.

Ac-KFLR (SEQ ID NO: 5) Ketothiazole (5d)

(yield: 43%)$^1$H NMR (400 MHz, DEUTERIUM OXIDE) δ ppm 0.85 (d, J=6.26 Hz, 3H) 0.90 (d, J=6.26 Hz, 3H) 1.13-1.38 (m, 2H) 1.40-1.77 (m, 9H) 1.78-1.91 (m, 1H) 1.99 (s, 3H) 2.04-2.17 (m, 1H) 2.82-3.05 (m, 3H) 3.09-3.32 (m, 3H) 4.08-4.21 (m, 1H) 4.37 (dd, J=8.80, 6.06 Hz, 1H) 4.65 (dd, J=8.61, 6.26 Hz, 1H) 5.44 (dd, J=9.19, 4.50 Hz, 1H) 7.15-7.43 (m, 5H) 8.08 (d, J=3.13 Hz, 1H) 8.13 (d, J=3.13 Hz, 1H). MS (ESI): found: [M+H]$^+$, 672.5.

Ac-NKLR (SEQ ID NO: 14) Ketothiazole (6d)

(yield: 39%)$^1$H NMR (400 MHz, DEUTERIUM OXIDE) δ ppm 0.85 (d, J=5.48 Hz, 3H) 0.91 (d, J=5.87 Hz, 3H) 1.32-1.48 (m, 2H) 1.48-1.91 (m, 10H) 1.93-2.17 (m, 4H) 2.62-2.84 (m, 2H) 2.98 (t, J=7.63 Hz, 2H) 3.14-3.30 (m, 2H) 4.20-4.42 (m, 2H) 4.63 (t, J=7.04 Hz, 1H) 5.45 (dd, J=9.39, 4.30 Hz, 1H) 8.06 (d, J=3.13 Hz, 1H) 8.11 (d, J=3.13 Hz, 1H). MS (ESI): found: [M+H]$^+$, 639.5.

Ac-RQLR (SEQ ID NO: 6) Ketothiazole (5e)

(yield: 13%)$^1$H NMR (400 MHz, DEUTERIUM OXIDE) δ ppm 0.85 (d, J=5.87 Hz, 3H) 0.91 (d, J=5.87 Hz, 3H) 1.45-1.89 (m, 10H) 1.90-2.19 (m, 6H) 2.35 (td, J=7.43, 3.91 Hz, 2H) 3.14-3.28 (m, 4H) 4.25 (dd, J=8.02, 6.06 Hz, 1H) 4.30-4.43 (m, 2H) 5.47 (dd, J=9.39, 4.30 Hz, 1H) 8.07 (d, J=3.13 Hz, 1H) 8.12 (d, J=3.13 Hz, 1H). MS (ESI): found: [M+H]$^+$, 681.5.

Ac-WQLR (SEQ ID NO: 3) Ketothiazole (5b)

(yield: 13%)$^1$H NMR (400 MHz, DEUTERIUM OXIDE) δ ppm 0.81 (d, J=5.87 Hz, 3H) 0.88 (d, J=5.48 Hz, 3H) 1.37-1.69 (m, 6H) 1.70-1.91 (m, 3H) 1.91-2.10 (m, 5H) 2.98-3.35 (m, 4H) 3.92-4.06 (m, 1H) 4.11-4.23 (m, 1H) 4.48 (t, J=6.65 Hz, 1H) 5.39 (m, 1H) 7.09 (t, J=7.24 Hz, 1H) 7.14-7.26 (m, 2H) 7.43 (d, J=8.22 Hz, 1H) 7.52 (d, J=7.43 Hz, 1H) 8.00 (d, J=2.74 Hz, 1H) 8.05 (d, J=2.74 Hz, 1H). MS (ESI): found: [M+H]$^+$, 711.5.

Ac-KHLR (SEQ ID NO: 2) Ketothiazole (5a)

(yield: 52%)$^1$H NMR (400 MHz, DEUTERIUM OXIDE) δ ppm 0.82 (d, J=4.30 Hz, 3H) 0.87 (d, J=4.70 Hz, 3H) 1.22-1.44 (m, 2H) 1.44-1.73 (m, 9H) 1.74-1.87 (m, 1H) 1.96 (s, 3H) 2.06 (m, 1H) 2.83-2.99 (m, 2H) 3.02-3.36 (m, 4H) 4.06-4.22 (m, 1H) 4.34 (m, 1H) 4.58-4.72 (m, 1H) 5.43 (dd, J=8.61, 4.30 Hz, 1H) 7.23 (s, 1H) 8.03 (d, J=2.35 Hz, 1H) 8.08 (d, J=2.35 Hz, 1H) 8.58 (s, 1H). MS (ESI): found: [M+H]$^+$, 662.5.

Ac-SKLR (SEQ ID NO: 10) Ketothiazole (6)

(yield: 57%)$^1$H NMR (400 MHz, DEUTERIUM OXIDE) δ ppm 0.81 (d, J=4.70 Hz, 3H) 0.87 (d, J=4.30 Hz, 3H) 1.26-1.91 (m, 12H) 1.93-2.16 (m, 4H) 2.94 (t, J=7.43 Hz, 2H) 3.18 (m, 2H) 3.79 (t, J=6.46 Hz, 2H) 4.18-4.46 (m, 3H) 5.43 (dd, J=9.00, 3.91 Hz, 1H) 8.03 (d, J=2.74 Hz, 1H) 8.08 (d, J=2.74 Hz, 1H). MS (ESI): found: [M+H]$^+$, 612.5.

Ac-SHLR (SEQ ID NO: 11) Ketothiazole (6a)

(yield: 32%)$^1$H NMR (400 MHz, DEUTERIUM OXIDE) δ ppm 0.81 (d, J=5.09 Hz, 3H) 0.86 (d, J=5.09 Hz, 3H) 1.41-1.60 (m, 3H) 1.60-1.72 (m, 2H) 1.73-1.88 (m, 1H) 1.90-2.15 (m, 4H) 2.99-3.37 (m, 4H) 3.63-3.83 (m, 2H) 4.20-4.41 (m, 2H) 4.68 (dd, J=8.61, 5.48 Hz, 1H) 5.44 (dd, J=8.61, 3.13 Hz, 1H) 7.24 (s, 1H) 8.03 (d, J=2.35 Hz, 1H) 8.08 (d, J=2.35 Hz, 1H) 8.57 (s, 1H). MS (ESI): found: [M+H]$^+$, 621.5.

Ac-SKFR (SEQ ID NO: 13) Ketothiazole (6c)

(yield: 46%)$^1$H NMR (400 MHz, DEUTERIUM OXIDE) δ ppm 1.25 (m, 2H) 1.42-1.81 (m, 7H) 1.86-2.11 (m, 4H) 2.80-3.06 (m, 4H) 3.13 (m, 2H) 3.64-3.86 (m, 2H) 4.17-4.28 (m, 1H) 4.32 (t, J=5.67 Hz, 1H) 4.56 (t, J=7.83 Hz, 1H) 5.38 (dd, J=8.61, 4.30 Hz, 1H) 7.00-7.36 (m, 5H) 8.04 (d, J=2.74 Hz, 1H) 8.07 (d, J=2.74 Hz, 1H). MS (ESI): found: [M+H]$^+$, 646.5.

Ac-WKLR (SEQ ID NO: 12) Ketothiazole (6b)

(yield: 38%)$^1$H NMR (400 MHz, DEUTERIUM OXIDE) δ ppm 0.86 (d, J=5.48 Hz, 3H) 0.93 (d, J=5.48 Hz, 3H)

1.09-1.20 (m, 2H) 1.39-1.71 (m, 9H) 1.73-1.88 (m, 1H) 1.98 (s, 3H) 2.01-2.14 (m, 1H) 2.80-2.94 (m, 2H) 3.10-3.27 (m, 4H) 4.04-4.13 (m, 1H) 4.15-4.24 (m, 1H) 4.45-4.59 (m, 1H) 5.42 (dd, J=9.00, 3.91 Hz, 1H) 7.08-7.17 (m, 1H) 7.18-7.28 (m, 2H) 7.47 (d, J=7.83 Hz, 1H) 7.57 (d, J=7.83 Hz, 1H) 7.93 (dd, J=13.50, 6.85 Hz, 1H) 8.05 (d, J=2.74 Hz, 1H) 8.09 (d, J=2.74 Hz, 1H). MS (ESI): found: [M+H]$^+$, 711.8.

Ac-KQLR (SEQ ID NO: 1) Ketothiazole (5)

(yield: 32%) $^1$H NMR (400 MHz, DEUTERIUM OXIDE) δ ppm 0.80 (d, J=5.09 Hz, 3H) 0.86 (d, J=5.09 Hz, 3H) 1.26-1.84 (m, 12H) 1.84-2.13 (m, 6H) 2.29 (m, 2H) 2.93 (t, J=7.43 Hz, 2H) 3.17 (m, 2H) 4.18 (t, J=7.04 Hz, 1H) 4.23-4.37 (m, 2H) 5.35-5.51 (m, 1H) 8.01 (d, J=2.74 Hz, 1H) 8.07 (d, J=2.74 Hz, 1H). MS (ESI): found: [M+H]$^+$, 653.5.

Ac-KRLR (SEQ ID NO: 8)-Ketothiazole (5g)

(yield: 44%) $^1$H NMR (400 MHz, DEUTERIUM OXIDE) δ ppm 0.77-0.91 (m, 6H) 1.26-1.45 (m, 3H) 1.46-1.58 (m, 5H) 1.58-1.70 (m, 7H) 1.70-1.85 (m, 4H) 1.97 (s, 3H) 1.99-2.11 (m, 2H) 2.93 (t, J=7.63 Hz, 2H) 3.15 (dt, J=13.79, 6.99 Hz, 4H) 4.17 (dd, J=8.22, 5.87 Hz, 1H) 4.24-4.30 (m, 1H) 4.30-4.37 (m, 1H) 5.41 (dd, J=9.20, 4.11 Hz, 1H) 8.02 (d, J=2.74 Hz, 1H) 8.07 (d, J=3.13 Hz, 1H) MS (ESI): found: [M+H]$^+$, 681.7.

Ac-WRLR (SEQ ID NO: 9)-Ketothiazole (5h)

(yield: 24%) $^1$H NMR (400 MHz, DEUTERIUM OXIDE) δ ppm 0.82 (d, J=5.87 Hz, 3H) 0.89 (d, J=5.87 Hz, 3H) 1.10-1.32 (m, 3H) 1.34-1.45 (m, 2H) 1.48 (d, J=6.65 Hz, 3H) 1.53-1.68 (m, 3H) 1.68-1.83 (m, 1H) 1.95 (s, 3H) 2.02 (d, J=10.56 Hz, 1H) 2.97 (t, J=5.87 Hz, 2H) 3.12 (t, J=6.85 Hz, 2H) 3.15-3.22 (m, 2H) 4.02 (dd, J=8.02, 5.67 Hz, 1H) 4.15 (t, J=7.63 Hz, 1H) 4.47 (t, J=7.04 Hz, 1H) 5.37 (dd, J=9.00, 4.30 Hz, 1H) 7.02-7.12 (m, 1H) 7.17 (t, J=7.63 Hz, 1H) 7.21 (s, 1H) 7.42 (d, J=8.22 Hz, 1H) 7.51 (d, J=7.83 Hz, 1H) 8.00 (d, J=3.13 Hz, 1H) 8.05 (d, J=3.13 Hz, 1H) MS (ESI): found: [M+H]$^+$, 739.7.

Ac-SWLR (SEQ ID NO: 17)-Ketothiazole (6g)

(yield: 20%) $^1$H NMR (400 MHz, DEUTERIUM OXIDE) δ ppm 0.74 (d, J=6.65 Hz, 3H) 0.71 (d, J=6.26 Hz, 3H) 0.99-1.15 (m, 2H) 1.35 (t, J=7.04 Hz, 2H) 1.51-1.64 (m, 3H) 1.72 (s, 3H) 1.76 (br. s., 1H) 2.00 (dd, J=13.69, 4.70 Hz, 2H) 3.00-3.18 (m, 3H) 3.25 (d, J=5.48 Hz, 2H) 3.60-3.81 (m, 3H) 4.11-4.26 (m, 2H) 4.62 (t, J=5.87 Hz, 1H) 5.33 (dd, J=9.59, 4.11 Hz, 1H) 7.08-7.15 (m, 1H) 7.15 (s, 1H) 7.17-7.23 (m, 1H) 7.43 (d, J=8.22 Hz, 1H) 7.57 (d, J=8.22 Hz, 1H) 7.63 (br. s., 1H) 7.77 (br. s., 1H) 8.00 (d, J=3.13 Hz, 1H) 8.06 (d, J=2.74 Hz, 1H) MS (ESI): found: [M+H]$^+$, 670.5.

Ac-RKLR (SEQ ID NO: 18)-ketothiazole (6h)

(yield: 31%) $^1$H NMR (400 MHz, DEUTERIUM OXIDE) δ ppm 0.76-0.91 (m, 6H) 1.24-1.47 (m, 3H) 1.47-1.56 (m, 3H) 1.56-1.70 (m, 7H) 1.70-1.86 (m, 4H) 1.97 (s, 3H) 2.00-2.12 (m, 1H) 2.93 (t, J=7.63 Hz, 2H) 3.06-3.24 (m, 4H) 4.19 (t, J=7.04 Hz, 1H) 4.27 (dd, J=8.80, 6.06 Hz, 1H) 4.33 (d, J=9.00 Hz, 1H) 5.41 (dd, J=9.00, 4.70 Hz, 1H) 8.03 (d, J=3.13 Hz, 1H) 8.08 (d, J=3.13 Hz, 1H) MS (ESI): found: [M+H]$^+$, 681.7.

Example 3. Synthesis of Cyclic Peptides

The cyclic peptide is listed in Table 3.1 were synthesized in accordance with the general schemes 3A and 3B and cyclization schemes 3C, 3D, 3E, and 3F shown below and the procedures described below.

Scheme 3A

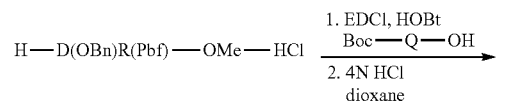

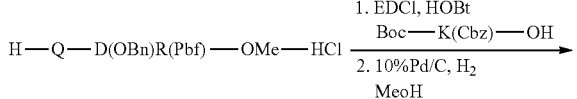

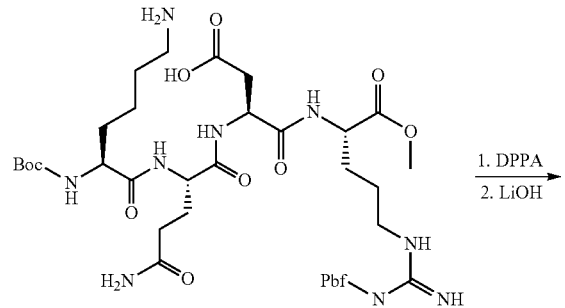

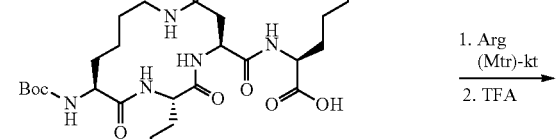

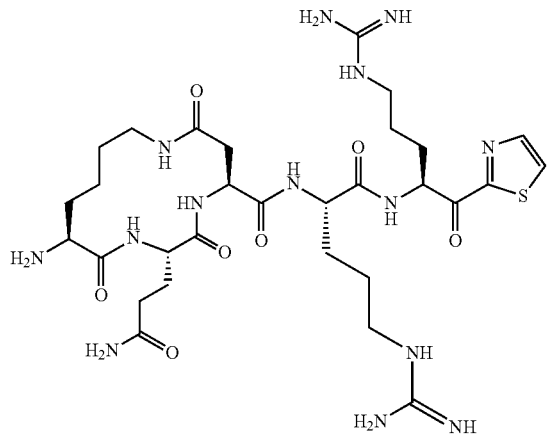

Scheme 3B

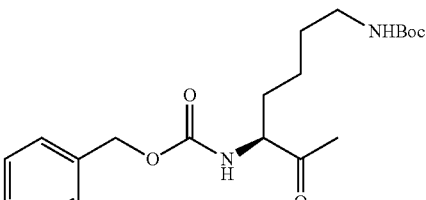

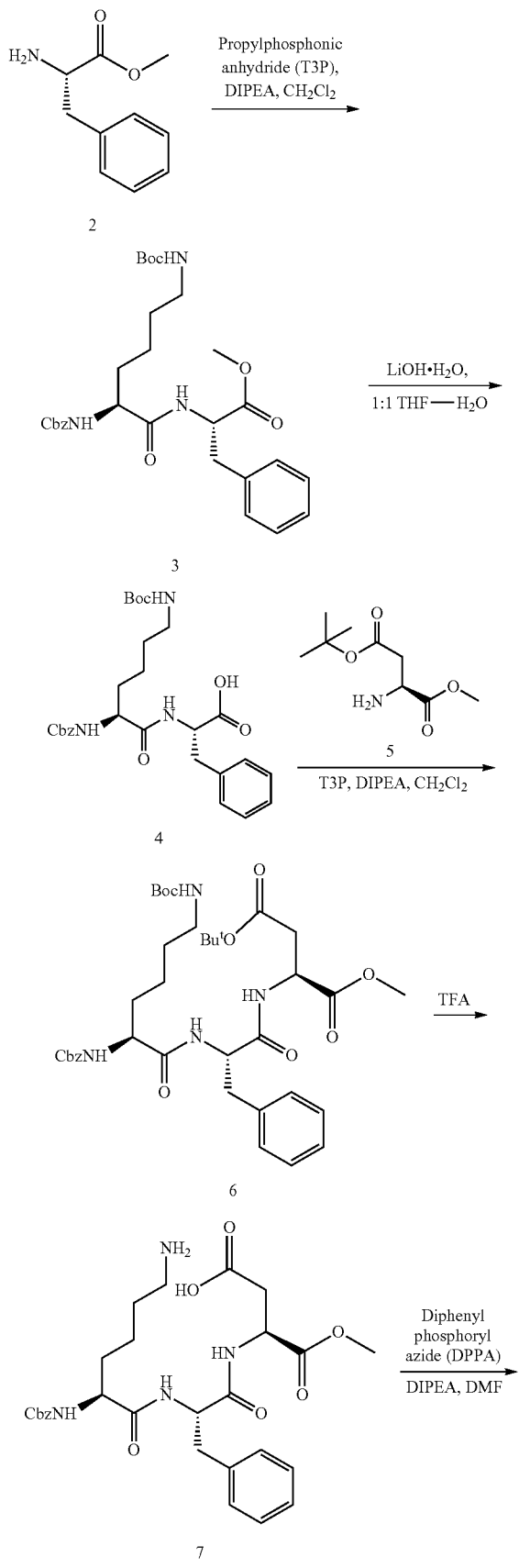

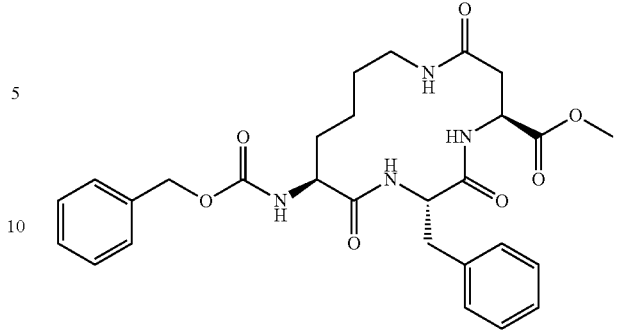

Chemical Formula: C$_{184}$H$_{247}$N$_{22}$O$_{50}$
Exact Mass: 3564.75
Molecular Weight: 3567.0
PK-1-71

TABLE 3.1

| | Y-P$_5$-P$_4$-P$_3$-P$_2$-P$_1$-Z | |
|---|---|---|
| Compound No. | Y-cyclo(P$_5$-P$_4$-P$_3$)-P$_2$-P$_1$-Z | Cyclization |
| 7074 | H-cyclo(KQD)RR-kt | P$_3$-P$_5$ |

Cbz-K(Boc)F—OMe (3):

Compound 1 (0.1 mmol) and compound 2 (0.1 mmol) was taken in dry CH$_2$Cl$_2$ (5 mL) and cooled to 0° C. and diisopropyletheylamine (DIPEA) (0.3 mmol) and propylphosphonic anhydride (T3P) (0.1 mmol, 50% solution in ethyl acetate) were added dropwise to the reaction mixture respectively. The reaction mixture was stirred for 1 hr at room temperature under nitrogen atmosphere. The completion of the reaction was confirmed by LCMS monitoring. On completion, the reaction mixture was diluted with 5 mL and washed with 10% citric acid, saturated Na$_2$CO$_3$ solution and brine respectively. The organic layer was dried over sodium sulfate and concentrated under reduced pressure to obtain the compound 3 as white solid (yield: 80%, Chemical Formula: C$_{29}$H$_{39}$N$_3$O$_7$, Exact Mass: 541.28, ESIMS: 564.6 [M+Na$^+$]).

Cbz-K(Boc)F—OH (4):

Compound 3 (0.1 mmol) was taken in 4 mL THF—H$_2$O (1:1) mixture and LiOH.H$_2$O (0.3 mmol) was added to the solution. The reaction mixture was stirred for 15 minutes at room temperature and the completion of the reaction was confirmed by LCMS monitoring. On completion, the THF was evaporated under reduced pressure and the water layer was cooled to 0° C. The water layer was brought to pH 6.5 by dropwise addition of cold 0.5 M HCl solution and kept on ice for 15 minutes to complete the precipitation of the product as white solid. The precipitate was isolated by filtration and dried under reduced pressure to obtain the compound 4 as white solid (Yield: 83%, Chemical Formula: C$_{28}$H$_{37}$N$_3$O$_7$, Exact Mass: 527.26, ESIMS: 528.3 [M+H$^+$]).

Cbz-K(Boc)FD(t-Bu)-OMe (6):

Compound 4 (0.1 mmol) and compound 5 (0.1 mmol) was taken in dry CH$_2$Cl$_2$ (5 mL) and cooled to 0° C. and diisopropyletheylamine (DIPEA) (0.3 mmol) and propylphosphonic anhydride (T3P) (0.1 mmol, 50% solution in ethyl acetate) were added dropwise to the reaction mixture respectively. The reaction mixture was stirred for 1 hr at room temperature under nitrogen atmosphere. The completion of the reaction was confirmed by LCMS monitoring. On completion, the reaction mixture was diluted with 5 mL and washed with 10% citric acid, saturated Na$_2$CO$_3$ solution and brine respectively. The organic layer was dried over sodium sulfate and concentrated under reduced pressure to obtain the compound 3 as white solid (yield: 80%, Chemical Formula: C$_{37}$H$_{52}$N$_4$O$_{10}$, Exact Mass: 712.37, ESIMS: 713.4 [M+H$^+$]).

Cbz-KFD-OMe (7):

Trifluoroacetic acid (TFA) (3 mL) was added to the compound 6 and the reaction mixture was stirred for 1 hr. The completion of the reaction was confirmed by LCMS monitoring. On completion, the TFA was evaporated under reduced pressure by azeotroping with toluene and the dry mass was triturated with diethyl ether to obtain the pure compound 7 as white solid (Yield: 92%, Chemical Formula: C$_{28}$H$_{36}$N$_4$O$_8$, Exact Mass: 556.25, ESIMS: 557.3 [M+H$^+$]).

Cbz-cyclo(KFD)-OH (PK-1-71):

Compound 7 (0.09 mmol) was taken in 25 mL DMF and DIPEA (0.27 mmol) and diphenyl phosphoryl azide (0.1 mmol) was added to the solution. The reaction mixture was stirred for 12 hr at room temperature under nitrogen atmosphere and the completion of the reaction was confirmed by LCMS monitoring. The DMF was evaporated under reduced pressure and the crude product was purified by normal phase column chromatography using silica gel column and 5% MeOH in dichloromethane as eluent to obtain the product PK-1-71 as white solid (yield: 68%, Chemical Formula: C$_{28}$H$_{34}$N$_4$O$_7$, Exact Mass: 538.24, ESIMS: 539.4 [M+H$^+$]) $^1$H NMR (400 MHz, METHANOL-d4) d 8.03 (s, 1H), 7.97 (s, 1H), 7.42-7.49 (m, 2H), 7.29-7.35 (m, 6H), 7.17-7.23 (m, J=7.80 Hz, 5H), 7.10-7.16 (m, 2H), 3.69 (td, J=6.65, 13.30 Hz, 1H), 3.19 (q, J=7.43 Hz, 1H), 2.98 (s, 1H), 2.85 (s, 1H), 2.74 (s, 1H), 1.36 (s, 3H), 1.34 (t, J=3.33 Hz, 8H).

((7S,10S,13S,Z)-13-acetamido-10-(3-amino-3-oxopropyl)-9,12-dioxo-2-oxa-8,11-diaza-1(1,4)-benzenacyclotetradecaphan-4-ene-7-carbonyl)-L-arginine (CJ-1-55)

methyl N2-((S)-2-((S)-2-((S)-2-acetamido-3-(4-(allyloxy)phenyl)propanamido)-5-amino-5-oxopentanamido) pent-4-enoyl)-Nw-((2,2,4,5,7-pentamethyl-2,3-dihydrobenzofuran-6-yl)sulfonyl)-L-argininate [calculated for Chemical Formula: C$_{44}$H$_{62}$N$_8$O$_{11}$S, Exact Mass: 910.43, MS(ESI): found: [M+H]$^+$, 911.4, (0.18 g, 0.2 mmol)] was dissolved in DCM (125 mL). Grubbs second generation catalyst (50 mg, 0.06 mmol) was added and then the stirred reaction mixture was heated to reflux. The reaction as filtered and purified by silica gel chromatography (17 mg, 0.019 mmol). The product was dissolved in water (1 mL) and THF (1 mL), then LiOH (2 mg, 0.084 mmol) was added, and the reaction stirred for 1 hour. The THF was removed and 2 drops of 3N HCl were added to precipitate the Pbf-protected acid. The solid was dissolved in 3 mL of TFA/water/thioanisole (95:2.5:2.5) and stirred for 3 hours. The solvent was removed under reduced pressure and the residue was purified by C18 reverse phase HPLC (5-95% Acetonitrile/water/0.05% TFA). After lyopholization of pure fractions the title compound (4.4 mg) was obtained as the TFA salt. Calculated for Chemical Formula: C$_{28}$H$_{40}$N$_8$O$_8$, Exact Mass: 616.30, MS(ESI): found: [M+H]$^+$ 617.3.

Scheme 3C

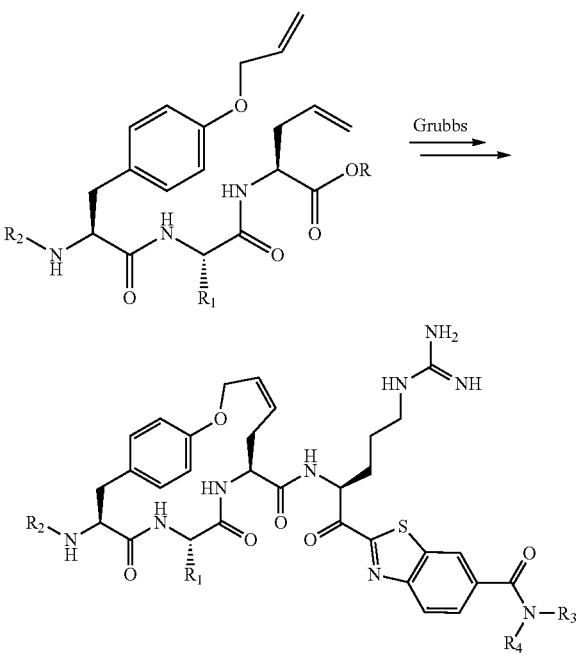

cyclo P2-P4

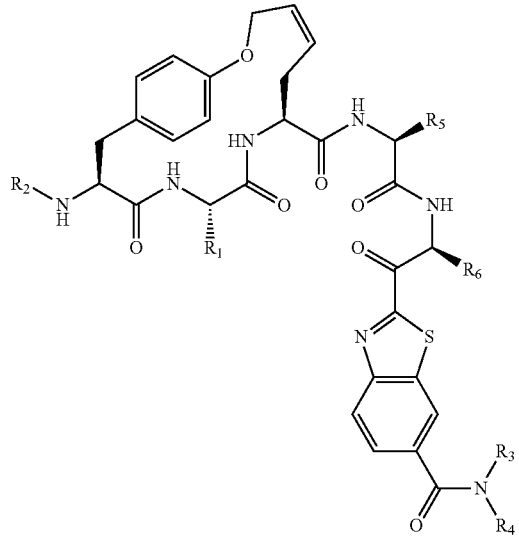

cyclo P3-P5

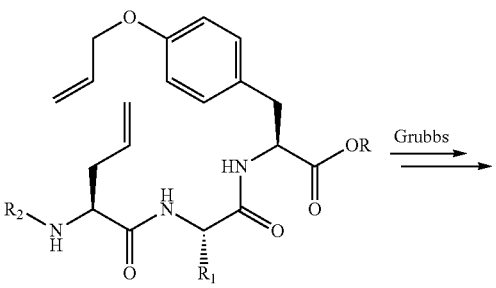

R = Me or Wang Resin

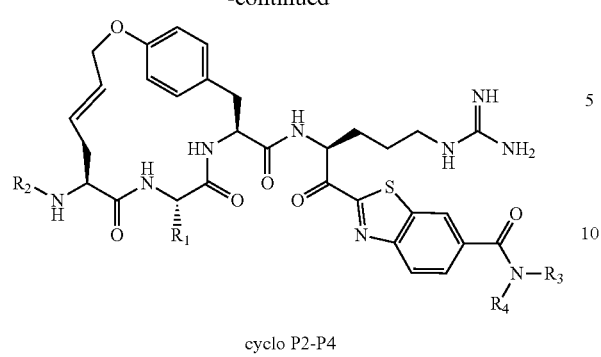
cyclo P2-P4
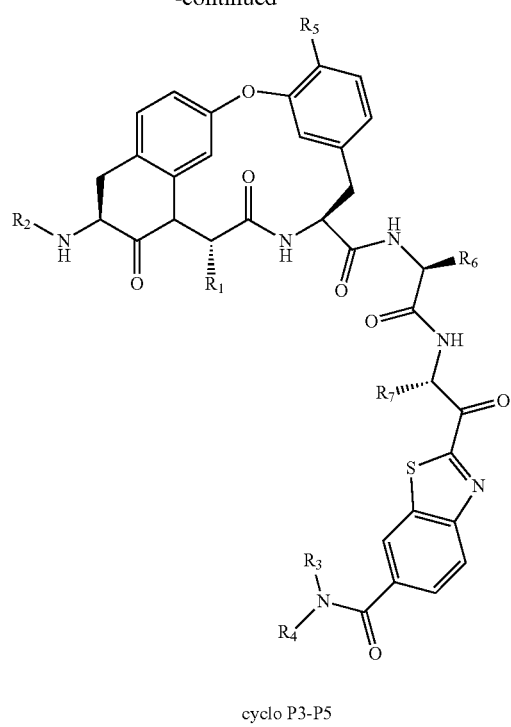
cyclo P3-P5
Scheme 3D
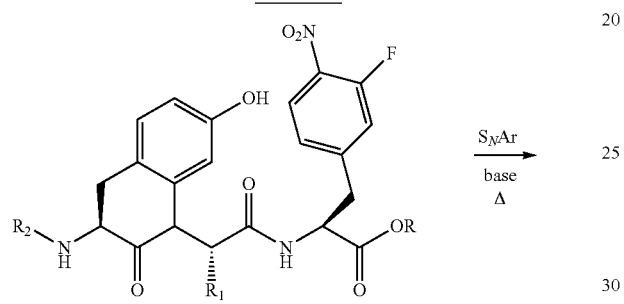
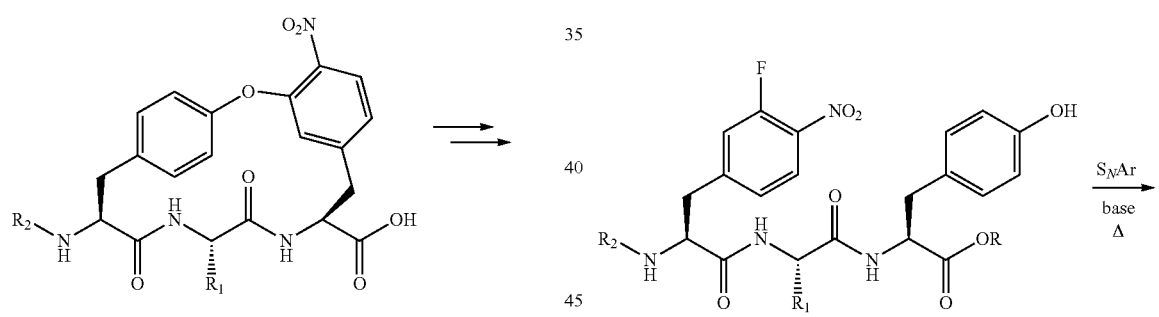
R = Me or Wang Resin
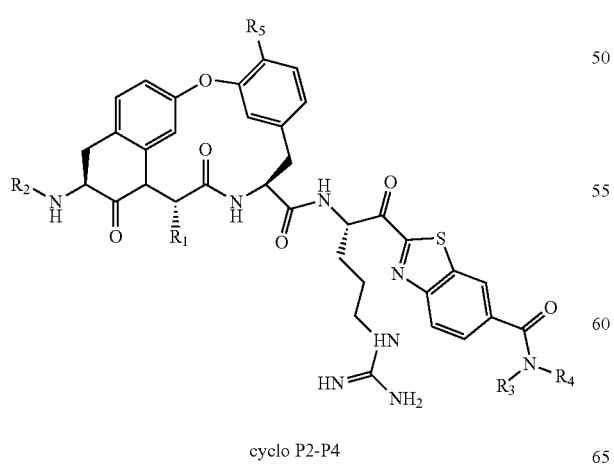
cyclo P2-P4
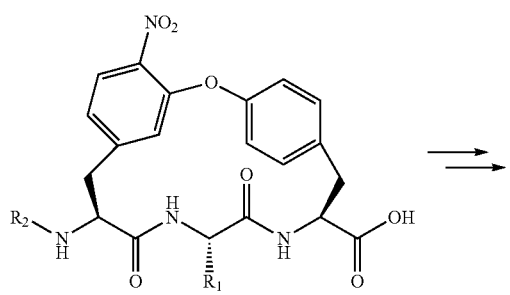

-continued

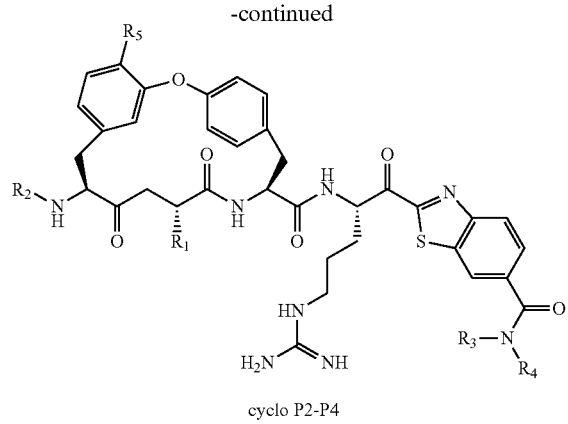

cyclo P2-P4

(2S,5S,13S)-13-amino-2-(3-amino-3-oxopropyl)-N—((S)-5-guanidino-1-(((S)-5-guanidino-1-oxo-1-(thiazol-2-yl)pentan-2-yl)amino)-1-oxopentan-2-yl)-3,7,14-trioxo-1,4,8-triazacyclotetradecane-5-carboxamide (7074)

A solution of (6S,9S,12S)-9-(3-amino-3-oxopropyl)-6-(4-aminobutyl)-12-(((S)-1-methoxy-1-oxo-5-(3-((2,2,4,5,7-pentamethyl-2,3-dihydrobenzofuran-6-yl)sulfonyl)guanidino)pentan-2-yl)carbamoyl)-2,2-dimethyl-4,7,10-trioxo-3-oxa-5,8,11-triazatetradecan-14-oic acid [calculated for Chemical Formula: $C_{40}H_{65}N_9O_{13}S$, Exact Mass: 911.44, MS(ESI): found: [M+H]$^+$, 912.4; (0.3 g, 0.33 mmol)] in DMF (10 mL) was slowly added to a stirred solution of DPPA (0.66 mmol, 0.15 mL) and DIPEA (0.66 mmol, 0.12 mL) in DMF (140 mL). The solvent was concentrated under reduced pressure and the residue purified by silica gel chromatography to give 100 mg of the fully protected cycloamide. This product (56 mg, 0.063 mmol) was dissolved in water (2 mL) and THF (2 mL) and then 2 mL of MeOH. LiOH (5 mg, 0.21 mmol) was added and the reaction stirred for 1 hour. 2 drops of 3N HCl was added and the reaction was then concentrated in vacuo to give 52 mg of Boc/Pbf-protected acid. This product (52 mg, 0.059 mmol) was dissolved in 5 mL of DMF, placed under a nitrogen atmosphere and cooled to with an ice-bath. To this stirred solution was added HATU (27 mg, 0.071 mmol), DIPEA (0.36 mmol, 0.063 mL), and then a solution of H-Arg(Mtr)-kt-HCl salt (29 mg, 0.06 mmol) in DMF. The reaction was allowed to come to room temperature and then stirred overnight. The reaction was added to water and the precipitate filtered to give the product as a mixture of two peaks by LCMS (51 mg crude). The solid was dissolved in 5 mL of TFA/water/thioanisole (95:2.5:2.5) and stirred for 6 hours. The solvent was removed under reduced pressure and the residue was purified by C18 reverse phase HPLC (5-95% Acetonitrile/water/0.05% TFA). After lyopholization of fractions, the title compound (12 mg) was obtained as a 3:1 ratio of D and L diastereomers (mixture of R and S isomers of the alpha keto carbon). Calculated for Chemical Formula: $C_{30}H_{50}N_{14}O_7S$, Exact Mass: 750.37, MS(ESI): found: [M+H]$^+$, 751.4.

Scheme 3E

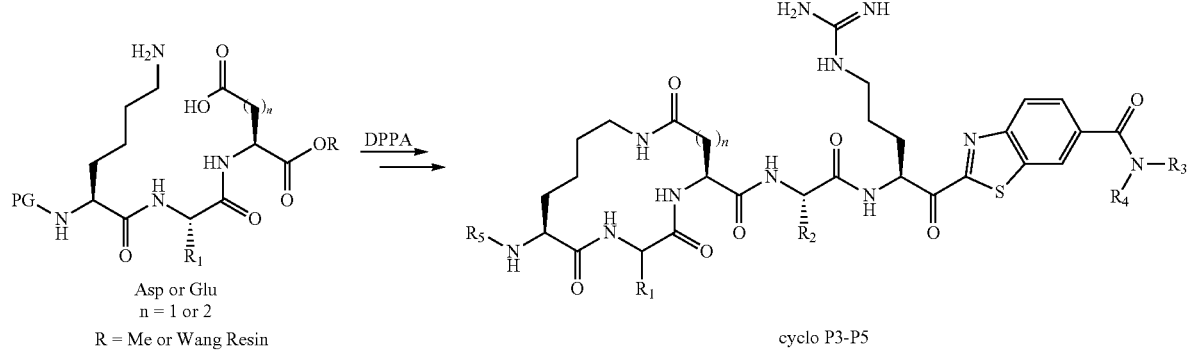

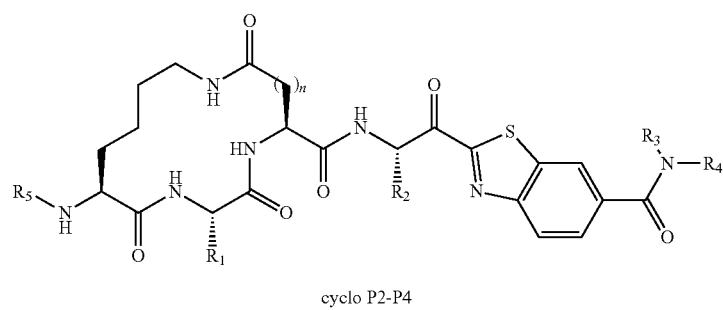

cyclo P2-P4

Scheme 3F
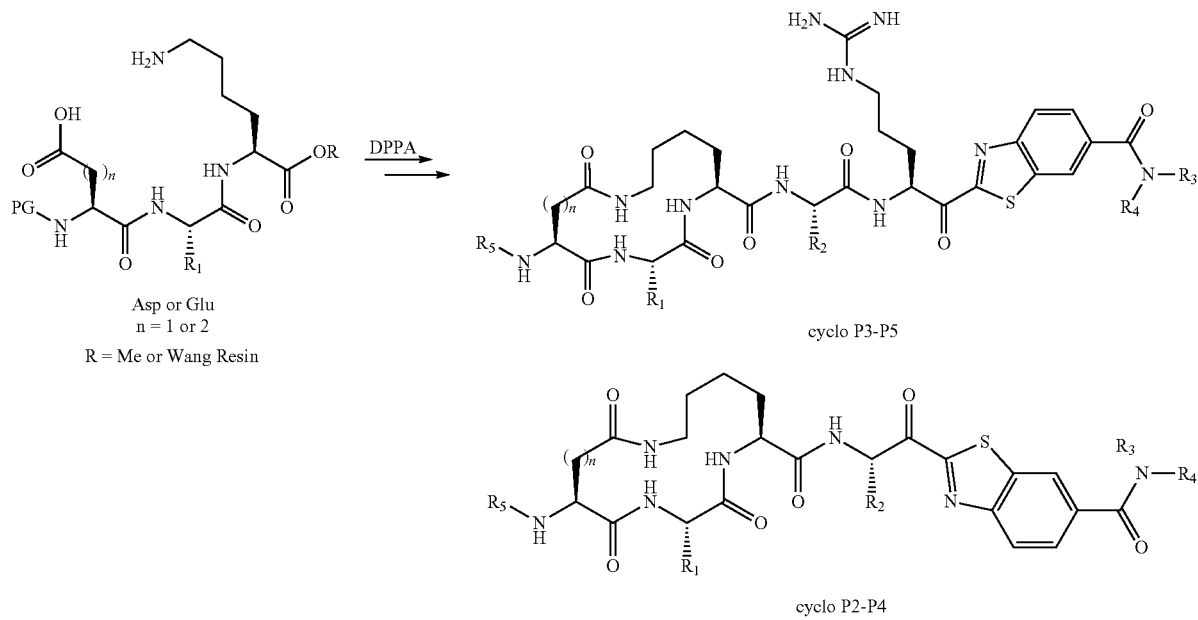
Scheme 3G
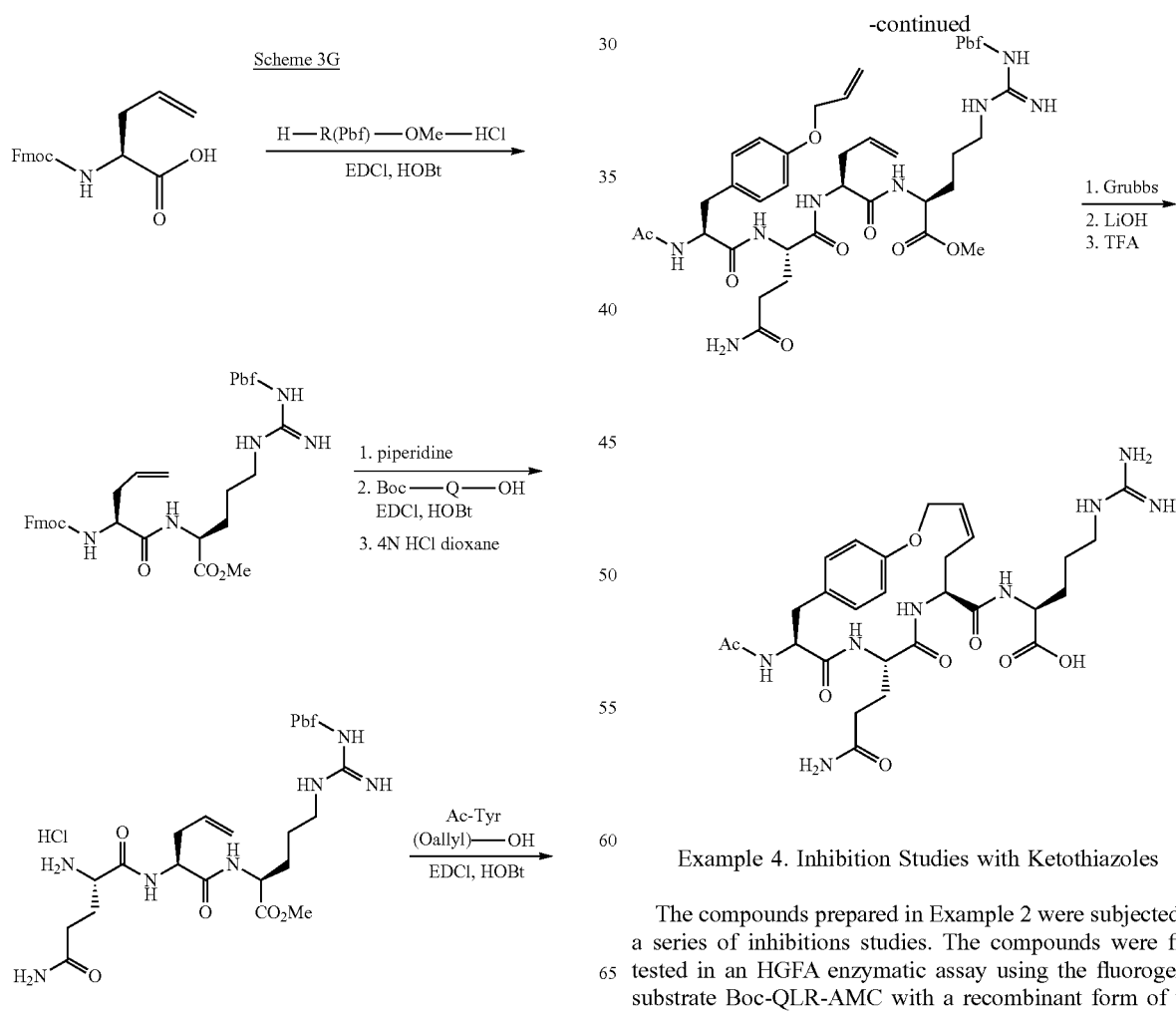
Example 4. Inhibition Studies with Ketothiazoles
The compounds prepared in Example 2 were subjected to a series of inhibitions studies. The compounds were first tested in an HGFA enzymatic assay using the fluorogenic substrate Boc-QLR-AMC with a recombinant form of the HGFA serine protease domain.

Synthesis of Boc-QLR-AMC Fluorogenic Substrate

Boc-R(NO$_2$)-AMC

Under nitrogen atmosphere, pyridine (60 mL) was added into the round bottom flask containing Boc-R(NO$_2$)—OH (4.653 g, 14.6 mmol) and 7-amino-4-methylcoumarin (3.829 g, 21.9 mmol). Diisopropylcarbodiimide (2.023 g, 16.0 mmol) was added and the mixture was stirred overnight. The mixture was filtered. The filtrate was concentrated then dried in vacuo. The resultant residue was purified by silica gel chromatography with dichloromethane/methanol combinations as eluent giving rise to Boc-R(NO$_2$)-AMC (2.964 g) in 43% yield. MS (ESI): found [M+H]$^+$, 477.4.

HCl.H$_2$N—R(NO$_2$)-AMC.

4 N HCl in dioxane (25 mL) was added into the round bottom flask containing Boc-R(NO$_2$)-AMC (2.964 g, 6.2 mmol) and the mixture stirred for 2 hours. The dioxane was removed in vacuo and to the resultant residue methanol was added then concentrated in vacuo three times, giving rise to the title compound in quantitative yield. MS (ESI): found [M+H]$^+$, 377.3.

Boc-QL-OH.

Under nitrogen atmosphere, anhydrous DMF (10 mL) was added into the round bottom flask containing Boc-Q-OH (0.500 g, 2.0 mmol), H-L-OMe HCl (0.406 g, 2.2 mmol), EDCI.HCl (0.467 g, 2.4 mmol), and HOBt (0.466 g, 3.1 mmol). N,N-diisopropylethylamine (0.787 g, 6.1 mmol) was added and the mixture was stirred overnight. The majority of DMF was removed in vacuo and to the resulting residue was added 20 mL of water. The precipitate was isolated by filtration then purified by silica gel chromatography with dichloromethane/methanol combinations as eluent to give Boc-QL-OMe (0.711 g) in 95% yield. MS (ESI): found [M+Na]$^+$, 396.4. Methanol/water (1:1 v/v, 10 mL) was added into the round bottom flask containing the Boc-QL-OMe (0.711 g, mmol) and LiOH (0.068 g, 2.8 mmol). The reaction was stirred overnight. The mixture was concentrated in vacuo and to the resulting residue was added 30 mL of water. 0.5 M HCl was added dropwise until pH=4.5 was reached, then the mixture was extracted three times with ethyl acetate. The ethyl acetate layers were collected, dried with Na$_2$SO$_4$, then concentrated in vacuo to give rise to Boc-QL-OH (0.603 g) in 49% yield. MS (ESI): found [M+Na]$^+$, 373.4.

Boc-QLR(NO$_2$)-AMC.

Under nitrogen atmosphere, anhydrous DMF (10 mL) was added into the round bottom flask containing Boc-QL-OH (0.603 g, 1.7 mmol), HCl.H$_2$N—R(NO$_2$)-AMC (0.406 g, 2.2 mmol), EDCI.HCl (0.322 g, 1.7 mmol), and HOBt (0.257 g, 1.7 mmol). N,N-diisopropylethylamine (0.904 g, 7.0 mmol) was added and the mixture was stirred overnight. The majority of DMF was removed in vacuo and to the resulting residue was added 20 mL of water. The mixture was extracted three times with ethyl acetate. The ethyl acetate layers were collected, dried with Na$_2$SO$_4$, then concentrated in vacuo. The resultant residue was purified by silica gel chromatography with dichloromethane/methanol combinations as eluent giving rise to Boc-QLR(NO$_2$)-AMC (0.250 g) in 20% yield. MS (ESI): found [M+H]$^+$, 718.5.

Boc-QLR-AMC.

Into the solution of Boc-QLR(NO$_2$)-AMC (0.250 g, 0.35 mmol) in MeOH (15 mL) was added Pd/C (10%) (0.111 g) followed by several drops of acetic acid. The mixture was stirred under hydrogen atmosphere for 21 hours. Additional Pd/C (10%) (0.184 g) was added with a few drops of acetic acid. The mixture stirred for 24 hours, then filtered. The filtrate was concentrated. 1/5 of the resulting residue was purified by HPLC (C18, 15*150 mm column; eluent: acetonitrile/water (0.05% TFA)) to give the title compound (0.037 g) in 78% yield. $^1$H NMR (400 MHz, METHANOL-d$_4$) δ ppm 0.92 (d, J=6.30 Hz, 3H) 0.98 (d, J=6.26 Hz, 3H) 1.45 (s, 9H) 1.54-2.14 (m, 9H) 2.25-2.41 (m, 2H) 2.49 (s, 3H) 3.17-3.29 (m, 2H) 4.00-4.14 (m, 1H) 4.34-4.47 (m, 1H) 4.49-4.61 (m, 1H) 6.28 (s, 1H) 7.46-7.60 (m, 1H) 7.71-7.80 (m, 1H) 7.80-7.89 (m, 1H). MS (ESI): found: [M+H]$^+$, 673.6.

Expression and Purification of N-Terminal His-Tag HGFA Serine Protease Domain:

Using primers identified as SEQ ID NO 1, SEQ ID NO 2, and standard PCR protocols, the nucleotide sequence encoding amino acids 373-655 of HGFA was synthesized. This PCR product was cloned into the SfoI-HindIII sites of a modified pFastBac HT baculovirus expression vector (Addgene, Cambridge, Mass.). This vector contains a six amino His tag followed by a seven amino spacer and a seven amino acid TEV cleavage site placed immediately downstream of the Honey Bee melittin signal peptide. Using a modified Bac to Bac Expression System (Life Technologies, Carlsbad, Calif.), recombinant HGFA bacmids were obtained by transforming DH10Bac *Escherichia coli* cells. To obtain HGFA containing baculovirus, purified bacmids were transfected into Sf9 insect cells. After 5 days in culture at 27° C., media was harvested from transfected Sf9 cells. This media was used to prepare baculovirus infected insect cells (BIICs). These BIICs were used to infect High 5 insect cells. Four days post infection, media was harvested and recombinant protein prepared as follows. Media was chilled to 4° C. and spun at 4000×g for 20 minutes (all subsequent steps were performed at 4° C. unless noted). Clarified media was passed first through a Whatman GF/B 1 um (#1821-047, GE Healthcare Life Sciences, Piscataway, N.J.) and then a 0.22 um PES membrane (#99955, TPP Techno Plastic Products AG, Trasadingen, Switzerland) and then concentrated using a Pall Centramate tangential flow system and Centramate T-series Cassette (#OS010T12, Pall Corporation, Port Washington, N.Y.). Concentrated media was then buffer exchanged in two steps, five volumes of 50 mM Na-phosphate, 500 mM NaCl, pH 6.2, followed by five volumes of 50 mM Na-phosphate, 500 mM NaCl, pH 7.5. The concentrated and buffered exchanged insect cell media was again filtered as above and made 25 mM imidazole (#1202, Sigma-Aldrich, St. Louis, Mo.) and was mixed with nickel agarose beads (#H-321-25, Gold Biotechnology, Inc., St. Louis Mo.). After mixing this slurry for 12 hours, nickel agarose beads were allowed to settle by gravity and then loaded into a column. Beads were washed with buffer (25 mM Na-phosphate, 500 mM NaCl, 25 mM imidazole, pH 8) and the bound protein eluted using (25 mM Na-phosphate, 500 mM NaCl, 250 mM imidazole, pH 8). Using a Amicon Ultra-4 Centrifugal filters (#UFC801008, Merck Millipore, Ltd., Tullagreen, Ireland), peak protein fractions were concentrated and run over a Superdex-200 10/300 GL column (GE Healthcare Life Sciences, Piscataway, N.J.) in 10 mM Tris, 200 mM NaCl, 0.2 mM EDTA, pH 8. HGFA containing fractions were pooled, concentrated, made 50% glycerol, and stored at minus 20° C. Protein was quantitated using a modified Lowry protein assay (#500-0006, Bio-Rad Laboratories, Hercules, Calif.).

Chromogenic Kinetic Enzyme Inhibitor Assays of HGFA:

The inhibitors (0-50 μM final concentration in reaction) were diluted in DMSO (2% DMSO final concentration in reaction) and then mixed with recombinant HGFA (12.5 nM final concentration in reaction) in TNC buffer (25 mM Tris, 150 mM NaCl, 5 mM CaCl$_2$, 0.01% TRITON X-100, pH 8).

After incubating for thirty minutes at 25° C., chromogenic substrate, Pefachrome FVIIa, (#093-01, Enzyme Research Laboratories, South Bend, Ind.)) was added to a final concentration of 250 µM in a final reaction volume of 40 microliters. Changes in absorbance at 405 nm were measured over time in a Biotek Synergy 2 plate reader (Winnoski, Vt.). Using Gen 5 2.00 software program (Biotek, Winnoski, Vt.), a four parameter curve fit was used to determine the inhibitor $IC_{50}$s from a plot of the mean reaction velocity versus the inhibitor concentration. The $IC_{50}$ values represent the average of three separate experimental determinations.

Chromogenic Kinetic Enzyme Assays of Thrombin and Factor Xa:

Inhibitors (11-pt serial dilutions, 0-20 µM final concentration) were serially diluted in DMSO (2% DMSO final concentration) and then mixed with recombinant thrombin (0.15 nM final concentration) or Factor Xa (0.35 nM final concentration) in TNC buffer (25 mM Tris, 150 mM NaCl, 5 mM $CaCl_2$, 0.01% TRITON X-100, pH 8) using clear 384 well plates. After incubating for 30 minutes at 25° C., the chromogenic substrate (S2238; D-Phe-Pip-Arg-pNA) for thrombin ($K_m$=14.5 µM) or (S2222; Bz-Ile-Glu-Gly-Arg-pNA) for Factor Xa ($K_m$=200 M) was added to a final concentration of $K_m$ (4×$K_m$ (50 µM) for thrombin) in a final reaction volume of 40 microliters. Changes in absorbance at 405 nm were measured over time in a Biotek Synergy 2 plate (Winnoski, Vt.). Using GraphPad Prism version 6.04 software program, (GraphPad Software, San Diego, Calif., www.graphpad.com), a four parameter curve fit was used to determine the inhibitor $IC_{50}$s from a plot of the mean reaction velocity versus the inhibitor concentration. $K_i$ values were calculated from the $IC_{50}$ values using the Cheng and Prusoff equation ($K_i$=$IC_{50}$/(1+[S]/$K_m$)).

TABLE 4.1

| Structure | HGFA $IC_{50}$ (µM) | Matriptase $IC_{50}$ (µM) | Hepsin $IC_{50}$ (µM) | Thrombin Ki (nM) | Factor Xa Ki (nM) |
|---|---|---|---|---|---|
| Nafamostat | 0.80 | 0.001 | 0.002 | | |
| Leupeptin (Ac-LLR-H | 0.535 | 1.150 | 0.256 | | |
| Ac-KQLR(SEQ ID NO: 1)-kt (5) | 0.445 | 0.005 | 0.002 | >20000 | 170 |
| Ac-KQLdR-kt (5-1) | 5.526 | — | — | — | — |
| Ac-KHLR(SEQ ID NO: 2)-kt (5a) | 0.650 | — | — | — | — |
| Ac-KHLdR-kt (5a-1) | 10.931 | — | — | — | — |
| Ac-WQLR(SEQ ID NO: 3)-kt (5b) | 0.471 | 0.049 | 0.001 | — | — |
| Ac-WQLdR-kt (5b-1) | 7.123 | — | — | — | — |
| Ac-KQFR(SEQ ID NO: 4)-kt (5c) | 0.470 | — | — | >20000 | 78.8 |
| Ac-KQFdR-kt (5c-1) | 7.824 | — | — | — | — |
| Ac-KFLR(SEQ ID NO: 5)-kt (5d) | 0.330 | 0.035 | 0.022 | — | — |
| Ac-RQLR(SEQ ID NO: 6)-kt (5e) | 0.270 | 0.001 | 0.001 | >20000 | 8.10 |
| Ac-RQLdR-kt (5e-1) | 3.118 | — | — | — | — |
| Ac-SQLR(SEQ ID NO: 7)-kt (5f) | 0.180 | — | — | — | — |
| Ac-KRLR(SEQ ID NO: 8)-kt (5g) | 0.225 | 0.014 | 0.005 | — | — |
| Ac-WRLR(SEQ ID NO: 9)-kt (5h) | 0.275 | 0.031 | 0.0003 | — | — |
| Ac-SKLR(SEQ ID NO: 10)-kt (6) | 0.56 | 0.048 | 0.00 | >20000 | 3062 |
| Ac-SKLdR-kt (6-1) | 6.311 | — | — | — | — |
| Ac-SHLR(SEQ ID NO: 11)-kt (6a) | 1.800 | 0.560 | 0.005 | — | — |
| Ac-SHLdR-kt (6a-1) | 21.218 | — | — | — | — |
| Ac-WKLR(SEQ ID NO: 12)-kt (6b) | 0.320 | 0.097 | 0.004 | — | — |
| Ac-WKLdR-kt (6b-1) | 6.500 | — | — | — | — |
| Ac-SKFR(SEQ ID NO: 13)-kt (6c) | 0.520 | 0.034 | 0.051 | >2000 | 530.00 |
| Ac-SKFdR-kt (6c-1) | 10.795 | — | — | — | — |
| Ac-NKLR(SEQ ID NO: 14)-kt (6d) | 0.397 | — | — | — | — |
| Ac-SRLR(SEQ ID NO: 15)-kt (6e) | 0.303 | 0.024 | 0.005 | — | — |
| Ac-SdRLR-kt (6e-1) | 1.420 | — | — | — | — |
| Ac-SRLdR-kt (6e-2) | 2.241 | — | — | — | — |
| Ac-SdRLdR-kt (6e-3) | 11.920 | — | — | — | — |
| Ac-TKLR(SEQ ID NO: 16)-kt (6f) | 0.567 | — | — | — | — |
| Ac-SWLR(SEQ ID NO: 17)-kt (6g) | 0.435 | 0.175 | 0.009 | 3698 | 759 |
| Ac-RKLR(SEQ ID NO: 18)-kt (6h) | 0.370 | — | — | — | — |
| Ac-NKLR(SEQ ID NO: 14)-kt | 0.4 | — | — | — | — |

TABLE 4.1-continued

| Structure | HGFA IC$_{50}$ (µM) | Matriptase IC$_{50}$ (µM) | Hepsin IC$_{50}$ (µM) | Thrombin Ki (nM) | Factor Xa Ki (nM) |
|---|---|---|---|---|---|
| H-KQLdR-kt | 11.31 | — | — | — | — |
| H-KQLR(SEQ ID NO: 1)-Kt | 0.44 | — | — | — | — |
| Ac-LLR-kt | 1.48 | | | | |

HGFA Competition Assay of Inhibitor Ac-KQLR (SEQ ID NO: 1)-Kt (5) and Substrate:

To determine whether the ketothiazoles are behaving as competitive inhibitors, different amounts of Ac-KQLR (SEQ ID NO: 1)-Kt (5) (0, 0.25, 0.5, and 1.0 µM) were mixed with Pefachrome serially diluted in TNC buffer. HGFA was added to 12.5 nM and changes in absorbance at 405 nm were measured over time in a Biotek Synergy 2 plate reader. From the plots of the mean reaction velocity versus substrate concentration and the Michaelis-Menten enzyme kinetics equation within GraphPad Prism version 6.04 for Windows, the reaction $V_{max}$ and subsequent $K_m$ for each concentration of inhibitor was determined as shown in the FIG. 1.

Fluorescent Kinetic Enzyme Inhibitor Assays of HGFA, Matriptase Hepsin, and Thrombin:

Inhibitors (11-pt serial dilutions, 0-20 µM final concentration in reaction) were serially diluted in DMSO (2% DMSO final concentration) and then mixed with either recombinant serine protease domain of HGFA [Z. Han, P. K. Harris, D. E. Jones, R. Chugani, T. Kim, M. Agarwal, W. Shen, S. A. Wildman, J. W. Janetka, Acs Med Chem Lett 2014, 5, 1219-1224], matriptase (Charles Craik, UCSF) or hepsin* (#4776-SE-010, R&D Systems, Minneapolis, Minn.) in black 384 well plates (Corning #3575. Corning, N.Y.). The final assay concentration for HGFA, matriptase and hepsin 7.5 nM, 0.2 nM, and 0.3 nM, respectively in TNC buffer (25 mM Tris, 150 mM NaCl, 5 mM CaCl$_2$, 0.01% TRITON X-100, pH 8). After thirty minutes incubation at room temperature, Boc-QLR-AMC substrate ($K_m$=37 µM) was added to the HGFA assays and Boc-QAR-AMC substrate was added to the matriptase ($K_m$=93 µM) and hepsin ($K_m$=156 µM) assays. The final substrate concentrations for all assays were at the $K_m$ for the respective enzymes. Changes in fluorescence (excitation at 380 nm and emission at 460 nm) were measured at room temperature over time in a Biotek Synergy 2 plate reader (Winnoski, Vt.). Using GraphPad Prism version 6.04 software program, (GraphPad Software, San Diego, Calif., www.graphpad.com), a four parameter curve fit was used to determine the inhibitor IC$_{50}$s from a plot of the mean reaction velocity versus the inhibitor concentration. The IC$_{50}$ values represent the average of three separate experimental determinations. K$_i$ values were calculated using the Cheng and Prusoff equation (K$_i$=IC$_{50}$/(1+[S]/K$_m$).

Hepsin Activation: Recombinant Hepsin (10 µg, 0.44 mg/mL as received from R&D Systems, Catalogue #4776-SE) was diluted to 2.4 µM in TNC buffer (25 mM Tris, 150 mM NaCl, 5 mM CaCl$_2$, 0.01% TRITON X-100, pH 8) and incubated at 37° C. After twenty-four hours, the hepsin was diluted in glycerol to 50%. This stock hepsin (1.2 µM) was stored in a –20° C. freezer and diluted in TNC buffer for use in assays.

As shown in the following table, the pro-HGF and pro-MSP tetrapeptides 5 and 6 showed K$_i$s of 53 nM and 81 nM, respectively. These results demonstrate that inhibitor 5 was competitive with substrate to the active-site. The majority of compounds evaluated are more selective for matriptase and hepsin; most pronounced with hepsin where some inhibitors having K$_i$s<1 nM. There are several compounds which are equipotent for HGFA compared to matriptase but leupeptin is 3-fold selective for HGFA over matriptase and only 3-fold favoring hepsin. The pro-HGF peptide (5) is 200-fold more potent for hepsin and 50-fold for matriptase while the pro-MSP peptide (6) is only slightly more potent for matriptase and 70-fold potent for hepsin versus HGFA. Ac-SWLR (SEQ ID NO: 17)-Kt (6g) is equipotent for both HGFA and matriptase with a K$_i$=66 nM but K$_i$=1.2 nM for hepsin. 6g, Ac-SKFR (SEQ ID NO: 13)-Kt (6c), Ac-KFLR (SEQ ID NO: 5)-Kt (5d) and Ac-SRLR (SEQ ID NO: 15)-Kt (6e) show HGFA selectivity over both hepsin and matriptase.

TABLE 4.2

| Structure | HGFA K$_i$ (nM) | Matriptase K$_i$ (nM) | Hepsin K$_i$ (nM) |
|---|---|---|---|
| Nafamostat | 25 | 0.02 | 0.53 |
| Leupeptin (Ac-LLR-H) | 188 | 696 | 61 |
| Ac-KQLR(SEQ ID NO: 1)-kt (5) | 70 | 1.60 | 0.19 |
| Ac-KQLdR-kt (5-1) | — | — | — |
| Ac-KHLR(SEQ ID NO: 2)-kt (5a) | 96 | 22.3 | 0.41 |
| Ac-KHLdR-kt (5a-1) | — | — | — |
| Ac-WQLR(SEQ ID NO: 3)-kt (5b) | 65 | 32.4 | 0.21 |
| Ac-WQLdR-kt (5b-1) | — | — | — |
| Ac-KQFR(SEQ ID NO: 4)-kt (5c) | 58 | 0.69 | 0.58 |
| Ac-KQFdR-kt (5c-1) | — | — | — |
| Ac-KFLR(SEQ ID NO: 5)-kt (5d) | 80 | 15 | 2.1 |
| Ac-RQLR(SEQ ID NO: 6)-kt (5e) | 60 | 0.32 | 0.28 |
| Ac-RQLdR-kt (5e-1) | — | — | — |
| Ac-SQLR(SEQ ID NO: 7)-kt (5f) | 182 | 9.2 | 0.34 |
| Ac-KRLR(SEQ ID NO: 8)-kt (5g) | 12 | 1.1 | 0.57 |
| Ac-WRLR(SEQ ID NO: 9)-kt (5h) | 21 | 5.5 | 0.21 |
| Ac-SKLR(SEQ ID NO: 10)(SEQ ID NO: 10)-kt (6) | 81 | 58 | 1.2 |
| Ac-SKLdR-kt (6-1) | — | — | — |
| Ac-SHLR(SEQ ID NO: 11)-kt (6a) | 332 | 104.2 | 0.60 |
| Ac-SHLdR-kt (6a-1) | — | — | — |
| Ac-WKLR(SEQ ID NO: 12)-kt (6b) | 56 | 8.6 | 0.55 |
| Ac-WKLdR-kt (6b-1) | — | — | — |
| Ac-SKFR(SEQ ID NO: 13)-kt (6c) | 57 | 3.03 | 8.5 |
| Ac-SKFdR-kt (6c-1) | — | — | — |
| Ac-NKLR(SEQ ID NO: 14)-kt (6d) | 79 | 12 | 1.4 |
| Ac-SRLR(SEQ ID NO: 15)-kt (6e) | 24 | 5.8 | 0.68 |
| Ac-SdRLR-kt (6e-2) | — | — | — |
| Ac-SRLdR-kt (6e-1) | — | — | — |
| Ac-SdRLdR-kt (6e-3) | — | — | — |
| Ac-TKLR(SEQ ID NO: 16)-kt (6f) | 103 | 8.7 | 0.61 |
| Ac-SWLR(SEQ ID NO: 17)-kt (6g) | 63 | 69 | 1.2 |
| Ac-RKLR(SEQ ID NO: 18)-kt (6h) | 17 | 0.83 | 0.47 |
| Ac-NKLR(SEQ ID NO: 14)-kt | 79 | 12.4 | 1.41 |
| Ac-LLR-kt | 253.00 | 27.950 | 2.288 |

Figure 2:
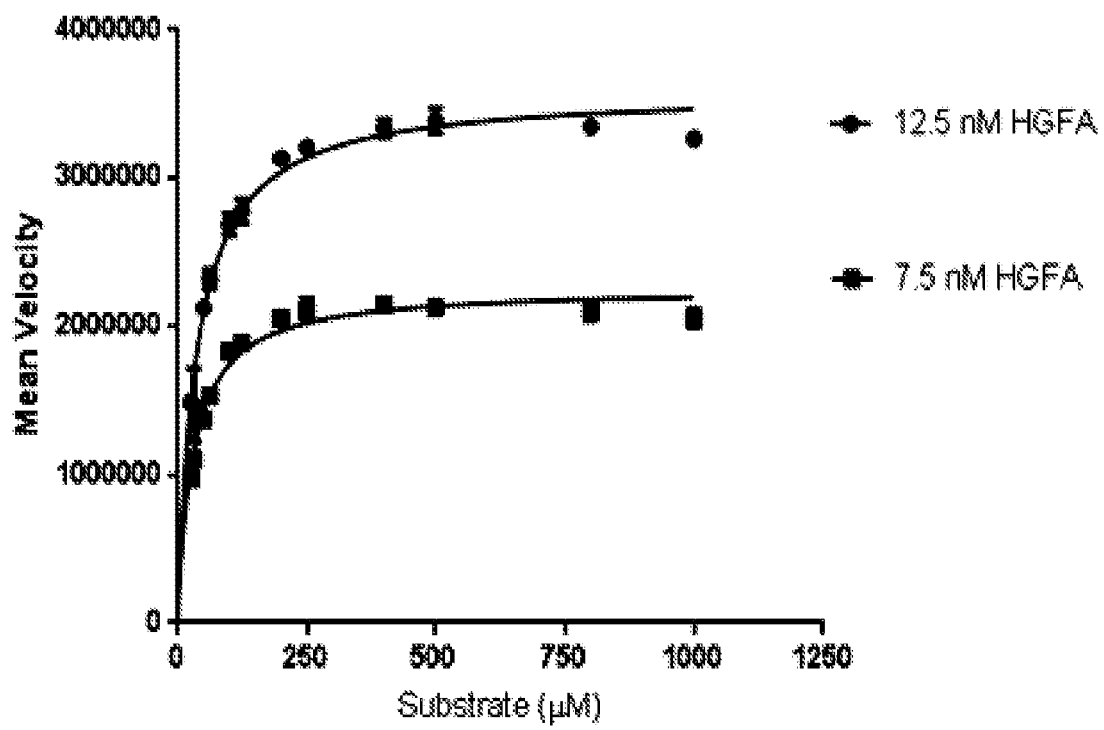
FIG. 2 presents a plot of the results for the fluorescent inhibitor assay for inhibitor Boc-QLR-AMC and HGFA.
Figure 3:
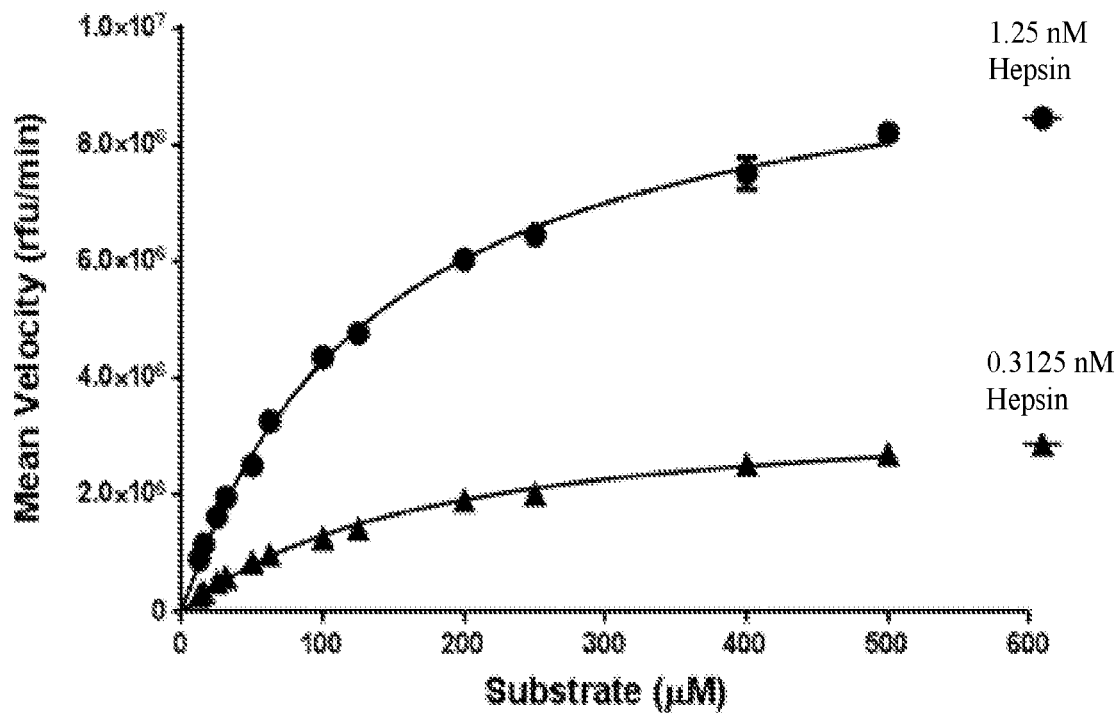
FIG. 3 presents a plot of the results for the fluorescent inhibitor assay for inhibitor Boc-QAR-AMC and hepsin.
Figure 4:
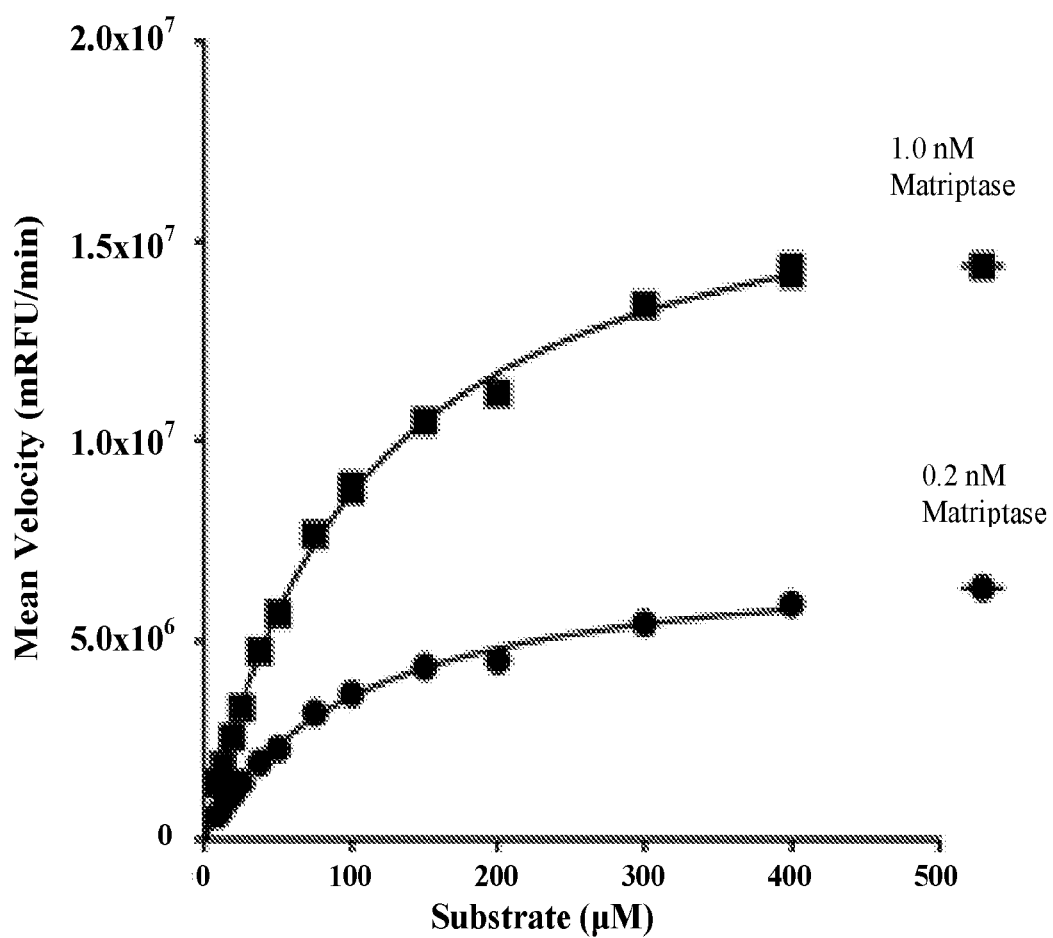
FIG. 4 presents a plot of the results for the fluorescent inhibitor assay for inhibitor Boc-QAR-AMC and matriptase.

— Not measured.
K$_m$ Determinations:

In black 384 well plates (Corning #3575), 12.5 nM HGFA was mixed with various amounts of Boc-QLR-AMC and 1 nM matriptase and 0.3 nM hepsin were mixed with various amounts of Boc-QAR-AMC. Changes in fluorescence (excitation at 380 nm and emission at 460 nn) were measured at room temperature over time in a Biotek Synergy 2 plate reader (Winnoski, Vt.). Using plots of the mean reaction velocity versus substrate concentration and the Michaelis- Menten enzyme kinetics equation within GraphPad Prism version 6.04 for Windows (GraphPad Software, San Diego, Calif., www.graphpad.com), the reaction $V_{max}$ and subsequent $K_m$ for each of the substrates were determined. The plots are presented in FIGS. 2-4.

Figure 5:
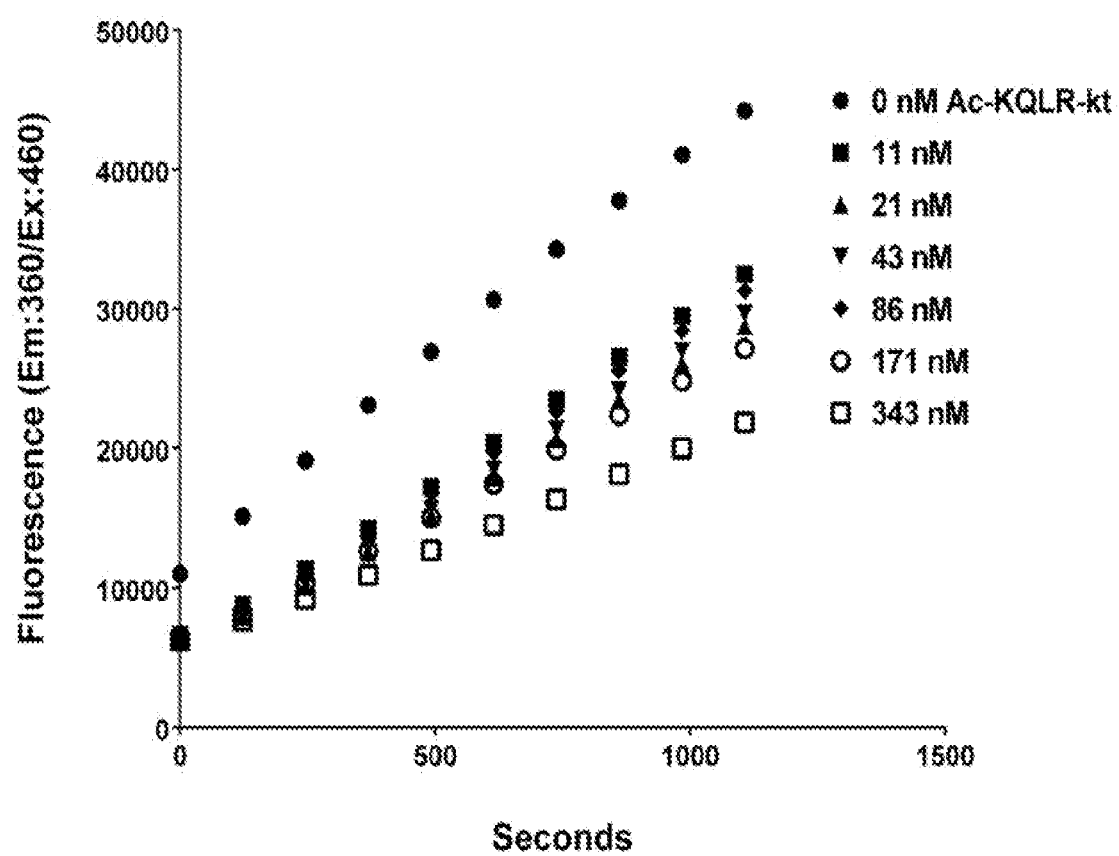
FIG. 5 presents a plot of the results of a dilution recovery experiments with Ac-KQLR (SEQ ID NO: 1)-Kt and HGFA.
Figure 6:
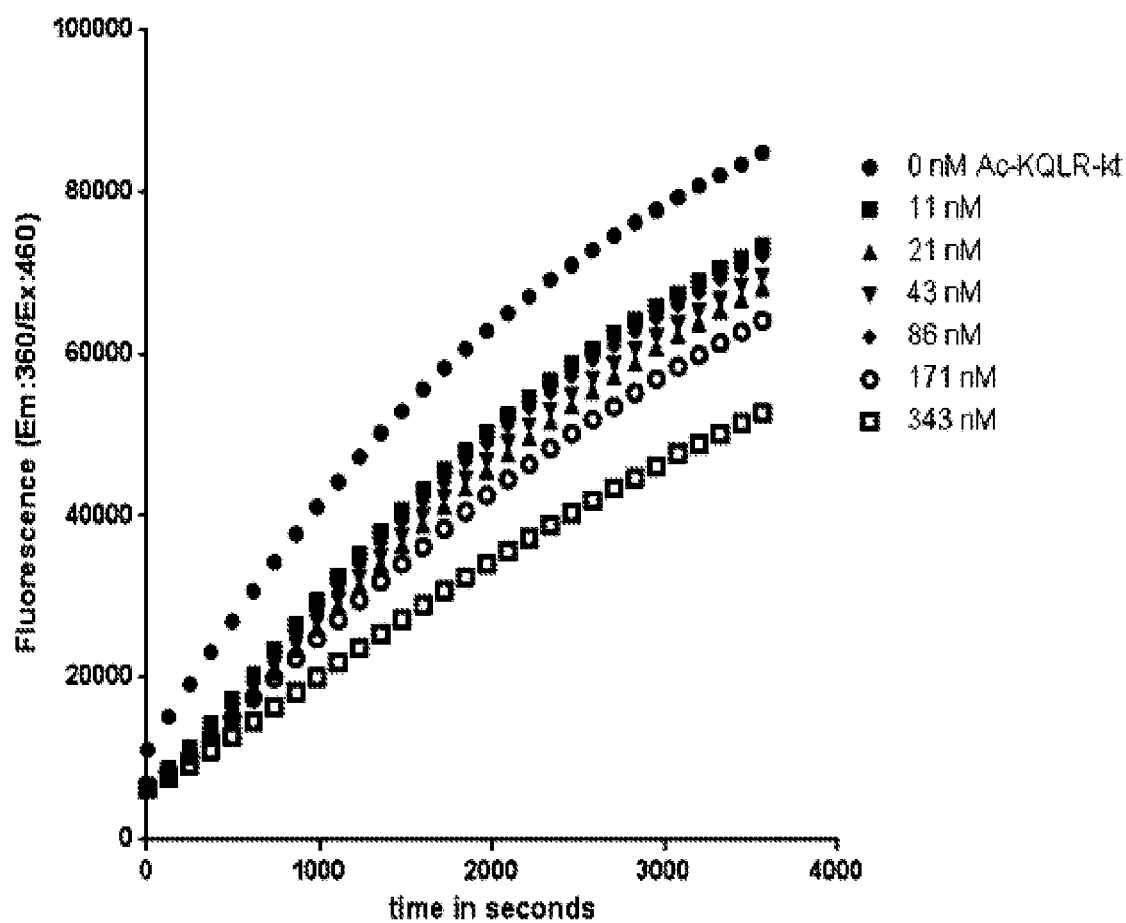
FIG. 6 presents a plot of the results of a dilution recovery experiments with Ac-KQLR (SEQ ID NO: 1)-Kt and HGFA.

Dilution Recovery Experiments with Ac-KQLR (SEQ ID NO: 1)-Kt (5) and HGFA:

To demonstrate reversibility of HGFA ketothiazole inhibitors and to examine the dissociation of the enzyme-inhibitor complex, dilution recovery experiments were performed. High concentration HGFA (7.5 µM) were mixed with different concentrations of Ac-KQLR (SEQ ID NO: 1)-Kt (5), between 0-120 µM. After incubating for 20 minutes at room temperature, these reactions were diluted rapidly (1:350) in TNC buffer containing 250 µM Boc-QLR-AMC substrate (~7 times $K_m$). Activity was monitored by recording the change in fluorescence (excitation at 380 nm and emission at 460 nn) over time in a Biotek Synergy 2 plate reader. GraphPad Prism was used to plot the change in fluorescence over time. The results are provided in FIGS. 5 and 6. These results show that Ac-KQLR (SEQ ID NO: 1)-Kt (5) is a reversible inhibitor of HGFA as the enzyme activity is recovered slowly over time even at an inhibitor concentrations 7× $K_i$.

Biochemical Assay for Proteolysis of Pro-HGF and Pro-MSP by HGFA:

A biochemical assay was employed in order to demonstrate that inhibitors can block the proteolytic activation of the endogenous growth factors, pro-HGF and pro-MSP by HGFA in a dose-dependent manner. In order to determine efficiency of our recombinant HGFA we performed a concentration response of HGFA using a fixed concentration of pro-HGF and pro-MSP. Since both the single chain inactive pro-HGF or pro-MSP and the active heterodimers have the same molecular weight, SDS gels were developed under reducing conditions.

For pro-HGF proteolysis, inhibitors (0-12.5 µM final concentration in reaction) were diluted in DMSO (2% DMSO final concentration in reaction) and then mixed with recombinant HGFA (1.0 nM final concentration) in TNC buffer. After 30 minutes incubation at room temperature (25° C.), 25 ng of pro-HGF (R&D Systems, NKG011306A) was added. After 1 hour incubation at 37° C., reactions were stopped by adding SDS gel loading buffer containing DTT (reducing) and then run on 12% PAGE. Proteins were transferred to Millipore Immobilon-P membranes (Billerica, Mass.) and then immunoblotted at 4° C. with anti-HGF antibody (R&D Systems, AF-294-NA) and HRP conjugated donkey anti-goat IgG (Santa Cruz, SC-2020) diluted 1:500 and 1:5000 in 5% milk/TBST (5% Carnation nonfat dried milk/10 mM Tris, 150 mM NaCl, 0.05% TWEEN 20, pH 8.0), respectively. Membranes were washed in TBST, immersed in Millipore Luminata Crescendo Western-HRP Substrate for 5 minutes, and then exposures made on a BioRad ChemiDoc MP Imaging System (Hercules, Calif.). For pro-MSP proteolysis assays, the procedures were similar, except that the HGFA concentration was 75 nM, pro-MSP (R&D Systems ZN081306A) concentration was 50 ng per reaction, and 1:500 dilution of anti-MSP antibody (R&D Systems, AF352) was used for MSP detection during immunoblotting.

Figure 7:
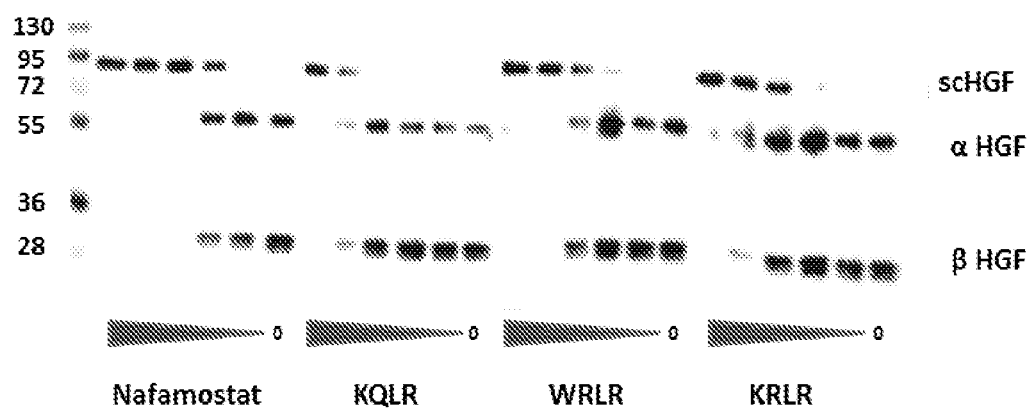
FIG. 7 shows the inhibition of HGFA-mediated scHGF (pro-HGF) cleavage by inhibitors. Immunoblot of scHGF cleavage reactions: Pro-HGF (30 ng) was cleaved with 1 nM HGFA in the presence of inhibitors (5-fold dilutions from 12.5 µM).
Figure 8:
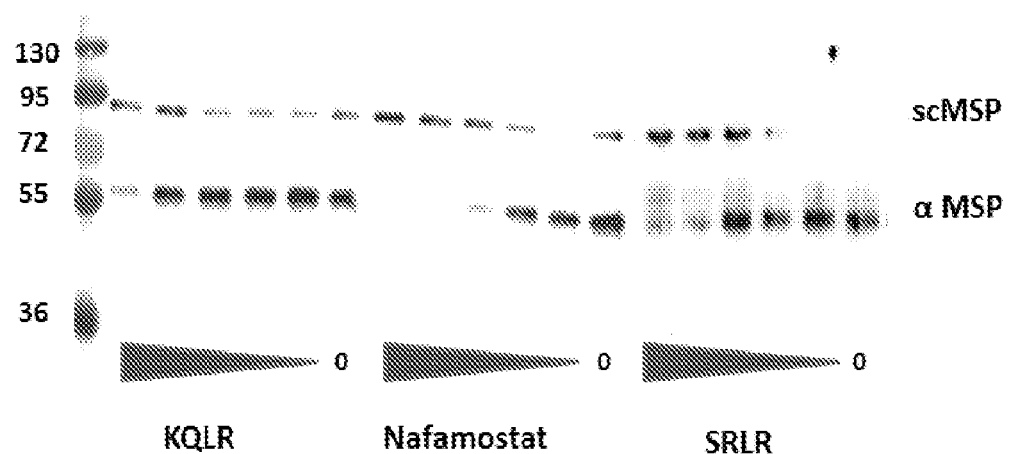
FIG. 8 shows the inhibition of HGFA-mediated scMSP (pro-MSP) cleavage by inhibitors. Immunoblot of scMSP cleavage reactions: Pro-MSP (50 ng) was cleaved with 10 nM HGFA in the presence of inhibitors (5-fold dilutions from 12.5 µM).

The results are shown in FIGS. 7 and 8 below. Lanes with pro-HGF (FIG. 7) and pro-MSP (FIG. 8) contain one band at 90 and 75 KDa, respectively, whereas activated HGF and MSP appear as two bands as the 60 KDa α-chain and 30 KDa β-chain in HGF and 50 KDa and 25 KDa for MSP (note: MSP Ab only recognizes the α-chain). Shown in FIG. 4, we found that nafamostat and the three inhibitors 5, 5h, 5g all showed a dose-dependent inhibition of pro-HGF activation with similar EC50 values in direct correlation with those found from the HGFA enzyme assay. These inhibitors in addition to 6e also all show dose-dependent inhibition of pro-MSP proteolysis by HGFA as shown in FIG. 7. While it is difficult to quantitate the level of MSP activation since the pro-MSP has some active two-chain MSP present, the EC50 values correlate with the level of potency seen in the enzyme assay. These results show the inhibitors inhibit the processing of both known protein substrates of HGFA.

c-MET Phosphorylation (Y1234/1235) in Cells Treated with HGFA Processed Pro-HGF and MSP:

To show the inhibition provided by the tetrapeptide compounds would have effects on cell signaling through c-MET kinase, a phosphorylation assay using the invasive breast cancer cell line, MDA-MB-231 was developed. This cell line has high expression of c-MET and pro-HGFA but not pro-HGF.

MDA-MB-231 cells were maintained in RPMI medium (Sigma-Aldrich R8758, St. Louis, Mo.) containing 10% fetal bovine serum (Sigma F2442) and 1× Penicillin/Streptomycin (Pen/Strep) antibiotics (Thermo Fisher SV30010). For cMet phosphorylation measurements, MDA-MB-231 cells were switched to starve medium (RPMI medium containing 1 mM Sodium Pyruvate (Corning 25-000-ci), 10 mM HEPES (Corning 25-060-ci), 0.225% Glucose (Corning 25-037-ci), IX PenStrep). After 18 hours, cells were switched to fresh starve media and then treated with HGFA Proteolysis reactions containing 1 nM HGFA, 50 ng pro-HGF and various amounts of inhibitors. After 15 minutes incubation, media was removed by aspiration and the remaining cells were washed twice with cold Dulbeccos Phosphate Buffered Saline (Life Technologies #14190-136). Next cells were scraped into in Lysis Buffer (50 mM Tris, 150 mM NaCl, 1 mM EDTA, 1% NP-40, 0.25% Sodium Deoxcholate, pH 7.5) containing 1 mM sodium fluoride, 1 mM sodium orthovanandate, 1× Sigma (P8340) Inhibitor Cocktail, and one Roche Complete Mini, EDTA-free Protease Inhibitor Cocktail tablet per 10 ml buffer and stored frozen. Lysate aliquots were mixed with reducing SDS gel loading buffer and run on 10% PAGE.

Immunoblots were performed as described previously, except primary antibodies, anti-phospho cMet (Cell Signaling, CS3077) and anti-total cMet (Cell Signaling, CS3127) were used and diluted in 5% BSA/TBST. Secondary antibodies, HRP-anti rabbit antibody (CS7074) and HRP-anti mouse (CS7076) were used, respectively. All antibodies were used at a 1:1000 dilution. Images were obtained and quantitated using BioRad ChemiDoc MP Imaging System. cMet phosphorylation signals were normalized using the total cMet signals and % inhibition calculated using the ratio of inhibited versus uninhibited HGFA Proteolytic reactions. Results were plotted in GraphPad Prism and a four parameter curve fit was used to determine the inhibitor $EC_{50}$s.

Figure 9:
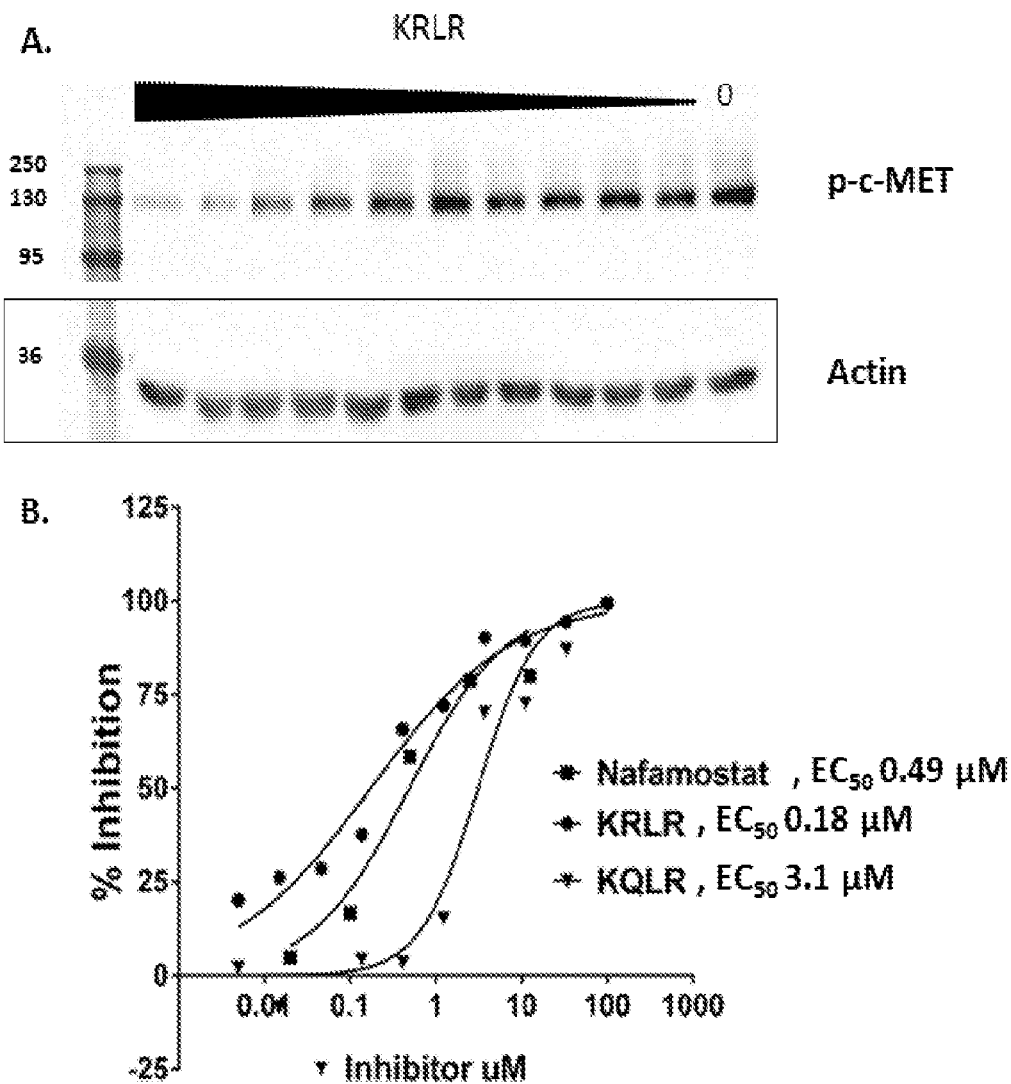
FIG. 9 shows MDA-MB-231 c-MET phosphorylation of cells treated with pro-HGF/HGFA reactions (3-fold dilutions of inhibitors starting at 100 µM). A. Immunoblot of pY1234/135 c-MET; B. % inhibition of c-MET phosphorylation.
Figure 10:
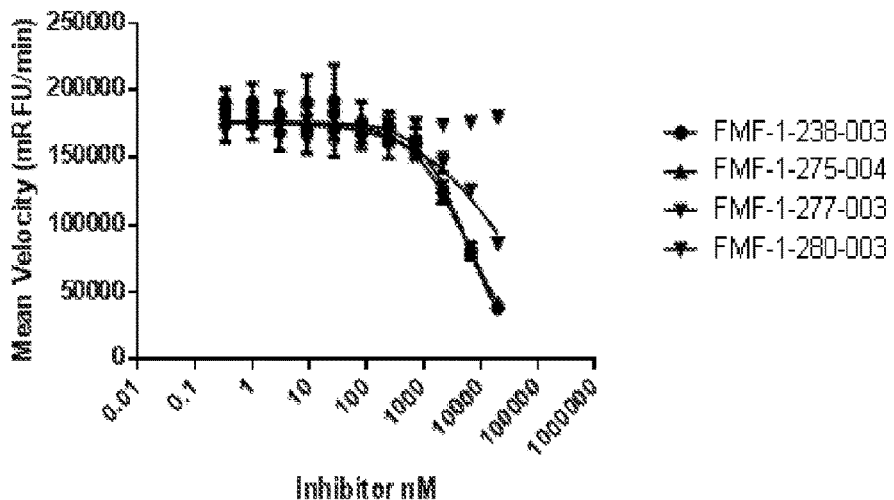
FIG. 10 presents a plot of the results of a chromogenic kinetic enzyme assay for matriptase and selected inhibitor compounds.
Figure 11:
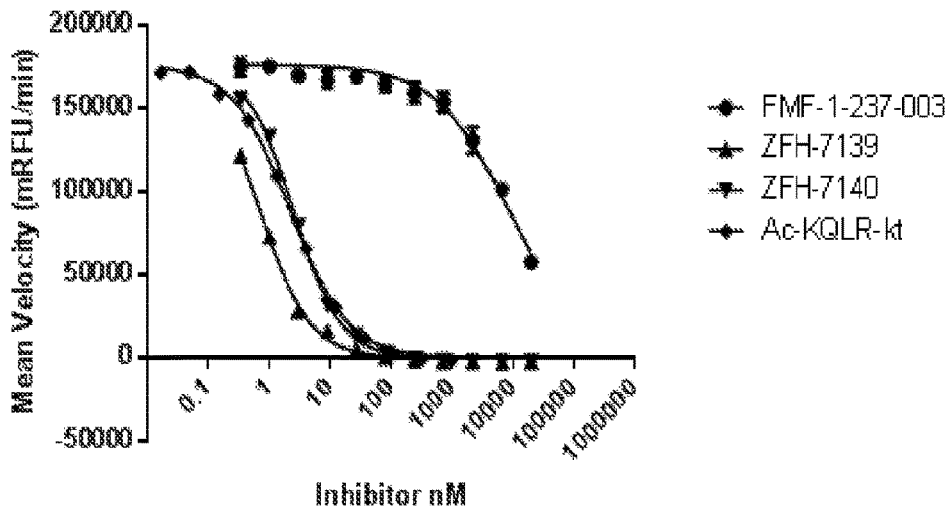
FIG. 11 presents a plot of the results of a chromogenic kinetic enzyme assay for matriptase and selected inhibitor compounds.
Figure 12:
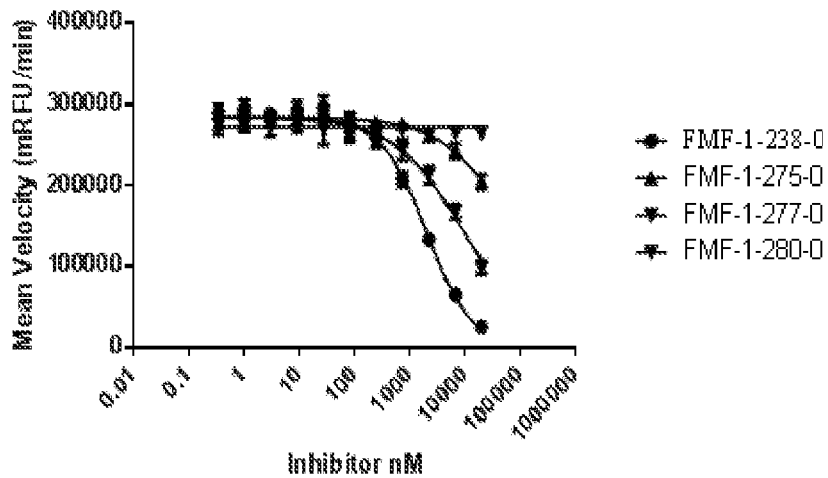
FIG. 12 presents a plot of the results of a chromogenic kinetic enzyme assay for hepsin and selected inhibitor compounds.
Figure 13:
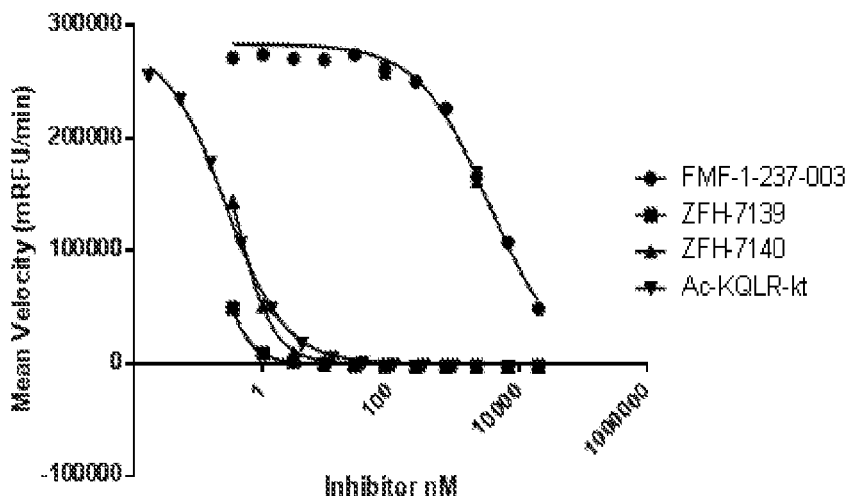
FIG. 13 presents a plot of the results of a chromogenic kinetic enzyme assay for matriptase and selected inhibitor compounds.
Figure 14:
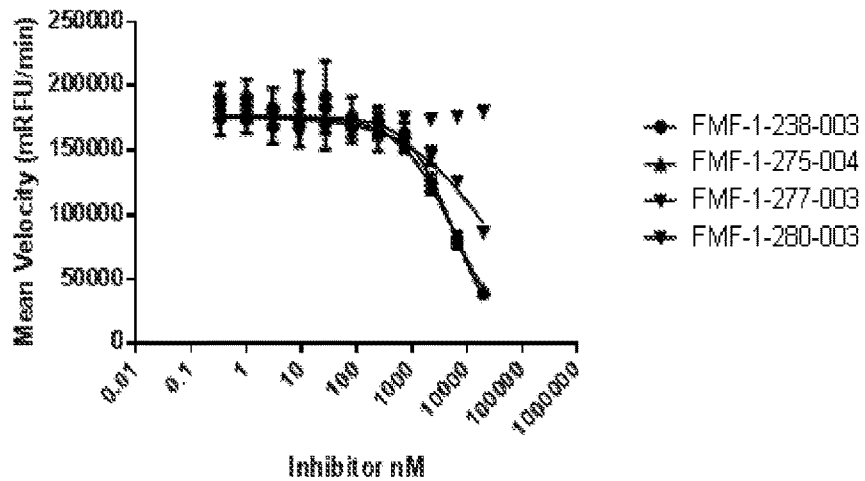
FIG. 14 presents a plot of the results of a chromogenic kinetic enzyme assay for matriptase and selected inhibitor compounds.
Figure 15:
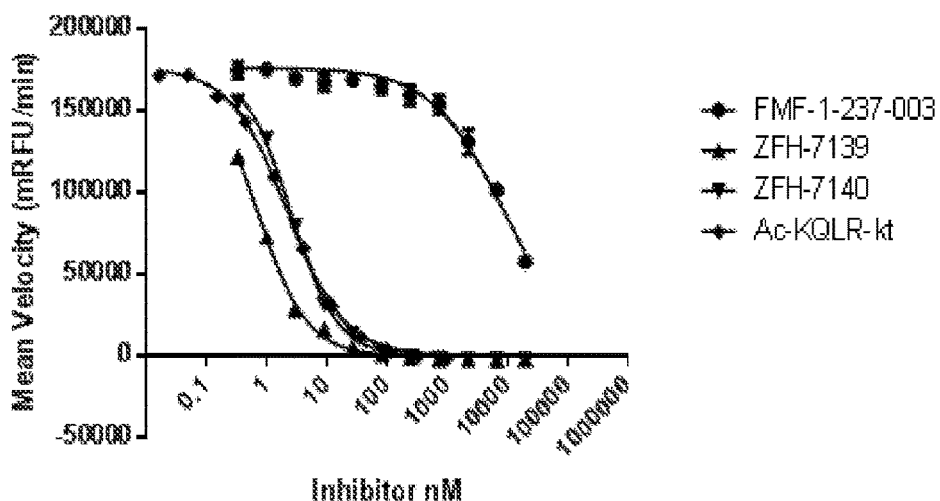
FIG. 15 presents a plot of the results of a chromogenic kinetic enzyme assay for matriptase and selected inhibitor compounds.
Figure 16:
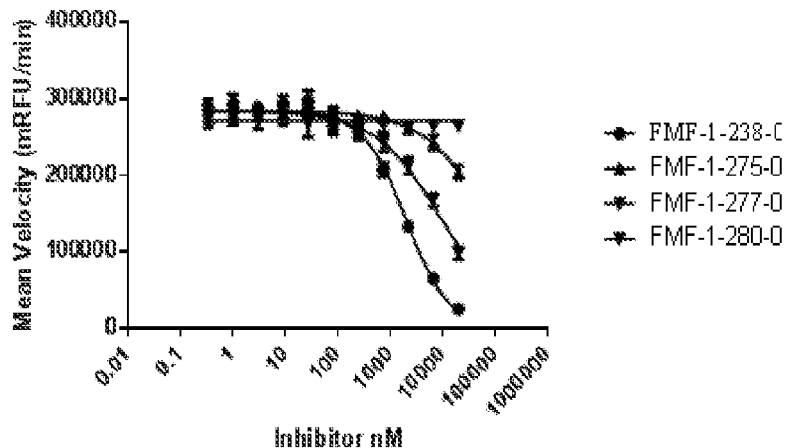
FIG. 16 presents a plot of the results of a chromogenic kinetic enzyme assay for hepsin and selected inhibitor compounds.
Figure 17:
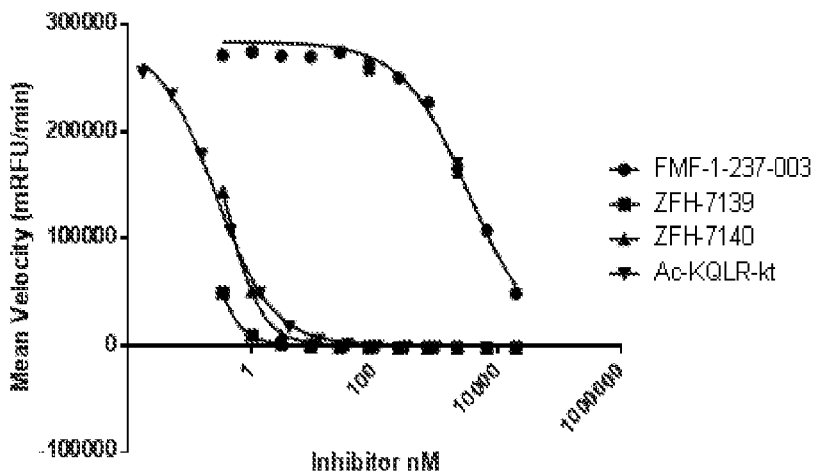
FIG. 17 presents a plot of the results of a chromogenic kinetic enzyme assay for hepsin and selected inhibitor compounds.

As shown in FIG. 9, several inhibitors were effective at decreasing c-MET phosphorylation in a dose-dependent manner. Thus, these results show that these inhibitors of HGFA can function as non-kinase inhibitors of HGF-mediated c-MET kinase signaling in cancer. The most potent compound 5g had an EC50 of 180 nM.

Example 5. Synthesis of Ketobenzothiazole Inhibitor Compounds

The polypeptide ketobenzothiazoles (kbt) listed in Table 5.1 were synthesized in accordance with the general scheme 5A shown below and the procedures described below.

TABLE 5.1

Polypeptide Compounds

Y—P3—P2—P1—[benzothiazole-W1]

| Compound No. | Ac-P3-P2-P1-Kt | W1 |
|---|---|---|
| 1-13A1 | H-WFR-kbt | H |
| 1-18A1 | H-dWFR-kbt | H |
| 1-15A1 | H-dWLR-kbt | H |
| 1-56A1 | H-WLR-kbt-COOH | COOH |
| 1-56A1 | H-dWLR-kbt-COOH | COOH |
| 1-54A1 | H-His(Bom)WLR-kbt | H |
| 7182 | H-LLR-kbt V amide | Val—NH2 |
| 7185-1 | Fmoc-AR-kbt | H |
| 7185-2 | Fmoc-RR-kbt | H |
| 7185-3 | Fmoc-NR-kbt | H |
| 7185-4 | Fmoc-DR-kbt | H |
| 7185-6 | Fmoc-QR-kbt | H |
| 7185-7 | Fmoc-ER-kbt | H |
| 7185-8 | Fmoc-GR-kbt | H |
| 7185-9 | Fmoc-HR-kbt | H |
| 7185-10 | Fmoc-IR-kbt | H |
| 7185-11 | Fmoc-LR-kbt | H |
| 7185-12 | Fmoc-KR-kbt | H |
| 7187-13 | Fmoc-MR-kbt | H |
| 7187-14 | Fmoc-FR-kbt | H |
| 7187-15 | Fmoc-PR-kbt | H |
| 7187-16 | Fmoc-SR-kbt | H |
| 7188-17 | Fmoc-TR-kbt | H |
| 7188-18 | Fmoc-WR-kbt | H |
| 7188-19 | Fmoc-YR-kbt | H |
| 7188-20 | Fmoc-VR-kbt | H |

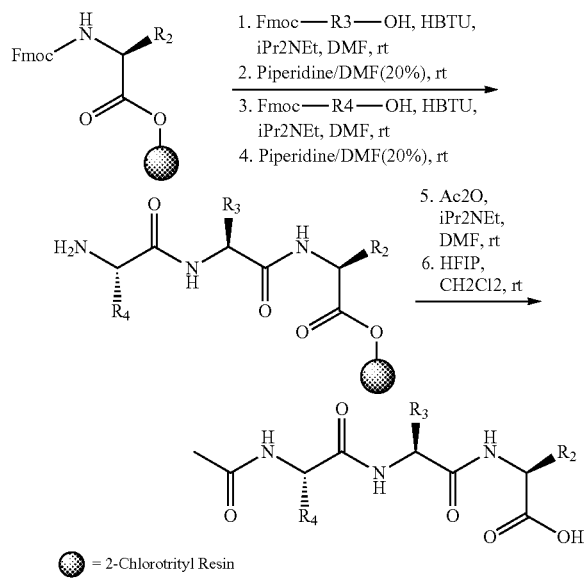

Scheme 5A

1. Fmoc—R3—OH, HBTU, iPr2NEt, DMF, rt
2. Piperidine/DMF(20%), rt
3. Fmoc—R4—OH, HBTU, iPr2NEt, DMF, rt
4. Piperidine/DMF(20%), rt
5. Ac2O, iPr2NEt, DMF, rt
6. HFIP, CH2Cl2, rt ● = 2-Chlorotrityl Resin Tripeptides were synthesized in 0.5 mmol scale through consecutive coupling of amino acid-preloaded 2-Cl-trityl resin with Fmoc protected amino acids followed by the deprotection of Fmoc group. In the coupling reaction, 5 equiv. Fmoc-amino acid/5 equiv. HBTU/10 equiv. $^{i}Pr_2NEt$ was used and the mixture was shaken at room temperature overnight. In the deprotection of Fmoc group, piperidine/DMF (20% v/v) was employed and the mixture was shaken from 1 to 4 hours at room temperature to ensure complete reaction.

Peptide Coupling and Deprotection Steps of the Fmoc Group:

Into the reaction vial (with a fritted glass resin support) containing H-Leu-2-Cl trityl, H-Phe-2-Cl trityl resin or H-Xxx-2-Cl trityl resin (0.714 g, 0.5 mmol), DMF/CH2Cl2 (15/15 mL) was added. The mixture was shaken at room temperature for 30 minutes, then filtered. The resulting resin was washed with DMF (10 mL) 2 times. Into another vial containing Fmoc-AA-OH (2.5 mmol) in DMF (20 mL), HBTU (0.853 g, 2.25 mmol) and $^{i}Pr_2NEt$ was added (0.87 mL, 5 mmol). The mixture was stirred at room temperature for 10 minutes, then added into the reaction vial containing the resin. The mixture was shaken at room temperature overnight, then filtered. The resin was washed with DMF (20 mL×4). To the resulting resin piperidine/DMF (20% v/v, 30 mL) was added. The mixture was shaken for 1-4 hours at room temperature, then filtered. The resin was washed with DMF (10 mL×4).

Acetyl Capping of the Tripeptides:

The tripeptide resin was suspended in 30 mL of 0.5 M Ac2O/DMF and 1 M $^{i}Pr_2NEt$/DMF. The mixture was shaken at room temperature for 1 hour. The resin was filtered and washed with DMF (10 mL×4) followed by CH2Cl2 (10 mL×4).

Cleavage of Tripeptide Resin:

Ac-capped tripeptide resin was suspended and shaken in 30 ml of 25% v/v HFIP/CH2Cl2 for 1 hour. The mixture was filtered. The filtrate was concentrated then dried in vacuo, giving rise to crude product of Acetyl-capped tripeptides.

Boc-WF—OMe:

Boc-Trp-OH (1 g, 3.28 mmol) and HCl.Phe-OMe (0.708 g, 3.28 mmol) was taken in dry dichloromethane (10 mL) under nitrogen atmosphere and the reaction mixture was cooled to 0° C. and N,N-diisopropylethylamine (1.7 mL, 9.84 mmol) and propylphosphonic anhydride (1.9 mL, 3.28 mmol, 50% solution in EtOAc) were added to the solution drop wise respectively. The reaction mixture was then stirred at 25° C. under nitrogen atmosphere for 1 hour and the completion of the reaction was confirmed by LC-MS monitoring. On completion the reaction mixture was diluted with 10 mL dichloromethane and washed with 10% citric acid solution, saturated sodium bicarbonate solution and brine respectively. The organic layer was dried over sodium sulfate and concentrated under reduced pressure. The crude product was triturated with hexane to obtain the title product in pure form as a white solid. Yield: 1.3 g (92.8%). Chemical formula: $C_{23}H_{33}N_3O_5$, Exact Mass: 465.55, MS(ESI): found: [M+Na]$^+$, 488.58.

Boc-WF—OH:

Boc-WF—OMe (0.130 g, 0.279 mmol) was taken in a 1:1 mixture of THF and water and LiOH.H2O (0.035 g, 0.873 mmol) was added to it. The reaction mixture was stirred for 30 minutes at 25° C. and the completion of the reaction was confirmed by LCMS monitoring. On completion, the THF was evaporated under reduced pressure and the remaining water layer was cooled to 0° C. The water layer was then brought to pH 6.5 by slow addition of 0.5 M HCl solution in water. The crude product precipitates out on addition of HCl and it was isolated by filtration. The crude product was dried under reduced pressure and triturated with diethyl ether to obtain the pure title product in pure form as white solid. Yield: 0.102 g (80%). Exact Mass: 451.21, MS(ESI): found: [M+H]$^+$, 452.26.

Boc-WFR(Mtr)-kbt:

Boc-WF—OH (35 mg, 0.077 mmol) and HATU (43.9 mg, 0.115 mmol) was taken in dry DMF under nitrogen atmosphere and the reaction mixture was cooled to 0° C. N,N-diisopropylethylamine (0.04 mL, 0.231 mmol) was then added drop wise to the reaction mixture and the reaction mixture was allowed to stir for 15 minutes followed by addition of HCl.Arg(Mtr)-kbt (41.75 mg, 0.077 mmol). The reaction mixture was stirred for 12 hours at 25° C. under nitrogen atmosphere and the completion of the reaction was confirmed by LC-MS monitoring. On completion, the reaction mixture was diluted with EtOAc and washed with 10% citric acid solution, saturated sodium bicarbonate solution and brine respectively. The organic layer was dried over sodium sulfate and concentrated under reduced pressure. The crude product was directly taken to the next step without further purification. Chemical formula: $C_{48}H_{56}N_8O_8S_2$, Exact Mass: 936.37, MS(ESI): found: $[M+H]^+$, 937.17.

H—WFR-kbt (1-13A1):

Boc-WFR(Mtr)-kbt (85 mg, crude product from previous step) was taken in 5 mL TFA:thioanisole:H$_2$O (95:2.5:2.5) and the reaction mixture was stirred for 6 hours at 25° C. The completion of the reaction was confirmed by LC-MS monitoring. On completion, the reaction mixture was concentrated under reduced pressure and triturated with diethyl ether to obtain the crude product as brown solid. The crude product was then subjected to reverse phase semi-preparative HPLC (Stationary phase: C18 column, mobile phase: H$_2$O-Acetonitrile with 0.1% TFA in each, 15-65% Acetonitrile in H$_2$O gradient for 20 minutes) to obtain the pure title product as yellow solid. Yield: 20 mg (41% over two steps). $^1$H NMR (400 MHz, CHLOROFORM-d) δ ppm 8.08 (br. s., 1H), 7.67 (d, J=8.22 Hz, 1H), 7.37 (d, J=8.22 Hz, 1H), 7.10-7.25 (m, 5H), 6.94-7.05 (m, 1H), 6.82 (d, J=7.04 Hz, 2H), 6.14-6.29 (m, 1H), 5.12 (d, J=2.74 Hz, 1H), 4.69-4.82 (m, 1H), 4.45 (br. s., 1H), 3.62 (s, 3H), 3.09-3.37 (m, 1H), 2.95 (d, J=5.48 Hz, 2H), 1.62 (s, 1H), 1.43 (br. s., 9H). Chemical formula: $C_{33}H_{36}N_8O_3S$, Exact Mass: 624.26, MS (ESI): found: $[M+H]^+$, 625.5.

Boc-dWF—OMe:

The title compound was synthesized using the same procedure as Boc-WF—OMe starting with Boc-dTrp-OH. Yield: 90%. Chemical formula: $C_{23}H_{33}N_3O_5$, Exact Mass: 465.55, MS(ESI): found: $[M+Na]^+$, 488.58.

Boc-dWF—OH:

The title compound was synthesized using the same procedure as Boc-WF—OH starting with Boc-dWF—OMe. Yield: 80%. Exact Mass: 451.21, MS(ESI): found: $[M+H]^+$, 452.26.

Boc-dWFR(Mtr)-kbt:

The title compound was synthesized using the same procedure as Boc-WFR(Mtr)-kbt starting with Boc-dWF—OH. The crude product was directly taken to the next step. Chemical formula: $C_{48}H_{56}N_8O_8S_2$, Exact Mass: 936.37, MS(ESI): found: $[M+H]^+$, 937.17.

H-dWFR-kbt (1-18A1):

The title compound was synthesized using the same procedure as H—WFR(Mtr)-kbt starting with Boc-dWF—OH. Yield: 25 mg (42% over two steps). Chemical formula: $C_{33}H_{36}N_8O_3S$, $^1$H NMR (400 MHz, METHANOL-d$_4$) δ ppm 8.21 (d, J=6.65 Hz, 1H), 8.11 (d, J=7.43 Hz, 1H), 7.57-7.67 (m, 4H), 7.12-7.36 (m, 10H), 7.01-7.08 (m, 2H), 6.84 (s, 1H), 4.48 (d, J=1.96 Hz, 1H), 3.13 (d, J=6.65 Hz, 4H), 3.01-3.07 (m, 1H), 2.75-2.84 (m, 1H), 2.65 (s, 2H), 2.03 (s, 5H), 1.41 (d, J=8.61 Hz, 1H) Exact Mass: 624.26, MS (ESI): found: $[M+H]^+$, 625.5.

Boc-dWL-OMe:

The title compound was synthesized using the same procedure as Boc-WF—OMe starting with Boc-dTrp-OH and HCl.H-Leu-OMe. Yield: 92%. Chemical formula: $C_{23}H_{33}N_3O_5$, Exact Mass: 431.24, MS(ESI): found: $[M+Na]^+$, 454.3.

Boc-dWL-OH:

The title compound was synthesized using the same procedure as Boc-WF—OH starting with Boc-dWF—OMe. Yield: 83%. Exact Mass: 417.23, MS(ESI): found: $[M+H]^+$, 418.26.

Boc-dWLR(Mtr)kbt:

The title compound was synthesized using the same procedure as Boc-WFR(Mtr)-kbt starting with Boc-dWL-OH. The crude product was directly taken to the next step. Chemical formula: $C_{45}H_{58}N_8O_8S_2$, Exact Mass: 902.38, MS(ESI): found: $[M+H]^+$, 903.5.

H-dWLR-kbt (1-15A1):

The title compound was synthesized using the same procedure as H—WFR(Mtr)-kbt starting with Boc-dWLR(Mtr)kbt. Yield: 22 mg (41% over two steps). Chemical formula: C $C_{30}H_{38}N_8O_3S$, $^1$H NMR (400 MHz, METHANOL-d$_4$) δ ppm 10.58 (br. s., OH), 8.82 (s, 1H), 8.22-8.32 (m, 2H), 7.70 (dd, J=8.02, 16.24 Hz, OH), 7.57-7.64 (m, 1H), 7.37 (d, J=6.26 Hz, 1H), 7.22 (d, J=13.30 Hz, OH), 7.11-7.18 (m, 2H), 7.02-7.10 (m, 1H), 5.55-5.67 (m, 1H), 4.47-4.58 (m, OH), 4.35 (dd, J=5.09, 10.17 Hz, OH), 4.05-4.31 (m, 2H), 3.37-3.55 (m, 1H), 3.07-3.27 (m, 3H), 2.65 (s, 1H), 2.18 (dd, J=6.06, 13.11 Hz, 1H), 1.57-1.95 (m, 3H), 1.16-1.52 (m, 2H), 1.06 (td, J=7.14, 13.89 Hz, 1H), 0.91-1.00 (m, 2H), 0.65-0.81 (m, 6H) Exact Mass: 624.26, MS (ESI): found: [M+H], 625.5.

H-dWFRkbt-COOH (1-45A1):

The title compound was synthesized using the same procedure as WFR(Mtr)kbt starting with Boc-dWFR(Mtr)kbt-COOH. Yield: 24 mg (43% over two steps). Chemical formula: $C_{34}H_{36}N_8O_5S$, $^1$H NMR (400 MHz, METHANOL-d4) δ ppm 10.58 (br. s., OH), 8.82 (s, 1H), 8.22-8.32 (m, 2H), 7.70 (dd, J=8.02, 16.24 Hz, OH), 7.57-7.64 (m, 1H), 7.37 (d, J=6.26 Hz, 1H), 7.22 (d, J=13.30 Hz, OH), 7.11-7.18 (m, 2H), 7.02-7.10 (m, 1H), 5.55-5.67 (m, 1H), 4.47-4.58 (m, OH), 4.35 (dd, J=5.09, 10.17 Hz, OH), 4.05-4.31 (m, 2H), 3.37-3.55 (m, 1H), 3.07-3.27 (m, 3H), 2.65 (s, 1H), 2.18 (dd, J=6.06, 13.11 Hz, 1H), 1.57-1.95 (m, 3H), 1.16-1.52 (m, 2H), 1.06 (td, J=7.14, 13.89 Hz, 1H), 0.91-1.00 (m, 2H), 0.65-0.81 (m, 6H) Exact Mass: 668.253, MS (ESI): found: $[M+H]^+$, 669.5.

H-WLRkbt-COOH (1-56A1):

The title compound was synthesized using the same procedure as WLR(Mtr)kbt starting with Boc-WLR(Mtr)kbt-COOH. Yield: 26 mg (44% over two steps). Chemical formula: $C_{31}H_{38}N_8O_5S$, $^1$H NMR (400 MHz, METHANOL-d4) δ ppm 8.77-8.84 (m, 1H), 8.22-8.32 (m, 3H), 7.57-7.71 (m, 1H), 7.31-7.42 (m, 2H), 7.04-7.23 (m, 3H), 4.09-4.13 (m, 1H), 3.48 (s, 1H), 3.22-3.27 (m, 2H), 3.13 (s, 1H), 2.65 (s, 2H), 1.62 (d, J=7.04 Hz, 1H), 1.17 (s, 1H), 0.90-1.00 (m, 6H), 0.65-0.80 (m, 7H) Exact Mass: 634.269, MS (ESI): found: $[M+H]^+$, 635.8.

H-dWLRkbt-COOH (1-56A1):

The title compound was synthesized using the same procedure as dWLR(Mtr)kbt starting with Boc-dWLR(Mtr)kbt-COOH. Yield: 25 mg (42% over two steps). Chemical formula: $C_{31}H_{38}N_8O_5S$, $^1$H NMR (400 MHz, METHANOL-d$_4$) δ ppm 10.58 (br. s., OH), 8.82 (s, 1H), 8.22-8.32 (m, 2H), 7.70 (dd, J=8.02, 16.24 Hz, OH), 7.57-7.64 (m, 1H), 7.37 (d, J=6.26 Hz, 1H), 7.22 (d, J=13.30 Hz, OH), 7.11-7.18 (m, 2H), 7.02-7.10 (m, 1H), 5.55-5.67 (m, 1H), 4.47-4.58 (n, OH), 4.35 (dd, J=5.09, 10.17 Hz, OH), 4.05-

4.31 (m, 2H), 3.37-3.55 (m, 1H), 3.07-3.27 (m, 3H), 2.65 (s, 1H), 2.18 (dd, J=6.06, 13.11 Hz, 1H), 1.57-1.95 (m, 3H), 1.16-1.52 (m, 2H), 1.06 (td, J=7.14, 13.89 Hz, 1H), 0.91-1.00 (m, 2H), 0.65-0.81 (m, 6H) Exact Mass: 634.269, MS (ESI): found: [M+H]$^+$, 635.8.

Fmoc-H(Bom)WL-OMe:

The title compound was synthesized using same procedure described as Boc-WF—OMe starting from Fmoc-His(Bom)-OH and HCl.H-WL-OMe. The crude product was directly taken to the next step. Chemical formula: $C_{47}H_{50}N_6O_7$, Exact Mass: 810.5, MS(ESI): found: [M+H]$^+$, 811.78.

Fmoc-H(Bom)WL-OH:

The title compound was synthesized using same procedure described as Boc-WF—OH starting from Fmoc-His(Bom)WL-OMe. Yield: 76%. Chemical formula: $C_{46}H_{48}N_6O_7$, Exact Mass: 796.35, MS(ESI): found: [M+H]$^+$, 797.78.

Fmoc-H(Bom)WLR(Mtr)-Kbt:

The title compound was synthesized using same procedure described as Boc-WF-RKbt starting from Fmoc-His(Bom)WL-OH and HCl.H-Arg(Mtr)-Kbt. Yield: 65%. Exact Mass: 1281.514, MS(ESI): found: [M+H]$^+$, 1262.7.

H(Bom)WLR-Kbt (1-54A1):

The title compound was synthesized using same procedure described as H—WF-RKbt starting from Fmoc-His(Bom)WLR(Mtr)Kbt, followed by a treatment with 4M HCl solution. Yield: 20% over three steps. Exact Chemical formula: $C_{44}H_{53}N_{11}O_5S$, $^1$H NMR (400 MHz, METHANOL-d$_4$) δ ppm 7.89 (d, J=7.83 Hz, 4H), 7.71 (d, J=7.43 Hz, 4H), 7.46-7.52 (m, 4H), 7.39-7.45 (m, 4H), 4.49 (t, J=5.28 Hz, 2H), 3.83 (d, J=5.48 Hz, 5H), 3.42 (d, J=12.13 Hz, 4H), 2.99 (t, J=11.54 Hz, 4H), 1.88 (br. s., 6H), 1.75 (br. s., 8H), 1.44-1.60 (m, 2H) Mass: 847.3, MS(ESI): found: [M+H]$^+$, 848.7.

H(Bom)dWLR-Kbt (1-58A1):

The title compound was synthesized using same procedure described as H—WF-RKbt starting from Fmoc-dHis(Bom)WLR(Mtr)Kbt, followed by a treatment with 4M HCl solution. Yield: 36% over three steps. Exact Chemical formula: $C_{44}H_{53}N_{11}O_5S$, $^1$H NMR (400 MHz, METHANOL-d$_4$) δ ppm 7.89 (d, J=7.83 Hz, 4H), 7.71 (d, J=7.43 Hz, 4H), 7.46-7.52 (m, 4H), 7.39-7.45 (m, 4H), 4.49 (t, J=5.28 Hz, 2H), 3.83 (d, J=5.48 Hz, 5H), 3.42 (d, J=12.13 Hz, 4H), 2.99 (t, J=11.54 Hz, 4H), 1.88 (br. s., 6H), 1.75 (br. s., 8H), 1.44-1.60 (m, 2H) Mass: 847.3, MS(ESI): found: [M+H]$^+$, 848.7.

Boc-LL-OMe:

The title compound was synthesized using the same procedure as Boc-dWL-OMe starting with Boc-Leu-OH and HCl.H-Leu-OMe.

Boc-LL-OH:

The title compound was synthesized using the same procedure as Boc-dWL-OH starting with Boc-LL-OMe. Exact Mass: 417.5 MS(ESI): found: [M+H]$^+$418.6

H-LLR-kbt V amide (7182).

Synthesized in a similar manner to H-WFRkbt from Boc-LLR(Mtr)-Kbt V amide. Yield 4.6 mg. Chemical Formula: $C_{31}H_{49}N_9O_5S$, Exact Mass: 659.36, MS(ESI): found: [M+H]$^+$, 660.6.

Boc-WL-OH:

The title compound was synthesized using the same procedure as Boc-dWL-OH starting with Boc-WL-OMe. Exact Mass: 417.2, MS(ESI): found: [M+H]$^+$, 418.3.

H-WLR-kbt V amide (7181).

Synthesized in a similar manner to H-dWLR-kbt from Boc-WLR(Mtr)-kbt V amide. Yield 4.5 mg. Chemical Formula: $C_{36}H_{48}N_{10}O_5S$, Exact Mass: 732.35, MS(ESI): found: [M+H]$^+$, 733.6.

Boc-R(Mtr)L-OH:

The title compound was synthesized using the same procedure as Boc-dWL-OH starting with Boc-R(Mtr)L-OMe. Exact Mass: MS(ESI): 599.7 found: [M+H]$^+$, 600.8.

H-RLR-kbt V amide (7180).

Yield 5 mg. $^1$H NMR (400 MHz, METHANOL-d$_4$) δ ppm 8.90 (d, J=7.04 Hz, OH), 8.65 (s, 1H), 8.35 (d, J=8.61 Hz, 1H), 8.28 (d, J=8.61 Hz, 1H), 8.10 (d, J=9.00 Hz, 1H), 5.53-5.61 (m, 1H), 4.42-4.55 (m, 2H), 3.92 (t, J=5.87 Hz, 1H), 3.18 (t, J=6.85 Hz, 2H), 2.20 (qd, J=6.81, 13.60 Hz, 2H), 1.86-1.98 (m, 3H), 1.70-1.82 (m, 3H), 1.56-1.68 (m, 3H), 1.07 (dd, J=4.30, 6.65 Hz, 6H), 0.96 (d, J=6.26 Hz, 16H). Chemical Formula: $C_{31}H_{50}N_{12}O_5S$, Exact Mass: 702.37, MS(ESI): found: [M+H]$^+$, 703.6.

Fmoc-A-R-kbt (7185-1).

Under nitrogen atmosphere, Fmoc-A-OH (0.02 mmol) was dissolved in DMF (10 mL) and then HATU (0.02 mmol) was added. After stirring for 10 minutes, H—R(Mtr)-kbt-HCl (0.0185 mmol) and N,N-diisopropylethylamine (0.1 mmol) were added. The mixture was stirred at room temperature for 4 hours. The solvent was removed and then 1.5 mL of cleavage cocktail (38:1:1 TFA/water/thioanisole) was added and then the reaction was stirred for 4 hours. After concentration in vacuo, the residue was purified by C18 reverse phase HPLC to give the title compound as a lyophilized white powder.

Fmoc-RR-kbt (7185-2).

The title compound was synthesized using the same procedure as (7185-1). Chemical formula $C_{34}H_{39}N_9O_4S$, Exact Mass 669.28, MS(ESI): found [M+H]$^+$ 670.4.

Fmoc-NR-kbt (7185-3).

The title compound was synthesized using the same procedure as (7185-1). Chemical formula $C_{32}H_{33}N_7O_5S$, Exact Mass 627.23, MS(ESI): found [M+H]$^+$ 628.3.

Fmoc-DR-kbt (7185-4).

The title compound was synthesized using the same procedure as (7185-1). Chemical formula $C_{32}H_{32}N_6O_6S$, Exact Mass, 628.21, MS(ESI): found [M+H]$^+$ 629.3.

Fmoc-QR-kbt (7185-6).

The title compound was synthesized using the same procedure as (7185-1). Chemical formula $C_{33}H_{35}N_7O_5S$, Exact Mass 641.24, MS(ESI): found [M+H]$^+$ 642.4.

Fmoc-ER-kbt (7185-7).

The title compound was synthesized using the same procedure as (7185-1). Chemical formula $C_{33}H_{34}N_6O_6S$, Exact Mass 642.23, MS(ESI): found [M+H]$^+$ 643.3.

Fmoc-GR-kbt (7185-8).

The title compound was synthesized using the same procedure as (7185-1). Chemical formula $C_{30}H_{30}N_6O_4S$, Exact Mass 570.2, MS(ESI): found [M+H]$^+$ 571.3.

Fmoc-HR-kbt (7185-9).

The title compound was synthesized using the same procedure as (7185-1). Chemical formula $C_{34}H_{34}N_8O_4S$, Exact Mass 650.24, MS(ESI): found [M+H]$^+$ 651.4.

Fmoc-IR-kbt (7185-10).

The title compound was synthesized using the same procedure as (7185-1). Chemical formula $C_{34}H_{38}N_6O_4S$, Exact Mass 626.27, MS(ESI): found [M+H]$^+$ 627.4.

Fmoc-LR-kbt (7185-11).

The title compound was synthesized using the same procedure as (7185-1). Chemical formula $C_{34}H_{38}N_6O_4S$, Exact Mass 626.27, MS(ESI): found [M+H]$^+$ 627.4.

Fmoc-KR-kbt (7185-12).
The title compound was synthesized using the same procedure as (7185-1). Chemical formula $C_{34}H_{39}N_7O_4S$, Exact Mass 641.28, MS(ESI): found $[M+H]^+$ 642.5.

Fmoc-MR-kbt (7187-13).
The title compound was synthesized using the same procedure as (7185-1). Chemical formula $C_{32}H_{34}N_6O_4S_2$, Exact Mass 630.21, MS(ESI): found $[M+H]^+$ 631.3.

Fmoc-FR-kbt (7187-14).
The title compound was synthesized using the same procedure as (7185-1). Chemical formula $C_{37}H_{36}N_6O_4S$, Exact Mass 660.25, MS(ESI): found $[M+H]^+$ 661.4.

Fmoc-PR-kbt (7187-15).
The title compound was synthesized using the same procedure as (7185-1). Chemical formula $C_{33}H_{34}N_6O_4S$, Exact Mass 610.24, MS(ESI): found $[M+H]^+$ 611.5.

Fmoc-SR-kbt (7187-16).
The title compound was synthesized using the same procedure as (7185-1). Chemical formula $C_{31}H_{32}N_6O_5S$, Exact Mass 600.22, MS(ESI): found $[M+H]^+$ 601.3.

Fmoc-TR-kbt (7188-17).
The title compound was synthesized using the same procedure as (7185-1). Chemical formula $C_{32}H_{34}N_6O_5S$, Exact Mass 614.23, MS(ESI): found $[M+H]^+$ 615.4.

Fmoc-WR-kbt (7188-18).
The title compound was synthesized using the same procedure as (7185-1). Chemical formula $C_{39}H_{37}N_7O_4S$, Exact Mass 699.26, MS(ESI): found $[M+H]^+$ 700.4.

Fmoc-YR-kbt (7188-19).
The title compound was synthesized using the same procedure as (7185-1). Chemical formula $C_{37}H_{36}N_6O_5S$, Exact Mass 676.25, MS(ESI): found $[M+H]^+$ 677.4.

Fmoc-VR-kbt (7188-20).
The title compound was synthesized using the same procedure as (7185-1). Chemical formula $C_{33}H_{36}N_6O_4S$, Exact Mass 612.25, MS(ESI): found $[M+H]^+$ 613.5.

The tetrapeptide ketothiazoles listed in Table 5.2 were synthesized in accordance with the procedures and schemes described below.

TABLE 5.2

Tetrapeptide ketobenzothiazoles.

$Y-P_4-P_3-P_2-P_1-$ benzothiazole with $W_1$ substituent

| Compound No. | Y-$P_4$-$P_3$-$P_2$-$P_1$-Z | $W_1$ |
|---|---|---|
| 7115 | Ac-KRLR(SEQ ID NO: 8)-Kbt-Val—NH$_2$ | Val-NH$_2$ structure |
| 7054 | Ac-KRLR(SEQ ID NO: 8)-Kbt | H |
| 7117 | H-WRLR(SEQ ID NO: 9)-Kbt | H |
| 1-45A1 | H-dWFR-kbt-COOH | COOH |
| 7055 | Ac-KQLR(SEQ ID NO: 1)-Kbt-Val—NH$_2$ | Val-NH$_2$ structure |
| 7116 | Ac-SKLR(SEQ ID NO: 10)-Kbt-Val—NH$_2$ | Val-NH$_2$ structure |
| 7124 | Ac-SKLR(SEQ ID NO: 10)-Kbt-Trp—NH$_2$ | Trp-NH$_2$ structure |

TABLE 5.2-continued

Tetrapeptide ketobenzothiazoles.

Y—P$_4$—P$_3$—P$_2$—P$_1$—[benzothiazole]—W$_1$

| Compound No. | Y-P$_4$-P$_3$-P$_2$-P$_1$-Z | W$_1$ |
|---|---|---|
| 7125 | Ac-SKLR(SEQ ID NO: 10)-Kbt-Phe—NH$_2$ | —NH—CH(CH$_2$Ph)—C(O)—NH$_2$ |
| 7006 | Ac-KQLR(SEQ ID NO: 1)-Kbt | H |
| 7126 | Ac-SKLR(SEQ ID NO: 10)-Kbt-4-pyridinylamide | —C(O)—NH-(4-pyridinyl) |
| 7053 | Ac-SKLR(SEQ ID NO: 10)-Kbt | H |
| 7063 | Ac-FLFR(SEQ ID NO: 19)-Kbt | H |
| 7118 | Ac-SKLR(SEQ ID NO: 10)-Kbt-COOH | —COOH |
| 7064 | Ac-WLFR(SEQ ID NO: 20)-Kbt | H |
| 7139 | Ac-SKLR(SEQ ID NO: 10)-Kbt-benzylamide | —C(O)—NH—CH$_2$-Ph |
| 7140 | Ac-SKLR(SEQ ID NO: 10)-Kbt-4-piperidinylamide | —C(O)—NH-(4-piperidinyl) |
| 7165 | Ac-KRLR(SEQ ID NO: 8)-Kbt-5-COOH | —C(O)—NH—CH$_2$-(3-COOH-phenyl) |

Procedure for the Preparation of Tetrapeptide Ketobenzothiazole:

Tripeptides were synthesized in 0.5 mmol scale through consecutive coupling of amino acid-preloaded 2-Cl-trityl resin with Fmoc protected amino acids followed by the deprotection of Fmoc group. In the coupling reaction, 5 equiv. Fmoc-amino acid/4.5 equiv. HBTU/10 equiv. $^i$Pr$_2$NEt was used and the mixture was shaken at room temperature overnight. In the deprotection of Fmoc group, piperidine/DMF (20% v/v) was employed and the mixture was shaken for 4 hours at room temperature.

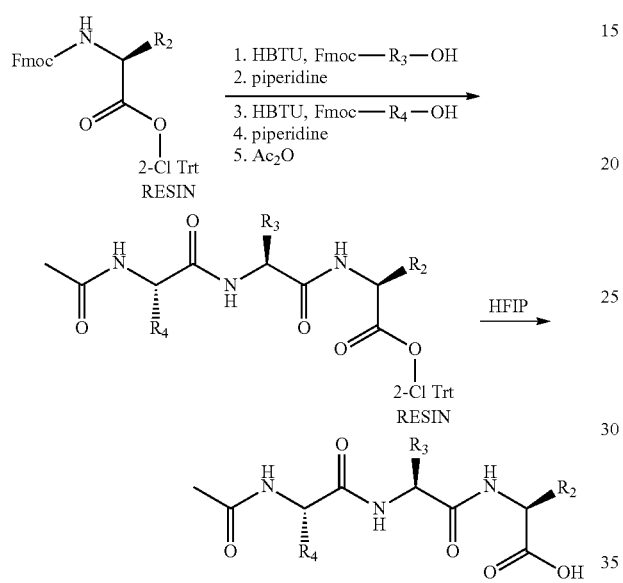

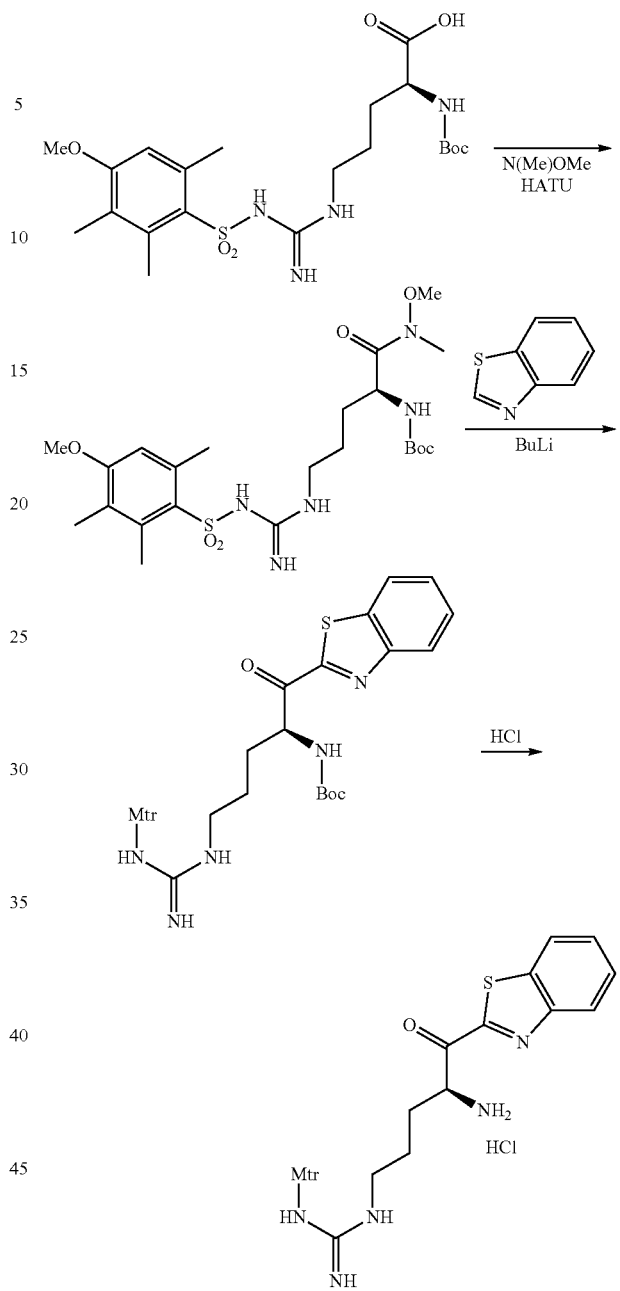

Peptide Coupling and Deprotection of Fmoc:

Into the reaction vial (with a fritted glass resin support) containing H-Leu-2-Cl-trityl resin (0.714 g, 0.5 mmol), DMF/CH$_2$Cl$_2$ (15/15 mL) was added. The mixture was shaken at room temperature for 30 minutes, then filtered. The resulting resin was washed with DMF (10 mL×2). Into another vial containing Fmoc-AA-OH (2.5 mmol) in DMF (20 mL), HBTU (0.853 g, 2.25 mmol) and $^i$Pr$_2$NEt was added (0.87 mL, 5 mmol). The mixture was stirred at room temperature for 10 minutes, then added into the reaction vial containing the resin. The mixture was shaken at room temperature overnight, then filtered. The resin was washed with DMF (20 mL×4). To the resulting resin piperidine/DMF (20% v/v, 30 mL) was added. The mixture was shaken for 4 hours at room temperature, then filtered. The resin was washed with DMF (10 mL×4).

Acetyl Capping of the Tripeptides:

The tripeptide resin was suspended in 30 mL of 0.5 M Ac$_2$O/DMF and 1 M $^i$Pr$_2$NEt/DMF. The mixture was shaken at room temperature for 1 hour. The resin was filtered and washed with DMF (10 mL×4) followed by CH$_2$Cl$_2$ (10 mL×4).

Cleavage of Tripeptide Resin:

Ac-capped tripeptide resin was suspended and shaken in 30 ml of 25% v/v HFIP/CH$_2$Cl$_2$ for 1 hour. The mixture was filtered. The filtrate was concentrated then dried in vacuo, giving rise to crude product of Ac-capped tripeptide.

BocHN-Arg(Mtr) ketobenzothiazole.

At −78° C., n-BuLi/Hex(2.5M) (14 mL, 35 mmol) was added dropwise into the solution of benzothiazole (4.87 g, 36 mmol) in THF (50 mL) over 15 minutes. After the mixture was stirred for additional half an hour, the solution of Boc-HN-Arg(Mtr) Weinreb amide (1.06 g, 2 mmol) in THF (15 mL) was added slowly over 50 min. For synthesis of Weinreb amide, see Han et al., "Inhibitors of HGFA, Matriptase, and Hepsin Serine Proteases: A Nonkinase Strategy to Block Cell Signaling in Cancer, *Acs Med Chem Lett* (2014) 5, 1219-1224. The mixture was stirred at −78° C. for additional 2 hours. The reaction was quenched with aqueous NH$_4$Cl and the aqueous layer was extracted with AcOEt. The organic phase was collected, dried with Na$_2$SO$_4$, then concentrated. The resulting residue was purified by silica gel chromatography with CHCl$_3$/MeOH combination as eluent to give the title compound (1.14 g) in 94% yield. 1H NMR (400 MHz, METHANOL-d₄) δ ppm 1.43 (s, 9H) 1.53-1.78 (m, 4H) 2.05 (s, 3H) 2.55 (s, 3H) 2.61 (s, 3H) 3.17-3.29 (m, 2H) 3.82 (s, 3H) 5.19-5.43 (m, 1H) 6.57 (s, 1H) 7.53-7.71 (m, 2H) 8.06-8.28 (m, 2H). MS(ESI): found: [M+H]⁺, 604.4.

HCl.H₂N-Arg(Mtr) ketobenzothiazole.

The mixture of BocHN-Arg(Mtr) ketobenzothiazole (1.0 g, 1.66 mmol) in 30 mL of HCl/dioxane (1.5 M) was stirred at room temperature. The reaction was monitored by LCMS until completion. The solvent was removed then the resulting residue was dried in vacuo to the tile product in quantitative yield. ¹H NMR (400 MHz, METHANOL-d₄) δ ppm 1.60-1.86 (m, 2H) 2.00-2.20 (m, 4H) 2.24-2.36 (m, 1H) 2.53 (s, 3H) 2.61 (s, 3H) 3.84 (s, 3H) 5.14-5.40 (m, 1H) 6.65 (s, 1H) 7.59-7.78 (m, 2H) 8.10-8.34 (m, 2H). MS(ESI): found: [M+H]⁺, 504.4.

1.90-2.26 (m, 3H) 2.02 (s, 3H) 2.26-2.44 (m, 2H) 2.87-2.97 (m, 2H) 3.20-3.40 (m, 2H) 4.21-4.29 (m, 1H) 4.31-4.38 (m, 1H) 4.39-4.48 (m, 1H) 5.63-5.78 (m, 1H) 7.54-7.74 (m, 2H) 8.08-8.16 (m, 1H) 8.19-8.29 (m, 1H). MS(ESI): found: [M+H]⁺, 703.6.

Ac-SKLR (SEQ ID NO: 10) ketobenzothiazole (7053).

(yield: 23%). Synthesized using the same procedure as for Ac-KQLR (SEQ ID NO: 1) ketobenzothiazole. ¹H NMR (400 MHz, METHANOL-d₄) δ ppm 0.87 (d, J=6.65 Hz, 3H) 0.91 (d, J=6.65 Hz, 3H) 1.36-2.08 (m, 12H) 2.01 (s, 3H) 2.10-2.29 (m, 1H) 2.82-3.04 (m, 2H) 3.22-3.38 (m, 2H) 3.65-3.93 (m, 2H) 4.24-4.53 (m, 3H) 5.58-5.74 (m, 1H) 7.56-7.71 (m, 2H) 8.08-8.16 (m, 1H) 8.18-8.25 (m, 1H). MS(ESI): found: [M+H]⁺, 662.5.

Ac-KRLR (SEQ ID NO: 8) ketobenzothiazole (7054).

(yield: 38%). Synthesized using the same procedure as for Ac-KQLR (SEQ ID NO: 1) ketobenzothiazole. ¹H NMR

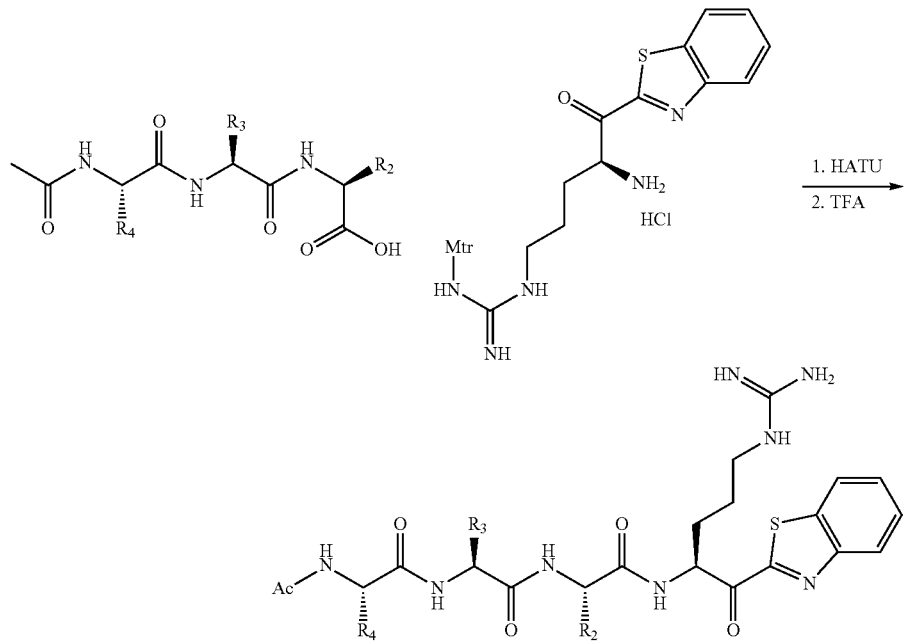

Ac-KQLR (SEQ ID NO: 1) ketobenzothiazole (7006).

Under nitrogen atmosphere, at 0° C. anhydrous DMF (5 mL) was added into the round bottom flask containing AcHN—K(Boc)-Q(Trt)-L-OH tripeptide (0.064 g, 0.083 mmol) and HATU (0.035 g, 0.091 mmol). After stirring for 10 minutes, Mtr-protected arginine ketobenzothiazole (0.068 g, 0.013 mmol), then N,N-diisopropylethylamine (0.053 g, 0.41 mmol) were added. The mixture was stirred at room temperature for 4 hours while being warmed to room temperature naturally. DMF was removed and to the resulting residue water (20 mL) was added. The precipitate formed was filtered and dried. To this precipitate 5 mL of TFA/thioanisole/water (95/2.5/2.5(v/v/v)) was added. The mixture was stirred at room temperature for 4 hours. Then cold ether (40 mL) was added. The resulting precipitate, which is the crude product, was collected by centrifugation, then by decanting out carefully ether solvent. The crude product was purified by HPLC (C18, 15*150 mm column; eluent: acetonitrile/water (0.05% TFA)) to give Ac-KQLR (SEQ ID NO: 1) ketobenzothiazole (0.030 g) in 43% yield. ¹H NMR (400 MHz, METHANOL-d₄) δ ppm 0.88 (d, J=6.26 Hz, 3H) 0.92 (d, J=6.26 Hz, 3H) 1.36-1.90 (m, 12H)

(400 MHz, METHANOL-d₄) δ ppm 0.90 (d, J=6.80 Hz, 3H) 0.94 (d, J=6.80 Hz, 3H) 1.36-1.96 (m, 16H) 1.99 (s, 3H) 2.09-2.34 (m, 1H) 2.87-2.98 (m, 2H) 3.14-3.23 (m, 2H) 3.25-3.33 (m, 2H) 4.20-4.30 (m, 1H) 4.33-4.52 (m, 2H) 5.54-5.76 (m, 1H) 7.59-7.70 (m, 2H) 8.10-8.16 (m, 1H) 8.18-8.23 (m, 1H). MS(ESI): found: [M+H]⁺, 731.7.

Ac-FLFR (SEQ ID NO: 19) ketobenzothiazole (7063).

(yield: 47%). Synthesized using the same procedure as for Ac-KQLR (SEQ ID NO: 1) ketobenzothiazole. ¹H NMR (400 MHz, METHANOL-d₄) δ ppm 0.85 (d, J=6.26 Hz, 3H) 0.90 (d, J=6.26 Hz, 3H) 1.36-1.63 (m, 3H) 1.66-1.99 (m, 3H) 1.91 (s, 3H) 2.05-2.25 (m, 1H) 2.80-2.91 (m, 1H) 2.92-3.02 (m, 1H) 3.02-3.18 (m, 2H) 3.20-3.33 (m, 2H) 4.19-4.39 (m, 1H) 4.47-4.70 (m, 2H) 5.64-5.75 (m, 1H) 7.01-7.33 (m, 10H) 7.57-7.71 (m, 2H) 8.10-8.17 (m, 1H) 8.19-8.25 (m, 1H). MS(ESI): found: [M+H]⁺, 741.6.

Ac-WLFR (SEQ ID NO: 20) ketobenzothiazole (7064).

(yield: 19%). Synthesized using the same procedure as for Ac-KQLR (SEQ ID NO: 1) ketobenzothiazole. ¹H NMR (400 MHz, METHANOL-d₄) δ ppm 0.79 (d, J=6.26 Hz, 3H) 0.84 (d, J=6.26 Hz, 3H) 1.32-1.50 (m, 3H) 1.62-1.91 (m, 3H) 1.95 (s, 3H) 2.06-2.21 (m, 1H) 2.88-3.00 (m, 1H) 3.05-3.29

(m, 5H) 4.14-4.33 (m, 1H) 4.50-4.72 (m, 2H) 5.61-5.77 (m, 1H) 6.96-7.03 (m, 1H) 7.04-7.20 (m, 7H) 7.29-7.37 (m, 1H) 7.54-7.71 (m, 3H) 7.85-7.97 (m, 1H) 8.10-8.16 (m, 1H) 8.18-8.26 (m, 1H). MS(ESI): found: [M+H]$^+$, 780.6.

WRLR (SEQ ID NO: 9) ketobenzothiazole (7117).

(yield: 39%). Synthesized using the same procedure as for Ac-KQLR (SEQ ID NO: 1) ketobenzothiazole, starting with the coupling of BocHN—W—R(Mtr)-L-OH tripeptide and Mtr-protected arginine ketobenzothiazole. $^1$H NMR (400 MHz, METHANOL-d$_4$) δ ppm 0.94 (d, J=6.65 Hz, 3H) 0.95 (d, J=6.65 Hz, 3H) 1.48-1.99 (m, 10H) 2.12-2.30 (m, 1H) 3.14-3.23 (m, 3H) 3.24-3.29 (m, 2H) 3.39-3.52 (m, 1H) 4.18-4.29 (m, 1H) 4.37-4.53 (m, 2H) 5.61-5.68 (m, 1H) 7.01-7.09 (m, 1H) 7.10-7.17 (m, 1H) 7.22 (s, 1H) 7.34-7.41 (m, 1H) 7.58-7.71 (m, 3H) 8.10-8.16 (m, 1H) 8.17-8.24 (m, 1H) 8.25-8.33 (m, 1H). MS(ESI): found: [M+H]$^+$, 747.7.

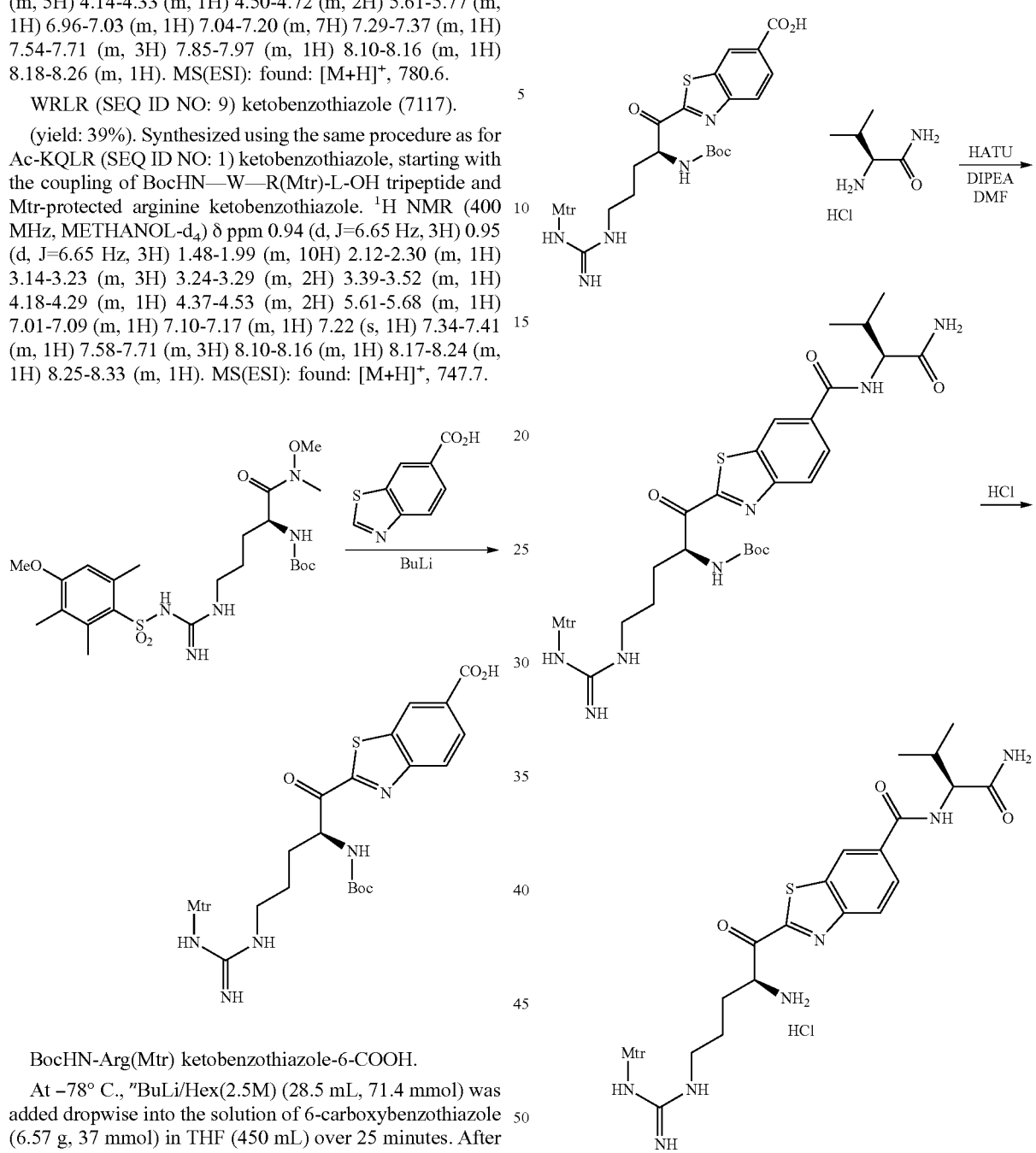

BocHN-Arg(Mtr) ketobenzothiazole-6-COOH.

At −78° C., "BuLi/Hex(2.5M) (28.5 mL, 71.4 mmol) was added dropwise into the solution of 6-carboxybenzothiazole (6.57 g, 37 mmol) in THF (450 mL) over 25 minutes. After the mixture was stirred for additional half an hour, the solution of Boc-HN-Arg(Mtr) Weinreb amide (1.63 g, 3.08 mmol) in THF (60 mL) was added slowly over 20 minutes at −78° C. After the addition then the mixture was stirred at −24° C. to −20° C. for 1.5 hours. The reaction was quenched with saturated aqueous NH$_4$Cl (270 mL). The layers were separated and the aqueous layer was extracted with AcOEt. The organic phase was collected and washed with water, 5% citric acid, then dried with Na$_2$SO$_4$ and concentrated. The resulting residue was purified by silica gel chromatography with CH$_2$Cl$_2$/MeOH combination as eluent to give the title compound (0.91 g) in 46% yield. $^1$H NMR (400 MHz, METHANOL-d$_4$) δ ppm 1.43 (s, 9H) 1.66 (m, 4H) 2.03 (s, 3H) 2.54 (s, 3H) 2.60 (s, 3H) 3.22-3.29 (m, 2H) 3.80 (s, 3H) 5.18-5.41 (m, 1H) 6.55 (s, 1H) 8.20 (m, 2H) 8.79 (s, 1H). MS(ESI): found: [M+H]$^+$, 648.4.

BocHN-Arg(Mtr) ketobenzothiazole-6-CONH-Val-amide.

Under nitrogen atmosphere, at 0° C. anhydrous DMF (5 mL) was added into the round bottom flask containing BocHN-Arg(Mtr) ketobenzothiazole-COOH (0.060 g, 0.093 mmol) and HATU (0.042 g, 0.11 mmol). After stirring for 10 minutes, L-valine amide hydrochloride (0.017 g, 0.11 mmol), then N,N-diisopropylethylamine (0.062 g, 0.55 mmol) were added. The mixture was stirred overnight while being warmed to room temperature naturally. DMF was removed and to the resulting residue 20 mL water was added. The precipitate formed was filtered and dried. The product was purified by silica gel chromatography with CHCl$_3$/MeOH combination as eluent to give the title compound (0.049 g) in 70% yield $^1$H NMR (400 MHz, METHANOL-d$_4$) δ ppm 1.06 (d, J=1.57 Hz, 3H) 1.08 (d, J=1.96 Hz, 3H) 1.42 (s, 9H) 1.56-1.79 (m, 4H) 2.04 (s, 3H) 2.15-2.30 (m, 1H) 2.55 (s, 3H) 2.60 (s, 3H) 3.20-3.28 (m, 2H) 3.80 (s, 3H) 4.45 (d, J=7.43 Hz, 1H) 5.19-5.41 (m, 1H) 6.57 (s, 1H) 8.00-8.12 (m, 1H) 8.13-8.29 (m, 1H) 8.62 (s, 1H). MS(ESI): found: [M+H]$^+$, 746.5.

HCl.H$_2$N-Arg(Mtr) ketobenzothiazole-6-CONH-Val-amide.

The mixture of BocHN-Arg(Mtr) ketobenzothiazole-(C═O)—V-amide (0.049 g, 0.066 mmol) in 10 mL of HCl/dioxane (2.5 M) was stirred at room temperature. The reaction was monitored by LCMS until completion. The solvent was removed then the resulting residue was dried in vacuo to the tile product in quantitative yield. $^1$H NMR (400 MHz, METHANOL-d$_4$) δ ppm 1.06 (d, J=3.13 Hz, 3H) 1.08 (d, J=3.13 Hz, 3H) 1.58-1.91 (m, 2H) 1.95-2.41 (m, 6H) 2.52 (s, 3H) 2.61 (s, 3H) 3.85 (s, 3H) 4.46 (d, J=7.40 Hz, 1H) 5.16-5.38 (m, 1H) 6.66 (bs, 1H) 7.99-8.18 (m, 1H) 8.22-8.39 (m, 1H) 8.55-8.78 (m, 1H). MS(ESI): found: [M+H]$^+$, 646.5.

(d, J=2.74 Hz, 3H) 1.08 (d, J=2.74 Hz, 3H) 1.37-2.14 (m, 14H) 2.02 (s, 3H) 2.14-2.43 (m, 4H) 2.87-3.00 (m, 2H) 3.22-3.38 (m, 2H) 4.20-4.29 (m, 1H) 4.29-4.38 (m, 1H) 4.39-4.50 (m, 2H) 5.58-5.75 (m, 1H) 8.05-8.14 (m, 1H) 8.24-8.33 (m, 1H) 8.62-8.67 (m, 1H). MS(ESI): found: [M+H]$^+$, 845.7.

Ac-SKLR (SEQ ID NO: 10) ketobenzothiazole-6-CONH-Val-amide (7116).

The title compound was synthesized using the same procedure as for Ac-KQLR (SEQ ID NO: 1) ketobenzothiazole-(C═O)—V-amide. Yield: 24%. $^1$H NMR (400 MHz, METHANOL-d$_4$) δ ppm 0.87 (d, J=6.46 Hz, 3H) 0.91 (d, J=6.46 Hz, 3H) 1.06 (d, J=2.54 Hz, 3H) 1.07 (d, J=2.54 Hz, 3H) 1.37-1.97 (m, 12H) 2.01 (s, 3H) 2.13-2.28 (m, 2H) 2.79-3.03 (m, 2H) 3.22-3.38 (m, 2H) 3.67-3.98 (m, 2H) 4.23-4.54 (m, 4H) 5.49-5.77 (m, 1H) 8.07-8.12 (m, 1H) 8.25-8.32 (m, 1H) 8.61-8.66 (m, 1H). MS(ESI): found: [M+H]$^+$, 804.7.

Ac-KRLR (SEQ ID NO: 8) ketobenzothiazole-6-CONH-Val-amide (7115).

The title compound was synthesized using the same procedure as for Ac-KQLR (SEQ ID NO: 1) ketobenzothi-

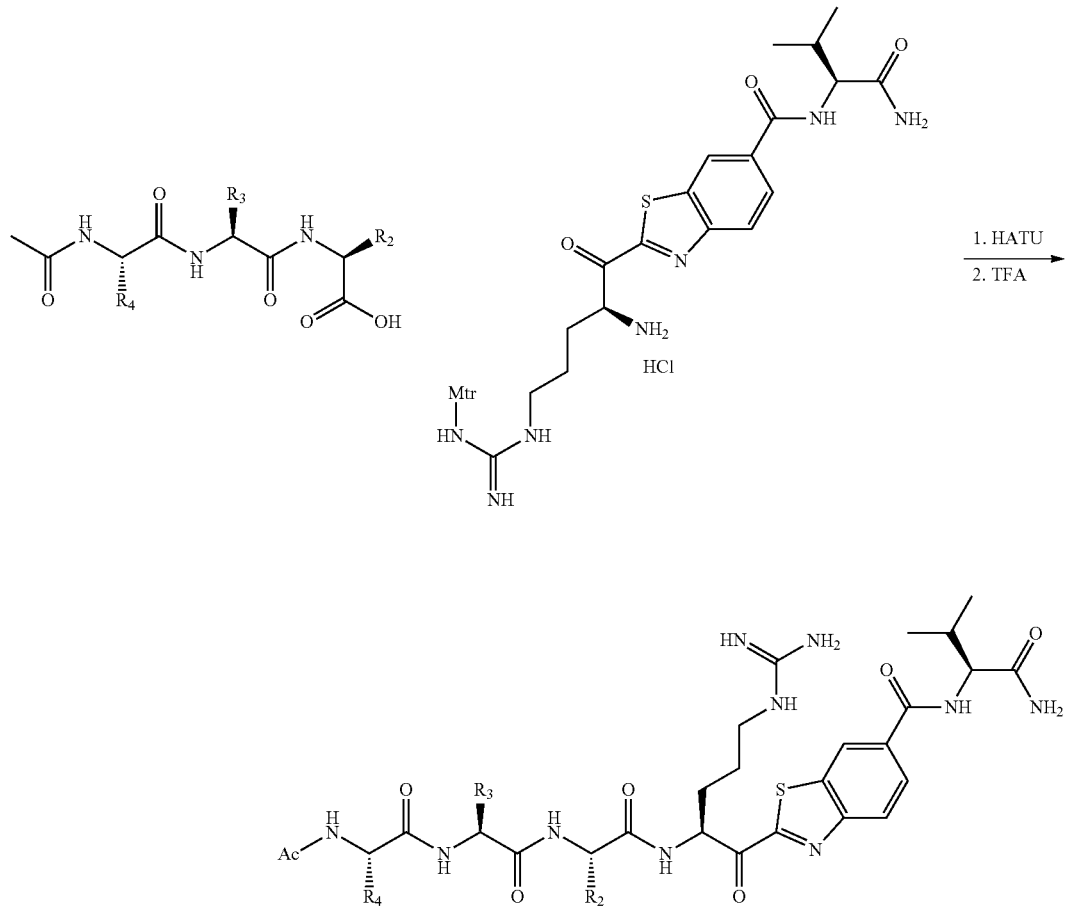

Ac-KQLR (SEQ ID NO: 1) ketobenzothiazole-6-CONH-Val-amide (7055).

The title compound was synthesized using the same procedure as for the tetrapeptide ketothiazoles, starting with the coupling of protected Ac-K(Boc)-Q(Trt)-L-OH tripeptide and HCl.H$_2$N-Arg(Mtr) ketobenzothiazole-(C═O)—V-amide. Yield: 11%. $^1$H NMR (400 MHz, METHANOL-d$_4$) δ ppm 0.87 (d, J=6.00 Hz, 3H) 0.92 (d, J=6.00 Hz, 3H) 1.06 azole-(C═O)—V-amide. Yield: 28%. $^1$H NMR (400 MHz, METHANOL-d$_4$) δ ppm 0.92 (dd, J=11.15, 6.46 Hz, 6H) 1.07 (dd, J=6.65, 2.74 Hz, 6H) 1.35-1.95 (m, 16H) 1.99 (s, 3H) 2.14-2.27 (m, 2H) 2.87-2.98 (m, 2H) 3.14-3.21 (m, 2H) 3.25-3.33 (m, 2H) 4.21-4.28 (m, 1H) 4.33-4.39 (m, 1H) 4.40-4.49 (m, 2H) 5.46-5.74 (m, 1H) 8.07-8.12 (m, 1H) 8.24-8.33 (m, 1H) 8.61-8.68 (m, 1H). MS(ESI): found: [M+H]$^+$, 873.7.

95 96
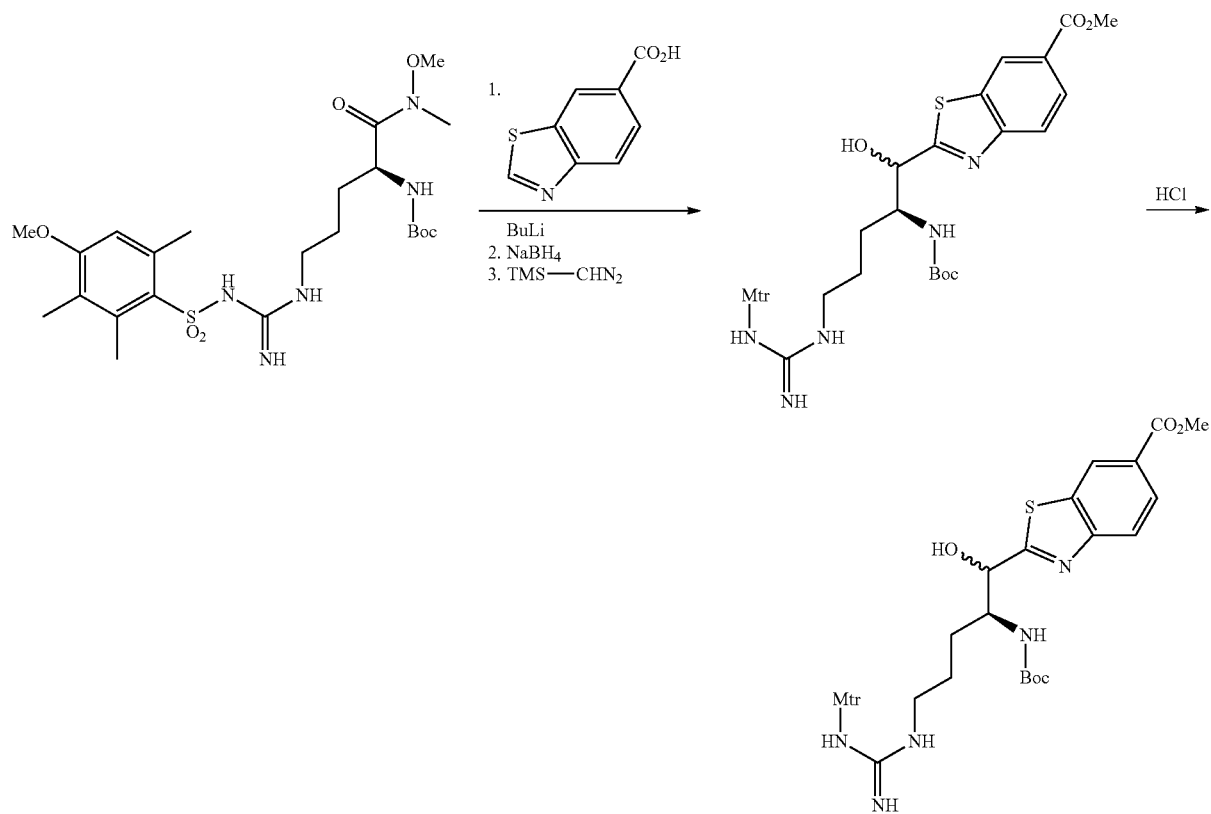
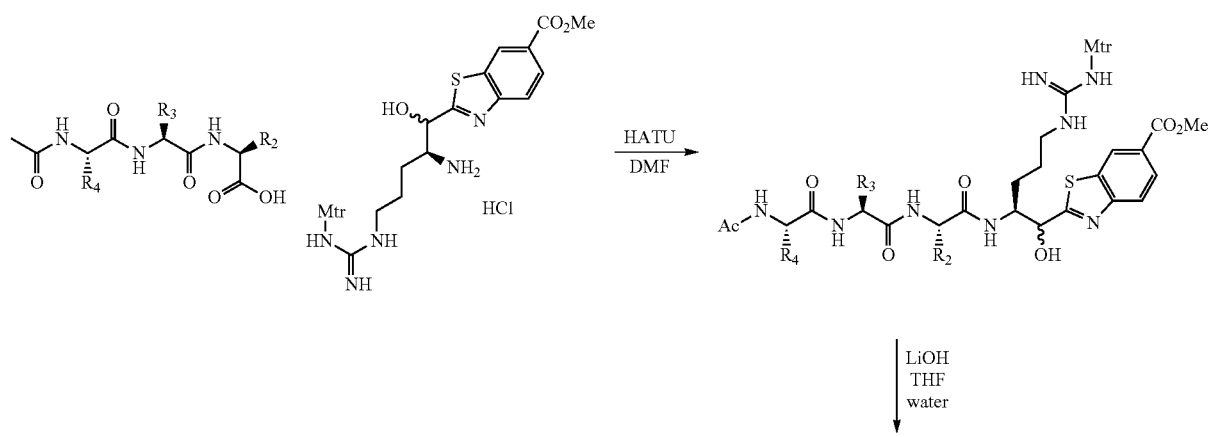
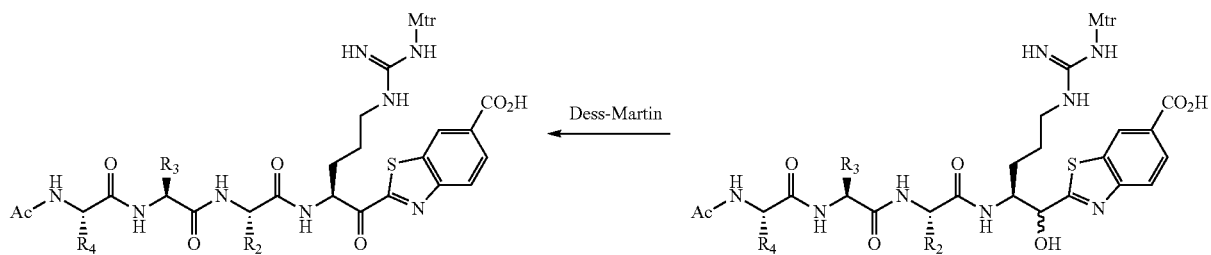

H—R (Mtr) ketobenzothiazole-(C=O)—NHBn(4-COOMe)-HCl.

The title compound was synthesized from using the same procedure as HCl.H-Arg(Mtr) ketobenzothiazole-6-CONH-Val-amide. Yield, 85 mg, MS(ESI): found: [M+H]$^+$, 695.4.

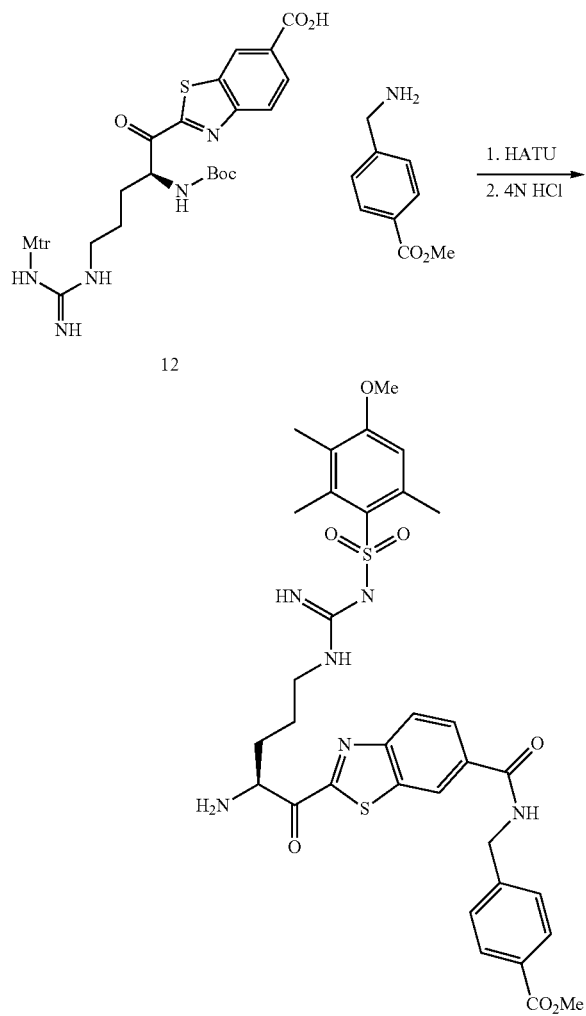

12

Ac-KRLR (SEQ ID NO: 8) ketobenzothiazole-(C=O)—NHBn(4-COOMe) (23a).

The title compound was synthesized from H—R ketobenzothiazole-(C=O)—NHBn(4-COOMe)-HCl using the same procedure as Ac-KQLR (SEQ ID NO: 1) ketobenzothiazole-6-CONH-Val-amide and was purified by HPLC. Yield: 23% over two steps. $^1$H NMR (400 MHz, METHANOL-d$_4$) δ ppm 0.90 (d, J=6.26 Hz, 3H) 0.93 (d, J=6.65 Hz, 3H) 1.37-1.95 (m, 16H) 1.99 (s, 3H) 2.13-2.28 (m, 1H) 2.87-2.97 (m, 2H) 3.13-3.23 (m, 2H) 3.25-3.32 (m, 2H) 3.89 (s, 3H) 4.21-4.28 (m, 1H) 4.32-4.41 (m, 1H) 4.41-4.50 (m, 1H) 4.69 (s, 2H) 5.56-5.66 (m, 1H) 7.50 (d, J=7.83 Hz, 2H) 8.00 (d, J=8.22 Hz, 2H) 8.09-8.13 (m, 1H) 8.27-8.32 (m, 1H) 8.62-8.67 (m, 1H). MS(ESI): found: [M+H]$^+$, 922.8.

H—R (Mtr) ketobenzothiazole-(C=O)—NHBn(3-COOMe)-HC.

The title compound was synthesized from using the same procedure as HCl.H-Arg(Mtr) ketobenzothiazole-6-CONH-Val-amide. Yield, 80 mg, MS(ESI): found: [M+H]$^+$, 695.4.

Ac-KRLR (SEQ ID NO: 8) ketobenzothiazole-(C=O)—NHBn(3-COOMe) (23b).

The title compound was synthesized from H—R ketobenzothiazole-(C=O)—NHBn(3-COOMe)-HCl using the same procedure as Ac-KQLR (SEQ ID NO: 1) ketobenzothiazole-6-CONH-Val-amide and was purified by HPLC. Yield: 19% over two steps. $^1$H NMR (400 MHz, METHANOL-d$_4$) δ ppm 0.90 (d, J=6.65 Hz, 3H) 0.93 (d, J=6.26 Hz, 3H) 1.40-1.95 (m, 16H) 1.99 (s, 3H) 2.13-2.27 (m, 1H) 2.88-2.97 (m, 2H) 3.13-3.23 (m, 2H) 3.25-3.31 (m, 2H) 3.89 (s, 3H) 4.21-4.28 (m, 1H) 4.33-4.41 (m, 1H) 4.41-4.50 (m, 1H) 4.68 (s, 2H) 5.57-5.66 (m, 1H) 7.43-7.52 (m, 1H) 7.61-7.69 (m, 1H) 7.90-7.97 (m, 1H) 8.03-8.08 (m, 1H) 8.09-8.13 (m, 1H) 8.26-8.31 (m, 1H) 8.58-8.68 (m, 1H). MS(ESI): found: [M+H]$^+$, 922.8.

Ac-KRLR (SEQ ID NO: 8) ketobenzothiazole-(C=O)—NHBn(3-COOH) (23c).

Compound 23b (0.01 g, 0.010 mmol) was taken in 0.5 mL 0.05M LiOH solution and the reaction mixture was stirred for 1.5 hours at room temperature. On completion, the pH of the reaction mixture was brought to 2 by dropwise addition of 1N HCl solution. The crude product was purified by HPLC. Yield: 44%. $^1$H NMR (400 MHz, METHANOL-d$_4$) δ ppm 0.90 (d, J=6.65 Hz, 3H) 0.93 (d, J=6.65 Hz, 3H) 1.37-1.93 (m, 16H) 1.99 (s, 3H) 2.13-2.27 (m, 1H) 2.88-2.96 (m, 2H) 3.14-3.21 (m, 2H) 3.25-3.30 (m, 2H) 4.20-4.28 (m, 1H) 4.32-4.41 (m, 1H) 4.41-4.50 (m, 1H) 4.64-4.73 (m, 2H) 5.56-5.65 (m, 1H) 7.43-7.50 (m, 1H) 7.61-7.67 (m, 1H) 7.91-7.97 (m, 1H) 8.04-8.09 (m, 1H) 8.09-8.15 (m, 1H) 8.26-8.31 (m, 1H) 8.62-8.67 (m, 1H). MS(ESI): found: [M+H]$^+$, 908.8.

Ac-KRLR (SEQ ID NO: 8) ketobenzothiazole-(C=O)—NHBn(4-COOH) (23d).

The title compound was synthesized using the same procedure as 23c starting with 23a. Yield: 44%. $^1$H NMR (400 MHz, METHANOL-d$_4$) δ ppm 0.91 (d, J=6.65 Hz, 3H) 0.93 (d, J=6.26 Hz, 3H) 1.33-1.95 (m, 16H) 1.99 (s, 3H) 2.14-2.27 (m, 1H) 2.88-2.96 (m, 2H) 3.14-3.21 (m, 2H) 3.25-3.30 (m, 2H) 4.19-4.28 (m, 1H) 4.33-4.41 (m, 1H) 4.41-4.50 (m, 1H) 4.61-4.76 (m, 2H) 5.54-5.69 (m, 1H) 7.46-7.52 (m, 2H) 7.98-8.04 (m, 2H) 8.09-8.15 (m, 1H) 8.27-8.32 (m, 1H) 8.62-8.68 (m, 1H). MS(ESI): found: [M+H]$^+$, 908.8.

Ac-S($^t$Bu)-K(Boc)-L-R(Mtr)-ketobenzothiazole-6-COOH.

Under nitrogen atmosphere at −78° C., "BuLi/Hex(2.5M) (28.5 mL, 71.4 mmol) was added dropwise into the solution of 6-carboxybenzothiazole (6.566 g, 37 mmol) in THF (450 mL) over 25 minutes. After the mixture was stirred for additional half an hour, the solution of Boc-HN-Arg(Mtr) Weinreb amide (1.633 g, 3.08 mmol) in THF (60 mL) was added slowly over 20 min at −78° C. After the addition then the mixture was stirred at −24° C. to −20° C. for 1.5 hours. The reaction was quenched with saturated aqueous NH$_4$Cl (270 mL). The layers were separated and the aqueous layer was extracted with AcOEt. The organic phase was collected and washed with water and brine, dried with Na$_2$SO$_4$, then concentrated in vacuo. To the resulting residue MeOH (50 mL) was added. The mixture was cooled at −25° C. and sodium borohydride (0.706 g, 18.7 mmol) was added. The mixture was stirred at −25-~20° C. for 1 hour. Acetone (10 mL) was added to quench the reaction and the mixture was stirred for 15 minutes then concentrated in vacuo. The residue was suspended in water, acidified to pH 3~4, and extracted with AcOEt. The organic phase was washed with brine, dried with Na$_2$SO$_4$, then concentrated in vacuo. The resulting residue was dissolved in CH$_2$Cl$_2$/MeOH (17/3 v/v, 40 mL), cooled to 0° C. Into it, (trimethylsilyl)diazomethane (2 M in hexane, 9.2 mL, 18.4 mmol) was added dropwise over 25 minutes. The mixture was stirred at 0° C. for 1 hour. MeOH (5 mL) was added and the mixture was concentrated in vacuo. The residue was purified by silica gel chromatography with CHCl$_3$/MeOH combination as eluent to give BocHN-Arg(Mtr)-CH(OH)benzothiazole-6-COOMe a (0.445 g, mixture of diastereomers) in 22% yield. MS(ESI): found: [M+H]$^+$, 664.5.

The mixture of a (0.44 g, 0.66 mmol) in TFA/CH$_2$Cl$_2$ (1/4 v/v, 18 mL) was stirred at room temperature for 2 hours. The solvents were removed and the residue was dried in vacuo to give TFA.H2N-Arg(Mtr)-CH(OH)benzothiazole-6-COOMe b (0.45 g, mixture of diastereomers) in quantitative yield. MS(ESI): found: [M+H]$^+$, 564.5.

Under nitrogen atmosphere, at 0° C. anhydrous DMF (13 mL) was added into the round bottom flask containing Ac-S($^t$Bu)-K(Boc)-L-OH (0.3650 g, 0.67 mmol) and HATU (0.255 g, 0.67 mmol). The mixture was stirred for 10 minutes, then b (0.40 g, 0.56 mmol) and N,N-diisopropylethylamine (0.49 mL, 2.8 mmol) were added sequentially. The mixture was stirred overnight while being warmed to room temperature naturally. DMF was removed and to the resulting residue, water (20 mL) was added. The precipitate formed was collected and purified by silica gel chromatography with CHCl$_3$/MeOH combination as eluent. The fractions with Ac-S($^t$Bu)-K(Boc)-L-Arg(Mtr)-CH(OH)benzothiazole-6-COOMe c (mixture of diastereomers) confirmed by LCMS [MS(ESI): found: [M+H]$^+$, 1090.8], were collected, and concentrated in vacuo. The residue c was dissolved in THF/H$_2$O (15 mL/10 mL) and LiOH (0.036 g, 1.5 mmol) was added. The mixture was stirred overnight, then concentrated. The concentrated mixture was acidified to pH 4.0 with 0.25 N HCl aqueous solution and extracted with AcOEt. The organic phase was collected, dried with Na$_2$SO$_4$ and concentrated in vacuo to give Ac-S($^t$Bu)-K(Boc)-L-Arg(Mtr)-CH(OH)benzothiazole-6-COOH d (mixture of diastereomers) (0.52 g) in 86% yield. MS(ESI): found: [M+H]$^+$, 1076.8. d was used in the next step without further purification.

Into the solution of d (0.30 g, 0.28 mmol) in CH$_2$Cl$_2$ (100 mL), Dess-Martin periodinane (DMP) (0.198 g, 0.47 mmol) was added. The mixture was stirred at room temperature for 3 hours, then additional DMP (0.12 g, 0.28 mmol) was added. The mixture was stirred overnight, then quenched with 1 M Na$_2$S$_2$O$_3$ aqueous solution. The organic phase was separated and the aqueous was extracted with CH$_2$Cl$_2$ 2 times. The organic phases were combined, dried with Na$_2$SO$_4$ and concentrated in vacuo. The resulting residue was purified by silica gel chromatography with CH$_2$Cl$_2$/MeOH combination as eluent to give the title compound Ac-S($^t$Bu)-K(Boc)-L-R(Mtr)-ketobenzothiazole-COOH (0.186 g) in 62% yield. $^1$H NMR (400 MHz, METHANOL-d$_4$) δ ppm 0.88 (d, J=5.87 Hz, 3H) 0.92 (d, J=6.26 Hz, 3H) 1.18 (s, 9H) 1.27-1.90 (m, 21H) 1.92-2.19 (m, 7H) 2.54 (s, 3H) 2.60 (s, 3H) 2.95-3.08 (m, 2H) 3.23-3.33 (m, 2H) 3.53-3.70 (m, 2H) 3.79 (s, 3H) 4.18-4.54 (m, 3H) 5.37-5.69 (m, 1H) 6.55 (s, 1H) 8.14-8.25 (m, 2H) 8.79 (s, 1H). MS(ESI): found: [M+H]$^+$, 1074.9.

Ac-SKLR (SEQ ID NO: 10)-ketobenzothiazole-6-COOH (7118).

To the crude Ac-S($^t$Bu)-K(Boc)-L-R(Mtr)-ketobenzothiazole-COOH received from the DMP oxidation of d (0.053 g, 0.049 mmol), 5 mL of TFA/thioanisole/water (95/2.5/2.5 (v/v/v)) was added. The mixture was stirred at room temperature for 4 hours. Then cold ether (40 mL) was added. The resulting precipitate, which is the crude product, was collected by centrifugation, then by decanting out carefully ether solvent. The crude product was purified by HPLC (C18, 15*150 mm column; eluent: acetonitrile/water (0.05% TFA)) to give the title compound (0.01 g) in 29% yield. $^1$H NMR (400 MHz, METHANOL-d$_4$) δ ppm 0.75-1.00 (m, 6H) 1.40-2.05 (m, 15H) 2.13-2.27 (m, 1H) 2.87-2.98 (m, 2H) 3.29-3.33 (m, 2H) 3.73-3.91 (m, 2H) 4.25-4.46 (m, 3H) 5.58-5.67 (m, 1H) 8.25-8.29 (m, 2H) 8.83 (s, 1H). MS(ESI): found: [M+H]$^+$, 706.5.

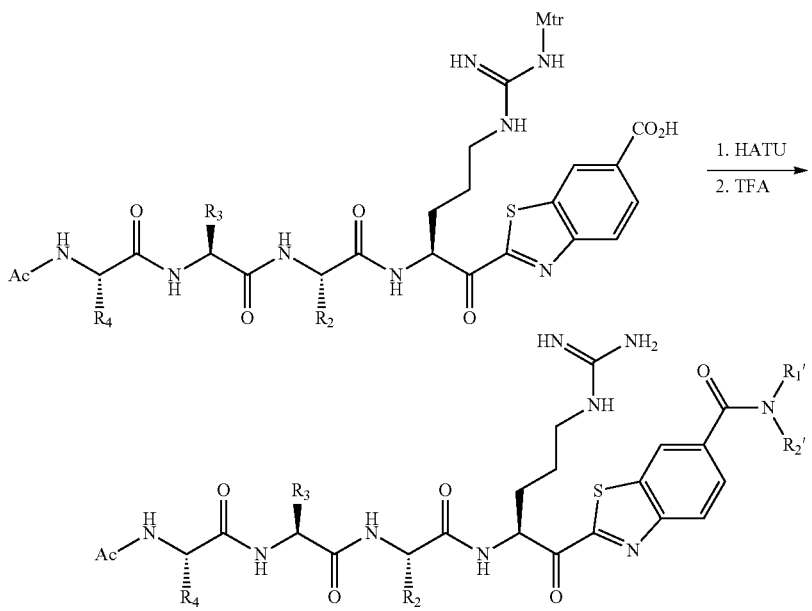

Ac-SKLR (SEQ ID NO: 10)-ketobenzothiazole-6-CONH-Phe-amide (7125).

The title compound was synthesized using the same procedure as for BocHN-Arg(Mtr) ketobenzothiazole-6-

CONH-Val-amide, starting with the coupling of Ac-S($^t$Bu)-K(Boc)-L-R(Mtr)-ketobenzothiazole-COOH and L-phenylalanine amide hydrochloride. Yield: 25%. $^1$H NMR (400 MHz, METHANOL-d$_4$) δ ppm 0.83-0.93 (m, 6H) 1.35-2.05 (m, 15H) 2.12-2.25 (m, 1H) 2.86-2.97 (m, 2H) 3.02-3.12 (m, 1H) 3.21-3.38 (m, 3H) 3.72-3.90 (m, 2H) 4.25-4.45 (m, 3H) 4.85-4.94 (m, 1H) 5.56-5.64 (m, 1H) 7.17-7.22 (m, 1H) 7.24-7.35 (m, 4H) 7.93-7.99 (m, 1H) 8.20-8.26 (m, 1H) 8.47-8.51 (m, 1H). MS(ESI): found: [M+H]$^+$, 852.7.

Ac-SKLR (SEQ ID NO: 10)-ketobenzothiazole-6-CONH-Trp-amide (7124).

The title compound was synthesized using the same procedure as for Ac-SKLR (SEQ ID NO: 10)-ketobenzothiazole-6-CONH-Phe-amide. Yield: 24%. $^1$H NMR (400 MHz, METHANOL-d$_4$) δ ppm 0.84-0.93 (m, 6H) 1.33-2.05 (m, 15H) 2.11-2.25 (m, 1H) 2.83-2.97 (m, 2H) 3.20-3.36 (m, 3H) 3.40-3.50 (m, 1H) 3.71-3.90 (m, 2H) 4.24-4.46 (m, 3H) 4.91-5.00 (m, 1H) 5.54-5.65 (m, 1H) 6.97-7.03 (m, 1H) 7.06-7.11 (m, 1H) 7.18 (s, 1H) 7.30-7.35 (m, 1H) 7.65-7.71 (m, 1H) 7.91-7.97 (m, 1H) 8.00-8.06 (m, 1H) 8.18-8.23 (m, 1H) 8.36-8.39 (m, 1H). MS(ESI): found: [M+H]$^+$, 891.7.

Ac-SKLR (SEQ ID NO: 10)-ketobenzothiazole-6-CONH-4-pyridine (7126).

The title compound was synthesized using the same procedure as for Ac-SKLR (SEQ ID NO: 10)-ketobenzothiazole-6-CONH-Phe-amide. Yield: 18%. $^1$H NMR (400 MHz, METHANOL-d$_4$) δ ppm 0.84-0.93 (m, 6H) 1.35-2.05 (m, 15H) 2.15-2.29 (m, 1H) 2.86-2.98 (m, 2H) 3.24-3.37 (m, 2H) 3.73-3.98 (m, 2H) 4.23-4.47 (m, 3H) 5.57-5.69 (m, 1H) 8.23-8.29 (m, 1H) 8.35-8.44 (m, 3H) 8.67-8.72 (m, 2H) 8.85 (s, 1H). MS(ESI): found: [M+H]$^+$, 782.7.

lethylamine (0.031 g, 0.24 mmol) were added sequentially. The mixture was stirred while being warmed to room temperature naturally. The reaction was monitored by LCMS until completion. DMF was removed and to the resulting residue, water (20 mL) was added. The precipitate formed was collected and purified by silica gel chromatography with CH$_2$Cl$_2$/MeOH combination as eluent to give Ac-S($^t$Bu)-K(Boc)-L-Arg(Mtr)-CH(OH)benzothiazole-6-CONH-4-1-Boc-piperidine e (0.088 g, mixture of diastereomers) in 86% yield. MS(ESI): found: [M+H]$^+$, 1259.0.

Into the solution of e (0.083 g, 0.066 mmol) in CH$_2$Cl$_2$ (15 mL), Dess-Martin periodinane (DMP) (0.042 g, 0.099 mmol) was added. The mixture was stirred at room temperature for 3 hours, then quenched with 1 M Na$_2$S$_2$O$_3$ aqueous solution. The organic phase was separated and the aqueous was extracted with CH$_2$Cl$_2$ 2 times. The organic phases were combined, dried with Na$_2$SO$_4$ and concentrated in vacuo. Into the resulting residue 3 mL of TFA/thioanisole/water (95/2.5/2.5(v/v/v)) was added. The mixture was stirred at room temperature for 4 hours. Then cold ether (40 mL) was added. The resulting precipitate, which is the crude product, was collected by centrifugation, then by decanting out carefully ether solvent. The crude product was purified by HPLC (C18, 15*150 mm column; eluent: acetonitrile/water (0.05% TFA)) to give the title compound Ac-SKLR (SEQ ID NO: 10)-ketobenzothiazole-6-CONH-4-piperidine (0.022 g) in 42% yield. $^1$H NMR (400 MHz, METHANOL-d$_4$) δ ppm 0.87 (d, J=6.26 Hz, 3H) 0.91 (d, J=6.26 Hz, 3H) 1.33-2.05 (m, 17H) 2.15-2.30 (m, 3H) 2.85-2.98 (m, 2H) 3.10-3.23 (m, 2H) 3.23-3.38 (m, 2H) 3.43-3.55 (m, 2H) 3.72-3.90 (m, 2H) 4.15-4.46 (m, 4H) 5.55-5.71 (m, 1H)

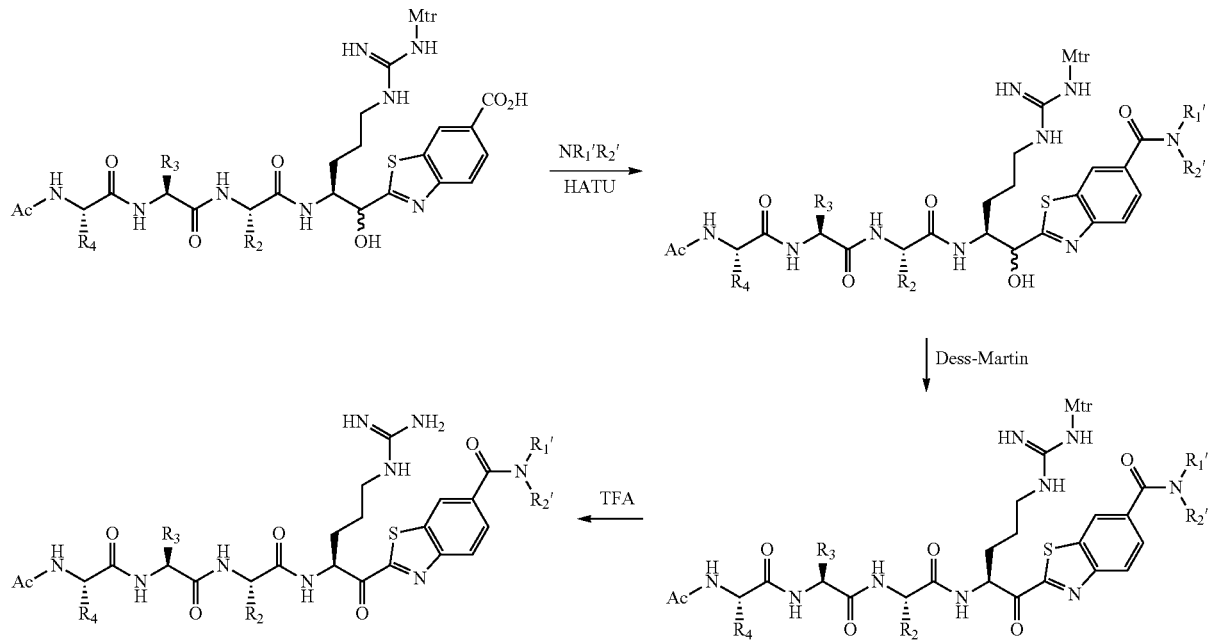

Ac-SKLR (SEQ ID NO: 10)-ketobenzothiazole-6-CONH-4-piperidine (7140).

Under nitrogen atmosphere, at 0° C. anhydrous DMF (5 mL) was added into the RB flask containing Ac-S($^t$Bu)(Boc)-L-Arg(Mtr)-CH(OH)benzothiazole-6-COOH d (0.088 g, 0.081 mmol) and HATU (0.037 g, 0.097 mmol). The mixture was stirred for 10 minutes, then 4-amino-1-Boc-piperidine (0.019 g, 0.097 mmol) and N,N-diisopropy- 8.06-8.11 (m, 1H) 8.25-8.30 (m, 1H) 8.60-8.63 (m, 1H) MS(ESI): found: [M+H]$^+$, 788.7.

Ac-SKLR (SEQ ID NO: 10)-ketobenzothiazole-6-CONH-Bn (7139).

The title compound was synthesized using the same procedure as for Ac-SKLR (SEQ ID NO: 10)-ketobenzothiazole-6-CONH-4-piperidine. Yield: 33%. $^1$H NMR (400 MHz, METHANOL-d$_4$) δ ppm 0.81-0.95 (m, 6H) 1.31-2.09

(m, 15H) 2.12-2.26 (m, 1H) 2.84-2.98 (m, 2H) 3.20-3.40 (m, 2H) 3.65-3.91 (m, 2H) 4.20-4.46 (m, 3H) 4.59-4.66 (m, 2H) 5.57-5.67 (m, 1H) 7.22-7.29 (m, 1H) 7.30-7.41 (m, 4H) 8.08-8.13 (m, 1H) 8.21-8.34 (m, 1H) 8.57-8.67 (m, 1H). MS(ESI): found: [M+H]$^+$, 795.6.

Cy5.5-KRLR (SEQ ID NO: 8)-OH (RSC-1177).

To H—K(Boc)R(Pbf)L-2-Cl Trt resin [(190 mg, 0.067 mmol), synthesized in a similar fashion to 7-AMINE)] was added 5 mL of DMF and 5 mL of DCM. After 30 min, the solvent was filtered and a solution of Cy5.5-NHS ester (71 mg, 0.10 mmol, Lumiprobe) in DMF (5 mL) and Hunig's Base (0.025 mL, 0.13 mmol) were added, then stirred overnight at room temperature. The solvent was filtered off and the resin washed thoroughly with DMF and DCM, then dried under vacuum. To the resin was added a 1:3 mixture of HFIP and DCM (15 mL) and after 45 minutes of gently shaking, the solvent was removed and then replenished. After 30 minutes of additional shaking, the solvent was removed. The combined filtrates were concentrated in vacuo to give 107 mg of crude material. Purification was achieved with 5-50% MeOH/DCM on silica gel. Yield 65 mg, 73%. Chemical Formula: $C_{76}H_{102}N_9O_{10}S$+Cl—, Exact Mass: 1332.75, MS(ESI): found: [M]$^+$, 1332.9.

Cy5.5-KRLR (SEQ ID NO: 8)-cmk (RSC-1179).

To a cooled (ice bath) solution of Cy5.5-KRLR (SEQ ID NO: 8)-OH (15 mg, 0.011 mmol) in THF (1 mL) was added N-methylmorpholine (0.011 mmol) and isopropyl chloroformate (0.011 mL, 1M solution in toluene. The reaction mixture was stirred for 10-15 minutes and then trimethylamine (0.011 mmol) and (S)—N—(N-(4-amino-6-chloro-5-oxohexyl)carbamimidoyl)-4-methoxy-2,3,6-trimethylbenzenesulfonamide hydrochloride [a E. Gherardi, W. Birchmeier, C. Birchmeier, G. Vande Woude, *Nature reviews. Cancer* 2012, 12, 89-103; b E. C. Smyth, F. Sclafani, D. Cunningham, *Oncotargets Ther* 2014, 7, 1001-1014.] (5 mg, 0.011 mmol) in DMF (0.2 mL) were added followed by stirring for an additional 2 hours. The solvent was removed and then 1.5 mL of cleavage cocktail (38:1:1 TFA/water/thioanisole) was added to the resin. After gentle shaking overnight, the solvent was removed in vacuo, triturated in toluene, and then concentrated in vacuo. The residue was purified by C18 reverse phase HPLC to give 10 mg of crude product which was re-purified to give 4 mg of pure title compound as the TFA salt. Chemical Formula: $C_{65}H_{91}ClN_{13}O_5$+Cl—, Exact Mass: 1168.69, MS(ESI): found: [M]$^+$, 1168.8.

Cy5.5-KRLR (SEQ ID NO: 8)-kbt (RSC-1178).

Synthesized in a similar manner to Ac-KQLR (SEQ ID NO: 1) kbt (3) from Cy5.5-KRLR (SEQ ID NO: 8)-OH.

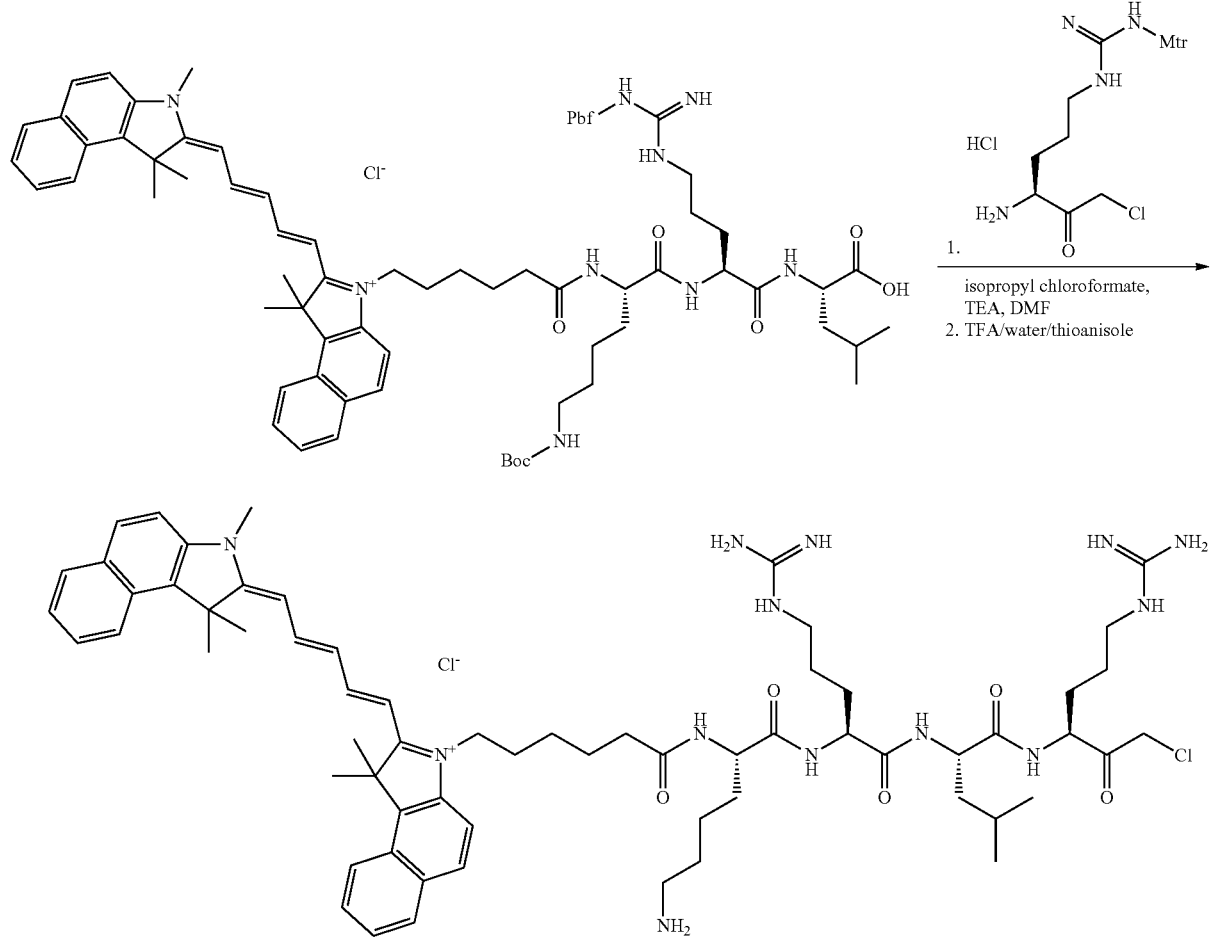

Chemical Formula: $C_{71}H_{93}N_{14}O_5S+Cl-$, Exact Mass: 1253.72, MS(ESI): found: $[M]^+$, 1253.7.

Example 6. Inhibition Studies with Polypeptide Ketobenzothiazoles

Fluorescent inhibitor and chromogenic proteolytic assays were performed in general accordance with the procedures described in Example 4 for compounds prepared in Examples 5 and 6.

The results of the assays are presented in Table 6.1. The results show increased potency of 2-fold of the ketobenzothiazoles over thiazole 5. More importantly when we substitute a Val on the benzothiazole ring 36c as in 8, we increase the HGFA potency another two-fold (Ki 13 nM) but decreased matriptase activity >10-fold (Ki 7 nM) and >3-fold for hepsin (Ki 0.3 nM). Ac-SKLR (SEQ ID NO: 10)-kbt V amide (9) showed a 4-fold enhancement in HGFA potency with no effect on hepsin or matriptase. We discovered Ac-KQLR (SEQ ID NO: 1)-kbt (7) improves potency 2-fold and further substitution of the benzothiazole ring with Valine, Ac-KQLR (SEQ ID NO: 1)-kbt V amide (8) increases potency another 2-fold for HGFA (Ki 13 nM) but decreased matriptase activity >10-fold (Ki 7 nM) and >3-fold for hepsin ($K_i$ 0.3 nM). This result demonstrates that these inhibitor compounds have improved selectivity for HGFA.

TABLE 6.1

| | | Fluorogenic Assay | | |
| --- | --- | --- | --- | --- |
| Compound No. | Y-P$_4$-P$_3$-P$_2$-P$_1$-Z | HGFA Ki (nM) | Matriptase Ki (nM) | Hepsin Ki (nM) |
| 7185-1 | Fmoc-AR-kbt | 7983.5 | 0.5 | 272.37 |
| 7185-2 | Fmoc-RR-kbt | 8633.5 | 2.0 | 99.92 |
| 7185-3 | Fmoc-NR-kbt | >20000 | 84.1 | 1.92 |
| 7185-4 | Fmoc-DR-kbt | >20000 | 397.9 | 232.92 |
| 7185-6 | Fmoc-QR-kbt | 6827 | 1.6 | 170.07 |
| 7185-7 | Fmoc-ER-kbt | >20000 | 8.4 | 337.63 |
| 7185-8 | Fmoc-GR-kbt | 9375 | 0.1 | 831.00 |
| 7185-9 | Fmoc-HR-kbt | 6356.19 | 66.7 | 268.07 |
| 7185-10 | Fmoc-IR-kbt | 6466.05 | 657.1 | 297.32 |
| 7185-11 | Fmoc-LR-kbt | 449.776 | 425.3 | 114.90 |
| 7185-12 | Fmoc-KR-kbt | >20000 | 0.2 | 159.25 |
| 7187-13 | Fmoc-MR-kbt | 1208.00 | 62.1 | 489.97 |
| 7187-14 | Fmoc-FR-kbt | 963.50 | 1281.5 | 777.88 |
| 7187-15 | Fmoc-PR-kbt | >20000 | 40.4 | 776.25 |
| 7187-16 | Fmoc-SR-kbt | >20000 | 90.00 | 885.50 |
| 7188-17 | Fmoc-TR-kbt | >20000 | 1217.00 | 436.75 |
| 7188-18 | Fmoc-WR-kbt | 3197.00 | 823.5 | 410.62 |
| 7188-19 | Fmoc-YR-kbt | 2961.00 | 331.6 | 217.38 |
| 7188-20 | Fmoc-VR-kbt | 4633.83 | 1488.0 | 313.60 |
| 1-13A1 | H-WFR-kbt | 5681.25 | 1871.5 | 240.15 |
| 1-18A1 | H-dWFR-kbt | 2250 | 135.3 | 369.80 |
| 1-15A1 | H-dWLR-kbt | 127.98 | 34.6 | 3.58 |
| 1-45A1 | H-WFR-kbt-COOH | 981 | 232 | 1.41 |
| 7171 | H-RLR-kbt | 83.07 | 3.3 | 0.50 |
| 1-56A1 | H-WLR-kbt-COOH | 1379 | 1206.5 | 446.30 |
| 1-57A1 | H-dWLR-kbt-COOH | 345.9 | 363.6 | 136.50 |
| 1-54A1 | H-His(Bom)-WLR-kbt | 3711.83 | 1549.8 | 2.08 |
| 1-58A1 | H-His(Bom)-dWLR-kbt | 2282.17 | 1504.7 | 1.13 |
| 7182 | H-LLR-kbt-Val-NH$_2$ | 82.09 | 23.6 | 0.88 |

TABLE 6.1-continued

| Compound No. | Y-$P_4$-$P_3$-$P_2$-$P_1$-Z | Fluorogenic Assay | | |
|---|---|---|---|---|
| | | HGFA Ki (nM) | Matriptase Ki (nM) | Hepsin Ki (nM) |
| 7181 | H-WLR-kbt-Val-$NH_2$ | 73.89 | 49.2 | 1.31 |
| 7180 | H-RLR-kbt-Val-$NH_2$ | 12.50 | 4.2 | 0.44 |
| 7170 | H-WLR-kbt | 103.98 | 33.5 | 1.52 |
| 7115 | Ac-KRLR(SEQ ID NO: 8)-kbt-Val-$NH_2$ | 5.83 | 7.415 | 0.2265 |
| 7054 | Ac-KRLR(SEQ ID NO: 8)-kbt | 6.00 | 0.540 | 0.112 |
| 7117 | H-WRLR(SEQ ID NO: 9)-kbt | 8.75 | 3.79 | 0.12 |
| 7055 | Ac-KQLR(SEQ ID NO: 1)kbt-Val-$NH_2$ | 12.00 | 6.98 | 0.29 |
| 7116 | Ac-SKLR(SEQ ID NO: 10)-kbt-Val-$NH_2$ | 12.98 | 10.3 | 0.19 |
| 7124 | Ac-SKLR(SEQ ID NO: 10)-kbt-Trp-$NH_2$ | 15.75 | 3.74 | 0.098 |
| 7125 | Ac-SKLR(SEQ ID NO: 10)-kbt-Phe-$NH_S$ | 17.28 | 6.26 | 0.14 |
| 7006 | Ac-KQLR(SEQ ID NO: 1)-kbt | 30.00 | 0.550 | 0.09 |
| 7126 | Ac-SKLR(SEQ ID NO: 10)-kbt-4-pyridinylamide | 31.76 | 3.95 | 0.14 |
| 7053 | Ac-SKLR(SEQ ID NO: 10)-kbt | 33.00 | 3.05 | 0.16 |
| 7063 | Ac-FLFR(SEQ ID NO: 19)-kbt | 114.00 | 3.60 | 1.44 |
| 7118 | Ac-SKLR(SEQ ID NO: 10)-kbt-COOH | 131.97 | 54.8 | 0.173 |
| 7064 | Ac-WLFR(SEQ ID NO: 20)-kbt | 133.00 | 5.960 | 0.347 |
| 7139 | Ac-SKLR(SEQ ID NO: 10)-kbt-benzylamide | 9.10 | 0.360 | 0.80 |
| 7140 | Ac-SKLR(SEQ ID NO: 10)-kbt-4-piperidinylamide | 7.70 | 1.28 | 0.20 |
| 7165 | Ac-KRLR(SEQ ID NO: 8)-kbt-Phe-COOH | 6.07 | 5.14 | 0.37 |
| 7164 | Ac-KRLR(SEQ ID NO: 8)-kbt-Benzyl-3-COOH | 3.33 | 3.60 | 0.30 |
| 7159 | Ac-KRLR(SEQ ID NO: 8)-kbt-Benzyl-3-COOMe | 7.76 | 1.80 | 0.36 |
| 7158 | Ac-KRLR(SEQ ID NO: 8)-kbt-Benzyl-4-COOMe | 5.85 | 0.98 | 0.26 |
| 1179 | Cy5.5-KRLR(SEQ ID NO: 8)-cmk | 34.14 | 172.2 | 323.53 |
| 1178-2 | Cy5.5-KRLR(SEQ ID NO: 8)-kbt | 608 | 87.5 | 3.89 |

The results of selectivity assays are presented in Table 6.2.

TABLE 6.2

| Compound No. | Y-$P_4$-$P_3$-$P_2$-$P_1$-Z | Fluorogenic Assay | | |
|---|---|---|---|---|
| | | Thrombin Ki (nM) | Factor Xa Ki (nM) | Trypsin Ki (nM) |
| 7118 | Ac-SKLR(SEQ ID NO: 10)-kbt-COOH | >2000 | 1247 | 0.03 |
| 7006 | Ac-KQLR(SEQ ID NO: 1)-kbt | >20000 | 129 | 0.24 |
| 7055 | Ac-KQLR(SEQ ID NO: 1)-kbt-Val-$NH_2$ | 3212 | 66 | 0.07 |
| 7053 | Ac-SKLR(SEQ ID NO: 10)-kbt | >20000 | 1901 | 0.16 |
| 7116 | Ac-SKLR(SEQ ID NO: 10)-kbt-Val-$NH_2$ | 4505 | 385 | 0.34 |
| 7117 | H-WRLR(SEQ ID NO: 9)-kbt | 4890 | 2.4 | 0.96 |
| 7063 | Ac-FLFR(SEQ ID NO: 19)-kbt | >20000 | 13.1 | 0.27 |
| 7054 | Ac-KRLR(SEQ ID NO: 8)-kbt | >20000 | 91.9 | 0.82 |

TABLE 6.2-continued

| Compound No. | Y-P$_4$-P$_3$-P$_2$-P$_1$-Z | Fluorogenic Assay | | |
| --- | --- | --- | --- | --- |
| | | Thrombin Ki (nM) | Factor Xa Ki (nM) | Trypsin Ki (nM) |
| 7064 | Ac-WLFR(SEQ ID NO: 20)-kbt | >20000 | 1.0 | |
| 7115 | Ac-KRLR(SEQ ID NO: 8)-kbt-Val-NH$_2$ | 1560 | 17.0 | |
| 7124 | Ac-SKLR(SEQ ID NO: 10)-kbt-Trp-NH$_2$ | 1231 | 163 | 0.02 |
| 7125 | Ac-SKLR(SEQ ID NO: 10)-kbt-Phe-NH$_2$ | 3640 | 544 | 0.27 |
| 7126 | Ac-SKLR(SEQ ID NO: 10)-kbt-pyridine-NH$_2$ | 3431 | 221 | 1.06 |
| 7139 | Ac-SKLR(SEQ ID NO: 10)-kbt-benzyl | 2467 | 190 | 0.05 |
| 7140 | Ac-SKLR(SEQ ID NO: 10)-kbt-piperidine | 2948 | 447 | 0.41 |
| 7158 | Ac-KRLR(SEQ ID NO: 8)-kbt-benzyl-4-COOMe | 20.92 | 9.0 | 0.05 |
| 7159 | Ac-KRLR(SEQ ID NO: 8)-kbt-Benzyl-3-COOMe | 85.38 | 14 | 0.04 |
| 7164 | Ac-KRLR(SEQ ID NO: 8)-kbt-benzyl-4-COOH | 1618 | | |
| 7170 | H-WLR-kbt | 457.00 | 532.00 | 0.050 |
| 7171 | H-RLR-kbt | 8198 | 56 | 0.13 |
| 7182 | H-LLR-Val-NH$_2$ | 101.4 | 159 | 0.61 |
| 7181 | H-WLR-kbt-Val-NH$_2$ | 41.04 | 159 | 0.01 |
| 7180 | H-RLR-kbt-Val-NH$_2$ | 548 | 18 | 0.31 |
| 7165 | Ac-KRLR(SEQ ID NO: 8)-kbt-benzyl-3-COOH | 1944 | 20.2 | 1.06 |
| 7187-14 | Fmoc-FR-kbt | >2000 | 28.4 | 14.350 |
| 7185-11 | Fmoc-LR-kbt | 995 | 410 | 19.78 |

Example 7. Inhibition Studies with Cyclic Peptides

Fluorescent inhibitor and chromogenic proteolytic assays were performed in general accordance with the procedures described in Example 4 for compounds prepared in Example 3. Table 7.1 presents the results for a cyclic peptide compound 7074.

TABLE 7.1

| Compound | Y-P$_5$-P$_4$-P$_3$-P$_2$-P$_1$-Z | Fluorogenic Assay | | |
| --- | --- | --- | --- | --- |
| | | HGFA Ki (nM) | Matriptase Ki (nM) | HGFA Ki (nM) |
| 7074 | H-cyclo(KQD)RR-kt | 5941.67 | 0.71 | 1.55 |

Example 8. Synthesis of Benzamidine Inhibitor Compounds

The benzamidine inhibitors listed in Table 8.1 were synthesized in accordance with the general scheme 8A shown below and the procedures described below. Phenylalanine naphthyl sulfonamides were synthesized in accordance with general scheme B and the procedures described below.

TABLE 8.1
Benzamidine inhibitors.
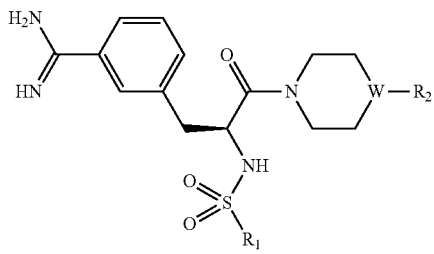
| Compound | R₁ | R₂ | W |
|---|---|---|---|
| 16 | 2-naphthyl | phenyl | C |
| 17a | 2-naphthyl | —C(O)NH-benzyl | N |
| 18* | 4-methylphenyl | —NH-C(O)-O-benzyl | C |
| 25a | 2-naphthyl | —C(O)NH-CH₂-(4-bromophenyl) | N |
| 25b | 4-methylphenyl | phenyl | C |
| 25c* | 4-methylphenyl | —C(O)NH-CH₂CH₂-phenyl | C |
| 25d | 2-naphthyl | —C(O)NH-hexyl | N |
| 25e | 2-naphthyl | —C(O)-benzothiophen-3-yl | N |

TABLE 8.1-continued
| Benzamidine inhibitors. |
| --- |
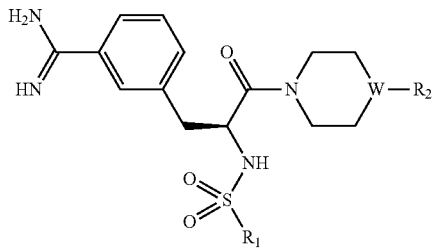
| Compound | R₁ | R₂ | W |
| --- | --- | --- | --- |
| 25f* | 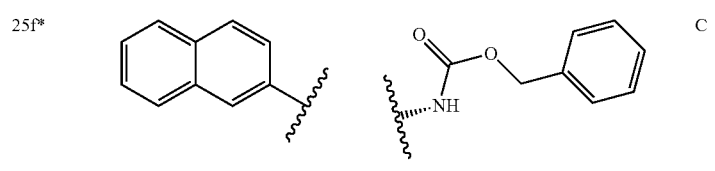 | | C |
| 25g | 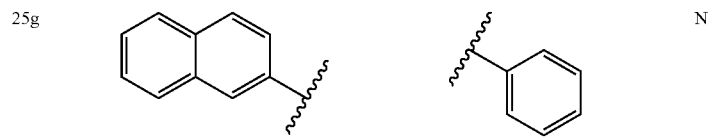 | | N |
| 25h | 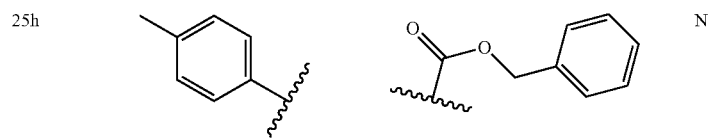 | | N |
| 26 | 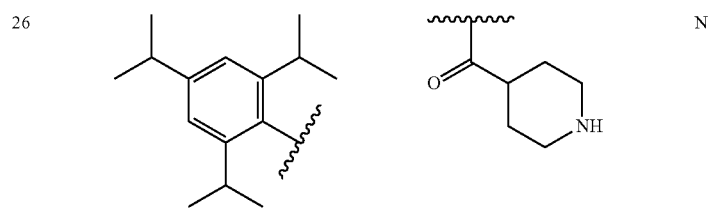 | | N |
| 27 | 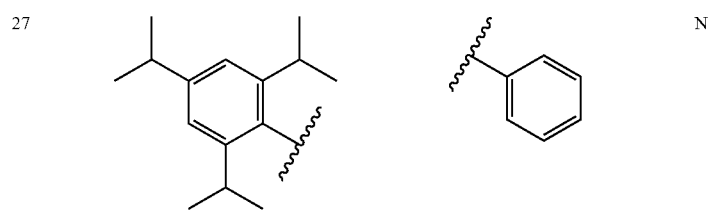 | | N |
*R₂ is substituted on the 3-position of the piperidine ring.

Scheme 8A. Synthesis of 3-amidinophenylalanine sulfonamide analogs
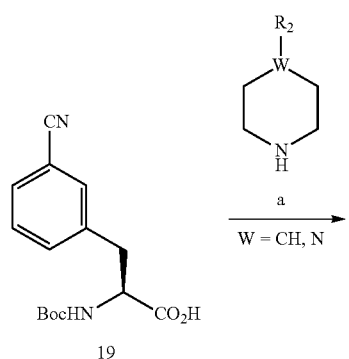
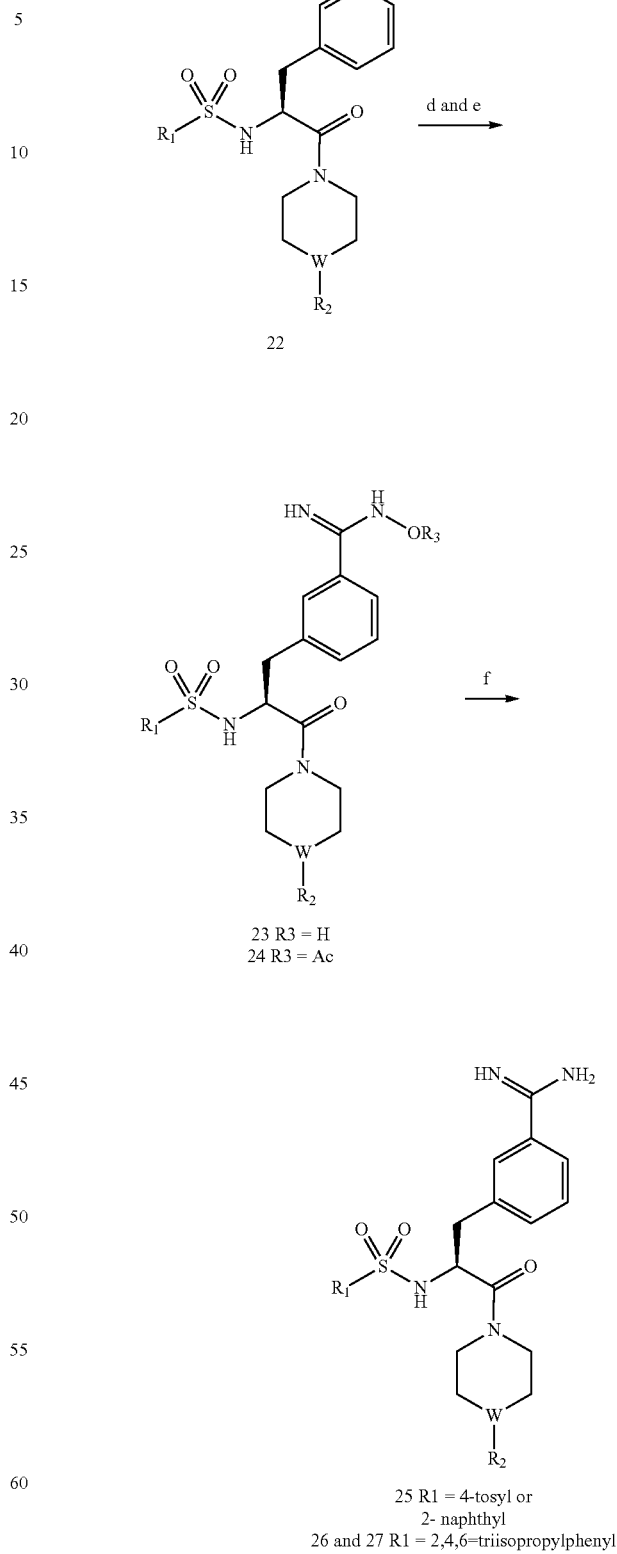
Reagents and conditions in Scheme A are as follows a) HATU, THF (or DMF), DIPEA; b) 4N HCl in 1,4-doxane; c) R₁SO₂Cl, DMAP, pyridine, THF; d) i. NH₂OH—HCl, K₂CO₃ (or DIPEA), EtOH; e) Ac₂O, AcOH; f) Zn, AcOH.

Scheme 8B. Synthesis of 3-amidinophenylalanine sulfonamide analogs

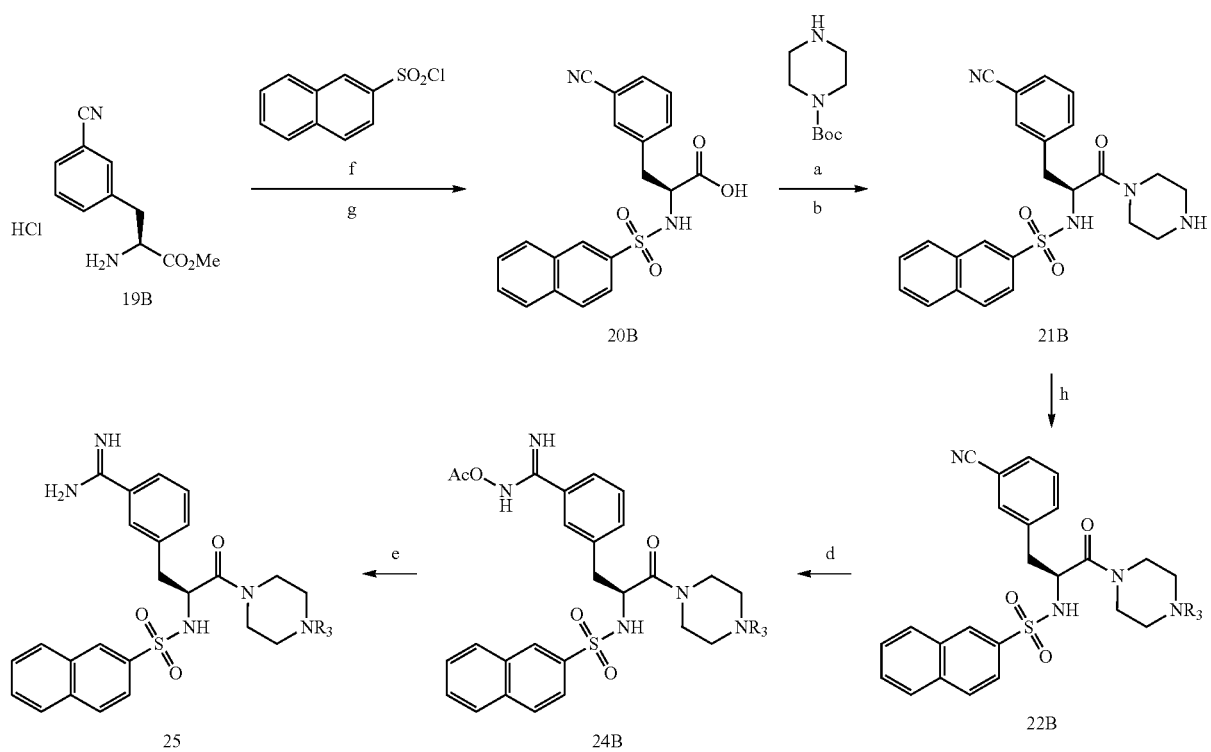

Reagents and conditions in Scheme B are as follows a) HATU, THF (or DMF), DIPEA; b) 4N HCl in 1,4-doxane; d) i. NH$_2$OH—HCl, K$_2$CO$_3$ (or DIPEA), EtOH; ii. Ac$_2$O, AcOH; e) Zn, AcOH; f) DMAP, pyridine, THF; g) LiOH, THF; h) HATU, RCO$_2$H (R$_3$ = COR) or R—N═C═O (R$_3$ = CONHR).

General Procedure A: General Procedure for the Synthesis of Amides (20):

A solution of N-Boc-3-cyanophenylalanine (19) in dry DMF (0.5 M) was added Hunig's Base (4.0 equiv) followed by HATU (1.3 equiv). The yellow solution was allowed to stir for 10 minutes and was then added amine (1.3 equiv). The resulting mixture was stirred at room temperature. After two hours, the reaction was checked by LCMS and was complete. The reaction mixture was diluted with ethyl acetate, washed with water (1×), brine (2×), dried (MgSO$_4$), filtered and concentrated to oil. The crude product was purified by MPLC (0-75% hexanes/ethyl acetate) to afford pure product.

General Procedure B: General procedure for BOC deprotection (21):

A solution of N-Boc protected amide in dioxane (0.4 M) was added 4.0 M HCl in dioxane (10 equiv). The resulting mixture was allowed to stir at room temperature. After 4 hours, the reaction was checked by LCMS and was complete. The solvent was removed under reduced pressure to afford pure product.

General Procedure C: General procedure for sulfonamide formation (22):

A mixture of amide in THF (0.2 M) was added Hunig's Base (10 equiv) and the mixture was stirred until all solids dissolved. The solution was then added DMAP (10 mol %) followed by arylsulfonyl chloride (1.1 equiv) and stirred at room temperature. After 2 hours the reaction was checked by LCMS and was complete. The reaction was diluted with ethyl acetate, washed with saturated NaHCO$_3$ (2×), brine (1×), dried (MgSO$_4$), filtered and concentrated under reduced pressure. The crude material was purified via MPLC (0-75% ethyl acetate/hexanes) to afford pure product as a solid.

General Procedure D: General Procedure for Formation of the Amidoxime (23):

A suspension of sulfonamide in dry ethanol (0.2M) was added hydroxylamine hydrochloride (2.2 equiv) followed by Hunig's base (2.3 equiv). The resulting mixture was heated to 75° C. for approximately 3 hours which resulted in a homogeneous solution. The reaction mixture was allowed to cool to room temperature, checked by LCMS and was complete. The solvent was removed under reduced pressure to afford the crude amidoxime intermediate as a white solid.

General Procedure E: General Procedure for Acetylation of Amidoxime (24).

A solution of crude amidoxime in acetic acid (0.2 M) was added acetic anhydride at room temperature. The resulting mixture was allowed to stir at room temperature. After approximately 2 hours the reaction was checked by LCMS and was complete. The solvent was removed under reduced pressure to afford the crude product.

General Procedure F: General procedure for preparation of amidines (25) and (26):

A solution of O-acetylamidoxime in acetic acid (0.2 M) was added zinc dust (15 equiv) at room temperature. The resulting suspension was stirred for 3 hours at room temperature. The reaction was checked by LCMS and was complete. The mixture was filtered and concentrated under reduced pressure to give the crude product as an oil. The crude product was purified via reverse phase HPLC (5-65% acetonitrile/water/0.05% trifluoroacetic acid) to afford pure product as a white solid after lyophilization.

(S)-3-(2-(Naphthalene-2-sulfonamido)-3-oxo-3-(4-phenylpiperidin-1-yl)propyl)benzimidamide (16)

Prepared from N-acetoxy-3-[(2S)-2-[(2-naphthylsulfonyl)amino]-3-oxo-3-(4-phenylpiperidin-1-yl)propyl]benzenecarboximidamide using General Procedure F. Purified by reversed-phase HPLC (5-75% acetonitrile/water/0.05% TFA), Yield (0.092 g, 52.5%). $^1$H NMR (300 MHz, DMSO-d$_6$) δ 9.40 (s, 2H), 9.26 (s, 2H), 8.23-8.50 (m, 2H), 7.94-8.10 (m, 2H), 7.56-7.78 (m, 4H), 7.35-7.56 (m, 2H), 7.07-7.33 (m, 3H), 6.96 (d, J=7.42 Hz, 1H), 6.78 (d, J=7.14 Hz, 1H), 4.49-4.79 (m, 1H), 3.82-4.21 (m, 2H), 3.61-3.79 (m, 1H), 3.41-3.56 (m, 2H), 2.89-3.06 (m, 1H), 2.72-2.89 (m, 1H), 2.59 (t, J=12.22 Hz, 1H), 1.31-1.64 (m, 2H), 0.75-1.08 (m, 1H), 0.38-0.67 (m, 1H). LRMS (ESI) $C_{31}H_{32}N_4O_3S$ found [M+H]: 541.2.

N-Acetoxy-3-[(2S)-2-[(2-naphthylsulfonyl)amino]-3-oxo-3-(4-phenylpiperidin-1-yl)propyl]benzenecarboximidamide Prepared from N-hydroxy-3-[(2S)-2-[(2-naphthylsulfonyl)amino]-3-oxo-3-(4-phenylpiperidin-1-yl)propyl]benzenecarboximidamide using General Procedure E. Purification by MPLC (0-90% EtOAc/hexanes). Yield (0.17 g, 47.7%). LRMS (ESI) $C_{33}H_{34}N_4O_5S$ found [M+H]: 599.2.

N-Hydroxy-3-[(2S)-2-[(2-naphthylsulfonyl)amino]-3-oxo-3-(4-phenylpiperidin-1-yl)propyl]benzenecarboximidamide Prepared from tert-butyl (S)-(3-(3-cyanophenyl)-1-oxo-1-(4-phenylpiperazin-1-yl)propan-2-yl)carbamate (0.312 g, 0.589 mmol) using General Procedure D. LRMS (ESI) $C_{31}H_{32}N_4O_4S$ found [M+H]: 557.2.

N-[(2S)-3-(3-Cyanophenyl)-1-oxo-1-(4-phenylpiperidin-1-yl)propan-2-yl]naphthalene-2-sulfonamide Prepared from 3-[(2S)-2-amino-3-oxo-3-(4-phenylpiperidin-1-yl)propyl]benzonitrile (4.1 g, 20.1 mmol) using General Procedure C. Yield (0.312 g, 79%). LRMS (ESI) $C_{31}H_{29}N_3O_3S$ found [M+H]: 524.2.

3-[(2S)-2-Amino-3-oxo-3-(4-phenylpiperidin-1-yl)propyl]benzonitrile

Prepared from tert-butyl [(2S)-3-(3-cyanophenyl)-1-oxo-1-(4-phenylpiperidin-1-yl)propan-2-yl]carbamate (0.67 g, 1.54 mmol) using General Procedure B. LRMS (ESI) $C_{21}H_{23}N_3O$ found [M+H]: 334.2.

tert-butyl [(2S)-3-(3-Cyanophenyl)-1-oxo-1-(4-phenylpiperidin-1-yl)propan-2-yl]carbamate Prepared from N-Boc-3-cyanophenylalanine (19) (0.56 g, 1.81 mmol) and N-phenylpiperidine (0.32 g, 2.01 mmol) using General Procedure A. Purified by MPLC (0-75% EtOAc/Hexanes). Yield (0.67 g, 85%). LRMS (ESI) $C_{26}H_{31}N_3O_3$ found [M+H]: 434.2.

(S)-3-(2-(Naphthalene-2-sulfonamido)-3-oxo-3-(4-phenylpiperazin-1-yl)propyl)benzimidamide (25g)

Prepared from (S)—N-acetoxy-3-(2-(naphthalene-2-sulfonamido)-3-oxo-3-(4-phenylpiperazin-1-yl)propyl)benzimidamide (0.123 g, 0.205 mmol) using General Procedure F. Purified by reversed-phase HPLC (5-60% acetonitrile/water/0.05% TFA), Yield (0.069 g, 54.7%). $^1$H NMR (300 MHz, DMSO-d$_6$) δ 9.42 (s, 2H), 9.29 (s, 2H), 8.22-8.51 (m, 2H), 7.85-8.12 (m, 3H), 7.36-7.74 (m, 7H), 7.08-7.28 (m, 2H), 6.61-6.90 (m, 3H), 4.49-4.75 (m, 1H), 3.37-3.61 (m, 1H), 3.19-3.37 (m, 1H), 3.03-3.18 (m, 1H), 2.96 (dd, J=7.00, 13.32 Hz, 2H), 2.52-2.89 (m, 4H), 2.25-2.45 (m, 1H). LRMS (ESI) $C_{30}H_{31}N_5O_3S$ found [M+H]: 542.2.

(S)—N-Acetoxy-3-(2-(naphthalene-2-sulfonamido)-3-oxo-3-(4-phenylpiperazin-1-yl)propyl)benzimidamide Prepared from N-hydroxy-3-[(2S)-2-[(2-naphthylsulfonyl)amino]-3-oxo-3-(4-phenylpiperidin-1-yl)propyl]benzenecarboximidamide (0.26 mmol) using General Procedure E. Purification by MPLC (0-40% EtOAc/hexanes). Yield (0.123 g, 79%). LRMS (ESI) $C_{32}H_{33}N_5O_5S$ found [M+H]: 600.2.

(S)—N-Hydroxy-3-(2-(naphthalene-2-sulfonamido)-3-oxo-3-(4-phenylpiperazin-1 yl)propyl)benzimidamide Prepared from (S)—N-(3-(3-cyanophenyl)-1-oxo-1-(4-phenylpiperazin-1-yl)propan-2-yl)naphthalene-2-sulfonamide (0.312 g, 0.589 mmol) using General Procedure D. LRMS (ESI) $C_{30}H_{31}N_5O_4S$ found [M+H]: 558.2.

(S)—N-(3-(3-Cyanophenyl)-1-oxo-1-(4-phenylpiperazin-1-yl)propan-2-yl)naphthalene-2-sulfonamide Prepared from (S)-3-(2-amino-3-oxo-3-(4-phenylpiperazin-1-yl)propyl)benzonitrile (0.121 g, 0.327 mmol) using General Procedure C. Purified by MPLC (0-75% EtOAc/Hexanes). Yield (0.133 g, 79.5%). LRMS (ESI) $C_{30}H_{28}N_4O_3S$ found [M+H]: 525.2.

(S)-3-(2-Amino-3-oxo-3-(4-phenylpiperazin-1-yl)propyl)benzonitrile

Prepared from tert-butyl [(2S)-3-(3-cyanophenyl)-1-oxo-1-(4-phenylpiperidin-1-yl)propan-2-yl]carbamate (0.347 g, 0.80 mmol) using General Procedure B. Purified product obtained by trituration in ether followed by filtration and drying. Yield (0.29 g, 97%). LRMS (ESI) $C_{20}H_{22}N_4O$ found [M+H]: 335.2.

tert-butyl (S)-(3-(3-Cyanophenyl)-1-oxo-1-(4-phenylpiperazin-1-yl)propan-2-yl)carbamate Prepared from N-Boc-3-cyanophenylalanine (19) (0.24 g, 0.83 mmol) and N-phenylpiperazine (0.92 mmol) using General Procedure A. Purified by MPLC (0-75% EtOAc/Hexanes). Yield (0.35 g, 96%). LRMS (ESI) $C_{25}H_{30}N_4O_3$ found [M+H]: 435.2.

(S)-Benzyl 4-(3-(3-carbamimidoylphenyl)-2-(4-methylphenylsulfonamido)propanoyl)piperazine-1-carboxylate (25h)

Prepared from benzyl (S)-4-(3-(3-(N-acetoxycarbamimidoyl)phenyl)-2-((4-methylphenyl)sulfonamido)propanoyl)piperazine-1-carboxylate (0.141 g, 0.228 mmol) using General Procedure F. Purified by reversed-phase HPLC (5-75% acetonitrile/water/0.05% TFA), Yield (0.058 g). $^1$H NMR (300 MHz, DMSO-d$_6$) δ 9.39 (br. s., 2H), 9.29 (br. s., 2H), 8.15 (d, J=9.34 Hz, 1H), 7.63-7.82 (m, 2H), 7.22-7.62 (m, 10H), 5.07 (s, 2H), 4.37-4.63 (m, 1H), 3.44-3.71 (m, 2H), 3.10-3.29 (m, 3H), 2.84-3.10 (m, 3H), 2.60-2.84 (m, 2H), 2.32 (s, 3H). LRMS (ESI) $C_{29}H_{33}N_5O_5S$ found [M+H]: 564.2.

Benzyl (S)-4-(3-(3-(N-acetoxycarbamimidoyl)phenyl)-2-((4-methylphenyl)sulfonamido)propanol)piperazine-1-carboxylate Prepared from benzyl (S)-4-(3-(3-(N-hydroxycarbamimidoyl)phenyl)-2-((4-methylphenyl)sulfonamido)propanoyl)piperazine-1-carboxylate (0.132 g, 0.228 mmol) using General Procedure E. LRMS (ESI) $C_{31}H_{35}N_5O_7S$ found [M+H]: 622.2.

Benzyl (S)-4-(3-(3-(N-hydroxycarbamimidoyl)phenyl)-2-((4-methylphenyl)sulfonamido)propanol)piperazine-1-carboxylate Prepared from benzyl (S)-4-(3-(3-cyanophenyl)-2-((4-methylphenyl)sulfonamido)propanoyl)piperazine-1-carboxylate (0.24 g, 0.228 mmol) using General Procedure D. LRMS (ESI) $C_{29}H_{33}N_5O_6S$ found [M+H]: 580.2.

Benzyl (S)-4-(3-(3-cyanophenyl)-2-((4-methylphenyl)sulfonamido)propanoyl)piperazine-1-carboxylate Prepared from benzyl (S)-4-(2-amino-3-(3-cyanophenyl)propanoyl)piperazine-1-carboxylate (0.243 g, 0.522 mmol) using General Procedure C. Purified by MPLC (0-75% EtOAc/Hexanes). Yield (0.124 g, 45.6%). LRMS (ESI) $C_{29}H_{30}N_4O_5S$ found [M+H]: 547.2.

Benzyl (S)-4-(2-amino-3-(3-cyanophenyl)propanoyl)piperazine-1-carboxylate

Prepared from benzyl (S)-4-(2-((tert-butoxycarbonyl)amino)-3-(3-cyanophenyl)propanoyl)piperazine-1-carboxylate (0.257 g, 0.522 mmol) using General Procedure B. LRMS (ESI) $C_{22}H_{24}N_4O_3$ found [M+H]: 393.2.

Benzyl (S)-4-(2-((tert-butoxycarbonyl)amino)-3-(3-cyanophenyl)propanoyl)piperazine-1-carboxylate Prepared from N-Boc-3-cyanophenylalanine (19) (1.02 g, 3.51 mmol) and N-carboxybenzyl piperazine (3.89 mmol) using General Procedure A. Purified by MPLC (0-80% EtOAc/Hexanes). Yield (0.257 g). LRMS (ESI) $C_{27}H_{32}N_4O_5$ found [M+H]: 493.2.

(S)-3-(3-Cyanophenyl)-2-(naphthalene-2-sulfonamido)propanoic acid (20B)

Prepared from methyl (S)-2-amino-3-(3-cyanophenyl)propanoate (19B) (4.1 g, 20.1 mmol) using General Procedure C to give methyl (S)-3-(3-cyanophenyl)-2-(naphthalene-2-sulfonamido)propanoate. Yield (8.19 g). LRMS (ESI) $C_{21}H_{18}N_2O_4S$ found [M+H]: 395.1. A solution of the crude ester in 1M HCl/AcOH (2:1) was refluxed for ~8 hours until no starting material was remaining by LCMS. After cooling to room temperature, the precipitate was filtered to give the title compound, Yield (8.0 g). LRMS (ESI) $C_{20}H_{16}N_2O_4S$ found [M+H]: 381.1.

(S)—N-(3-(3-Cyanophenyl)-1-oxo-1-(piperazin-1-yl)propan-2-yl)naphthalene-2-sulfonamide (21B)

Using General Procedure A, the crude 20B (2.0 g, 5.26 mmol) and N-tert-butoxycarbonyl-piperazine (0.98 g, 5.26 mmol) were combined to give tert-butyl (S)-4-(3-(3-cyanophenyl)-2-(naphthalene-2-sulfonamido)propanoyl)piperazine-1-carboxylate after MPLC (0-75% EtOAc/hexanes), Yield (2.15 g). LRMS (ESI) $C_{29}H_{32}N_4O_5S$ found [M+H]: 549.2. To a solution of the product in 1,4-dioxane was added HCl and stirred at room temperature overnight. After concentrating in vacuo, the residue was dissolved in MeOH and then concentrated to dryness. Purification by MPLC (0-10% MeOH/DCM gave the title product, Yield (0.8 g). $^1$H NMR (300 MHz, dmso-$d_6$) δ 2.30-2.47 (m, 2H) 2.71 (dd, J=13.46, 9.07 Hz, 2H) 2.87 (dd, J=13.46, 5.77 Hz, 2H) 3.09-3.21 (m, 1H) 3.31-3.43 (m, 3H) 4.51 (dd, J=8.65, 6.46 Hz, 1H) 7.33 (t, J=7.83 Hz, 1H) 7.49 (d, J=7.69 Hz, 2H) 7.57-7.74 (m, 5H) 7.93-8.10 (m, 3H) 8.24 (s, 1H) ppm. LRMS (ESI) $C_{24}H_{24}N_4O_3S$ found [M+H]: 449.2.

(S)—N-Benzyl-4-(3-(3-carbamimidoylphenyl)-2-(naphthalene-2-sulfonamido)propanoyl)piperazine-1-carboxamide (17a)

Prepared from (S)-4-(3-(3-(N-acetoxycarbamimidoyl)phenyl)-2-(naphthalene-2-sulfonamido)propanoyl)-N-benzylpiperazine-1-carboxamide using General Procedure F. Purification by reverse phase HPLC (10-60% acetonitrile/water/0.05% TFA). Yield: 24.2 mg (44%). $^1$H NMR (300 MHz, dmso-$d_6$) δ ppm 2.56-2.83 (m, 3H) 2.86-3.10 (m, 3H) 3.18 (br. s., 2H) 3.79-4.02 (m, 1H) 4.17 (m, 2H) 4.56 (m, 2H) 6.96 (s, 1H) 7.02-7.08 (m, 2H) 7.13-7.22-7.31 (m, 3H) 7.43 (m, 2H) 7.51-7.77 (m, 4H) 7.97 (br. s., 1H) 8.00-8.21 (m, 2H) 8.22-8.49 (m, 2H) 8.92 (m, 2H) 8.63 (br. S, 1H) 9.29 (br s, 1H). LRMS (ESI) $C_{32}H_{34}N_6O_4S$ found [M+H]: 599.2.

(S)-4-(3-(3-(N-Acetoxycarbamimidoyl)phenyl)-2-(naphthalene-2-sulfonamido)propanoyl)-N-benzylpiperazine-1-carboxamide Prepared from (S)—N-benzyl-4-(3-(3-(N-hydroxycarbamimidoyl)phenyl)-2-(naphthalene-2-sulfonamido)propanoyl)piperazine-1-carboxamide using General Procedure E. LRMS (ESI) $C_{34}H_{36}N_6O_6S$ found [M+H]: 657.2.

(S)—N-Benzyl-4-(3-(3-(N-hydroxycarbamimidoyl)phenyl)-2-(naphthalene-2-sulfonamido)propanoyl)piperazine-1-carboxamide Prepared from (S)—N-benzyl-4-(3-(3-cyanophenyl)-2-(naphthalene-2-sulfonamido)propanoyl)piperazine-1-carboxamide (54.4 mg, 0.094 mmol) using General Procedure D. LRMS (ESI) $C_{34}H_{36}N_6O_6S$ found [M+H]: 615.2.

(S)—N-Benzyl-4-(3-(3-cyanophenyl)-2-(naphthalene-2-sulfonamido)propanoyl)piperazine-1-carboxamide To a solution of 21B (50 mg, 0.119 mmol) in THF (1 mL) under a nitrogen atmosphere was added benzyl isocyanate (41 uL, 0.335 mmol). The reaction mixture was stirred overnight at room temperature. The reaction was concentrated in vacuo and the residue purified by MPLC (10-75% EtOAc/hexanes) to give the title compound. Yield (54.4 mg). LRMS (ESI) $C_{32}H_{31}N_5O_4S$ found [M+H]: 582.2.

(S)—N-(4-Bromobenzyl)-4-(3-(3-carbamimidoylphenyl)-2-(naphthalene-2-sulfonamido)propanoyl)piperazine-1-carboxamide (25a)

Prepared from (S)-4-(3-(3-(N-acetoxycarbamimidoyl)phenyl)-2-(naphthalene-2-sulfonamido)propanoyl)-N-(4- bromobenzyl)piperazine-1-carboxamide using General Procedure F. Purification by reverse phase HPLC (25-75% acetonitrile/water/0.05% TFA). Yield: 9.8 mg (12%). $^1$H NMR (300 MHz, dmso-$d_6$) δ ppm 2.56-2.83 (m, 3H) 2.83-3.00 (m, 2H) 3.04 (d, J=9.39 Hz, 1H) 3.11-3.28 (m, 2H) 3.39-3.51 (m, 1H) 3.57-3.76 (m, 1H) 4.11 (d, J=5.48 Hz, 1H) 4.42-4.61 (m, 1H) 6.99-7.27 (m, 3H) 7.27-7.52 (m, 4H) 7.52-7.74 (m, 4H) 7.82 (s, 1H) 7.89-8.17 (m, 3H) 8.17-8.43 (m, 2H) 9.09 (s, 2H) 9.32 (s, 2H). LRMS (ESI) $C_{32}H_{33}BrN_6O_4S$ found [M+H]: 677.1/679.1.

(S)-4-(3-(3-(N-Acetoxycarbamimidoyl)phenyl)-2-(naphthalene-2-sulfonamido)propanoyl)-N-(4-bromobenzyl)piperazine-1-carboxamide Prepared from (S)—N-(4-bromobenzyl)-4-(3-(3-(N-hydroxycarbamimidoyl)phenyl)-2-(naphthalene-2-sulfonamido)propanoyl)piperazine-1-carboxamide using General Procedure E. LRMS (ESI) $C_{34}H_{35}BrN_6O_6S$ found [M+H]: 635.1/637.1.

(S)—N-(4-Bromobenzyl)-4-(3-(3-(N-hydroxycarbamimidoyl)phenyl)-2-(naphthalene-2-sulfonamido) propanoyl)piperazine-1-carboxamide Prepared from (S)—N-(4-bromobenzyl)-4-(3-(3-cyanophenyl)-2-(naphthalene-2-sulfonamido)propanoyl)piperazine-1-carboxamide (78 mg, 0.112 mmol) using General Procedure D. LRMS (ESI) $C_{32}H_{33}BrN_6O_5S$ found [M+H]: 693.1/695.1.

(S)—N-(4-Bromobenzyl)-4-(3-(3-cyanophenyl)-2-(naphthalene-2-sulfonamido)propanoyl)piperazine-1-carboxamide To a solution of 21B (50 mg, 0.115 mmol) in THF (1 mL) under a nitrogen atmosphere was added 4-bromobenzyl isocyanate (32 μL, 0.23-0 mmol). The reaction mixture was stirred overnight at room temperature. The reaction was concentrated in vacuo and the triturated with THF, filtered, and dried to give the title compound. Yield (78 mg). LRMS (ESI) $C_{32}H_{30}BrN_5O_4S$ found [M+H]: 660.1/662.1.

(S)-4-(3-(3-Carbamimidoylphenyl)-2-(naphthalene-2-sulfonamido)propanoyl)-N-hexylpiperazine-1-carboxamide (25d)

Prepared from (S)-4-(3-(3-(N-acetoxycarbamimidoyl)phenyl)-2-(naphthalene-2-sulfonamido)propanoyl)-N-hexylpiperazine-1-carboxamide using General Procedure F. The crude product was purified using MPLC (0-10% MeOH/DCM) to the give the title compound. Yield: 20 mg (50%). $^1$H NMR (300 MHz, dmso-$d_6$) δ ppm 0.75-0.93 (m, 3H) 1.12-1.31 (m, 5H) 1.72 (s, 3H) 2.54 (s, 4H) 2.62-2.74 (m, 2H) 2.86 (d, J=7.43 Hz, 1H) 2.93 (d, J=7.04 Hz, 2H) 3.00 (s, 1H) 3.50 (s, 1H) 4.28 (br. s., 1H) 4.45 (br. s., 1H) 4.56 (d, J=7.43 Hz, 1H) 6.41 (br. s., 2H) 6.54-6.79 (m, 2H) 6.95 (d, J=8.61 Hz, 1H) 7.14 (d, J=7.04 Hz, 1H) 7.23 (br. s., 1H) 7.34 (br. s., 1H) 7.54 (br. s., 1H) 7.57-7.75 (m, 2H) 7.89-8.13 (m, 2H) 8.22-8.38 (m, 1H) 8.49 (s, 1H). LRMS (ESI) $C_{31}H_{40}N_6O_4S$ found [M+H]: 593.3.

(S)-4-(3-(3-(N-Acetoxycarbamimidoyl)phenyl)-2-(naphthalene-2-sulfonamido)propanoyl)-N-hexylpiperazine-1-carboxamide Prepared from (S)—N-hexyl-4-(3-(3-(N-hydroxycarbamimidoyl)phenyl)-2-(naphthalene-2-sulfonamido)propanoyl) piperazine-1-carboxamide using General Procedure E. LRMS (ESI) $C_{33}H_{42}N_6O_6S$ found [M+H]: 651.3.

(S)—N-Hexyl-4-(3-(3-(N-hydroxycarbamimidoyl) phenyl)-2-(naphthalene-2-sulfonamido)propanoyl) piperazine-1-carboxamide Prepared from (S)-4-(3-(3-cyanophenyl)-2-(naphthalene-2-sulfonamido)propanoyl)-N-hexylpiperazine-1-carboxamide (40 mg, 0.069 mmol) using General Procedure D. LRMS (ESI) $C_{31}H_{40}N_6O_5S$ found [M+H]: 609.3.

(S)-4-(3-(3-Cyanophenyl)-2-(naphthalene-2-sulfonamido)propanoyl)-N-hexylpiperazine-1-carboxamide To a solution of 21B (50 mg, 0.115 mmol) in THF (1 mL) under a nitrogen atmosphere was added hexyl isocyanate (49 uL, 0.335 mmol). The reaction mixture was stirred overnight at room temperature. The reaction was concentrated in vacuo and the residue purified by MPLC (10-70% EtOAc/hexanes) to give the title compound. Yield (40 mg). LRMS (ESI) $C_{31}H_{37}N_5O_4S$ found [M+H]: 576.3.

(S)-3-(3-(4-(Benzo[b]thiophene-3-carbonyl)piperazin-1-yl)-2-(naphthalene-2-sulfonamido)-3-oxopropyl)benzimidamide (25e)

Prepared from (S)—N-acetoxy-3-(3-(4-(benzo[b]thiophene-3-carbonyl)piperazin-1-yl)-2-(naphthalene-2-sulfonamido)-3-oxopropyl)benzimidamide using General Procedure F. Purification by reverse phase HPLC (5-60% acetonitrile/water/0.05% TFA). Yield: 11 mg (21%). $^1$H NMR (300 MHz, dmso-$d_6$) δ ppm 2.71 (br. s., 1H) 2.74-2.86 (m, 1H) 2.87-2.96 (m, 1H) 3.00 (br. s., 1H) 3.15 (d, J=19.17 Hz, 2H) 3.92 (s, 2H) 4.54 (s, 2H) 6.57 (s, 2H) 7.04-7.20 (m, 1H) 7.20-7.34 (m, 1H) 7.34-7.54 (m, 2H) 7.59 (br. s., 1H) 7.63-7.77 (m, 2H) 7.87 (s, 2H) 7.97-8.22 (m, 3H) 8.33 (br. s., 1H) 8.39 (m, 1H) 8.60 (m, 1H) 8.90 (m, 2H) 9.25 (m, 2H). LRMS (ESI) $C_{33}H_{31}N_5O_4S_2$ found [M+H]: 626.2.

(S)—N-Acetoxy-3-(3-(4-(benzo[b]thiophene-3-carbonyl)piperazin-1-yl)-2-(naphthalene-2-sulfonamido)-3-oxopropyl)benzimidamide Prepared from (S)-1-(3-(4-(benzo[b]thiophene-3-carbonyl)piperazin-1-yl)-2-(naphthalene-2-sulfonamido)-3-oxopropyl)-N-hydroxy-1l4-pyran-3-carboximidamide using General Procedure E. LRMS (ESI) $C_{35}H_{33}N_5O_6S_2$, found [M+H]: 684.2.

(S)-1-(3-(4-(Benzo[b]thiophene-3-carbonyl)piperazin-1-yl)-2-(naphthalene-2-sulfonamido)-3-oxopropyl)-N-hydroxy-1l4-pyran-3-carboximidamide Prepared from (S)—N-(1-(4-(benzo[b]thiophene-3-carbonyl)piperazin-1-yl)-3-(3-cyanophenyl)-1-oxopropan-2-yl)naphthalene-2-sulfonamide (51 mg, 0.0139 mmol) using General Procedure D. LRMS (ESI) $C_{33}H_{31}N_5O_5S_2$, found [M+H]: 642.2.

(S)—N-(1-(4-(Benzo[b]thiophene-3-carbonyl)piperazin-1-yl)-3-(3-cyanophenyl)-1-oxopropan-2-yl) naphthalene-2-sulfonamide To a solution of 3-carboxybenzothiophene (18 mg, 0.101 mmol), HBTU (42 mg, 0.115 mmol), and DIPEA (88 uL, 0.506 mmol) in THF (1.5 mL) under a nitrogen atmosphere, was added 21B (50 mg, 0.115 mmol). The reaction mixture was stirred overnight at room temperature. The reaction was concentrated in vacuo and the residue purified by MPLC (10-70% EtOAc/hexanes) to give the title compound. Yield (51 mg). LRMS (ESI) $C_{33}H_{28}N_4O_4S_2$ found [M+H]: 609.2.

(S)-3-(3-Oxo-3-(4-phenylpiperazin-1-yl)-2-((2,4,6-triisopropylphenyl)sulfonamido)propyl)benzimidamide (27)

Prepared from (S)—N-acetoxy-3-(3-oxo-3-(4-phenylpiperazin-1-yl)-2-((2,4,6-triisopropylphenyl)sulfonamido)propyl)benzimidamide using General Procedure F. Purified by reversed-phase HPLC (5-80% acetonitrile/water/0.05% TFA), Yield (0.166 g, 42.8%). $^1$H NMR (300 MHz, DMSO-$d_6$) δ 9.08-9.47 (m, 4H), 8.15-7.91 (d, 1H), 7.57-7.74 (m, 2H), 7.39-7.56 (m, 2H), 7.07-7.29 (m, 4H), 6.71-6.91 (m, 3H), 4.41-4.64 (m, 1H), 3.93-4.20 (m, 2H), 3.27-3.52 (m, 2H), 3.15-3.27 (m, 2H), 2.99-3.15 (m, 2H), 2.78-2.99 (m, 4H), 2.59-2.78 (m, 2H), 0.98-1.31 (m, 18H). LRMS (ESI), $C_{35}H_{47}N_5O_3S$, [M+H]: 618.3.

(S)—N-Acetoxy-3-(3-oxo-3-(4-phenylpiperazin-1-yl)-2-((2.4.6-triisoproplphenyl)sulfonamido)propyl)benzimidamide Prepared from (S)—N-hydroxy-3-(3-oxo-3-(4-phenylpiperazin-1-yl)-2-((2,4,6-triisopropylphenyl)sulfonamido)propyl)benzimidamide using General Procedure E. LRMS (ESI), $C_{37}H_{49}N_5O_5S$, [M+H]: 676.3.

(S)—N-Hydroxy-3-(3-oxo-3-(4-phenylpiperazin-1-yl)-2-((2,4,6-triisopropylphenyl)sulfonamido)propyl)benzimidamide Prepared from (S)—N-(3-(3-cyanophenyl)-1-oxo-1-(4-phenylpiperazin-1-yl)propan-2-yl)-2,4,6-triisopropylbenzenesulfonamide using General Procedure D. LRMS (ESI), $C_{35}H_{47}N_5O_4S$, [M+H]: 634.3

(S)—N-(3-(3-Cyanophenyl)-1-oxo-1-(4-phenylpiperazin-1-yl)propan-2-yl)-2,4,6-triisopropylbenzenesulfonamide Prepared from (S)-3-(3-cyanophenyl)-2-((2,4,6-triisopropylphenyl)sulfonamido)propanoic acid (0.36 g, 0.96 mmol) and 4-phenyl piperazine (1.19 mmol) using General Procedure A. Purification by MPLC (0-50% EtOAc/hexanes), Yield (0.34 g, 72%). LRMS (ESI), $C_{35}H_{44}N_4O_3S$, [M+H]: 601.3

(S)-3-(2-(4-Methylphenylsulfonamido)-3-oxo-3-(4-phenylpiperidin-1-yl)propyl)benzimidamide (25b)

Prepared from using General Procedure F. Yield (0.13 g, 55%). $^1$H NMR (300 MHz, DMSO-$d_6$) δ 9.32 (s, 2H), 9.37 (s, 2H), 8.00-8.36 (m, 1H), 7.63-8.00 (m, 2H), 7.40-7.63 (m, 4H), 7.06-7.40 (m, 5H), 7.00 (d, J=7.42 Hz, 1H), 4.41-4.73 (m, 1H), 4.21-4.39 (m, 1H), 3.92 (t, J=9.75 Hz, 1H), 3.63-3.81 (m, 1H), 2.90-3.02 (m, 1H), 2.49-2.88 (m, 4H), 2.36 (s, 2H), 1.95-2.33 (m, 1H), 1.65 (d, J=11.81 Hz, 1H), 1.39-1.60 (m, 1H), 1.08-1.39 (m, 1H), 0.78-1.08 (m, 1H). LRMS (ESI), $C_{28}H_{32}N_4O_3S$, [M+H]: 505.2.

(S)—N-Acetoxy-3-(2-((4-methylphenyl)sulfonamido)-3-oxo-3-(4-phenylpiperidin-1-yl)propyl)benzimidamide Prepared from (S)—N-hydroxy-3-(2-((4-methylphenyl)sulfonamido)-3-oxo-3-(4-phenylpiperidin-1-yl)propyl)benzimidamide using General Procedure E. Purification by MPLC (0-90% EtOAc/hexanes). Yield (0.24 g, 89%). LRMS (ESI), $C_{30}H_{34}N_4O_5S$, [M+H]: 563.2.

(S)—N-Hydroxy-3-(2-((4-methylphenyl)sulfonamido)-3-oxo-3-(4-phenylpiperidin-1-yl)propyl)benzimidamide Prepared from (S)—N-(3-(3-cyanophenyl)-1-oxo-1-(4-phenylpiperidin-1-yl)propan-2-yl)-4-methylbenzenesulfonamide using General Procedure D. LRMS (ESI), $C_{28}H_{32}N_4O_4S$, [M+H]: 521.2.

(S)—N-(3-(3-Cyanophenyl)-1-oxo-1-(4-phenylpiperidin-1-yl)propan-2-yl)-4-methylbenzenesulfonamide Prepared from 3-[(2S)-2-amino-3-oxo-3-(4-phenylpiperidin-1-yl)propyl]benzonitrile (0.256 g, 0.69 mmol) using General Procedure C. Yield (0.23 g, 68%). LRMS (ESI), $C_{28}H_{29}N_3O_3S$, [M+H]: 488.2.

Benzyl (S)-1-((S)-3-(3-carbamimidoylphenyl)-2-(4-methylphenylsulfonamido)propanoyl)piperidin-3-ylcarbamate (18)

Prepared from benzyl ((S)-1-((S)-3-(3-(N-acetoxycarbamimidoyl)phenyl)-2-((4-methylphenyl)sulfonamido)propanoyl)piperidin-3-yl)carbamate using General Procedure F. Yield (0.14 g, 44%). $^1$H NMR (300 MHz, DMSO-$d_6$) δ 9.13-9.47 (m, 4H), 7.60-7.77 (m, 2H), 7.40-7.59 (m, 4H), 7.12-7.40 (m, 7H), 5.00 (s, 1H), 4.29-4.60 (m, 1H), 3.95-4.15 (m, 1H), 3.62-3.85 (m, 2H), 3.56 (d, J=1.10 Hz, 1H), 3.29-3.46 (m, 2H), 2.64-2.99 (m, 3H), 2.53-2.63 (m, 1H), 2.34 (s, 3H), 1.69-1.98 (m, 1H), 1.56-1.69 (m, 1H), 1.26-1.49 (m, 1H), 1.08-1.24 (m, 1H). LRMS (ESI), $C_{30}H_{35}N_5O_5S$, [M+H]: 578.2.

Benzyl ((S)-1-((S)-3-(3-(N-acetoxycarbamimidoyl)phenyl)-2-((4-methylphenyl)sulfonamido)propanoyl)piperidin-3-yl)carbamate Prepared from benzyl ((S)-1-((S)-3-(3-(N-hydroxycarbamimidoyl)phenyl)-2-((4-methylphenyl)sulfonamido)propanoyl)piperidin-3-yl)carbamate using General Procedure E. LRMS (ESI), $C_{32}H_{37}N_5O_7S$, [M+H]: 636.2.

Benzyl ((S)-1-((S)-3-(3-(N-hydroxycarbamimidoyl)phenyl)-2-((4-methylphenyl)sulfonamido)propanoyl)piperidin-3-yl)carbamate Prepared from benzyl ((S)-1-((S)-3-(3-cyanophenyl)-2-((4-methylphenyl)sulfonamido)propanoyl)piperidin-3-yl)carbamate using General Procedure D. LRMS (ESI), $C_{30}H_{35}N_5O_6S$, [M+H]: 594.2.

Benzyl ((S)-1-((S)-3-(3-cyanophenyl)-2-((4-methylphenyl)sulfonamido)propanoyl)piperidin-3-yl)carbamate Prepared from benzyl ((S)-1-((S)-2-amino-3-(3-cyanophenyl)propanoyl)piperidin-3-yl)carbamate using General Procedure C. Purification by MPLC (0-75% EtOAc/hexanes). Yield (0.27 g, 69%). LRMS (ESI), $C_{30}H_{32}N_4O_5S$, [M+H]: 561.2.

Benzyl ((S)-1-((S)-2-amino-3-(3-cyanophenyl)propanoyl)piperidin-3-yl)carbamate Prepared from benzyl ((S)-1-((S)-2-((tert-butoxycarbonyl)amino)-3-(3-cyanophenyl)propanoyl)piperidin-3-yl)carbamate using General Procedure B. LRMS (ESI), $C_{23}H_{26}N_4O_3$, [M+H]: 407.2.

Benzyl ((S)-1-((S)-2-((tert-butoxycarbonyl)amino)-3-(3-cyanophenyl)propanoyl)piperidin-3-yl)carbamate Prepared from 19 (0.46 g, 1.59 mmol) and benzyl (S)-piperidin-3-ylcarbamate (0.48 g, 2.04 mmol) using General Procedure A. LRMS (ESI), $C_{28}H_{34}N_4O_5$, [M+H]: 507.2.

Benzyl (R)-1-((S)-3-(3-carbamimidoylphenyl)-2-(naphthalene-2-sulfonamido)propanoyl)piperidin-3-ylcarbamate (25f)

Prepared from benzyl ((R)-1-((S)-3-(3-(N-acetoxycarbamimidoyl)phenyl)-2-(naphthalene-2-sulfonamido)propanoyl)piperidin-3-yl)carbamate using General Procedure F. Yield (0.136 g, 53%). $^1$H NMR (300 MHz, DMSO-$d_6$) δ 9.20-9.48 (m, 3H), 9.15 (br. s., 1H), 8.15-8.43 (m, 2H), 7.85-8.15 (m, 3H), 7.77 (br. s., 1H), 7.55-7.69 (m, 3H), 7.29-7.53 (m, 8H), 4.86-5.23 (m, 3H), 4.35-4.68 (m, 1H), 3.87-4.17 (m, 1H), 3.57-3.87 (m, 1H), 2.81-3.09 (m, 2H), 2.52-2.81 (m, 3H), 1.74-1.94 (m, 1H), 1.58-1.74 (m, 1H), 1.34-1.58 (m, 1H), 0.90-1.29 (m, 2H). LRMS (ESI), $C_{33}H_{35}N_5O_5S$, [M+H]: 614.2.

Benzyl ((R)-1-((S)-3-(3-(N-acetoxycarbamimidol)phenyl)-2-(naphthalene-2-sulfonamido)propanoyl)piperidin-3-yl)carbamate Prepared from benzyl ((R)-1-((S)-3-(3-(N-hydroxycarbamimidoyl)phenyl)-2-(naphthalene-2-sulfonamido)propanoyl)piperidin-3-yl)carbamate using General Procedure E. LRMS (ESI), $C_{35}H_{37}N_5O_7S$, [M+H]: 672.2.

Benzyl ((R)-1-((S)-3-(3-(N-hydroxycarbamimidoyl)phenyl)-2-(naphthalene-2-sulfonamido)propanoyl)piperidin-3-yl)carbamate Prepared from benzyl ((R)-1-((S)-3-(3-cyanophenyl)-2-(naphthalene-2-sulfonamido)propanoyl)piperidin-3-yl)carbamate using General Procedure D. LRMS (ESI), $C_{33}H_{35}N_5O_6S$, [M+H]: 630.2.

Benzyl ((R)-1-((S)-3-(3-cyanophenyl)-2-(naphthalene-2-sulfonamido)propanol)piperidin-3-yl)carbamate Prepared from benzyl ((R)-1-((S)-2-amino-3-(3-cyanophenyl)propanoyl)piperidin-3-yl)carbamate using General Procedure C. Purification by MPLC (0-85% EtOAc/hexanes). Yield (0.22 g, 57%). LRMS (ESI), $C_{33}H_{32}N_4O_5S$, [M+H]: 597.2.

Benzyl ((R)-1-((S)-2-amino-3-(3-cyanophenyl)propanoyl)piperidin-3-yl)carbamate Prepared from benzyl ((R)-1-((S)-2-((tert-butoxycarbonyl)amino)-3-(3-cyanophenyl)propanoyl)piperidin-3-yl)carbamate using General Procedure B. Yield (0.29 g). LRMS (ESI), $C_{23}H_{26}N_4O_3$, [M+H]: 407.2.

Benzyl ((R)-1-((S)-2-((tert-butoxycarbonyl)amino)-3-(3-cyanophenyl)propanoyl)piperidin-3-yl)carbamate Prepared from 19 (0.42 g, 1.46 mmol) and benzyl (R)-piperidin-3-ylcarbamate (0.48 g, 2.04 mmol) using General Procedure A. Purification by MPLC (5-80% EtOAc/hexanes), Yield (0.346 g, 47%). LRMS (ESI), $C_{28}H_{34}N_4O_5$, [M+H]: 507.2.

1-((S)-3-(3-Carbamimidoylphenyl)-2-(4-methylphenylsulfonamido)propanoyl)-N-phenethylpiperidine-3-carboxamide (25c)

Prepared from 1-((S)-3-(3-(N-acetoxycarbamimidoyl)phenyl)-2-((4-methylphenyl)sulfonamido)propanoyl)-N-phenethylpiperidine-3-carboxamide using General Procedure F. Yield (0.28 g, 39%). $^1$H NMR (300 MHz, DMSO-$d_6$) δ 9.52-9.78 (m, 2H), 9.30-9.52 (m, 2H), 8.03-8.40 (m, 2H), 7.76-7.98 (m, 2H), 7.49-7.76 (m, 4H), 7.24-7.49 (m, 7H), 4.51-4.78 (m, 1H), 3.90-4.36 (m, 1H), 3.78-3.90 (m, 1H), 3.59-3.68 (m, 1H), 3.29-3.46 (m, 2H), 3.00-3.19 (m, 1H), 2.69-3.00 (m, 4H), 2.56-2.69 (m, 1H), 2.01-2.25 (m, 1H), 1.80-2.01 (m, 1H), 1.23-1.80 (m, 3H), 0.30-1.21 (m, 1H). LRMS (ESI), $C_{31}H_{37}N_5O_4S$, [M+H]: 576.3.

1-((S)-3-(3-(N-Acetoxycarbamimidoyl)phenyl)-2-((4-methylphenyl)sulfonamido)propanoyl)-N-phenethylpiperidine-3-carboxamide Prepared from 1-((S)-3-(3-(N-hydroxycarbamimidoyl)phenyl)-2-((4-methylphenyl)sulfonamido)propanoyl)-N-phenethylpiperidine-3-carboxamide using General Procedure E. LRMS (ESI), $C_{33}H_{39}N_5O_6S$, [M+H]: 634.3.

1-((S)-3-(3-(N-Hydroxycarbamimidoyl)phenyl)-2-((4-methylphenyl)sulfonamido)propanoyl)-N-phenethylpiperidine-3-carboxamide Prepared from 1-((S)-3-(3-cyanophenyl)-2-((4-methylphenyl)sulfonamido)propanoyl)-N-phenethylpiperidine-3-carboxamide using General Procedure D. LRMS (ESI), $C_{31}H_{37}N_5O_5S$, [M+H]: 592.3.

1-((S)-3-(3-Cyanophenyl)-2-((4-methylphenyl)sulfonamido)propanoyl)-N-phenethylpiperidine-3-carboxamide Prepared from (S)-3-(3-cyanophenyl)-2-((4-methylphenyl)sulfonamido)propanoic acid (0.67 g, 1.95 mmol) and N-phenethylpiperidine-3-carboxamide (0.68 g, 2.53 mmol) using General Procedure A. Yield (0.96 g, 88%). LRMS (ESI), $C_{31}H_{34}N_4O_4S$, [M+H]: 559.2.

(S)-3-(3-Cyanophenyl)-2-((4-methylphenyl)sulfonamido)propanoic acid

To a solution of methyl (S)-3-(3-cyanophenyl)-2-((4-methylphenyl)sulfonamido)propanoate (1.85 g, 5.17 mmol) in THF (30 mL) was added LiOH (0.80 g) in water (10 mL). The reaction was stirred at room temperature for 2 h. The organic layer was extracted with water and the combined aqueous fractions were adjusted to pH 3 with conc. HCl and then extracted with EtOAc. The combined organic layers were dried over MgSO4, filtered and the filtrate concentrated in vacuo to give the title compound. Yield (1.68 g, 95%). LRMS (ESI), $C_{17}H_{16}N_2O_4S$, [M+H]: 345.1.

Methyl (S)-3-(3-cyanophenyl)-2-((4-methylphenyl)sulfonamido)propanoate

Prepared from 19B (1.53 g, 6.36 mmol) using General Procedure C. Yield (1.85 g, 81%) LRMS (ESI), $C_{18}H_{18}N_2O_4S$, [M+H]: 359.1.

Example 9 Inhibition Studies with Benzamidine Compounds

Fluorescent inhibitor and chromogenic proteolytic assays were performed in general accordance with the procedures described in Example 4 for compounds prepared in Example 8.

The results for these studies are presented in Tables 9.1, 9.2, and 9.3 and FIGS. 10-17.

The results for selective studies are presented in Table 9.4.

TABLE 9.1

| Compound No. | $R_1$ | $R_2$ | W | Fluorogenic Assay HGFA $K_i$ (μM) | Matriptase $K_i$ (μM) | Hepsin $K_i$ (μM) |
|---|---|---|---|---|---|---|
| 16 (DEJ-1-69-002) | 2-naphthyl | phenyl | C | 10.1 | 0.3 | 3.28 |
| 17a (FMF-1-279-003) | 2-naphthyl | C(O)NH-benzyl | N | 14.0 | 2.06 | 1.0 |
| 25a (FMF-1-236-003) | 2-naphthyl | C(O)NH-CH2-(4-Br-phenyl) | N | 16.2 | 4.2 | 0.048 |
| 25b (DEJ-1-65-001) | 4-methylphenyl | phenyl | C | 19.85 | 0.57 | 4.8 |
| 25d (FMF-1-278-003) | 2-naphthyl | C(O)NH-hexyl | N | >50 | 14.9 | 1.3 |
| 25e (FMF-1-281-003) | 2-naphthyl | C(O)-benzothiophen-3-yl | N | >50 | 1.2 | 3.75 |

TABLE 9.1-continued

| Compound No. | R₁ | R₂ | W | Fluorogenic Assay | | |
|---|---|---|---|---|---|---|
| | | | | HGFA $K_i$ (μM) | Matriptase $K_i$ (μM) | Hepsin $K_i$ (μM) |
| 25g (DEJ-1-63-001) | naphthalen-2-yl | phenyl | N | 18.3 | 1.8 | 7.0 |
| 25h (DEJ-1-112-004) | p-tolyl | benzyl ester | N | >50 | 0.43 | 2.4 |
| 26 (JJ-I-134-2) | 2,4,6-triisopropylphenyl | piperidin-4-yl carbonyl | N | 5.5 | 0.12 | 8.14 |
| JWJ-I-135 | 2,4,6-triisopropylphenyl | 1-carbamimidoyl-piperidin-4-yl carbonyl | N | 17.84 | 0.0043 | 1.58 |
| JJ-I-134-2 | 2,4,6-triisopropylphenyl | piperidin-4-yl carbonyl | N | 5.45 | 0.12 | 8.13 |
| 27 (DEJ-1-173-004) | 2,4,6-triisopropylphenyl | phenyl | N | 22.2 | 0.76 | 7.4 |

TABLE 9.1-continued

| Compound No. | R₁ | R₂ | W | Fluorogenic Assay | | |
|---|---|---|---|---|---|---|
| | | | | HGFA $K_i$ (μM) | Matriptase $K_i$ (μM) | Hepsin $K_i$ (μM) |
| 28 (FMF-1-238-003) | naphthyl | 4-methoxybenzyl-CH₂-C(O)- | N | | 2.286-002 | |
| 29 (FMF-1-276-003) | naphthyl | isopropyl-C(O)- | N | | >20 | >20 |
| 30 (FMF-1-277-004) | naphthyl | isobutyl | N | | 12.4 | 4.9 |
| 31 (FMF-1-280-003) | naphthyl | 3-hydroxyphenyl-CH₂-C(O)- | N | | 4.4 | 1.7 |
| 32 (FMF-1-237-003) | naphthyl | 4-fluorophenyl-CH₂-C(O)- | N | | 2.8 | 1.0 |
| FMF-1-275-004 | naphthyl | -CH₂-C(O)-O-Et | N | | 2.78 | 39.5 |
| FMF-1-279-003 | naphthyl | -C(O)-NH-CH₂-Ph | N | 14.03 | 2.56 | 1.04 |
| FMF-1-278-003 | naphthyl | -C(O)-NH-hexyl | N | >50 | 14.87 | 1.28 |

TABLE 9.2

| Compound No. | R₁ | R₂ | Fluorogenic Assay | | |
|---|---|---|---|---|---|
| | | | HGFA Ki (μM) | Matriptase Ki (μM) | Hepsin Ki (μM) |
| 25f* (DEJ-1-86-002) | naphthyl | benzyl carbamate (NH) | >50 | 4.9 | 2.8 |
| 18* (DEJ-1-85-002) | p-tolyl | benzyl carbamate (NH) | >50 | 1 | 2.3 |
| 25c* (DEJ-1-194-002) | p-tolyl | phenethyl amide | >50 | 1.3 | 0.67 |

TABLE 9.3

| Compound No. | R₁ | R₂ | W | Fluorogenic Assay | | |
|---|---|---|---|---|---|---|
| | | | | HGFA Ki (μM) | Matriptase Ki (μM) | Hepsin Ki (μM) |
| (FMF-1-254-004) | naphthyl | benzyl amide | N | >50 | >10 | >10 |

TABLE 9.4

| Compound No. | Thrombin $K_i$ (nM) | Factor Xa $K_i$ (nM) | Trypsin $K_i$ (nM) |
|---|---|---|---|
| FMF-1-236-003 | 3106.0 | 4564.0 | 2.20 |
| JWJ-1-135 | >2000 | — | 1.93 |

Example 10. Tumor Microenvironment and Drug Sensitivity

The microenvironment of solid tumors is characterized by the presence of activated stromal cells, which produce an abundance of inflammatory mediators and growth factors that have been shown to play a critical role in tumor progression. Macrophages and myofibroblasts are two major components of the tumor microenvironment. HGF and other factors produced by macrophages and myofibroblasts that modulate oncogenic signaling pathways in tumor cells, include MET were investigated. An objective of this example is to understand the nature of tumor-derived factors that are responsible for activation of stromal cells and determine how the presence of genetic alterations in tumor cells alters communication of tumor cells with the stroma. In addition to their effect on tumor growth, HGF or MSP from the tumor microenvironment are also important regulators of responsiveness of cancer cells to antineoplastic therapies.

RON Phosphorylation and Migration and Invasion Assays of Breast Cancer Cells:

RON receptor tyrosine kinase activation confers resistance to tamoxifen in the MCF7 and T47D breast cancer cell lines. MDA-MB-231 express RON but we have not been able to detect phosphorylated RON (pRON) following MSP stimulation.

Detection and quantification of pRON in T47D cells was performed using a sandwich ELISA assay. RON capture antibody (R&D Systems, AF691) was immobilized on high protein binding 96-well plates. Next, cell lysates are added to wells, followed by incubation with an anti-phosphotyrosine-HRP antibody and then addition of a TMB substrate. Optical density of wells was determined by reading plates at 450 nm in a plate reader.

Figure 18:
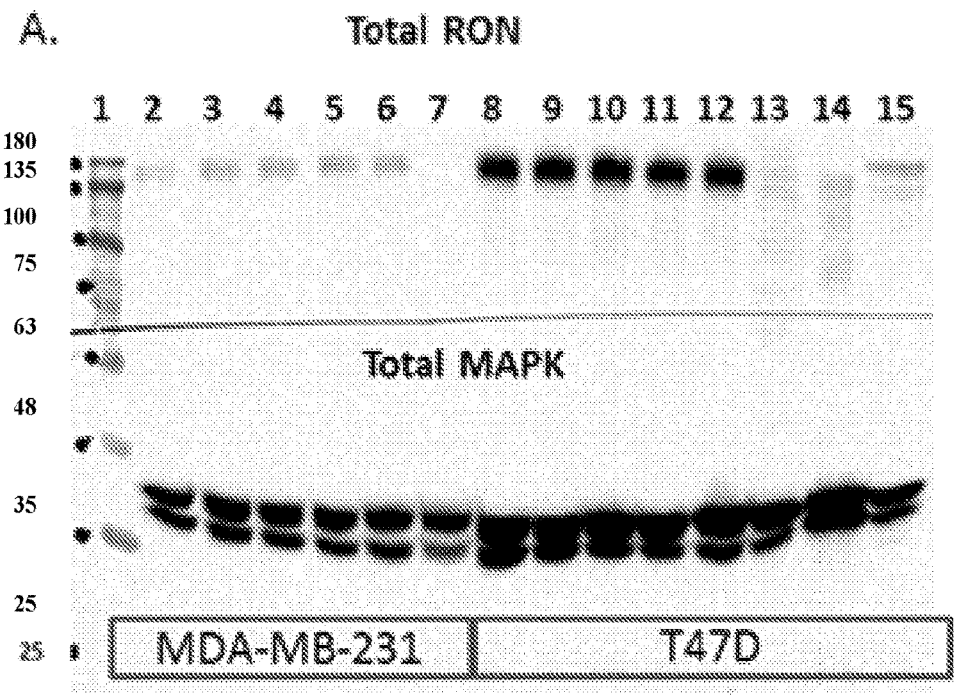
FIG. 18 shows MDA-MB-231 vs T47D breast cancer cells following MSP stimulation. A. Immunoblot of total RON and MAPK of breast cancer cells; B. RON phosphorylation ELISA assay.
Figure 18:
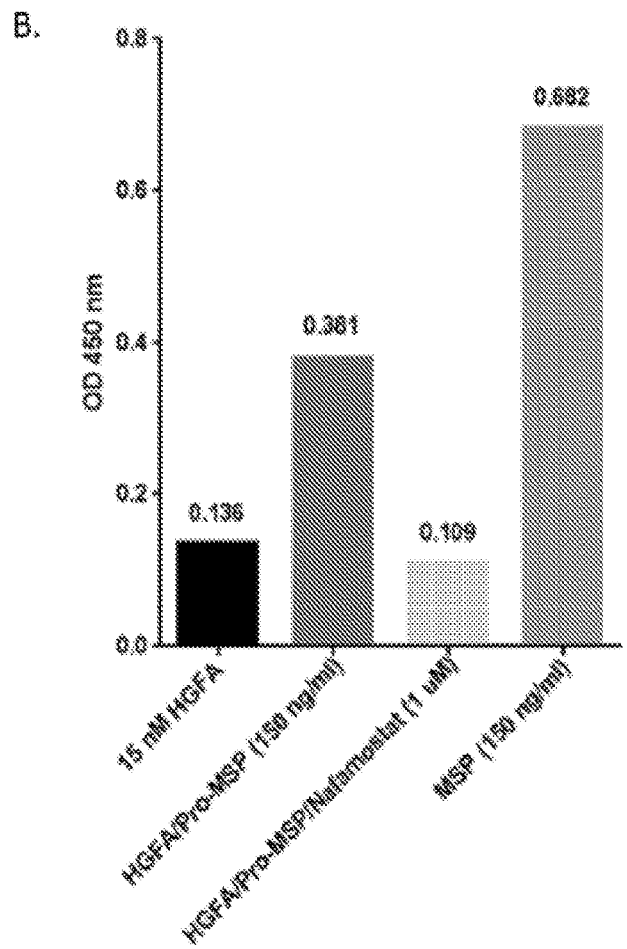

It can be seen in FIG. 18 that RON phosphorylation in T47D cells following active MSP stimulation, or HGFA-mediated pro-MSP stimulation, results in similar levels of RON phosphorylation. Inhibition with the triplex HGFA, matriptase, hepsin inhibitor Nafamostat, reduces pRON to background levels.

Triple-negative MDA-MB-231 breast cancer cells co-express MET, hepsin and HGFA but lower levels of RON and matriptase while T47D cells have good expression of RON.

MRC5 fibroblasts were plated in the bottom well of a Boyden chamber, and incubated overnight to condition the attractant media. The following day, MDA-MB-231 or T47D cells+/−inhibitors were plated above on Matrigel coated inserts (8.0 μm membrane inserts, 12-well; Corning 3422) and incubated in FBS media overnight. Inhibitors were added to fresh media and then cells were plated above on the inserts. The cells were fixed and stained at the 24 hour time point. The inserts were then removed and mounted on glass plates where the number of migrated cells were imaged and counted at 4 fields per membrane using a light microscope at 20x.

Figure 19:
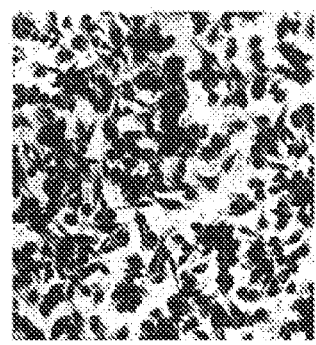
FIG. 19 shows the inhibition of MRC-5 mediated/pro-HGF migration and invasion of triple negative human MDA-MB-231 breast cancer cells using selected inhibitor compounds.
Figure 19:
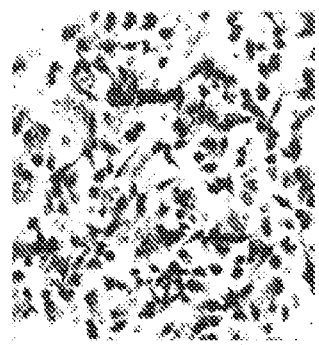
Figure 19:
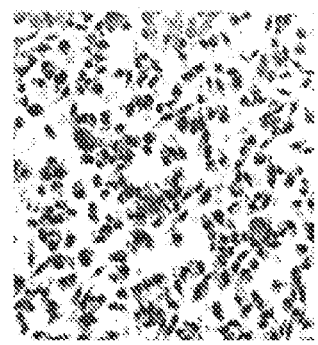

It can be seen in FIG. 19 that the two triplex inhibitors of HGFA, matriptase, and hepsin, 7115 and 7054 (1 μM) abrogate the MRC5-mediated migration and invasion of MDA-MB-231 cells through Matrigel by blocking active HGF production. The inhibitors tested are as effective as HAI-1, an endogenous inhibitor of matriptase, hepsin, and HGFA.

Example 11. PS-SCL and MSP-MS Substrate Screening of Natural and Unnatural Amino Acids Characterization of Hepsin and HGFA P4-P2 Substrate Specificity Using HyCoSuL.:

Each of the $P_4$, $P_3$, and $P_2$ sublibraries were screened at the 100 μM concentration with hepsin either HGFA in a 100 μL final volume per well (99 μL of protease in buffer+1 μL of 10 mM substrates mixture). The total time of the assay was 30 minutes, however only linear portions of the progress curve (5-15 minutes) were used for velocity (RFU/s) calculations. Each sublibrary screening was repeated at least 3-times and the average value calculated from each measurement was used to create the substrate specificity matrix—the best recognized amino acid in each position was set to 100%, and other amino acids were adjusted accordingly.

Recombinant human hepsin (10 μg in 20 uL, 4776-SE-010, R&D Systems) was added to the 100 μL of activation buffer (0.1 M Tris, 0.15 M NaCl, 0.01 M $CaCl_2$, 0.05% TRITON-X, pH=8.0) and incubated at 37° C. for 24 hours (hepsin concentration in activation buffer 2 μM). Once activated hepsin was diluted in assay buffer (0.05 M Tris, pH=9.0) to the final concentration of 4 nM and incubated at 37° C. for 15 minutes before added to a substrate.

HFGA enzyme was diluted in the assay buffer (0.15 M NaCl, 0.025 M Tris, 0.005 M $CaCl_2$, pH=8.0) to the final concentration of 10-20 nM (depending of sublibrary) and incubated at 25° C. for 30 minutes before added to a substrate.

Characterization of Hepsin and HGFA P1 Substrate Specificity Using Ac-Ala-Arg-Leu-P1-ACC Individual Substrate Library:

The 142-membered Ac-Ala-Arg-Leu-P1-ACC fluorogenic substrate library containing 19 natural (except cysteine) and 123 unnatural amino acids was used to determine hepsin and HGFA preferences in $P_1$ position. The protocol for both enzymes activation and incubation are as the same as in HyCoSuL screening. The $P_1$ individual substrate library was used at the final concentration of 5 μM. The total time of the assay was 30 min, however only linear portions of the progress curve (5-15 minutes) were used for velocity (RFU/s) calculations. Each screening for hepsin either HGFA was repeated 3-times and the average value for each measurement was used to create the substrate specificity matrix.

The detailed protocol for the use of ACC-labeled combinatorial peptide libraries in protease substrate specificity screening can be found in: Poreba M, Szalek A, Kasperkiewicz P, Drag M., *Methods Mol Biol.* 2014, 1133, 41-59, which is incorporated herein by reference.

Figure 20:
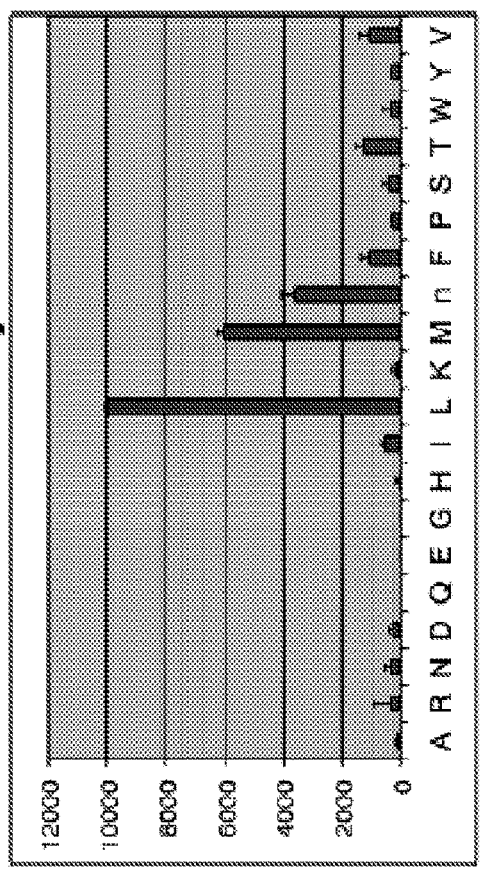
FIG. 20 shows the MSP-MS profiling for HGFA substrate cleavage and specificity.
Figure 20:
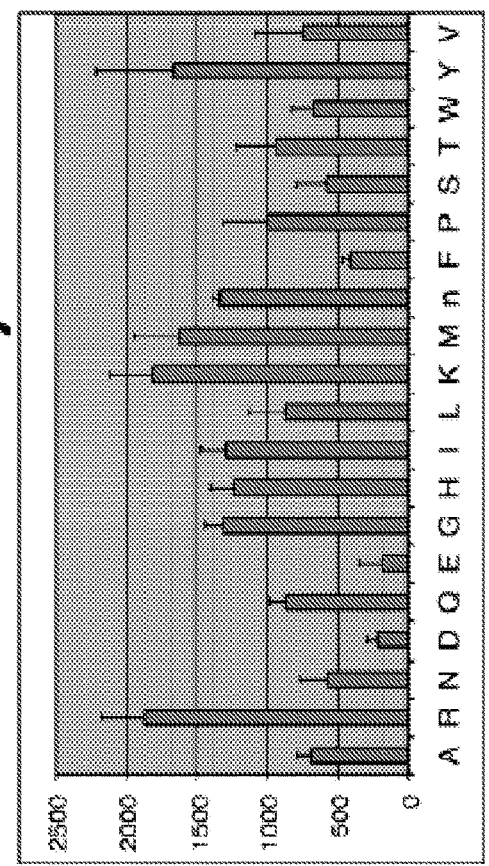
Figure 20:
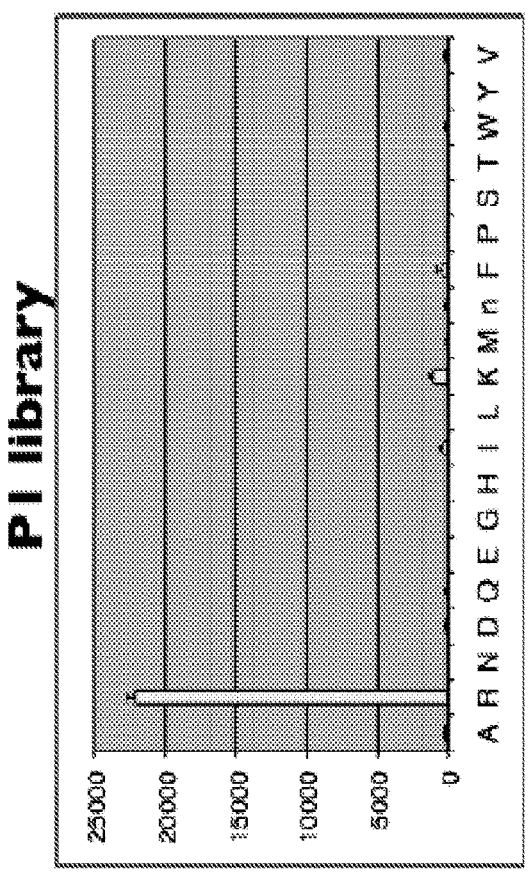
Figure 20:
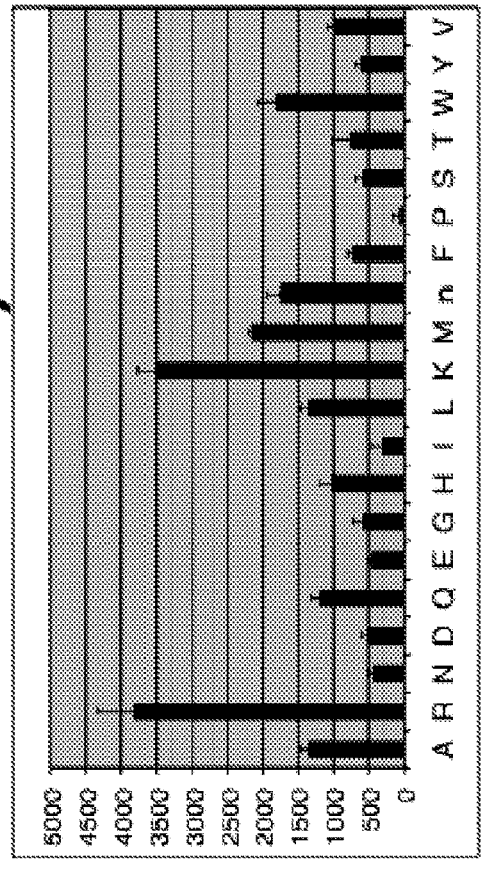
Figure 21:
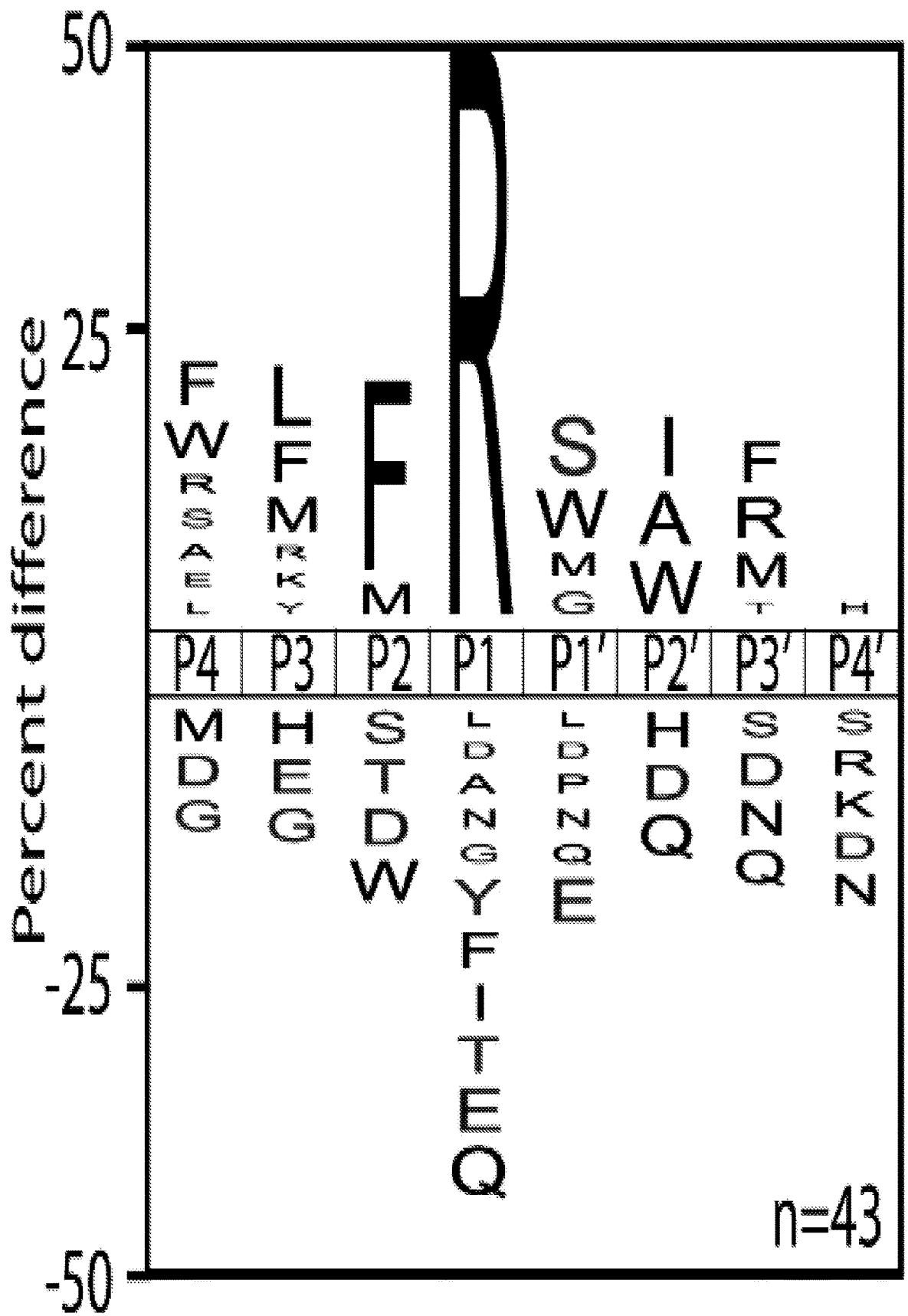
FIG. 21 shows iceLogo figures. A. Shows frequency at which specific amino acids are present at each position. B. Comparision of P4 and P4' amino acid frequency of the 22 peptides that were cleaved versus all possible peptides that contained an arginine.
Figure 21:
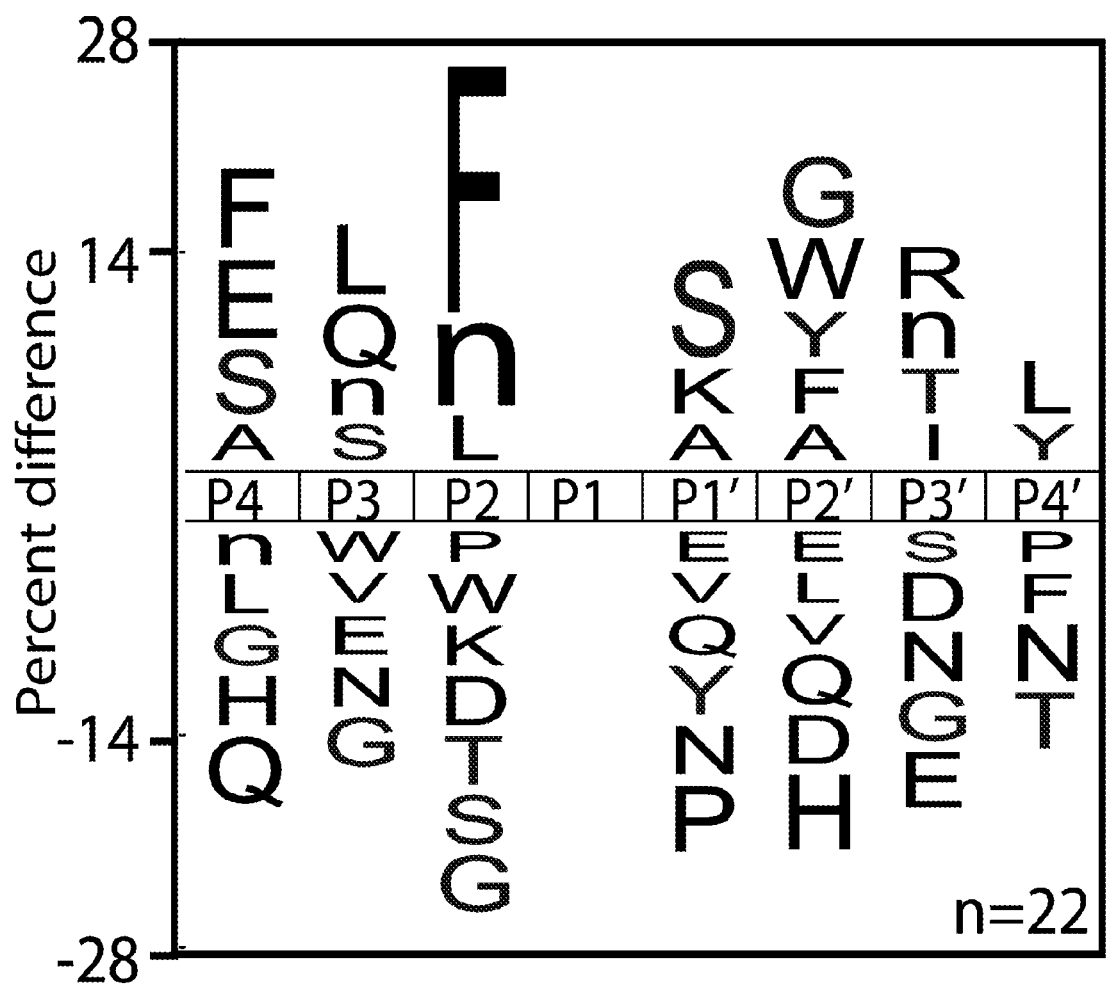

Results for MSP-MS profiling for HGFA substrate cleavage and specificity can be seen in FIG. 20 and Tables 11.1-11.4. IceLogo graphs can be seen in FIGS. 21A and 21B.

TABLE 11.1

| P4-P4'-All | P4-P4'-Cleaved by HGFA (4 hr) |
|---|---|
| ADARKYWN | AMFRKYPI |
| AGKRRDWX | ASMRIYIE |
| AMFRKYPI | EIFRKWHX |
| AMWRLDII | ESARDXXX |
| ASHRMGKN | EYFRMIRW |
| ASMRIYIE | FLVRTWKM |
| DAQRWKNI | FRIRSGTX |
| DEPRGHMY | FTQRAGIL |
| DQVRRMNX | IDLRWMAY |
| DSIRHQGP | KLFRFNWX |
| EIFRKWHX | NFLRGPXX |
| EKQRFHPX | NQMRGFXX |
| ELGRSANA | PQRRGMXX |
| ESARDXXX | RMIRWAVL |
| EVARPLGX | SLYRMIRQ |
| EYFRMIRW | SYMRWPXX |
| EYPRPQEW | TYFRAWXX |
| FDNRVGKW | VQHRLFTY |
| FHWRIMQG | WAFRSRYH |
| FLVRTWKM | WPQRRGMX |
| FPVRPTEX | XKARSAFA |
| FRIRSGTX | YAFRSTMV |

TABLE 11.2

| | P1 position % activity | |
|---|---|---|
| Amino Acid | Hepsin | HGFA |
| L-Ala (A) | 0.49 | 0.00 |
| L-Arg (R) | 100.00 | 100.00 |
| L-Asn (N) | 0.00 | 0.00 |
| L-Asp (D) | 0.00 | 0.00 |
| L-Gln (Q) | 0.00 | 0.00 |
| L-Glu (E) | 0.13 | 0.00 |
| Gly (G) | 0.07 | 0.00 |
| L-His (H) | 0.17 | 0.00 |
| L-Ile (I) | 0.08 | 0.00 |
| L-Leu (L) | 0.03 | 0.00 |
| L-Lys (K) | 2.34 | 0.99 |
| L-Nle | 0.07 | 0.00 |
| L-Phe (F) | 0.12 | 0.00 |
| L-Pro (P) | 0.04 | 0.00 |
| L-Ser (S) | 0.20 | 0.00 |
| L-Thr (T) | 0.45 | 0.00 |
| L-Trp (W) | 0.70 | 0.73 |
| L-Tyr (Y) | 0.30 | 0.00 |
| L-Val (V) | 0.00 | 0.00 |
| L-MeAla | 0.09 | 0.00 |
| B-Ala | 0.00 | 0.00 |
| dhPro 2/2 | 0.00 | 0.00 |
| L-Oic | 0.00 | 2.10 |
| L-Hyp | 0.00 | 0.00 |
| L-Hyp(Bzl) | 0.00 | 0.30 |
| L-Gla | 0.00 | 0.00 |
| L-Asp(Me) | 2.77 | 3.11 |
| L-Asp(Oall) | 2.34 | 0.00 |
| L-Asp(Bzl) | 0.93 | 12.28 |
| L-Glu(Me) | 0.41 | 0.00 |
| L-Glu(All) | 1.26 | 0.00 |
| L-Glu(Ochx) | 0.17 | 0.00 |
| L-Glu(Bzl) | 0.09 | 0.00 |
| L-Aad | 0.00 | 0.00 |
| L-Api | 0.00 | 0.00 |
| L-Dap | 0.03 | 0.00 |
| L-Orn | 0.00 | 0.00 |
| L-Cit | 0.42 | 0.00 |
| L-hCit | 0.13 | 0.00 |
| L-Lys(Ac) | 0.00 | 0.00 |
| L-Lys(tfa) | 0.00 | 0.00 |
| L-Lys(2-Cl-Z) | 0.09 | 0.00 |
| His(Bzl) | 0.12 | 0.00 |
| Arg(Me) | 0.00 | 0.00 |
| Arg(Me)2½ sym | 0.00 | 0.00 |
| L-hArg | 0.24 | 0.00 |
| L-3-Pal | 0.00 | 0.00 |
| L-4-Pal | 0.00 | 0.00 |
| L-Phe(4-NH2) | 0.08 | 0.00 |
| L-Phe(2-F) | 0.04 | 0.00 |
| L-Phe(3-F) | 0.01 | 0.00 |
| L-Phe(4-F) | 0.08 | 0.00 |
| L-Phe(3,4-F2) | 0.25 | 0.00 |
| L-Phe(F5) | 0.00 | 0.00 |
| L-Phe(2-Cl) | 0.04 | 0.00 |
| L-Phe(3-Cl) | 0.21 | 0.00 |
| L-Phe(4-Cl) | 0.07 | 0.00 |
| L-Phe(3,4-Cl2) | 0.02 | 0.00 |
| L-Phe(3-I) | 0.00 | 0.00 |
| L-Phe(4-I) | 0.34 | 0.00 |
| L-Phe(4-Br) | 0.10 | 0.00 |
| L-Phe(NO2) | 0.39 | 1.37 |
| L-Phe(guan) | 9.45 | 0.00 |
| L-Phe(4-Me) | 0.00 | 0.00 |
| L-hPhe | 0.16 | 0.00 |
| L-Ala(2th) | 0.28 | 0.42 |
| L-Ser(Bzl) | 0.30 | 0.00 |
| L-Hse(Bzl) | 0.06 | 0.00 |
| L-Thr(Bzl) | 0.04 | 0.00 |
| L-Cys(Bzl) | 0.00 | 0.00 |
| L-Cys(Me-Bzl) | 0.13 | 0.00 |
| L-Cys(4-MeOBzl) | 0.25 | 0.00 |
| L-Tyr(Bzl) | 0.45 | 0.00 |
| L-Dht | 0.00 | 0.00 |
| L-Trp(Me) | 0.13 | 0.48 |
| L-Tyr(Me) | 0.14 | 0.00 |
| L-hTyr(Me) | 0.00 | 0.56 |
| L-Tyr(2,6-Cl-Bzl) | 0.41 | 0.00 |
| L-Abu(Bth) | 0.00 | 0.00 |
| L-Bip | 0.13 | 0.00 |
| L-Bpa | 0.56 | 1.57 |
| Nle(Obzl) | 0.15 | 0.00 |
| L-1-Nal | 0.20 | 0.00 |
| L-2-Nal | 0.61 | 0.00 |
| L-Hse | 0.00 | 0.00 |
| L-Hnv | 1.55 | 0.00 |
| L-Met (M) | 0.00 | 0.00 |
| L-Met(O) | 0.00 | 0.00 |
| L-Met(O$_2$) | 0.00 | 0.00 |
| L-2-Abu | 0.00 | 0.00 |
| L-Nva | 0.14 | 0.00 |
| L-Tle | 0.42 | 0.00 |
| L-hLeu | 0.00 | 0.00 |
| L-2-Aoc | 2.82 | 0.00 |
| AC5C | 0.15 | 6.43 |
| L-Chg | 0.00 | 0.00 |
| L-Cha | 0.00 | 0.00 |
| L-hCha | 0.21 | 0.00 |
| L-Thyr | 0.28 | 0.00 |
| L-Inp | 0.07 | 0.00 |
| D-Ala | 0.00 | 0.00 |
| D-Asn | 0.00 | 0.00 |
| D-Asp | 0.05 | 0.00 |
| D-Gln | 0.00 | 0.00 |
| D-Glu | 0.00 | 0.00 |
| D-Leu | 0.00 | 0.00 |
| D-Lys | 0.23 | 0.00 |
| D-Phe | 0.38 | 0.00 |
| D-Pro | 1.08 | 0.00 |
| D-Phe | 0.09 | 0.00 |
| D-Ser | 0.02 | 0.00 |
| D-Thr | 0.24 | 0.00 |
| D-Trp | 0.50 | 0.00 |
| D-Tyr | 0.23 | 0.00 |
| D-Pip | 0.42 | 5.57 |
| D-Tic | 0.14 | 1.12 |
| D-Gla | 0.00 | 0.00 |
| D-Chg | 0.60 | 0.65 |
| D-Cha | 0.13 | 0.00 |

TABLE 11.2-continued

| | P1 position % activity | |
|---|---|---|
| Amino Acid | Hepsin | HGFA |
| D-Phg | 0.09 | 0.00 |
| D-3-Pal | 0.00 | 0.00 |
| D-4-Pal | 0.00 | 0.00 |
| D-Phe(4-Me) | 0.48 | 0.00 |
| D-Phe(2-F) | 0.00 | 0.00 |
| D-Phe(3-F) | 0.44 | 0.00 |
| D-Phe(4-F) | 0.00 | 0.00 |
| D-Phe(3,4-F2) | 0.31 | 0.00 |
| D-Phe(F5) | 0.34 | 0.00 |
| D-Phe(2-Cl) | 0.66 | 0.00 |
| D-Phe(3-Cl) | 0.12 | 0.00 |
| D-Phe(4-Cl) | 0.00 | 0.00 |
| D-Phe(3,4-Cl2) | 0.07 | 0.00 |
| D-Phe(4-I) | 0.32 | 0.00 |
| D-Phe(4-Br) | 0.11 | 4.00 |
| D-Phe(4-NO2) | 1.45 | 0.74 |
| D-Ser(Bzl) | 0.00 | 0.00 |
| D-Thr(Bzl) | 0.00 | 0.00 |
| D-hPhe | 0.04 | 0.00 |
| D-Bip | 0.30 | 0.00 |
| D-Bpa | 0.34 | 0.00 |
| D-1-Nal | 0.23 | 0.49 |
| D-2-Nal | 0.11 | 0.00 |

TABLE 11.3

| | P4 Position % Activity | | P3 Position % Activity | | P2 Position % Activity | |
|---|---|---|---|---|---|---|
| Amino Acid | Hepsin | HGFA | Hepsin | HGFA | Hepsin | HGFA |
| L-Ala (A) | 41.30 | 6.68 | 28.07 | 8.97 | 17.85 | 2.37 |
| L-Arg (R) | 80.32 | 23.62 | 70.75 | 43.98 | 57.23 | 2.08 |
| L-Asn (N) | 25.25 | 8.20 | 24.47 | 6.12 | 63.72 | 4.79 |
| L-Asp (D) | 0.22 | 1.90 | 3.89 | 2.81 | 0.33 | 1.21 |
| L-Gln (Q) | 29.82 | 9.01 | 58.69 | 15.98 | 12.19 | 3.35 |
| L-Glu (E) | 0.76 | 1.96 | 16.72 | 3.47 | 0.00 | 0.89 |
| Gly (G) | 29.19 | 10.84 | 26.14 | 10.42 | 0.00 | 1.14 |
| L-His (H) | 25.35 | 8.90 | 43.05 | 11.93 | 31.24 | 4.00 |
| L-Ile (I) | 47.02 | 14.09 | 11.37 | 9.06 | 45.68 | 4.94 |
| L-Leu (L) | 33.10 | 10.18 | 19.51 | 13.71 | 100.00 | 100.00 |
| L-Lys (K) | 75.43 | 18.29 | 80.71 | 44.63 | 46.70 | 1.04 |
| L-Nle | 40.93 | 11.76 | 24.09 | 19.15 | 62.04 | 45.52 |
| L-Phe (F) | 30.80 | 9.42 | 2.91 | 13.51 | 25.22 | 16.60 |
| L-Pro (P) | 56.00 | 10.30 | 2.09 | 2.04 | 13.10 | 2.21 |
| L-Ser (S) | 31.63 | 7.04 | 38.70 | 14.57 | 18.40 | 3.24 |
| L-Thr (T) | 29.29 | 7.67 | 35.34 | 14.51 | 70.75 | 8.87 |
| L-Trp (W) | 6.82 | 8.78 | 0.00 | 17.50 | 6.00 | 4.04 |
| L-Tyr (Y) | 22.39 | 16.47 | 7.75 | 11.59 | 22.79 | 3.17 |
| L-Val (V) | 43.08 | 11.66 | 16.77 | 9.51 | 51.85 | 8.33 |
| D-Ala | 18.44 | 7.11 | 48.09 | 9.84 | 0.00 | 0.00 |
| D-Arg | 44.37 | 23.20 | 66.08 | 29.10 | 0.00 | 0.00 |
| D-Asn | 18.48 | 7.38 | 38.75 | 15.16 | 0.00 | 0.00 |
| D-Asp | 1.98 | 2.25 | 17.18 | 5.37 | 0.00 | 0.00 |
| D-Gln | 20.13 | 8.03 | 97.80 | 13.84 | 0.00 | 0.00 |
| D-Glu | 2.98 | 2.62 | 34.55 | 3.61 | 0.00 | 0.00 |
| D-His | 19.33 | 7.79 | 40.09 | 11.09 | 0.00 | 0.00 |
| D-Leu | 24.76 | 10.56 | 20.14 | 7.08 | 0.00 | 0.00 |
| D-Lys | 49.84 | 17.66 | 64.56 | 21.11 | 0.00 | 0.00 |
| D-Phe | 13.15 | 8.13 | 24.92 | 15.22 | 0.00 | 0.00 |
| D-Pro | 20.45 | 10.30 | 38.88 | 4.96 | 0.00 | 0.00 |
| D-Ser | 21.84 | 7.94 | 54.84 | 10.86 | 11.55 | 0.00 |
| D-Phg | 22.48 | 9.06 | 57.07 | 40.01 | 13.53 | 4.40 |
| D-Thr | 25.74 | 8.61 | 36.69 | 6.45 | 0.00 | 0.00 |
| D-Trp | 1.48 | 7.65 | 24.90 | 87.59 | 0.00 | 0.00 |
| D-Tyr | 12.66 | 10.09 | 29.94 | 17.32 | 0.00 | 0.00 |
| D-Val | 22.58 | 8.25 | 27.04 | 5.76 | 0.00 | 0.00 |

TABLE 11.3-continued

| | P4 Position % Activity | | P3 Position % Activity | | P2 Position % Activity | |
|---|---|---|---|---|---|---|
| Amino Acid | Hepsin | HGFA | Hepsin | HGFA | Hepsin | HGFA |
| β-Ala | 30.74 | 10.07 | 22.78 | 15.95 | 0.00 | 0.24 |
| L-Hyp | 37.81 | 10.66 | 4.70 | 2.18 | 38.67 | 3.95 |
| L-Hyp(Bzl) | 33.33 | 8.91 | 1.29 | 4.34 | 32.68 | 4.39 |
| L-Thz | 45.46 | 12.65 | 9.93 | 7.76 | 6.16 | 2.80 |
| L-Oic | 53.72 | 16.76 | 2.92 | 2.78 | 0.67 | 20.71 |
| L-Idc | 0.00 | 32.64 | 0.00 | 6.43 | 0.00 | 0.96 |
| L-Pip | 34.68 | 9.25 | 1.64 | 0.83 | 10.66 | 1.75 |
| L-Tic | 13.31 | 10.84 | 8.10 | 25.13 | 2.45 | 3.58 |
| dhAbu | 44.51 | 24.45 | 7.29 | 9.44 | 7.72 | 14.12 |
| dhLeu | 52.44 | 42.50 | 5.85 | 11.02 | 0.00 | 0.48 |
| L-Dap | 35.65 | 13.31 | 48.71 | 24.27 | 10.01 | 1.49 |
| L-Dab | 47.53 | 16.76 | 48.55 | 29.40 | 13.49 | 0.50 |
| L-Dab(Z) | 96.34 | 16.55 | 31.58 | 21.38 | 20.86 | 4.84 |
| L-Cit | 36.68 | 6.44 | 29.53 | 13.41 | 32.27 | 6.32 |
| L-hCit | 40.51 | 10.53 | 27.31 | 19.71 | 36.25 | 7.59 |
| L-Orn | 84.52 | 20.23 | 79.70 | 54.04 | 78.48 | 0.00 |
| L-Lys(TFA) | 50.71 | 11.66 | 35.84 | 21.11 | 38.29 | 5.16 |
| L-Lys(Ac) | 35.02 | 8.71 | 29.15 | 16.02 | 23.04 | 7.36 |
| L-Lys(2-ClZ) | 41.91 | 47.56 | 2.55 | 14.21 | 21.20 | 29.53 |
| L-Agp | 98.08 | 80.01 | 97.35 | 74.18 | 35.36 | 11.83 |
| L-Agb | 37.96 | 11.59 | 26.80 | 19.62 | 3.53 | 1.05 |
| L-Arg(NO2) | 82.11 | 8.33 | 41.82 | 16.01 | 17.44 | 2.76 |
| L-Arg(Z)2 | 61.73 | 16.44 | 50.93 | 33.31 | 52.91 | 4.93 |
| L-hArg | 56.24 | 22.07 | 47.00 | 100.00 | 57.96 | 5.83 |
| L-His(3-Bom) | 38.40 | 100.00 | 15.18 | 13.20 | 0.00 | 0.43 |
| L-Phe(NH2) | 24.64 | 9.11 | 11.65 | 17.32 | 30.51 | 2.45 |
| L-Phe(guan) | 35.43 | 20.91 | 9.10 | 42.11 | 34.36 | 11.74 |
| L-Trp(Me) | 0.00 | 2.49 | 0.00 | 18.14 | 7.81 | 1.12 |
| L-Dht | 1.56 | 10.19 | 0.00 | 58.65 | 13.91 | 20.10 |
| L-Asp(Me) | 18.55 | 9.31 | 13.81 | 10.52 | 0.00 | 0.75 |
| L-Asp(Chx) | 27.32 | 10.34 | 19.99 | 22.46 | 0.79 | 2.16 |
| L-Asp(Bzl) | 19.34 | 9.60 | 7.29 | 6.92 | 0.00 | 1.35 |
| L-Glu(Me) | 36.79 | 9.13 | 64.70 | 32.95 | 13.49 | 6.65 |
| L-Glu(Chx) | 45.93 | 11.19 | 43.91 | 30.08 | 14.72 | 6.42 |
| L-Glu(Bzl) | 60.31 | 13.89 | 50.15 | 33.35 | 36.33 | 6.88 |
| L-Phe(2-F) | 24.33 | 10.49 | 7.80 | 13.39 | 1.78 | 5.98 |
| L-Phe(3-F) | 24.03 | 10.21 | 10.43 | 15.12 | 30.55 | 11.72 |
| L-Phe(4-F) | 27.78 | 11.22 | 5.16 | 15.01 | 32.86 | 4.84 |
| L-Phe(3,4-F2) | 19.65 | 8.79 | 0.71 | 15.06 | 38.16 | 3.73 |
| L-Phe(F5) | 26.60 | 12.25 | 5.13 | 22.36 | 0.36 | 1.55 |
| L-Phe(2-Cl) | 14.92 | 10.91 | 0.98 | 10.78 | 2.71 | 11.87 |
| L-Phe(3-Cl) | 9.26 | 10.25 | 0.35 | 21.45 | 33.86 | 12.49 |
| L-Phe(4-Cl) | 26.01 | 12.60 | 0.31 | 13.32 | 2.85 | 1.74 |
| L-Phe(3,4-Cl2) | 2.40 | 9.92 | 0.00 | 16.15 | 0.00 | 2.22 |
| L-Phe(4-Br) | 5.08 | 13.65 | 0.00 | 13.96 | 2.42 | 2.41 |
| L-Phe(4-Me) | 15.51 | 11.98 | 2.39 | 16.82 | 6.44 | 0.97 |
| L-3-Pal | 31.27 | 7.69 | 28.37 | 11.00 | 17.32 | 4.29 |
| L-4-Pal | 33.68 | 9.27 | 21.91 | 14.57 | 0.11 | 4.34 |
| L-Ala(2th) | 35.30 | 11.16 | 11.54 | 20.51 | 10.54 | 11.48 |
| L-Ala(Bth) | 14.64 | 10.26 | 20.97 | 23.90 | 6.52 | 2.16 |
| L-Bta | 13.63 | 9.79 | 0.13 | 24.11 | 0.00 | 3.71 |
| L-Abu | 38.68 | 9.87 | 28.98 | 15.31 | 0.00 | 1.81 |
| L-Abu(Bth) | 38.68 | 11.84 | 4.21 | 21.63 | 0.64 | 14.29 |
| L-Ser(Ac) | 37.96 | 7.56 | 42.09 | 21.69 | 6.73 | 1.67 |
| L-Ser(Bzl) | 21.57 | 14.49 | 11.56 | 19.45 | 20.43 | 5.27 |
| L-hSer | 26.55 | 7.34 | 33.48 | 16.59 | 31.76 | 2.12 |
| L-hSer(Bzl) | 40.00 | 12.03 | 21.24 | 20.03 | 46.09 | 17.39 |
| L-Thr(Bzl) | 40.13 | 13.14 | 16.36 | 21.72 | 36.14 | 7.19 |
| L-Cys(Bzl) | 23.44 | 16.89 | 3.06 | 25.14 | 1.50 | 7.46 |
| L-Cys(MeBzl) | 15.53 | 13.63 | 0.87 | 17.21 | 3.49 | 6.24 |
| L-Cys(4-MeOBzl) | 12.84 | 13.88 | 0.10 | 16.76 | 7.07 | 9.44 |
| L-Nle(O-Bzl) | 91.83 | 16.90 | 82.17 | 30.67 | 0.00 | 0.00 |
| L-Phg | 34.01 | 11.24 | 28.27 | 23.25 | 48.33 | 14.18 |
| L-hPhe | 44.79 | 11.14 | 10.63 | 61.77 | 4.71 | 32.14 |
| L-Chg | 46.64 | 25.12 | 6.60 | 18.69 | 10.88 | 27.27 |
| L-Cha | 25.44 | 13.42 | 3.64 | 22.61 | 74.49 | 6.03 |
| L-hCha | 5.44 | 12.92 | 0.13 | 73.74 | 0.00 | 2.90 |
| L-Igl | 25.47 | 10.62 | 0.00 | 52.15 | 2.20 | 19.79 |
| L-1-Nal | 5.18 | 6.36 | 0.00 | 23.07 | 3.00 | 4.19 |
| L-2-Nal | 1.34 | 11.72 | 0.00 | 12.75 | 0.00 | 5.10 |
| L-Bpa | 0.86 | 12.77 | 0.00 | 8.16 | 0.00 | 1.57 |

TABLE 11.3-continued

| Amino Acid | P4 Position % Activity | | P3 Position % Activity | | P2 Position % Activity | |
|---|---|---|---|---|---|---|
| | Hepsin | HGFA | Hepsin | HGFA | Hepsin | HGFA |
| L-2-Aoc | 19.98 | 12.15 | 12.74 | 33.06 | 8.90 | 14.37 |
| L-hLeu | 41.61 | 14.86 | 13.84 | 23.44 | 14.44 | 72.69 |
| L-NptGly | 27.66 | 8.34 | 9.92 | 12.95 | 37.46 | 53.86 |
| L-Hnv | 33.75 | 7.92 | 33.40 | 15.07 | 34.62 | 5.49 |
| L-Tle | 38.05 | 9.71 | 7.48 | 6.70 | 0.00 | 0.00 |
| L-Tyr(Me) | 31.38 | 9.54 | 4.55 | 17.41 | 10.89 | 1.79 |
| L-Tyr(2,6Cl2-Z) | 0.08 | 9.94 | 0.09 | 4.47 | 0.00 | 2.83 |
| L-Tyr(Bzl) | 3.10 | 9.39 | 0.00 | 14.03 | 0.28 | 3.71 |
| L-Tyr(2-Br-Z) | 22.51 | 12.67 | 8.05 | 17.09 | 7.72 | 2.39 |
| L-hTyr | 31.56 | 13.69 | 7.46 | 73.59 | 0.00 | 42.92 |
| L-hTyr(Me) | 36.30 | 10.62 | 10.00 | 25.48 | 0.00 | 23.13 |
| L-Nva | 41.99 | 11.78 | 25.85 | 17.60 | 58.40 | 39.80 |
| L-Met(O) | 22.86 | 6.64 | 68.16 | 16.63 | 11.40 | 1.68 |

TABLE 11.4

| | Ac-Ala-Arg-Leu-Arg-ACC | NH$_2$-Leu-DTrp-Nle-Arg-ACC | Ac-His(3Bom)-Agp-hLeu-Arg-ACC | Ac-Agp-hArg-Leu-Arg-ACC |
|---|---|---|---|---|
| $K_M$ | 107.2 | 73.4 | 52.1 | 37.8 |
| $k_{cat}$ | 0.337 | 1.30 | 1.47 | 1.56 |
| $k_{cat}/K_M$ | 3,144 | 17,662 | 28,140 | 41,254 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying figures shall be interpreted as illustrative and not in a limiting sense.

What is claimed is:

1. A compound of Formula (II):

wherein
Y is acetyl, tert-butyloxycarbonyl, benzyloxymethyl acetyl, carboxybenzyl, fluorenylmethoxycarbonyl (FMOC), benzyl, or a fluorophore;
$P_1$ is a residue of an amino acid selected from the group consisting of Arg and D-Arg;
$P_2$ is a residue of an amino acid selected from the group consisting of Leu and hLeu;
$P_3$ is a residue of an amino acid selected from the group consisting of Arg, Lys, Trp, Leu, Gln, Phe, His, hArg, D-Trp, His(3-Bom), and L-Phe($NO_2$);
P4 is a residue of an amino acid selected from the group consisting of Arg, Lys, Trp, Ser, Phe, Thr, Asn, His(3-Bom), and D-Trp; and
Z is a

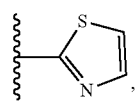 , 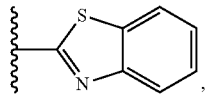 , or a benzothiazole of Formula (IV) or (V)

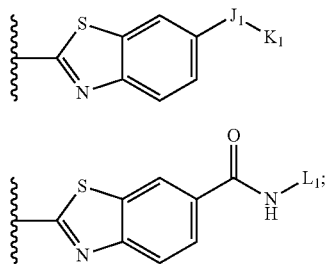

wherein
$J_1$ is C(O), $SO_2$, $CH_2$, or heterocyclo;
$K_1$ is a D- or L-amino acid, wherein the C-terminus is —COOH, —C(O)$NH_2$, —OH, —$OR_{10}$, —$NH_2$, —$NR_{11}R_{12}$, —H, or heterocyclo;
$R_{10}$ is $C_1$ to $C_{12}$ alkyl, cycloalkyl, alkylaryl, or aryl;
$R_{11}$ and $R_{12}$ are each independently H, $C_1$ to $C_{12}$ alkyl, cycloalkyl, alkylaryl, aryl, or heterocyclo; and $R_{11}$ and $R_{12}$ optionally form a ring; and
$L_1$ is H, alkyl, cycloalkyl, alkylaryl, benzyl, substituted benzyl, 2- or 3- or 4-piperdinyl, 2- or 3- or 4-pyridinyl, aryl, heterocyclo, or heteroaryl.

2. The compound of claim 1 wherein Y is acetyl and/or Z is

Z is 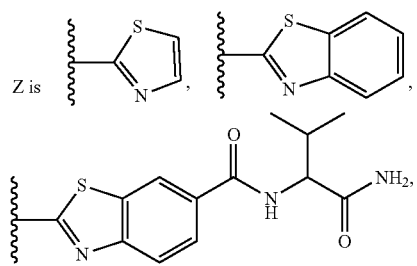

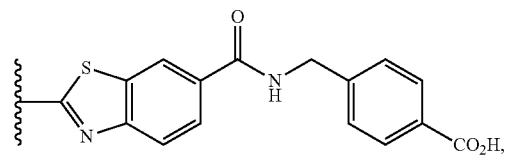

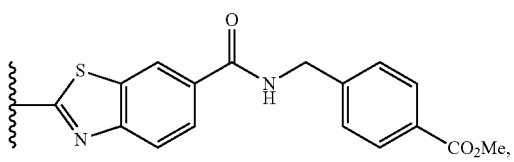

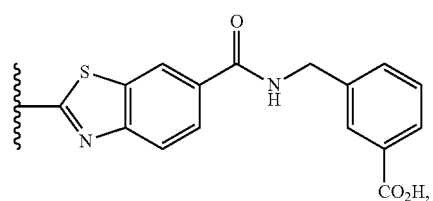

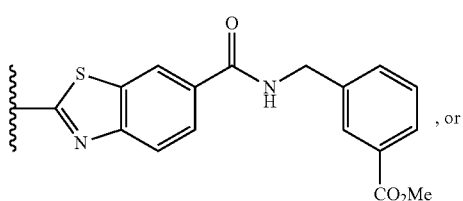

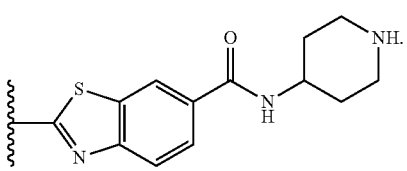

3. The compound of claim 1 wherein $P_1$ is an amino acid residue of Arg; $P_2$ is an amino acid residue of Leu; $P_3$ is an amino acid residue of His, Gln, Arg, Lys, Leu, Phe, or Trp; and $P_4$ is an amino acid residue of Ser, Lys, Phe, Trp, or His(3-Bom).

4. The compound of claim 2 wherein $P_1$ is an amino acid residue of Arg; $P_2$ is an amino acid residue of Leu; $P_3$ is an amino acid residue of Arg, Leu, Trp, Phe, His, Gln, or Lys; and $P_4$ is an amino acid residue of Phe, Trp, Ser, Lys, or His(3-Bom).

5. The compound claim 1 wherein $P_1$ is an amino acid residue of Arg; $P_2$ is an amino acid residue of Leu; $P_3$ is an amino acid residue of Leu, Trp, Phe, His, Gln, or Lys; and $P_4$ is an amino acid residue of Phe, Lys, or His(3-Bom).

6. The compound of claim 1 wherein $P_4$-$P_3$-$P_2$-$P_1$ of Formula (II) is a tetrapeptide selected from the group consisting of SEQ ID NO 1, SEQ ID NO 2, SEQ ID NO 3, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 14, SEQ ID NO 15, SEQ ID NO 16, SEQ ID NO 17, and SEQ ID NO 18.

7. The compound of claim 1 wherein Z is a benzothiazole of Formula (IV) or Formula (V).

8. The compound of claim 1 wherein $L_1$ is a substituted benzyl group.

9. The compound of claim 2 wherein Z is
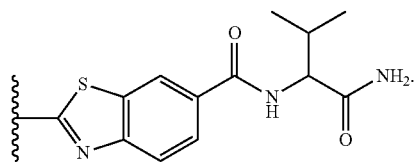 [SMILES: *c1nc2ccc(C(=O)NC(C(N)=O)C(C)C)cc2s1]
10. The compound of claim 6 wherein Y is acetyl and Z is a
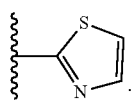
11. The compound of claim 1, wherein the compound is selected from the group consisting of:
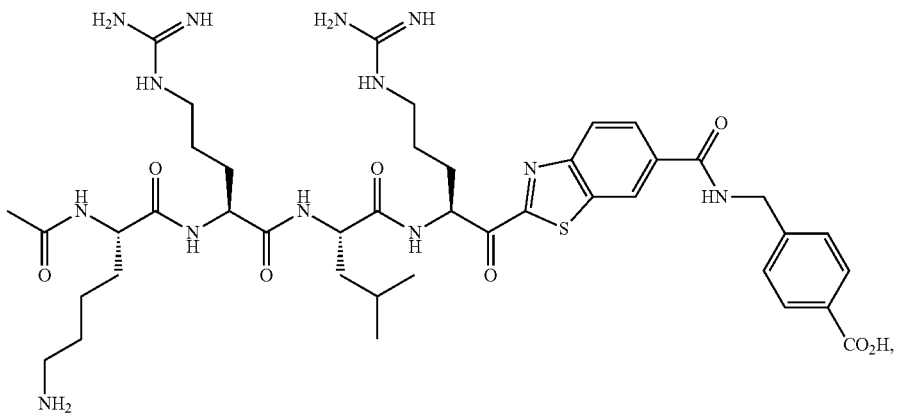
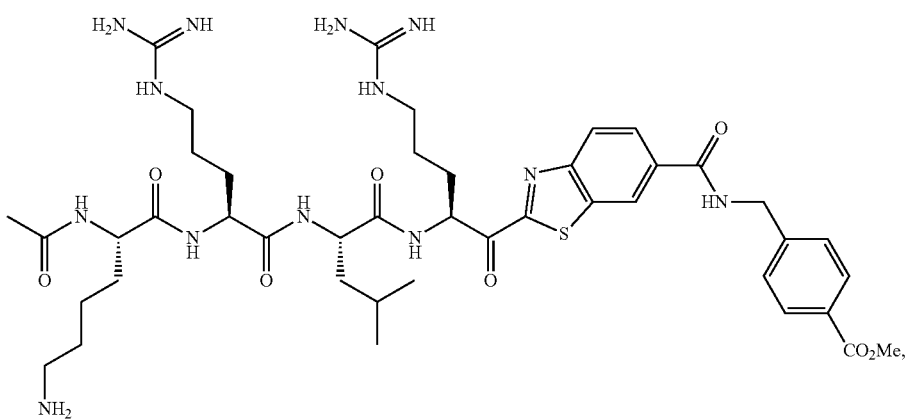
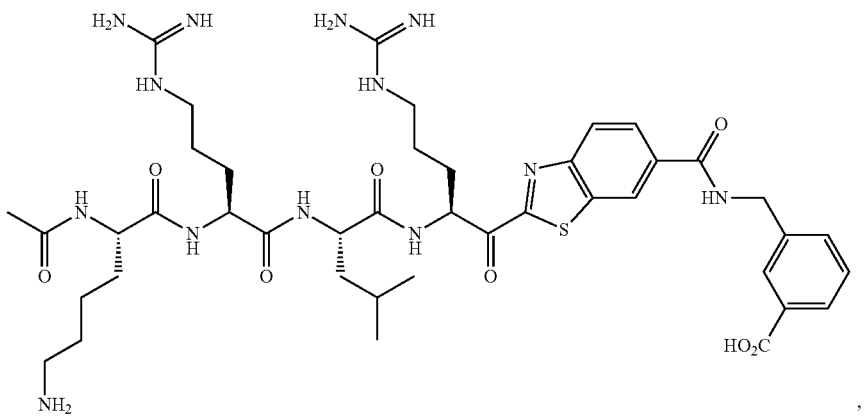
, -continued
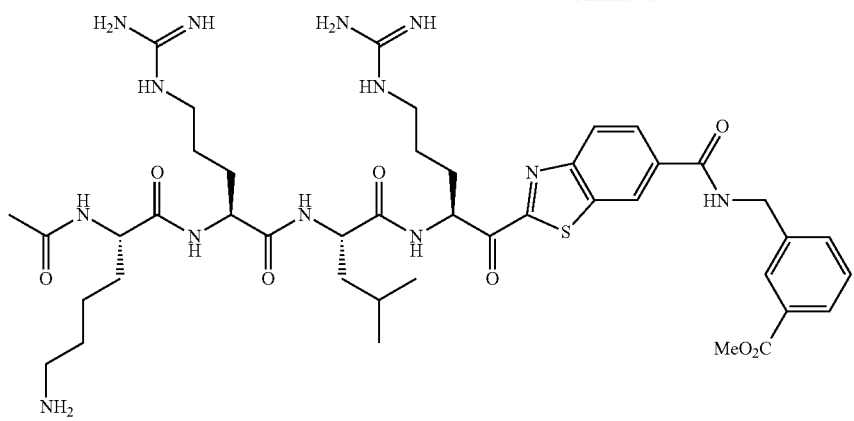
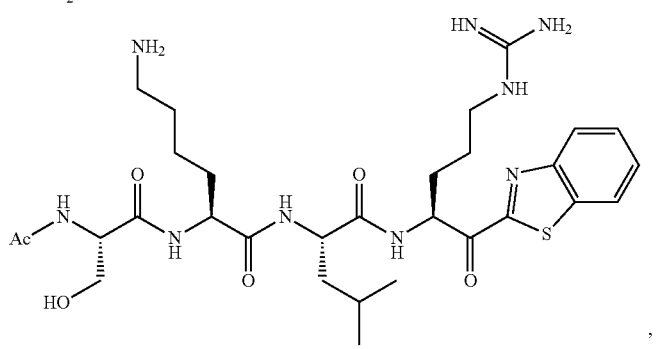
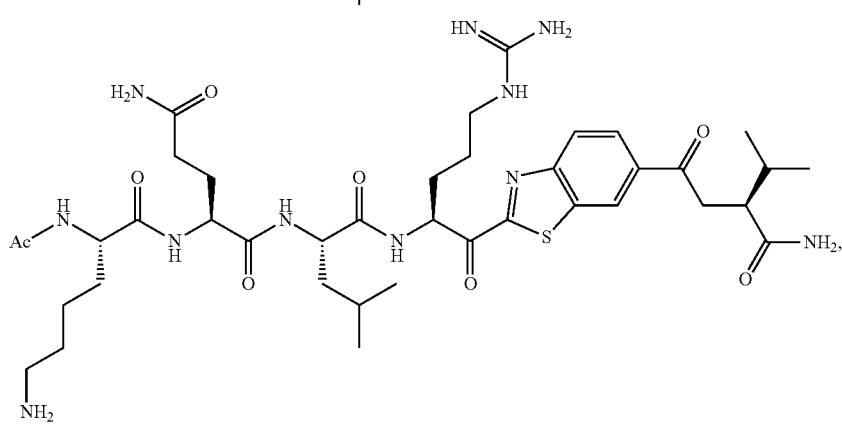
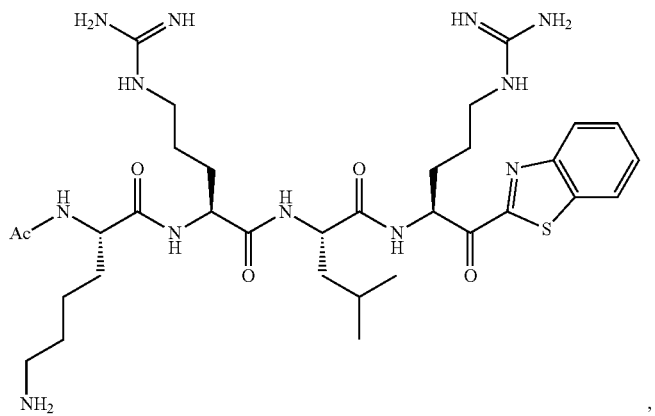

-continued
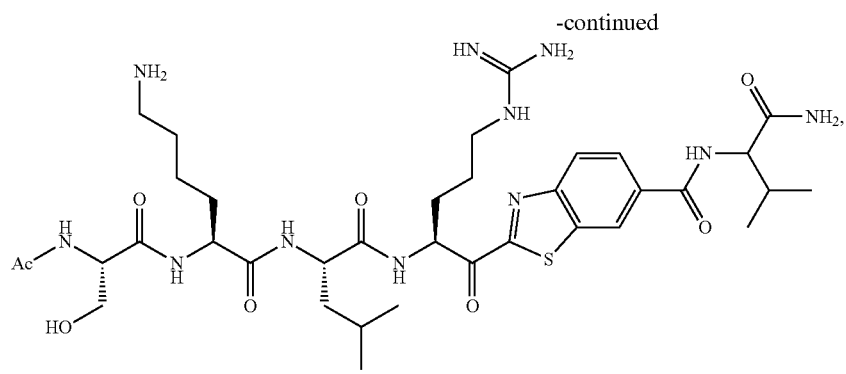
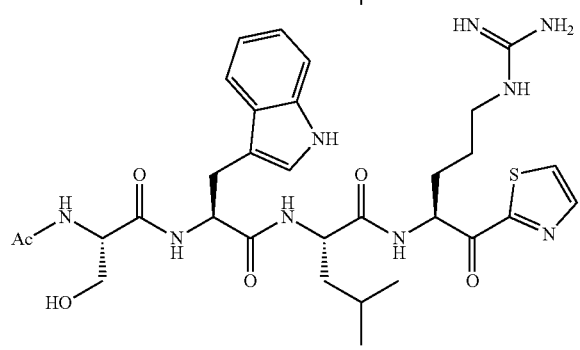
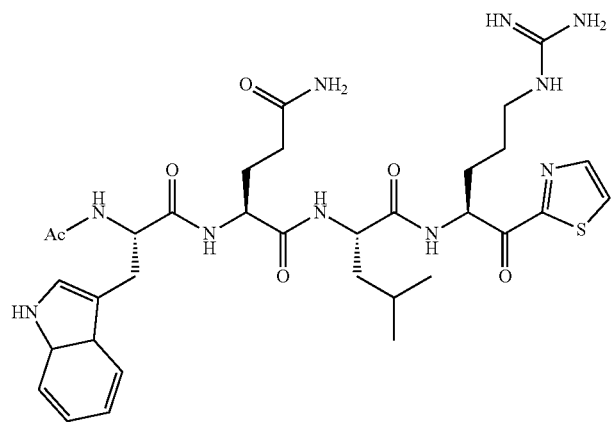
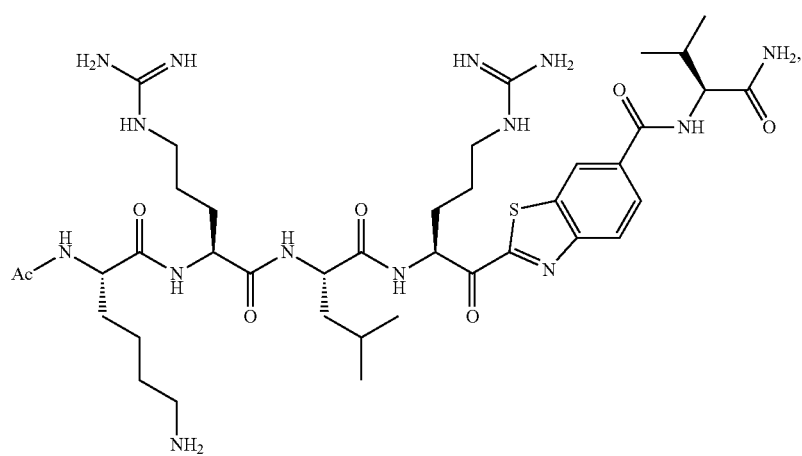

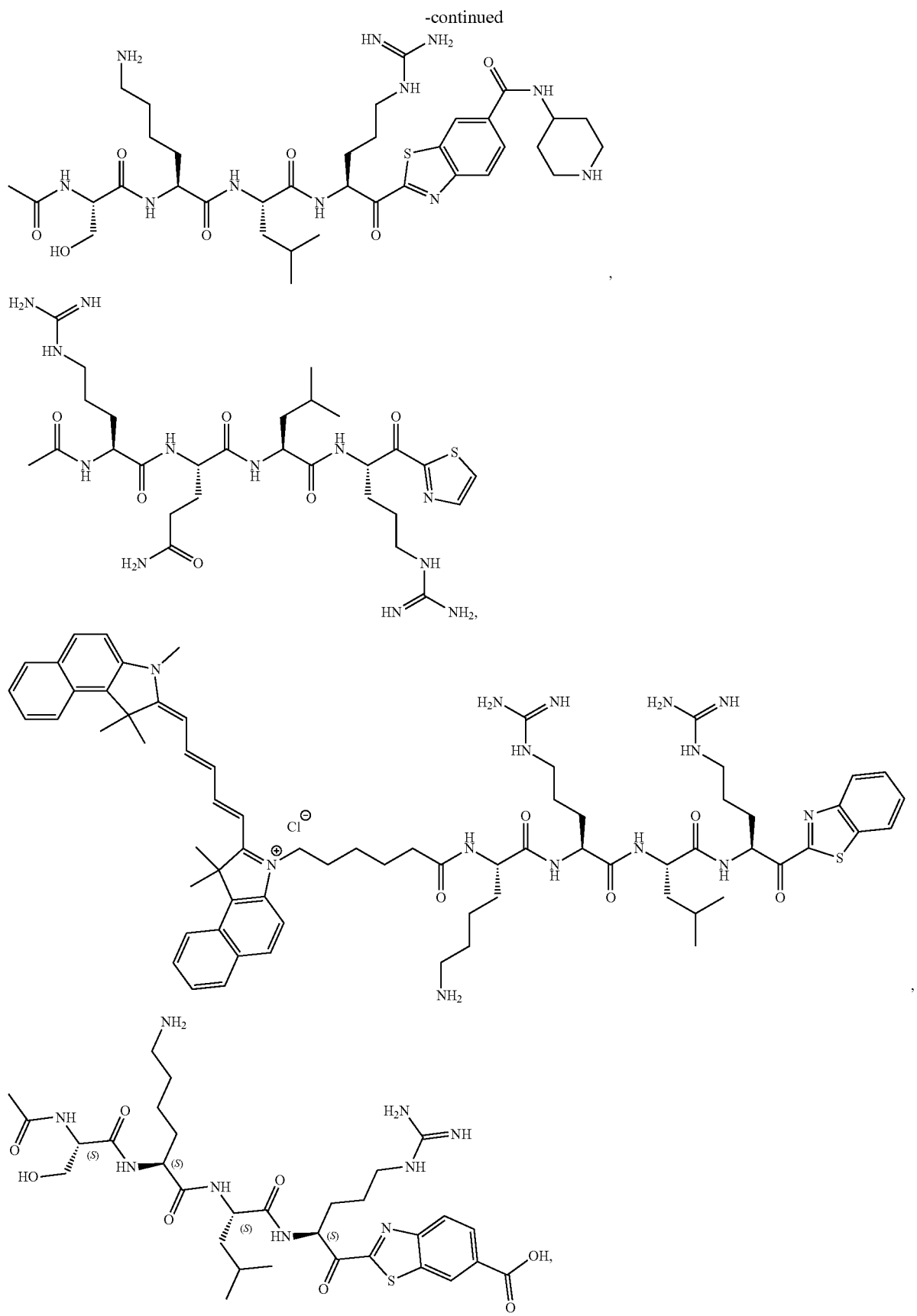

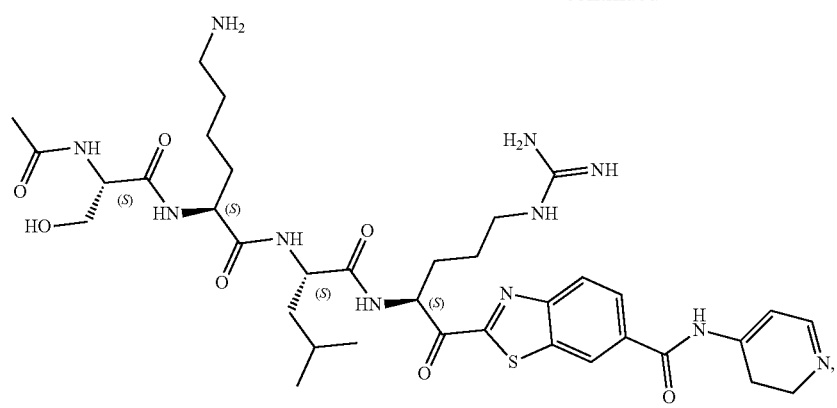
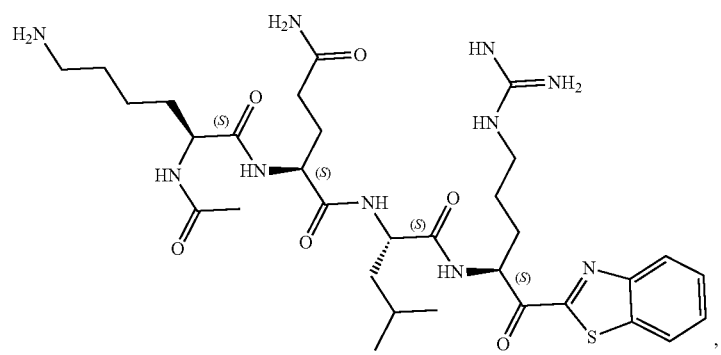
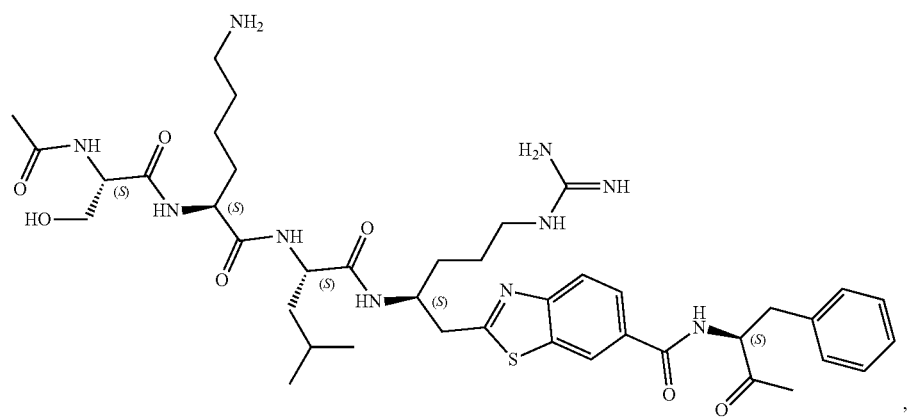

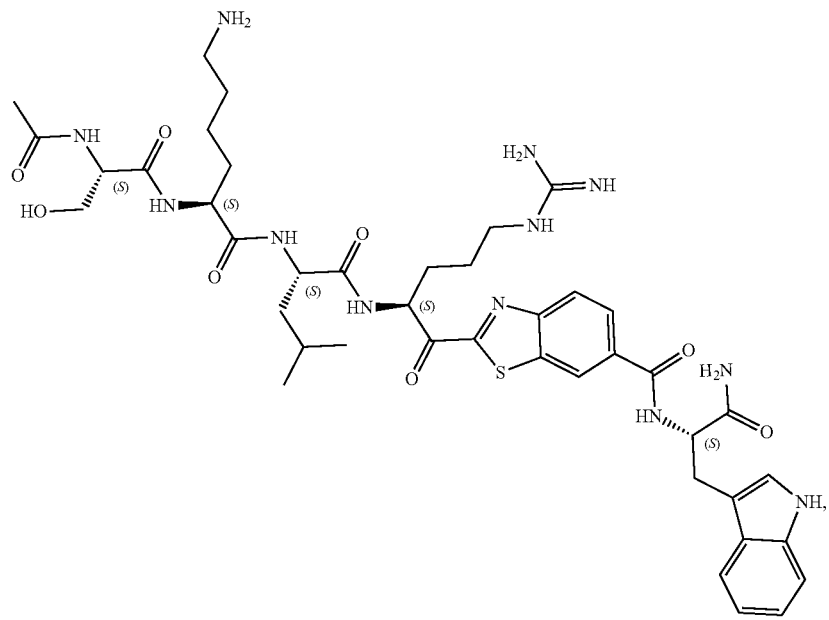
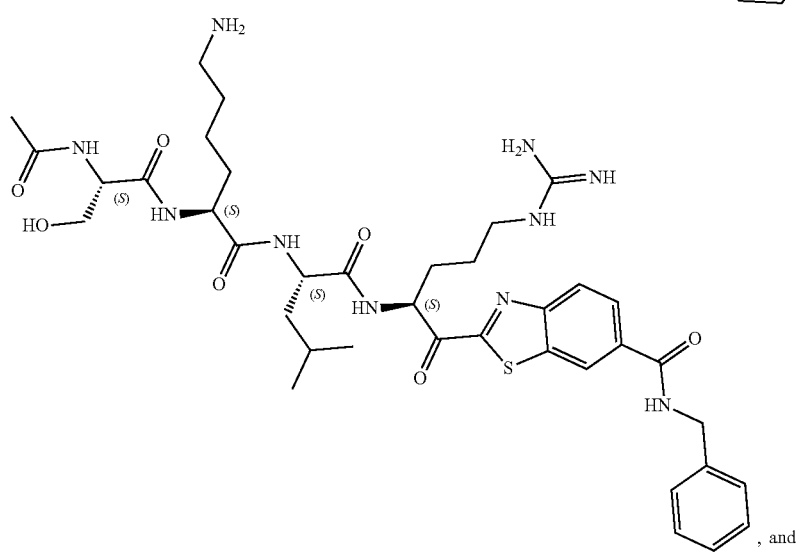
, and
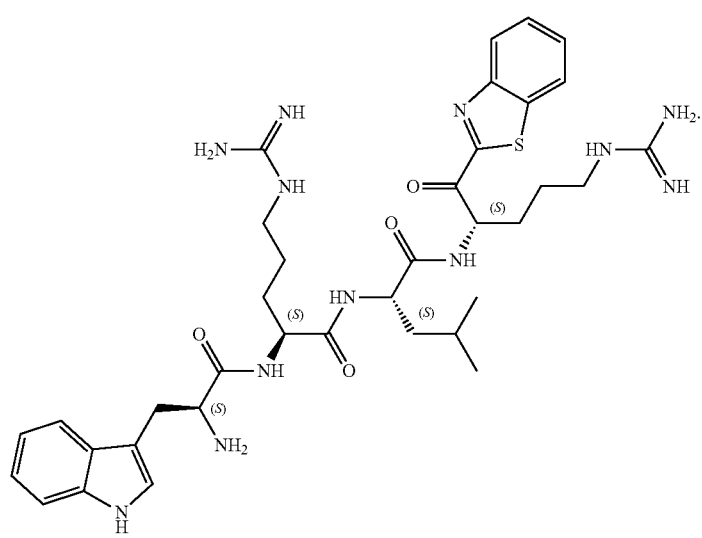

12. A method of inhibiting tumor progression comprising administering to the subject in need thereof a pharmaceutical composition comprising a therapeutically effective amount of at least one compound of claim 1.

13. A method of treating a cancer in a subject comprising administering to the subject in need thereof a pharmaceutical composition comprising a therapeutically effective amount of at least one compound of claim 1.

14. The method of claim 13, wherein the cancer is selected from the group consisting of breast, ovarian, prostate, endometrial, colon, pancreatic, head and neck, gastric, renal, brain, liver, bladder, kidney, lung, esophageal, leukemias, multiple myeloma, lymphoma, and melanoma.

15. A pharmaceutical composition comprising a therapeutically effective amount of at least one compound of claim 1.

16. A fluorescent imaging composition comprising a compound of Formula (II) of claim 1 and a fluorophore selected from the group consisting of Cy3, Cy3.5, Cy5, Cy5.5, Cy7, and Cy7.5.

17. A method of detecting imaging cancer comprising:
administering to a subject the fluorescent imaging composition of claim 16;
detecting fluorescence of the fluorescent imaging composition within the body of the subject,
wherein fluorescence of the fluorescent imaging composition indicates the existence of cancer.

18. A radiolabeled imaging composition comprising a compound of Formula (II) of claim 1 and a radioisotope selected from the group consisting of $^{11}$C, $^{13}$N, $^{15}$O, $^{18}$F, $^{75}$Br, $^{124}$I, $^{125}$I, and $^{131}$I.

19. A method of imaging cancer comprising:
administering to a subject the radiolabeled imaging composition of claim 18; and
detecting radiation of the radiolabeled imaging composition within the body of the subject,
wherein the radiation of the radiolabeled imaging composition indicates the existence of cancer.

20. The compound of claim 1 wherein Z is a benzothiazole of Formula (IV).

21. The compound of claim 1 wherein $P_2$ forms a bond with $P_4$ to form a cyclic peptide.

22. The compound of claim 1 wherein the compound has the following formula:

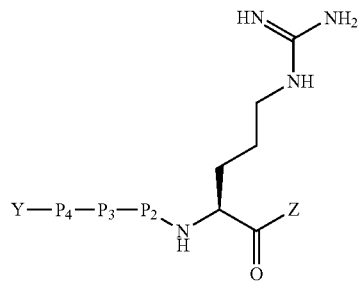

wherein
Y is acetyl;
$P_2$ is a residue of an amino acid selected from the group consisting of Leu and hLeu;
$P_3$ is a residue of an amino acid selected from the group consisting of Arg, Lys, Trp, Leu, Gln, Phe, His, His(3-Bom), and L-Phe(NO$_2$);
$P_4$ is a residue of an amino acid selected from the group consisting of Arg, Lys, Trp, Ser, Phe, His(3-Bom); and Z is

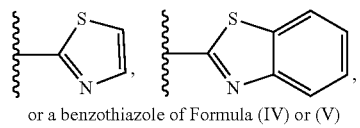

or a benzothiazole of Formula (IV) or (V)

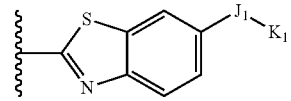

(IV)

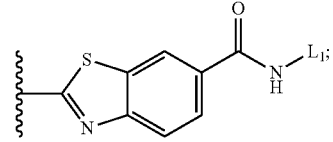

(V)

wherein
$J_1$ is C(O), SO$_2$, CH$_2$, or heterocyclo,
$K_1$ is a D- or L-amino acid, wherein the C-terminus is —COOH, —C(O)NH$_2$, —OH, —OR$_{10}$, —NH$_2$, —NR$_{11}$R$_{12}$, —H, or heterocyclo;
$R_{10}$ is $C_1$ to $C_{12}$ alkyl, cycloalkyl, alkylaryl, or aryl;
$R_{11}$ and $R_{12}$ are each independently H, $C_1$ to $C_{12}$ alkyl, cycloalkyl, alkylaryl, aryl, or heterocyclo; and $R_{11}$ and $R_{12}$ optionally form a ring; and
$L_1$ is H, alkyl, cycloalkyl, alkylaryl, benzyl, substituted benzyl, 2- or 3- or 4-piperdinyl, 2- or 3- or 4-pyridinyl, aryl, heterocyclo, or heteroaryl.

23. A compound of Formula (II):

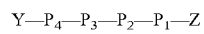

Y—P$_4$—P$_3$—P$_2$—P$_1$—Z (II)

wherein
Y is acetyl, tert-butyloxycarbonyl, benzyloxymethyl acetyl, carboxybenzyl, fluorenylmethoxycarbonyl (FMOC), benzyl, or a fluorophore;
$P_1$ is a residue of Arg;
$P_2$ is a residue of an amino acid selected from the group consisting of Leu or hLeu;
$P_3$ is a residue of an amino acid selected from the group consisting of Gln, Agp, Nle(O-Bzl), Orn, Met(O), Arg, hArg, Trp, hCha, hTyr, hPhe, and Lys;
$P_4$ is a residue of an amino acid selected from the group consisting of Agp, DAB(Z), Nle(O-Bzl), Orn, Arg(NO$_2$), Arg, Lys, L-Arg(Z)2, L-Glu(Bzl), His(3-Bom), Lys(2-Cl—Z), dhLeu, Idc, Chg, dhAbu, and L-hArg; and Z is

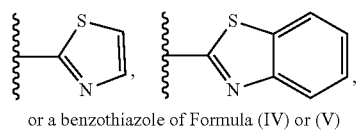

or a benzothiazole of Formula (IV) or (V)

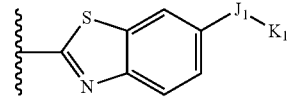

(IV)

-continued

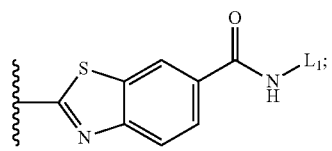
(V)

wherein
- $J_1$ is C(O), $SO_2$, $CH_2$, or heterocyclo;
- $K_1$ is a D- or L-amino acid, wherein the C-terminus is —COOH, —C(O)NH$_2$, —OH, —OR$_{10}$, —NH$_2$, —NR$_{11}$R$_{12}$, —H, or heterocyclo;
- $R_{10}$ is $C_1$ to $C_{12}$ alkyl, cycloalkyl, alkylaryl, or aryl;
- $R_{11}$ and Ria are each independently H, $C_1$ to $C_{12}$ alkyl, cycloalkyl, alkylaryl, aryl, or heterocyclo; and $R_{11}$ and $R_{12}$ optionally form a ring; and
- $L_1$ is H, alkyl, cycloalkyl, alkylaryl, benzyl, substituted benzyl, 2- or 3- or 4-piperdinyl, 2- or 3- or 4-pyridinyl, aryl, heterocyclo, or heteroaryl.

* * * * *

SEQUENCE LISTING

```
<160> NUMBER OF SEQ ID NOS: 25

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Lys Gln Leu Arg
1

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Lys His Leu Arg
1

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Trp Gln Leu Arg
1

<210> SEQ ID NO 4
<211> LENGTH: 4
<212> TYPE: PRT
<213> ORGANISM: Artificial Sequence
<220> FEATURE:
<223> OTHER INFORMATION: Synthetic
```

```
<400> SEQUENCE: 4

Lys Phe Leu Arg
1

<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Lys Phe Leu Arg
1

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Arg Gln Leu Arg
1

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Ser Gln Leu Arg
1

<210> SEQ ID NO 8
<211> LENGTH: 4
<212> TYPE: PRT
<213> ORGANISM: Artificial Sequence
<220> FEATURE:
<223> OTHER INFORMATION: Synthetic

<400> SEQUENCE: 8

Lys Arg Leu Arg
1

<210> SEQ ID NO 9
<211> LENGTH: 4
<212> TYPE: PRT
<213> ORGANISM: Artificial Sequence
<220> FEATURE:
<223> OTHER INFORMATION: Synthetic

<400> SEQUENCE: 9

Trp Arg Leu Arg
1

<210> SEQ ID NO 10
<211> LENGTH: 4
<212> TYPE: PRT
<213> ORGANISM: Artificial Sequence
<220> FEATURE:
<223> OTHER INFORMATION: Synthetic

<400> SEQUENCE: 10
```

Ser Lys Leu Arg
1

<210> SEQ ID NO 11
<211> LENGTH: 4
<212> TYPE: PRT
<213> ORGANISM: Artificial Sequence
<220> FEATURE:
<223> OTHER INFORMATION: Synthetic

<400> SEQUENCE: 11

Ser His Leu Arg
1

<210> SEQ ID NO 12
<211> LENGTH: 4
<212> TYPE: PRT
<213> ORGANISM: Artificial Sequence
<220> FEATURE:
<223> OTHER INFORMATION: Synthetic

<400> SEQUENCE: 12

Trp Lys Leu Arg
1

<210> SEQ ID NO 13
<211> LENGTH: 4
<212> TYPE: PRT
<213> ORGANISM: Artificial Sequence
<220> FEATURE:
<223> OTHER INFORMATION: Synthetic

<400> SEQUENCE: 13

Ser Lys Phe Arg
1

<210> SEQ ID NO 14
<211> LENGTH: 4
<212> TYPE: PRT
<213> ORGANISM: Artificial Sequence
<220> FEATURE:
<223> OTHER INFORMATION: Synthetic

<400> SEQUENCE: 14

Asn Lys Leu Arg
1

<210> SEQ ID NO 15
<211> LENGTH: 4
<212> TYPE: PRT
<213> ORGANISM: Artificial Sequence
<220> FEATURE:
<223> OTHER INFORMATION: Synthetic

<400> SEQUENCE: 15

Ser Arg Leu Arg
1

<210> SEQ ID NO 16
<211> LENGTH: 4
<212> TYPE: PRT
<213> ORGANISM: Artificial Sequence
<220> FEATURE:
<223> OTHER INFORMATION: Synthetic

<400> SEQUENCE: 16

```
Thr Lys Leu Arg
1

<210> SEQ ID NO 17
<211> LENGTH: 4
<212> TYPE: PRT
<213> ORGANISM: Artificial Sequence
<220> FEATURE:
<223> OTHER INFORMATION: Synthetic

<400> SEQUENCE: 17

Ser Trp Leu Arg
1

<210> SEQ ID NO 18
<211> LENGTH: 4
<212> TYPE: PRT
<213> ORGANISM: Artificial Sequence
<220> FEATURE:
<223> OTHER INFORMATION: Synthetic

<400> SEQUENCE: 18

Arg Lys Leu Arg
1

<210> SEQ ID NO 19
<211> LENGTH: 4
<212> TYPE: PRT
<213> ORGANISM: Artificial Sequence
<220> FEATURE:
<223> OTHER INFORMATION: Synthetic

<400> SEQUENCE: 19

Phe Leu Phe Arg
1

<210> SEQ ID NO 20
<211> LENGTH: 4
<212> TYPE: PRT
<213> ORGANISM: Artificial Sequence
<220> FEATURE:
<223> OTHER INFORMATION: Synthetic

<400> SEQUENCE: 20

Trp Leu Phe Arg
1

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
gtccaactgt caccggatct c                                         21

<210> SEQ ID NO 22
<211> LENGTH: 35
<212> TYPE: DNA
<213> ORGANISM: Artificial Sequence
<220> FEATURE:
<223> OTHER INFORMATION: Synthetic

<400> SEQUENCE: 22
ccgccgaaca ccgagggagg actttcgaac ggcgg                           35
```

-continued

```
<210> SEQ ID NO 23
<211> LENGTH: 655
<212> TYPE: PRT
<213> ORGANISM: Homo sapiens

<400> SEQUENCE: 23

Met Gly Arg Trp Ala Trp Val Pro Ser Pro Trp Pro Pro Gly Leu
1               5                   10                  15

Gly Pro Phe Leu Leu Leu Leu Leu Leu Leu Leu Leu Pro Arg Gly
            20                  25                  30

Phe Gln Pro Gln Pro Gly Gly Asn Arg Thr Glu Ser Pro Glu Pro Asn
            35                  40                  45

Ala Thr Ala Thr Pro Ala Ile Pro Thr Ile Leu Val Thr Ser Val Thr
50                  55                  60

Ser Glu Thr Pro Ala Thr Ser Ala Pro Glu Ala Glu Gly Pro Gln Ser
65                  70                  75                  80

Gly Gly Leu Pro Pro Pro Arg Ala Val Pro Ser Ser Ser Pro
            85                  90                  95

Gln Ala Gln Ala Leu Thr Glu Asp Gly Arg Pro Cys Arg Phe Pro Phe
            100                 105                 110

Arg Tyr Gly Gly Arg Met Leu His Ala Cys Thr Ser Glu Gly Ser Ala
            115                 120                 125

His Arg Lys Trp Cys Ala Thr Thr His Asn Tyr Asp Arg Asp Arg Ala
            130                 135                 140

Trp Gly Tyr Cys Val Glu Ala Thr Pro Pro Gly Gly Pro Ala Ala
145                 150                 155                 160

Leu Asp Pro Cys Ala Ser Gly Pro Cys Leu Asn Gly Gly Ser Cys Ser
                165                 170                 175

Asn Thr Gln Asp Pro Gln Ser Tyr His Cys Ser Cys Pro Arg Ala Phe
                180                 185                 190

Thr Gly Lys Asp Cys Gly Thr Glu Lys Cys Phe Asp Glu Thr Arg Tyr
            195                 200                 205

Glu Tyr Leu Glu Gly Gly Asp Arg Trp Ala Arg Val Arg Gln Gly His
            210                 215                 220

Val Glu Gln Cys Glu Cys Phe Gly Gly Arg Thr Trp Cys Glu Gly Thr
225                 230                 235                 240

Arg His Thr Ala Cys Leu Ser Ser Pro Cys Leu Asn Gly Gly Thr Cys
                245                 250                 255

His Leu Ile Val Ala Thr Gly Thr Thr Val Cys Ala Cys Pro Pro Gly
            260                 265                 270

Phe Ala Gly Arg Leu Cys Asn Ile Glu Pro Asp Glu Arg Cys Phe Leu
            275                 280                 285

Gly Asn Gly Thr Gly Tyr Arg Gly Val Ala Ser Thr Ser Ala Ser Gly
            290                 295                 300

Leu Ser Cys Leu Ala Trp Asn Ser Asp Leu Leu Tyr Gln Glu Leu His
305                 310                 315                 320

Val Asp Ser Val Gly Ala Ala Ala Leu Leu Gly Leu Gly Pro His Ala
                325                 330                 335

Tyr Cys Arg Asn Pro Asp Asn Asp Glu Arg Pro Trp Cys Tyr Val Val
            340                 345                 350

Lys Asp Ser Ala Leu Ser Trp Glu Tyr Cys Arg Leu Glu Ala Cys Glu
            355                 360                 365

Ser Leu Thr Arg Val Gln Leu Ser Pro Asp Leu Leu Ala Thr Leu Pro
            370                 375                 380
```

```
Glu Pro Ala Ser Pro Gly Arg Gln Ala Cys Gly Arg Arg His Lys Lys
385                 390                 395                 400

Arg Thr Phe Leu Arg Pro Arg Ile Ile Gly Ser Ser Ser Leu Pro
            405                 410                 415

Gly Ser His Pro Trp Leu Ala Ala Ile Tyr Ile Gly Asp Ser Phe Cys
            420                 425                 430

Ala Gly Ser Leu Val His Thr Cys Trp Val Val Ser Ala Ala His Cys
            435                 440                 445

Phe Ser His Ser Pro Pro Arg Asp Ser Val Ser Val Val Leu Gly Gln
        450                 455                 460

His Phe Phe Asn Arg Thr Thr Asp Val Thr Gln Thr Phe Gly Ile Glu
465                 470                 475                 480

Lys Tyr Ile Pro Tyr Thr Leu Tyr Ser Val Phe Asn Pro Ser Asp His
                485                 490                 495

Asp Leu Val Leu Ile Arg Leu Lys Lys Lys Gly Asp Arg Cys Ala Thr
            500                 505                 510

Arg Ser Gln Phe Val Gln Pro Ile Cys Leu Pro Glu Pro Gly Ser Thr
        515                 520                 525

Phe Pro Ala Gly His Lys Cys Gln Ile Ala Gly Trp Gly His Leu Asp
    530                 535                 540

Glu Asn Val Ser Gly Tyr Ser Ser Leu Arg Glu Ala Leu Val Pro
545                 550                 555                 560

Leu Val Ala Asp His Lys Cys Ser Ser Pro Glu Val Tyr Gly Ala Asp
                565                 570                 575

Ile Ser Pro Asn Met Leu Cys Ala Gly Tyr Phe Asp Cys Lys Ser Asp
                580                 585                 590

Ala Cys Gln Gly Asp Ser Gly Gly Pro Leu Ala Cys Glu Lys Asn Gly
            595                 600                 605

Val Ala Tyr Leu Tyr Gly Ile Ile Ser Trp Gly Asp Gly Cys Gly Arg
            610                 615                 620

Leu His Lys Pro Gly Val Tyr Thr Arg Val Ala Asn Tyr Val Asp Trp
625                 630                 635                 640

Ile Asn Asp Arg Ile Arg Pro Pro Arg Leu Val Ala Pro Ser
                645                 650                 655

<210> SEQ ID NO 24
<211> LENGTH: 855
<212> TYPE: PRT
<213> ORGANISM: Homo sapiens

<400> SEQUENCE: 24

Met Gly Ser Asp Arg Ala Arg Lys Gly Gly Gly Gly Pro Lys Asp Phe
1               5                   10                  15

Gly Ala Gly Leu Lys Tyr Asn Ser Arg His Glu Lys Val Asn Gly Leu
            20                  25                  30

Glu Glu Gly Val Glu Phe Leu Pro Val Asn Asn Val Lys Lys Val Glu
        35                  40                  45

Lys His Gly Pro Gly Arg Trp Val Val Leu Ala Ala Val Leu Ile Gly
    50                  55                  60

Leu Leu Leu Val Leu Leu Gly Ile Gly Phe Leu Val Trp His Leu Gln
65                  70                  75                  80

Tyr Arg Asp Val Arg Val Gln Lys Val Phe Asn Gly Tyr Met Arg Ile
                85                  90                  95

Thr Asn Glu Asn Phe Val Asp Ala Tyr Glu Asn Ser Asn Ser Thr Glu
```

```
            100                 105                 110
Phe Val Ser Leu Ala Ser Lys Val Lys Asp Ala Leu Lys Leu Leu Tyr
            115                 120                 125

Ser Gly Val Pro Phe Leu Gly Pro Tyr His Lys Glu Ser Ala Val Thr
            130                 135                 140

Ala Phe Ser Glu Gly Ser Val Ile Ala Tyr Tyr Trp Ser Glu Phe Ser
145                 150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
                180                 185                 190

Val Thr Ser Val Val Ala Phe Pro Thr Asp Ser Lys Thr Val Gln Arg
                195                 200                 205

Thr Gln Asp Asn Ser Cys Ser Phe Gly Leu His Ala Arg Gly Val Glu
        210                 215                 220

Leu Met Arg Phe Thr Thr Pro Gly Phe Pro Asp Ser Pro Tyr Pro Ala
225                 230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
                260                 265                 270

Ser Asp Leu Val Thr Val Tyr Asn Thr Leu Ser Pro Met Glu Pro His
                275                 280                 285

Ala Leu Val Gln Leu Cys Gly Thr Tyr Pro Pro Ser Tyr Asn Leu Thr
            290                 295                 300

Phe His Ser Ser Gln Asn Val Leu Leu Ile Thr Leu Ile Thr Asn Thr
305                 310                 315                 320

Glu Arg Arg His Pro Gly Phe Glu Ala Thr Phe Phe Gln Leu Pro Arg
                325                 330                 335

Met Ser Ser Cys Gly Gly Arg Leu Arg Lys Ala Gln Gly Thr Phe Asn
                340                 345                 350

Ser Pro Tyr Tyr Pro Gly His Tyr Pro Pro Asn Ile Asp Cys Thr Trp
                355                 360                 365

Asn Ile Glu Val Pro Asn Asn Gln His Val Lys Val Arg Phe Lys Phe
            370                 375                 380

Phe Tyr Leu Leu Glu Pro Gly Val Pro Ala Gly Thr Cys Pro Lys Asp
385                 390                 395                 400

Tyr Val Glu Ile Asn Gly Glu Lys Tyr Cys Gly Glu Arg Ser Gln Phe
                405                 410                 415

Val Val Thr Ser Asn Ser Asn Lys Ile Thr Val Arg Phe His Ser Asp
                420                 425                 430

Gln Ser Tyr Thr Asp Thr Gly Phe Leu Ala Glu Tyr Leu Ser Tyr Asp
            435                 440                 445

Ser Ser Asp Pro Cys Pro Gly Gln Phe Thr Cys Arg Thr Gly Arg Cys
            450                 455                 460

Ile Arg Lys Glu Leu Arg Cys Asp Gly Trp Ala Asp Cys Thr Asp His
465                 470                 475                 480

Ser Asp Glu Leu Asn Cys Ser Cys Asp Ala Gly His Gln Phe Thr Cys
                485                 490                 495

Lys Asn Lys Phe Cys Lys Pro Leu Phe Trp Val Cys Asp Ser Val Asn
                500                 505                 510

Asp Cys Gly Asp Asn Ser Asp Glu Gln Gly Cys Ser Cys Pro Ala Gln
                515                 520                 525
```

```
Thr Phe Arg Cys Ser Asn Gly Lys Cys Leu Ser Lys Ser Gln Gln Cys
            530                 535                 540

Asn Gly Lys Asp Asp Cys Gly Asp Gly Ser Asp Glu Ala Ser Cys Pro
545                 550                 555                 560

Lys Val Asn Val Val Thr Cys Thr Lys His Thr Tyr Arg Cys Leu Asn
                565                 570                 575

Gly Leu Cys Leu Ser Lys Gly Asn Pro Glu Cys Asp Gly Lys Glu Asp
            580                 585                 590

Cys Ser Asp Gly Ser Asp Glu Lys Asp Cys Asp Cys Gly Leu Arg Ser
            595                 600                 605

Phe Thr Arg Gln Ala Arg Val Val Gly Gly Thr Asp Ala Asp Glu Gly
            610                 615                 620

Glu Trp Pro Trp Gln Val Ser Leu His Ala Leu Gly Gln Gly His Ile
625                 630                 635                 640

Cys Gly Ala Ser Leu Ile Ser Pro Asn Trp Leu Val Ser Ala Ala His
            645                 650                 655

Cys Tyr Ile Asp Asp Arg Gly Phe Arg Tyr Ser Asp Pro Thr Gln Trp
            660                 665                 670

Thr Ala Phe Leu Gly Leu His Asp Gln Ser Gln Arg Ser Ala Pro Gly
            675                 680                 685

Val Gln Glu Arg Arg Leu Lys Arg Ile Ile Ser His Pro Phe Phe Asn
690                 695                 700

Asp Phe Thr Phe Asp Tyr Asp Ile Ala Leu Leu Glu Leu Glu Lys Pro
705                 710                 715                 720

Ala Glu Tyr Ser Ser Met Val Arg Pro Ile Cys Leu Pro Asp Ala Ser
                725                 730                 735

His Val Phe Pro Ala Gly Lys Ala Ile Trp Val Thr Gly Trp Gly His
            740                 745                 750

Thr Gln Tyr Gly Gly Thr Gly Ala Leu Ile Leu Gln Lys Gly Glu Ile
            755                 760                 765

Arg Val Ile Asn Gln Thr Thr Cys Glu Asn Leu Leu Pro Gln Gln Ile
            770                 775                 780

Thr Pro Arg Met Met Cys Val Gly Phe Leu Ser Gly Gly Val Asp Ser
785                 790                 795                 800

Cys Gln Gly Asp Ser Gly Gly Pro Leu Ser Ser Val Glu Ala Asp Gly
                805                 810                 815

Arg Ile Phe Gln Ala Gly Val Val Ser Trp Gly Asp Gly Cys Ala Gln
            820                 825                 830

Arg Asn Lys Pro Gly Val Tyr Thr Arg Leu Pro Leu Phe Arg Asp Trp
            835                 840                 845

Ile Lys Glu Asn Thr Gly Val
    850                 855

<210> SEQ ID NO 25
<211> LENGTH: 417
<212> TYPE: PRT
<213> ORGANISM: Homo sapiens

<400> SEQUENCE: 25

Met Ala Gln Lys Glu Gly Gly Arg Thr Val Pro Cys Cys Ser Arg Pro
1               5                   10                  15

Lys Val Ala Ala Leu Thr Ala Gly Thr Leu Leu Leu Thr Ala Ile
            20                  25                  30

Gly Ala Ala Ser Trp Ala Ile Val Ala Val Leu Leu Arg Ser Asp Gln
```

```
                35                  40                  45
Glu Pro Leu Tyr Pro Val Gln Val Ser Ser Ala Asp Ala Arg Leu Met
 50                  55                  60

Val Phe Asp Lys Thr Glu Gly Thr Trp Arg Leu Cys Ser Ser Arg
 65                  70                  75                  80

Ser Asn Ala Arg Val Ala Gly Leu Ser Cys Glu Glu Met Gly Phe Leu
                 85                  90                  95

Arg Ala Leu Thr His Ser Glu Leu Asp Val Arg Thr Ala Gly Ala Asn
                100                 105                 110

Gly Thr Ser Gly Phe Phe Cys Val Asp Glu Gly Arg Leu Pro His Thr
                115                 120                 125

Gln Arg Leu Leu Glu Val Ile Ser Val Cys Asp Cys Pro Arg Gly Arg
130                 135                 140

Phe Leu Ala Ala Ile Cys Gln Asp Cys Gly Arg Arg Lys Leu Pro Val
145                 150                 155                 160

Asp Arg Ile Val Gly Gly Arg Asp Thr Ser Leu Gly Arg Trp Pro Trp
                165                 170                 175

Gln Val Ser Leu Arg Tyr Asp Gly Ala His Leu Cys Gly Gly Ser Leu
                180                 185                 190

Leu Ser Gly Asp Trp Val Leu Thr Ala Ala His Cys Phe Pro Glu Arg
                195                 200                 205

Asn Arg Val Leu Ser Arg Trp Arg Val Phe Ala Gly Ala Val Ala Gln
210                 215                 220

Ala Ser Pro His Gly Leu Gln Leu Gly Val Gln Ala Val Val Tyr His
225                 230                 235                 240

Gly Gly Tyr Leu Pro Phe Arg Asp Pro Asn Ser Glu Glu Asn Ser Asn
                245                 250                 255

Asp Ile Ala Leu Val His Leu Ser Ser Pro Leu Pro Leu Thr Glu Tyr
                260                 265                 270

Ile Gln Pro Val Cys Leu Pro Ala Ala Gly Gln Ala Leu Val Asp Gly
                275                 280                 285

Lys Ile Cys Thr Val Thr Gly Trp Gly Asn Thr Gln Tyr Tyr Gly Gln
                290                 295                 300

Gln Ala Gly Val Leu Gln Glu Ala Arg Val Pro Ile Ile Ser Asn Asp
305                 310                 315                 320

Val Cys Asn Gly Ala Asp Phe Tyr Gly Asn Gln Ile Lys Pro Lys Met
                325                 330                 335

Phe Cys Ala Gly Tyr Pro Glu Gly Gly Ile Asp Ala Cys Gln Gly Asp
                340                 345                 350

Ser Gly Gly Pro Phe Val Cys Glu Asp Ser Ile Ser Arg Thr Pro Arg
                355                 360                 365

Trp Arg Leu Cys Gly Ile Val Ser Trp Gly Thr Gly Cys Ala Leu Ala
370                 375                 380

Gln Lys Pro Gly Val Tyr Thr Lys Val Ser Asp Phe Arg Glu Trp Ile
385                 390                 395                 400

Phe Gln Ala Ile Lys Thr His Ser Glu Ala Ser Gly Met Val Thr Gln
                405                 410                 415

Leu
```